US009643972B2

(12) United States Patent
Beck et al.

(10) Patent No.: US 9,643,972 B2
(45) Date of Patent: May 9, 2017

(54) IMMUNOREGULATORY AGENTS

(71) Applicant: Flexus Biosciences, Inc., Princeton, NJ (US)

(72) Inventors: Hilary Plake Beck, Emerald Hills, CA (US); Juan Carlos Jaen, Burlingame, CA (US); Maksim Osipov, Belmont, CA (US); Jay Patrick Powers, Pacifica, CA (US); Maureen Kay Reilly, Belmont, CA (US); Hunter Paul Shunatona, San Francisco, CA (US); James Ross Walker, Menlo Park, CA (US); Mikhail Zibinsky, Lodi, CA (US); James Aaron Balog, Lambertville, NJ (US); David K. Williams, Delran, NJ (US); Jay A. Markwalder, Lahaska, PA (US); Emily Charlotte Cherney, Newtown, PA (US); Weifang Shan, Princeton, NJ (US); Audris Huang, New Hope, PA (US)

(73) Assignee: Flexus Biosciences, Inc., Princeton, NJ (US)

( * ) Notice: Subject to any disclaimer, the term of this patent is extended or adjusted under 35 U.S.C. 154(b) by 0 days.

(21) Appl. No.: 14/933,863

(22) Filed: Nov. 5, 2015

(65) Prior Publication Data
US 2016/0137652 A1 May 19, 2016

Related U.S. Application Data

(60) Provisional application No. 62/075,671, filed on Nov. 5, 2014, provisional application No. 62/098,022, filed on Dec. 30, 2014.

(51) Int. Cl.
| A61K 31/4709 | (2006.01) |
| C07D 487/04 | (2006.01) |
| C07D 215/06 | (2006.01) |
| A61K 31/47 | (2006.01) |
| C07D 231/56 | (2006.01) |
| A61K 31/416 | (2006.01) |
| C07D 215/233 | (2006.01) |
| C07D 471/04 | (2006.01) |
| A61K 31/437 | (2006.01) |
| C07D 239/74 | (2006.01) |
| A61K 31/517 | (2006.01) |
| A61K 31/4375 | (2006.01) |
| C07D 217/04 | (2006.01) |
| C07D 405/08 | (2006.01) |
| C07D 417/08 | (2006.01) |
| C07D 401/12 | (2006.01) |
| C07D 401/14 | (2006.01) |
| A61K 31/506 | (2006.01) |
| A61K 31/496 | (2006.01) |
| A61K 31/519 | (2006.01) |
| A61K 45/06 | (2006.01) |

(52) U.S. Cl.
CPC .......... *C07D 487/04* (2013.01); *A61K 31/416* (2013.01); *A61K 31/437* (2013.01); *A61K 31/4375* (2013.01); *A61K 31/47* (2013.01); *A61K 31/4709* (2013.01); *A61K 31/496* (2013.01); *A61K 31/506* (2013.01); *A61K 31/517* (2013.01); *A61K 31/519* (2013.01); *A61K 45/06* (2013.01); *C07D 215/06* (2013.01); *C07D 215/233* (2013.01); *C07D 217/04* (2013.01); *C07D 231/56* (2013.01); *C07D 239/74* (2013.01); *C07D 401/12* (2013.01); *C07D 401/14* (2013.01); *C07D 405/08* (2013.01); *C07D 417/08* (2013.01); *C07D 471/04* (2013.01)

(58) Field of Classification Search
CPC .............. A61K 31/4709; A61K 31/496; A61K 31/519; A61K 31/506; A61K 45/06; C07D 401/14; C07D 401/12; C07D 417/08
See application file for complete search history.

(56) References Cited

U.S. PATENT DOCUMENTS

| 5,455,273 A | 10/1995 | Maier et al. |
| 5,723,464 A | 3/1998 | Brightwell et al. |
| 7,645,771 B2 | 1/2010 | Kazmierski et al. |
| 8,088,803 B2 | 1/2012 | Combs et al. |
| 2002/0016463 A1 | 2/2002 | Zablocki et al. |
| 2003/0190298 A1 | 10/2003 | Bradley et al. |
| 2004/0029887 A1 | 2/2004 | Bhatia et al. |
| 2004/0234623 A1 | 11/2004 | Munn et al. |
| 2006/0258719 A1 | 11/2006 | Combs et al. |
| 2007/0129347 A1 | 6/2007 | Hinze et al. |

(Continued)

FOREIGN PATENT DOCUMENTS

| EP | 0596298 B1 | 1/2002 |
| EP | 1781656 B1 | 12/2007 |
| WO | WO 99/29310 | 6/1999 |
| WO | WO 00/56727 | 9/2000 |
| WO | WO 01/92204 | 12/2001 |

(Continued)

OTHER PUBLICATIONS

Corsello, J Clin Endocrinol Metab, 98(4), 1361-1375, 2013.*

(Continued)

*Primary Examiner* — D M Seaman
(74) *Attorney, Agent, or Firm* — Baker & Hostetler, LLP

(57) ABSTRACT

Compounds that modulate the oxidoreductase enzyme indoleamine 2,3-dioxygenase, and compositions containing the compounds, are described herein. The use of such compounds and compositions for the treatment and/or prevention of a diverse array of diseases, disorders and conditions, including cancer- and immune-related disorders, that are mediated by indoleamine 2,3-dioxygenase is also provided.

47 Claims, 15 Drawing Sheets

(56) References Cited

U.S. PATENT DOCUMENTS

| | | |
|---|---|---|
| 2007/0197584 A1 | 8/2007 | Schwink et al. |
| 2008/0039453 A1 | 2/2008 | Putman |
| 2008/0146569 A1 | 6/2008 | Blake et al. |
| 2009/0275523 A1 | 11/2009 | Schudok et al. |
| 2010/0008866 A1 | 1/2010 | Blum et al. |
| 2010/0233166 A1 | 9/2010 | Prendergast et al. |
| 2011/0218183 A1 | 9/2011 | Chen |
| 2011/0306644 A1 | 12/2011 | Hoekstra et al. |
| 2013/0197095 A1 | 8/2013 | Nolte et al. |
| 2013/0217706 A1 | 8/2013 | Tran et al. |
| 2014/0212444 A1 | 7/2014 | Holoshitz et al. |
| 2016/0137653 A1 | 5/2016 | Beck et al. |

FOREIGN PATENT DOCUMENTS

| | | |
|---|---|---|
| WO | WO 2004/094409 | 11/2004 |
| WO | WO 2005/080317 | 9/2005 |
| WO | WO 2006/018279 | 2/2006 |
| WO | WO 2006/029879 | 3/2006 |
| WO | WO 2006/105021 | 10/2006 |
| WO | WO 2007/005874 | 1/2007 |
| WO | WO 2008/132601 | 11/2008 |
| WO | WO 2009/009116 | 1/2009 |
| WO | WO 2009/044273 | 4/2009 |
| WO | WO 2009/052320 | 4/2009 |
| WO | WO 2010/015655 | 2/2010 |
| WO | WO 2010/019570 | 2/2010 |
| WO | WO 2010/075376 A2 | 7/2010 |
| WO | WO 2010/077634 | 7/2010 |
| WO | WO 2011/028683 | 3/2011 |
| WO | WO 2011/070024 | 6/2011 |
| WO | WO 2011/107553 | 9/2011 |
| WO | WO 2011/109400 | 9/2011 |
| WO | WO 2011/131407 | 10/2011 |
| WO | WO 2011/140249 | 11/2011 |
| WO | WO 2012/032433 | 3/2012 |
| WO | WO 2012/145493 | 10/2012 |
| WO | WO 2013/079174 | 6/2013 |
| WO | WO 2013/079425 | 6/2013 |
| WO | WO 2013/087699 | 6/2013 |
| WO | WO 2013/119716 | 8/2013 |
| WO | WO 2013/132044 | 9/2013 |
| WO | WO 2013/169264 | 11/2013 |
| WO | WO 2014/008218 | 1/2014 |
| WO | WO 2014/036357 | 3/2014 |
| WO | WO 2014/036412 | 3/2014 |
| WO | WO 2014/150677 | 9/2014 |
| WO | WO 2014/160967 | 10/2014 |
| WO | WO2015/188085 A1 | 12/2015 |
| WO | WO 2016/071283 | 5/2016 |
| WO | WO 2016/073738 | 5/2016 |
| WO | WO 2016/073770 | 5/2016 |
| WO | WO 2016/073774 | 5/2016 |

OTHER PUBLICATIONS

Kohrt, Blood, VOl 123(5), 678-686, 2014.*
Stucchi, ACS Med Chem Lett, vol. 6, 882-887, 2015.*
https://pubchem.ncbi.nlm.nih.gov/compound/70339979#section=top; Pub Chem Open Chemistry Database; Compound Summary for CID 70339979; Dec. 20, 2015; 3 pages.
International Search Report dated Mar. 17, 2016 issued in PCT/US15/59311, 3 pages.
International Search Report dated May 17, 2016 issued in PCT/US15/59316, 2 pages.
International Search Report dated Dec. 10, 2015 issued in PCT/US15/34449, 1 page.
International Search Report dated May 13, 2016 issued in PCT/US15/59271, 3 pages.
Pubchem CID 57911539, Aug. 19, 2012, pp. 1-11 [online], [retrieved on Dec. 17, 2015], Retrieved from the Internet <URL:https://pubchem.ncbi.nlm.nih.gov/compound/57911539#section=Top.>; p. 3.
National Center for Biotechnology Information, Pubchem Compound Database; CID=24231423, https://pubchem.ncbi.nlm.nih.gov/compound/24231423 (accessed Jun. 23, 2016). 9 pages.
Pubchem SID=162741420, May 22, 2013, pp. 1-5 [online], [retrieved on Dec. 21, 2015], retrieved from the Internet <URL: https://pubchem.ncbi.nlm.nih.gov/substance/162741420>; p. 3. (accessed Jul. 11, 2016).
Serafini, P. et al., Myeloid suppressor cells in cancer: recruitment, phenotype, properties, and mechanisms of immune suppression. Seminars in Cancer Biology, 16(1):53-65 Feb. 2006.
Ball, H.J. et al., Characterization of an indoleamine 2, 3-dioxygenase-like protein found in humans and mice, Gene, 396(1):203-213 Jul. 2007.
Brandacher, G. et al., Prognostic value of indoleamine 2,3-dioxygenase expression in colorectal cancer: effect on tumor-infiltrasting T cells, Clin. Cancer Res., 12(4):1144-1151 Feb. 2006.
Berge, S. M. et al., Pharmaceutical Salts, J. Pharm. Sci., 66:1-19, Jan. 1977.
Munsen et al., Ligand a versatile computerized approach for characterization of ligand-binding systems, Analytical Biochemistry, 107(1), 220-239, Sep. 1980.
Platten, M. et al., Tryptophan catabolism in cancer: beyond IDO and tryptophan depletion, Cancer Research, 72(21):5435-5440, Nov. 2012.
Ishiyama, et al., Palladium (0)-catalyzed cross-coupling reaction of alkoxydiboron with halorenes: a direct procedure for arylboronic esters., J. Org. Chem., 60, 7508-7510, Nov. 1995.
El-Faham, et al., Peptide coupling reagents, more than a letter soup, Chemical Reviews, 111.11, 6557-6602, Aug. 2011.
Evans, et al., Asymmetric alkylation reactions of chiral imide enolates. A practical approach to the enantioselective synthesis of alpha-substituted carboxylic acid derivatives, Journal of the American Chemical Society, 104(6), pp. 1737-1739, Mar. 1982.
Chiang et al., An Fc Domain Protein-Small Molecule Conjugate as an Enhanced Immunomodular, Journal of the American Chemical Society, 136(9):3370-3373, Feb. 2014.
Li, W. et al., Current drug research on PEGylation with small molecular agents, Progress in Polymer Science, 38:421-444, Apr. 2013.
Ramirez-Montagut et al., Immunity to melanoma: unraveling the relation of tumor immunity and autoimmunity, Oncogene, 22(20):3180-3187, May 2003.
Sawaya et al., Risk of cervical cancer associated with extending the interval between cervical-cancer screenings, New England Journal of Medicine, 349(16): 1501-1509, Oct. 2003.
Pardoll, The blockade of immune checkpoints in cancer immunotherapy, Nature Reviews Cancer, 12(4):252-264, Apr. 2012.
Sarkar, et al., Induction of indoleamine 2, 3-dioxygenase by interferon-y in human islets, Diabetes, 56(1):72-79, Jan. 2007.
Littlejohn, et al., Expression and Purification of Recombinant Human Indoleamine 2,3-Dioxygenase, Protein Expression and Purification, 19(1):22-29, Jun. 2000.
Fox, et al., Discovery of 6-phenylpyrimido [4,5-b][1,4] oxazines as potent and selective acyl CoA: diacylglycerol acytransferase 1 (DGAT1) inhibitors with in vivo efficacy in rodents, Journal of Medical Chemistry, 57(8):3464-3483, Apr. 2014.
Yamamoto, et al., Additional reaction of arylboronic acid to aldehydes and α,β-unsaturated carbonyl compounds catalyzed by conventional palladium complexes in the presence of chloroform, J Organomet, Chem., 69(9)4:1325-1332, Apr. 2009.
Li, G. et al., Discovery of novel orally active ureido NPY Y5 receptor antagonists, Bioorganic & Medical Chemistry Letters, 18(3):1146-1150, Feb. 2008.
Kawamura et al., Iron-catalysed cross-coupling of halohydrins with aryl aluminum reagents: a protecting-group-free strategy attaining remarkable rate enhancement and diastereoinduction, Chemical Communications, 48(75):9376-9378, Aug. 2012.
Vilums, Design and synthesis of novel small molecule CCR2 antagonists: Evaluation of 4-aminopiperidine derivatives, Bioorganic Medical Chemistry Letters, 24(23):5377, Dec. 2014.
Robinson et al, Kinetic Resolution Strategies using non-enzymatic Catalysts, Tetrahedron, Jun. 2003, 14(1), 1407-1446.

(56) References Cited

OTHER PUBLICATIONS

Qureshi et al., Indoleamine 2,3-dioxygenase; potential in cancer immunotherapy, Science Vision, 2013, vol. 19(1,2), pp. 33-40.
Kotha et al, Recent applications of Suzuki-Miyaura cross-coupling reaction in organic synthesis, Tetrahedron, Nov. 2002, 58:9633-9695.
Kinzel et al., A new palladium precatalyst allows for the fast Suzuki-Miyaura coupling reactions of unstable polyfluorophenyl and 2-heteroaryl boronic acids, Jouranl of the American Chemical Society, Sep. 2010, 132(40), 14073-14075.
Evans et al., Contrasteric carboximide hydrolysis with lithium hydroperoxide, Tetrahedron Letters, Dec. 1987, 28(49), 6141-6144.
Stocks et al., Evidence for a Common Non-Heme Chelatable-Iron-Dependent Activation Mechanism for Semisynthetic and Synthetic Endoperoxide Antimalarial Drugs, Angew. Chem. Int. Ed., Aug. 2007, 46(33), 6278-6283.
Barlind et al., Design and optimization of pyrazinecarboxamide-based inhibitors of diacylglycerol acyltransferase 1 (DGAT1) leading to a clinical candidate dimethylpyrazinecarboxamide phenylcyclohexylacetic acid (AZD7687), Journal of medicinal chemistry, Nov. 2012, 55(23), 10610-10629.

\* cited by examiner

IMMUNOREGULATORY AGENTS

CROSS-REFERENCE TO RELATED APPLICATIONS

This application claims priority to U.S. Provisional Application Ser. No. 62/075,671, filed Nov. 5, 2014, and 62/098,022, filed Dec. 30, 2014, respectively, the entire content of which are incorporated herein by reference.

BACKGROUND OF THE INVENTION

Indoleamine 2,3-dioxygenase (IDO; also known as IDO1) is an IFN-γ target gene that plays a role in immunomodulation. IDO is an oxidoreductase and one of two enzymes that catalyze the first and rate-limiting step in the conversion of tryptophan to N-formyl-kynurenine. It exists as a 41 kD monomer that is found in several cell populations, including immune cells, endothelial cells, and fibroblasts. IDO is relatively well-conserved between species, with mouse and human sharing 63% sequence identity at the amino acid level. Data derived from its crystal structure and site-directed mutagenesis show that both substrate binding and the relationship between the substrate and iron-bound dioxygenase are necessary for activity. A homolog to IDO (IDO2) has been identified that shares 44% amino acid sequence homology with IDO, but its function is largely distinct from that of IDO. (See, e.g., Serafini P, et al., *Semin. Cancer Biol.*, 16(1):53-65 (February 2006) and Ball, H. J. et al., *Gene*, 396(1):203-213 (July 2007)).

IDO plays a major role in immune regulation, and its immunosuppressive function manifests in several manners. Importantly, IDO regulates immunity at the T cell level, and a nexus exists between IDO and cytokine production. In addition, tumors frequently manipulate immune function by upregulation of IDO. Thus, modulation of IDO can have a therapeutic impact on a number of diseases, disorders and conditions.

A pathophysiological link exists between IDO and cancer. Disruption of immune homeostasis is intimately involved with tumor growth and progression, and the production of IDO in the tumor microenvironment appears to aid in tumor growth and metastasis. Moreover, increased levels of IDO activity are associated with a variety of different tumors (Brandacher, G. et al., *Clin. Cancer Res.*, 12(4):1144-1151 (Feb. 15, 2006)).

Treatment of cancer commonly entails surgical resection followed by chemotherapy and radiotherapy. The standard treatment regimens show highly variable degrees of long-term success because of the ability of tumor cells to essentially escape by regenerating primary tumor growth and, often more importantly, seeding distant metastasis. Recent advances in the treatment of cancer and cancer-related diseases, disorders and conditions comprise the use of combination therapy incorporating immunotherapy with more traditional chemotherapy and radiotherapy. Under most scenarios, immunotherapy is associated with less toxicity than traditional chemotherapy because it utilizes the patient's own immune system to identify and eliminate tumor cells.

In addition to cancer, IDO has been implicated in, among other conditions, immunosuppression, chronic infections, and autoimmune diseases or disorders (e.g., rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV). Although their roles are not as well defined, IDO inhibitors may also find use in the treatment of patients with neurological or neuropsychiatric diseases or disorders (e.g., depression).

Small molecule inhibitors of IDO have been developed to treat or prevent IDO-related diseases. For example, the IDO inhibitors 1-methyl-DL-tryptophan; p-(3-benzofuranyl)-DL-alanine; p-[3-benzo(b)thienyl]-DL-alanine; and 6-nitro-L-tryptophan have been used to modulate T cell-mediated immunity by altering local extracellular concentrations of tryptophan and tryptophan metabolites (WO 99/29310). Compounds having IDO inhibitory activity are further reported in WO 2004/094409.

In view of the role played by indoleamine 2,3-dioxygenase in a diverse array of diseases, disorders and conditions, and the limitations (e.g., efficacy) of current IDO inhibitors, new IDO modulators, and compositions and methods associated therewith, are needed.

BRIEF SUMMARY OF THE INVENTION

The present invention relates to compounds that modulate the oxidoreductase enzyme indoleamine 2,3-dioxygenase (IDO), and compositions (e.g., pharmaceutical compositions) comprising the compounds. Such compounds, including methods of their synthesis, and compositions are described in detail below.

The present invention also relates to the use of such compounds and compositions for the treatment and/or prevention of a diverse array of diseases, disorders and conditions mediated, in whole or in part, by IDO. Such diseases, disorders and conditions are described in detail elsewhere herein. Unless otherwise indicated, when uses of the compounds of the present invention are described herein, it is to be understood that such compounds may be in the form of a composition (e.g., a pharmaceutical composition).

As discussed hereafter, although the compounds of the present invention are believed to effect their activity by inhibition of IDO, a precise understanding of the compounds' underlying mechanism of action is not required to practice the invention. It is envisaged that the compounds may alternatively effect their activity through inhibition of tryptophan-2,3-dioxygenase (TDO) activity. It is also envisaged that the compounds may effect their activity through inhibition of both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

In one aspect, the present invention provides compounds represented by formula (I):

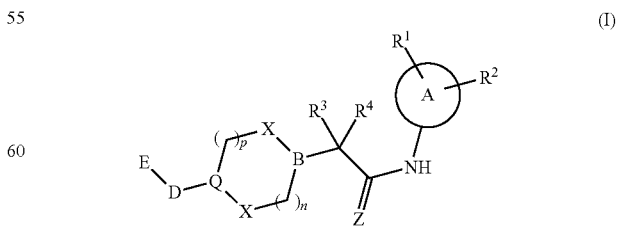

or a pharmaceutically acceptable salt, hydrate or solvate thereof, wherein, the subscript n is 1 or 0; the subscript p is 1 or 0; the ring designated as A is phenyl, 5- or 6-membered heteroaryl, or $C_{5-7}$ cycloalkyl; Z is O; B is N, $C(OR^{5a})$, or $C(R^{3a})$; each X is independently $NR^{5a}$, O, $CHR^5$, $C(O)$, or $CH(OR^{5a})$; Q is N, $C(CN)$, or $CR^6$; D is a bond, O, $C(R^5)_2$, or $NR^{5a}$; E is an optionally substituted 9- or 10-membered fused bicyclic heteroaryl; $R^1$ and $R^2$ are independently hydrogen, halogen, $C_1$-$C_4$ haloalkyl, $C_3$-$C_6$ cycloalkyl, 3- to 6-membered cycloheteroalkyl, optionally substituted phenyl, optionally substituted heteroaryl, optionally substituted $C_1$-$C_4$ alkyl, $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl; $R^3$, $R^{3a}$ and $R^4$ are independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, optionally substituted $C_3$-$C_6$ cycloalkyl-$C_1$-$C_4$ alkyl, optionally substituted aryl-$C_1$-$C_6$ alkyl, fluorine, OH, CN, $CO_2H$, $C(O)NH_2$, $N(R^5)_2$, optionally substituted —O—$C_1$-$C_6$ alkyl, —$(CR^5R^5)_m$—OH, —$(CR^5R^5)_m$—$CO_2H$, —$(CR^5R^5)_m$—$C(O)NH_2$, —$(CR^5R^5)_m$—$C(O)NHR^5$, —$(CR^5R^5)_m N(R^5)_2$, —$NH(CR^5R^5)_m CO_2H$ or —$NH(CR^5R^5)_m$—$C(O)NH_2$; each $R^5$ is independently H, F, OH, or optionally substituted $C_1$-$C_6$ alkyl; each $R^{5a}$ is independently H, or optionally substituted $C_1$-$C_6$ alkyl; $R^6$ is H, OH, F, optionally substituted $C_1$-$C_6$ alkyl, optionally substituted —O—$C_1$-$C_6$ alkyl, or —$N(R^{5a})_2$; and each m is independently 1, 2, or 3.

In yet another aspect, the present invention provides compositions in which compounds of formula (I), are combined with one or more pharmaceutically acceptable excipients.

In some embodiments, the present invention contemplates methods for treating or preventing cancer in a subject (e.g., a human) comprising administering to the subject a therapeutically effective amount of at least one IDO inhibitor described herein. The present invention includes methods of treating or preventing a cancer in a subject by administering to the subject an IDO inhibitor in an amount effective to reverse or stop the progression of IDO-mediated immunosuppression. In some embodiments, the IDO-mediated immunosuppression is mediated by an antigen-presenting cell (APC).

Examples of the cancers that may be treated using the compounds and compositions described herein include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma. In some embodiments of the present invention, the cancer is melanoma, colon cancer, pancreatic cancer, breast cancer, prostate cancer, lung cancer, leukemia, a brain tumor, lymphoma, sarcoma, ovarian cancer, or Kaposi's sarcoma. Cancers that are candidates for treatment with the compounds and compositions of the present invention are discussed further hereafter.

The present invention contemplates methods of treating a subject receiving a bone marrow transplant or peripheral blood stem cell transplant by administering a therapeutically effective amount of an IDO inhibitor sufficient to increase the delayed-type hypersensitivity reaction to tumor antigen, delay the time-to-relapse of post-transplant malignancy, increase relapse-free survival time post-transplant, and/or increase long-term post-transplant survival.

In certain embodiments, the present invention contemplates methods for treating or preventing an infective disorder (e.g., a viral infection) in a subject (e.g., a human) comprising administering to the subject a therapeutically effective amount of at least one IDO inhibitor (e.g., a novel inhibitor of the instant invention). In some embodiments, the infective disorder is a viral infection (e.g., a chronic viral infection), a bacterial infection, or a parasitic infection. In certain embodiments, the viral infection is human immunodeficiency virus or cytomegalovirus. In other embodiments, the bacterial infection is a *Mycobacterium* infection (e.g., *Mycobacterium leprae* or *Mycobacterium tuberculosis*). In still other embodiments, the parasitic infection is *Leishmania donovani, Leishmania tropica, Leishmania major, Leishmania aethiopica, Leishmania mexicana, Plasmodium falciparum, Plasmodium vivax, Plasmodium ovale*, or *Plasmodium malariae*. In further embodiments, the infective disorder is a fungal infection.

In still other embodiments, the present invention contemplates methods for treating or preventing an immune-related disease, disorder or condition in a subject (e.g., a human), comprising administering to the subject a therapeutically effective amount of at least one IDO inhibitor (e.g., preferably a novel inhibitor of the instant invention). Examples of immune-related diseases, disorders and conditions are described hereafter.

Other diseases, disorders and conditions that may be treated or prevented, in whole or in part, by modulation of IDO activity are candidate indications for the IDO inhibitor compounds that are described herein.

The present invention further contemplates the use of the IDO inhibitors described herein in combination with one or more additional agents. The one or more additional agents may have some IDO modulating activity and/or they may function through distinct mechanisms of action. In some embodiments, such agents comprise radiation (e.g., localized radiation therapy or total body radiation therapy) and/or other treatment modalities of a non-pharmacological nature. When combination therapy is utilized, the IDO inhibitor(s) and the one additional agent(s) may be in the form of a single composition or multiple compositions, and the treatment modalities may be administered concurrently, sequentially, or through some other regimen. By way of example, the present invention contemplates a treatment regimen wherein a radiation phase is followed by a chemotherapeutic phase. The combination therapy may have an additive or synergistic effect. Other benefits of combination therapy are described hereafter.

In some embodiments, the present invention further comprises the use of the IDO inhibitors described herein in combination with bone marrow transplantation, peripheral blood stem cell transplantation, or other types of transplantation therapy.

In particular embodiments, the present invention contemplates the use of the inhibitors of IDO function described herein in combination with immune checkpoint inhibitors. The blockade of immune checkpoints, which results in the amplification of antigen-specific T cell responses, has been shown to be a promising approach in human cancer therapeutics. Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors. Immune checkpoint inhibitors, and combination therapy therewith, are discussed in detail elsewhere herein.

In other embodiments, the present invention provides methods for treating cancer in a subject, comprising administering to the subject a therapeutically effective amount of at least one IDO inhibitor and at least one chemotherapeutic agent, such agents including, but not limited to alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nucleoside analogs (e.g., gemcitabine); nitroso ureas such as carmustine, lomustine, and streptozocin; topoisomerase 1 inhibitors (e.g., irinotecan); platinum complexes such as cisplatin and carboplatin; bioreductive alkylators such as mitomycin, procarbazine, dacarbazine and altretamine); DNA strand-breakage agents (e.g., bleomycin); topoisomerase II inhibitors (e.g., amsacrine, dactinomycin, daunorubicin, idarubicin, mitoxantrone, doxorubicin, etoposide, and teniposide); DNA minor groove binding agents (e.g., plicamydin); antimetabolites (e.g., folate antagonists such as methotrexate and trimetrexate; pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, estramustine, vinblastine, docetaxol, epothilone derivatives, and paclitaxel); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, anti-androgen agents such as flutamide; and antiadrenal agents such as mitotane and aminoglutethimide). The present invention also contemplates the use of the IDO inhibitors in combination with other agents known in the art (e.g., arsenic trioxide) and other chemotherapeutic agents developed in the future.

In some embodiments drawn to methods of treating cancer, the administration of a therapeutically effective amount of an IDO inhibitor in combination with at least one chemotherapeutic agent results in a cancer survival rate greater than the cancer survival rate observed by administering either alone. In further embodiments drawn to methods of treating cancer, the administration of a therapeutically effective amount of an IDO inhibitor in combination with at least one chemotherapeutic agent results in a reduction of tumor size or a slowing of tumor growth greater than reduction of the tumor size or tumor growth observed by administration of one agent alone.

In further embodiments, the present invention contemplates methods for treating or preventing cancer in a subject, comprising administering to the subject a therapeutically effective amount of at least one IDO inhibitor and at least one signal transduction inhibitor (STI). In a particular embodiment, the at least one STI is selected from the group consisting of bcr/abl kinase inhibitors, epidermal growth factor (EGF) receptor inhibitors, her-2/neu receptor inhibitors, and farnesyl transferase inhibitors (FTIs). Other candidate STI agents are set forth elsewhere herein.

The present invention also contemplates methods of augmenting the rejection of tumor cells in a subject comprising administering an IDO inhibitor in conjunction with at least one chemotherapeutic agent and/or radiation therapy, wherein the resulting rejection of tumor cells is greater than that obtained by administering either the IDO inhibitor, the chemotherapeutic agent or the radiation therapy alone.

In further embodiments, the present invention provides methods for treating cancer in a subject, comprising administering to the subject a therapeutically effective amount of at least one IDO inhibitor and at least one immunomodulator other than an IDO inhibitor. In particular embodiments, the at least one immunomodulator is selected from the group consisting of CD40L, B7, B7RP1, ant-CD40, anti-CD38, anti-ICOS, 4-IBB ligand, dendritic cell cancer vaccine, IL2, IL12, ELC/CCL19, SLC/CCL21, MCP-1, IL-4, IL-18, TNF, IL-15, MDC, IFN-α/13, M-CSF, IL-3, GM-CSF, IL-13, and anti-IL-10. Other candidate immunomodulator agents are set forth elsewhere herein.

The present invention contemplates embodiments comprising methods for treating or preventing an infective disorder (e.g., a viral infection) in a subject (e.g., a human) comprising administering to the subject a therapeutically effective amount of at least one IDO inhibitor and a therapeutically effective amount of an anti-infective agent(s)

In some embodiments of the present invention, the additional therapeutic agent is a cytokine, including, for example, granulocyte-macrophage colony stimulating factor (GM-CSF) or flt3-ligand. The present invention also contemplates methods for treating or preventing a viral infection (e.g., a chronic viral infection) including, but not limited to, hepatitis C virus (HCV), human papilloma virus (HPV), cytomegalovirus (CMV), Epstein-Barr virus (EBV), varicella zoster virus, coxsackie virus, and human immunodeficiency virus (HIV). The use of the IDO inhibitors described herein to treat (either alone or as a component of combination therapy) infection is discussed further hereafter.

In additional embodiments, treatment of an infective disorder is effected through the co-administration of a vaccine in combination with administration of a therapeutically effective amount of an IDO inhibitor of the present invention. In some embodiments, the vaccine is an anti-viral vaccine, including, for example, an anti-HIV vaccine. In other embodiments, the vaccine is effective against tuberculosis or malaria. In still other embodiments, the vaccine is a tumor vaccine (e.g., a vaccine effective against melanoma); the tumor vaccine may comprise genetically modified tumor cells or a genetically modified cell line, including genetically modified tumor cells or a genetically modified cell line that has been transfected to express granulocyte-macrophage stimulating factor (GM-CSF). In particular embodiments, the vaccine includes one or more immunogenic peptides and/or dendritic cells.

In some embodiments, the present invention contemplates methods of using the IDO inhibitors disclosed herein in combination with one or more antimicrobial agents.

In certain embodiments drawn to treatment of an infection by administering an IDO inhibitor and at least one additional therapeutic agent, a symptom of infection observed after administering both the IDO inhibitor and the additional therapeutic agent is improved over the same symptom of infection observed after administering either alone. In some embodiments, the symptom of infection observed may be reduction in viral load, increase in CD4+ T cell count, decrease in opportunistic infections, increased survival time, eradication of chronic infection, or a combination thereof.

DETAILED DESCRIPTION OF THE INVENTION

Figure 1A:
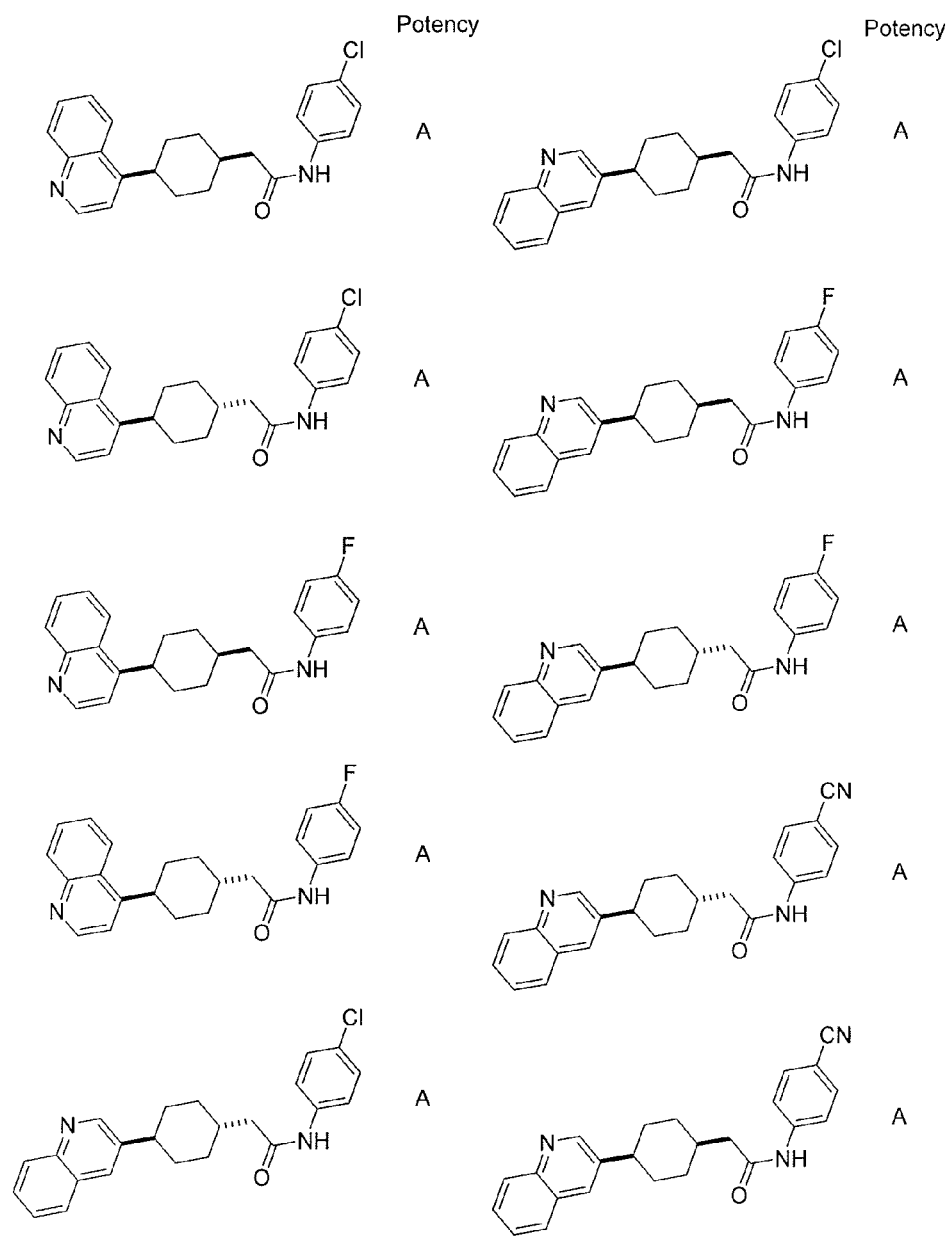
FIG. 1A-1P provides a structure and biological activity for compounds described herein. Measured inhibitory potencies for compounds of the invention in the assay described in Example 251 are provided below in FIG. 1A-1P, wherein potency levels are provided as follows: (IDO potency: $IC_{50}$: A<0.1 µM; B<1 µM; C<10 µM).
Figure 1B:
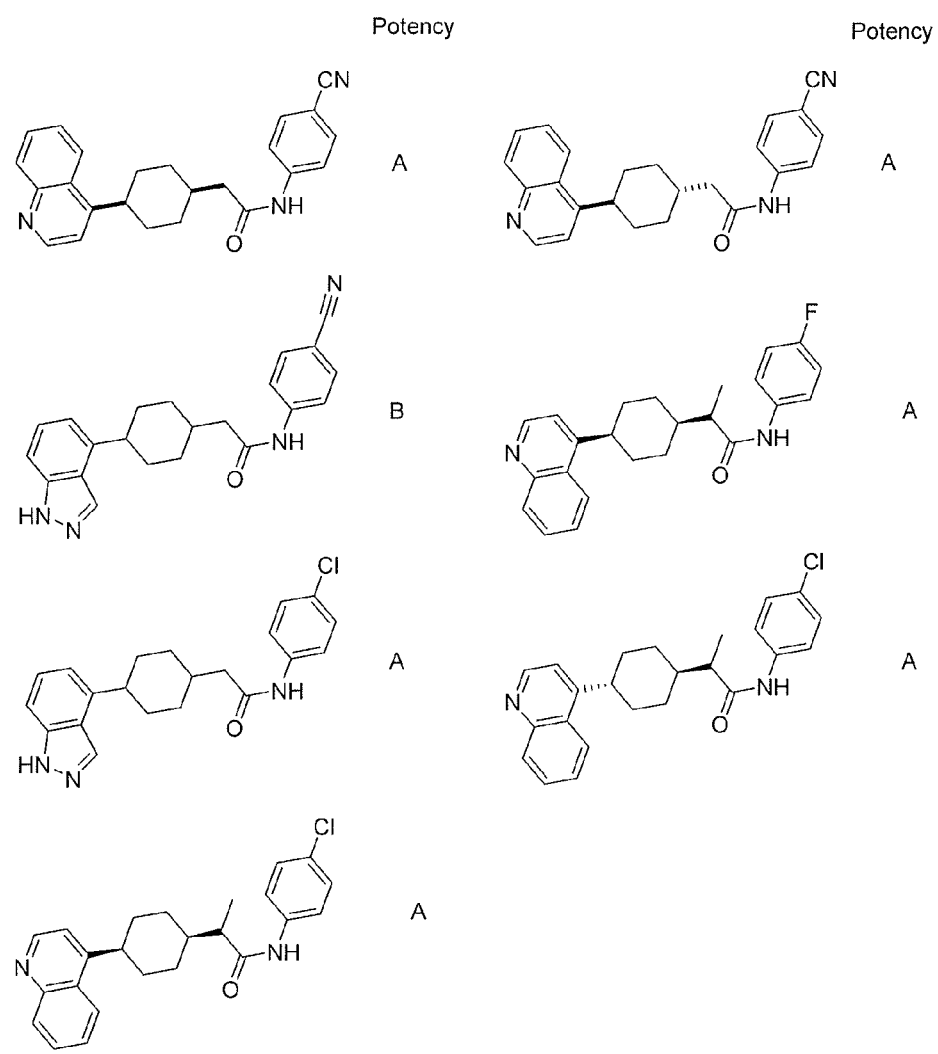
Figure 1C:
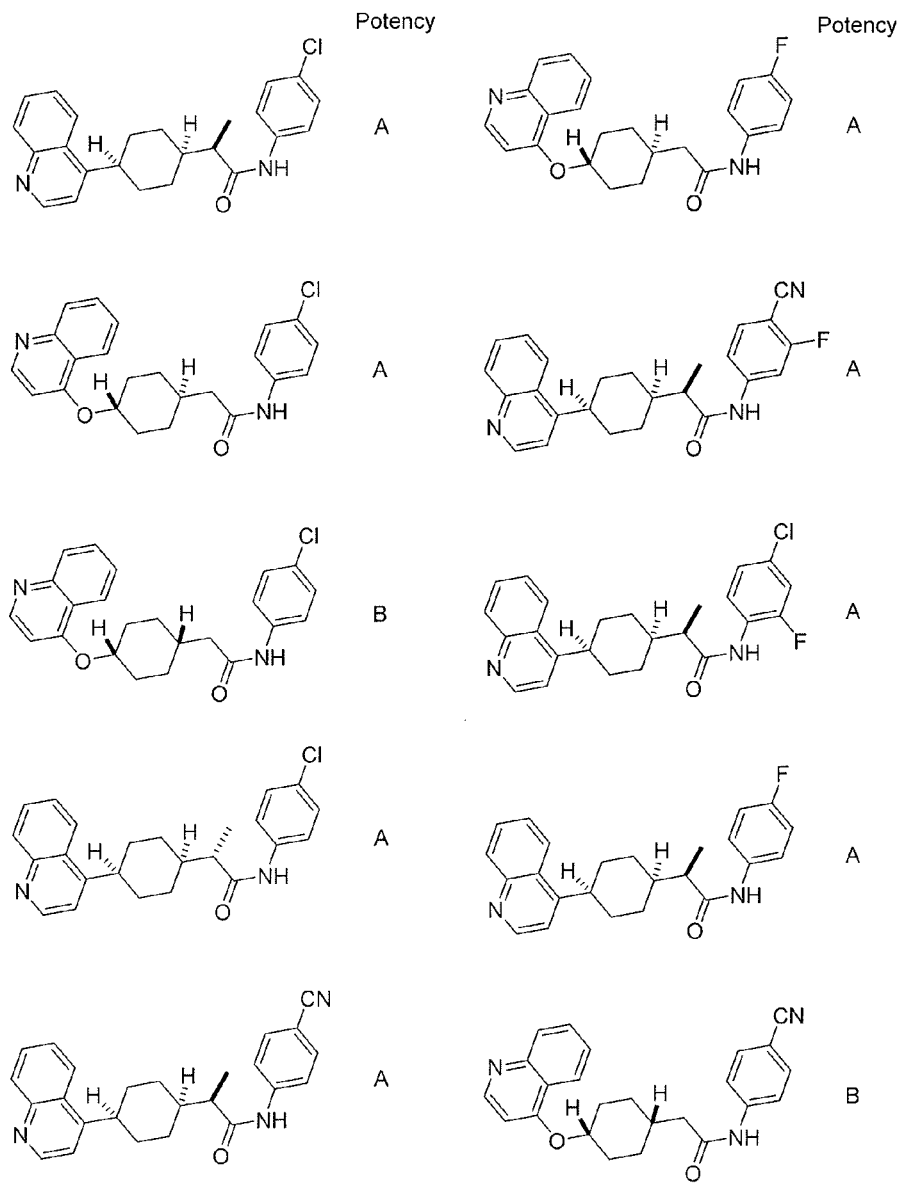
Figure 1D:
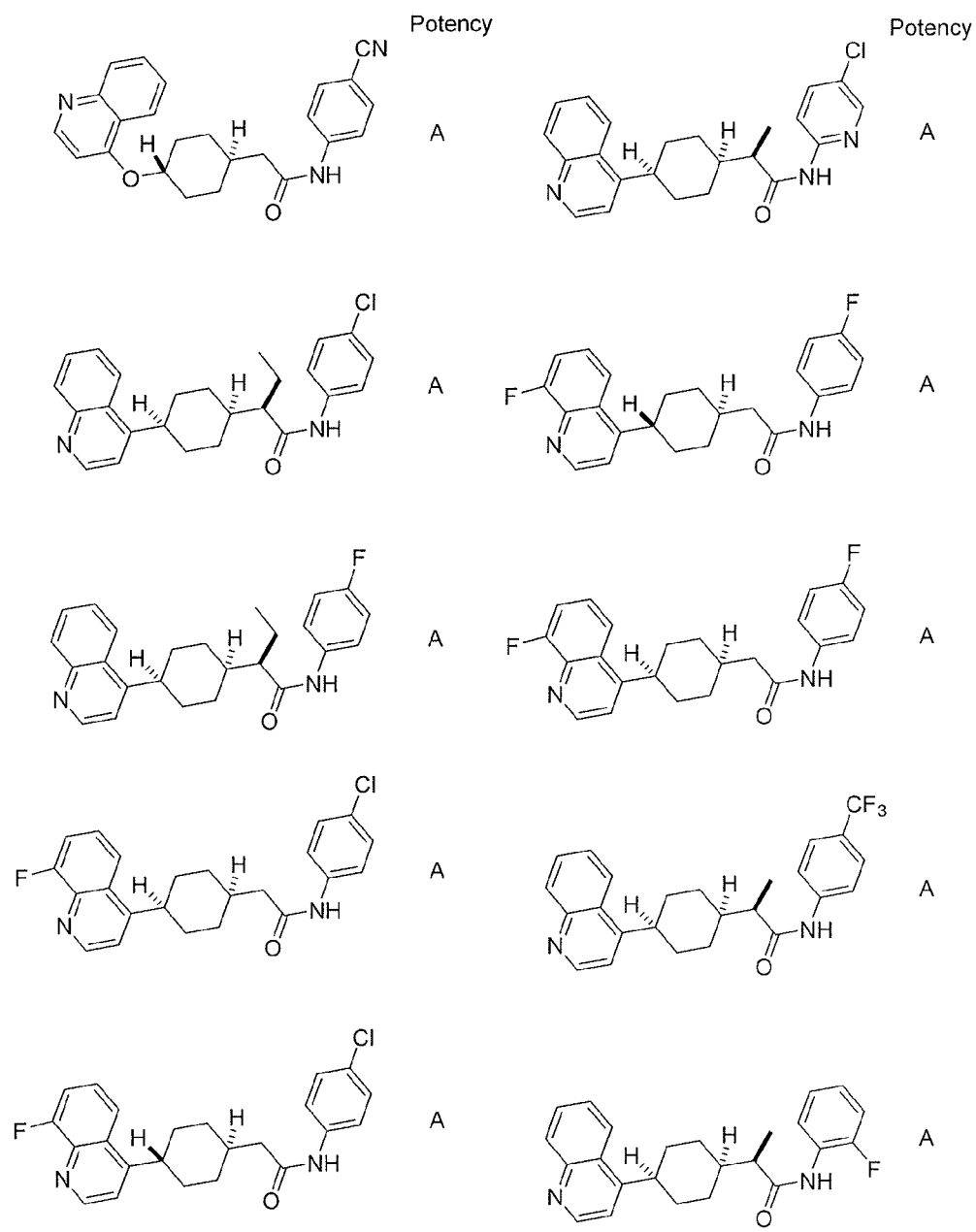
Figure 1E:
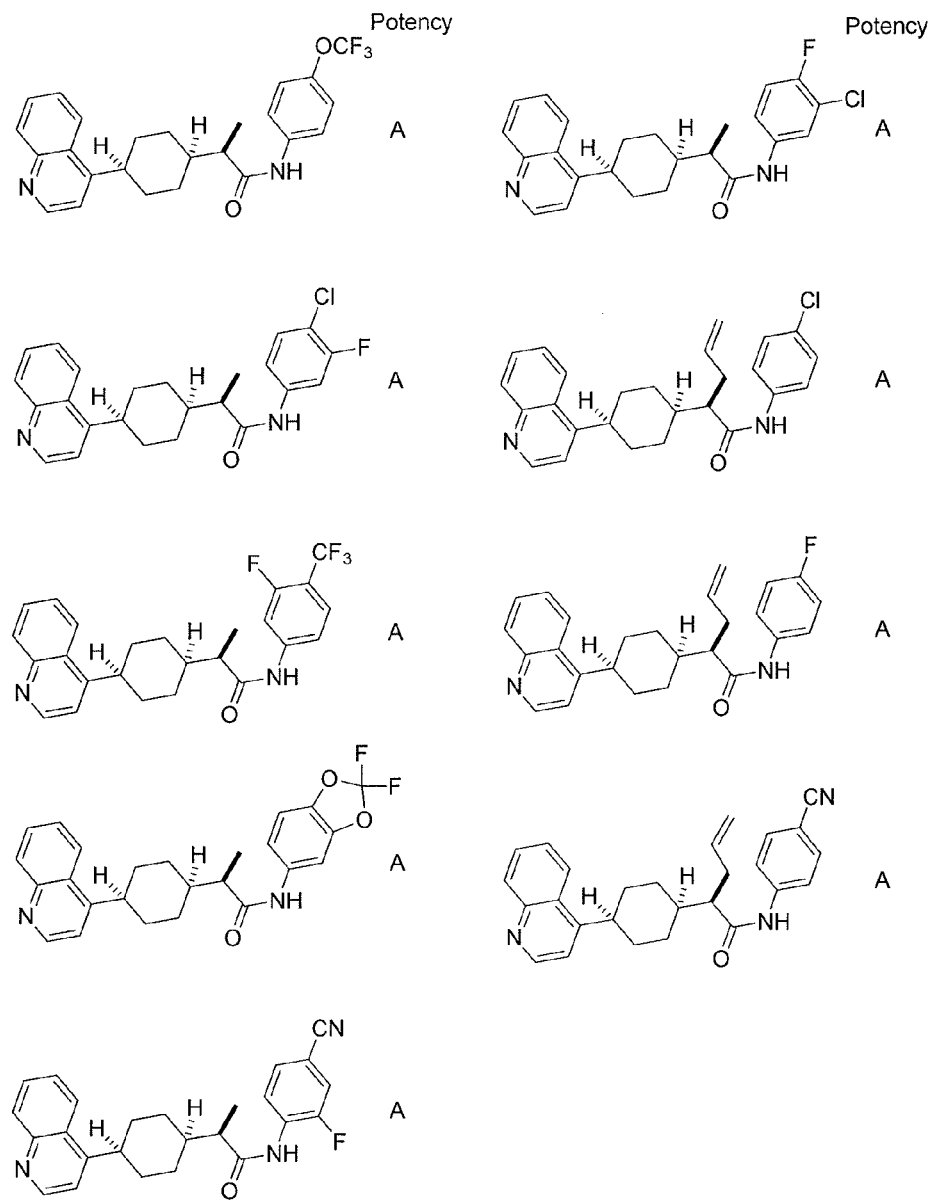
Figure 1F:
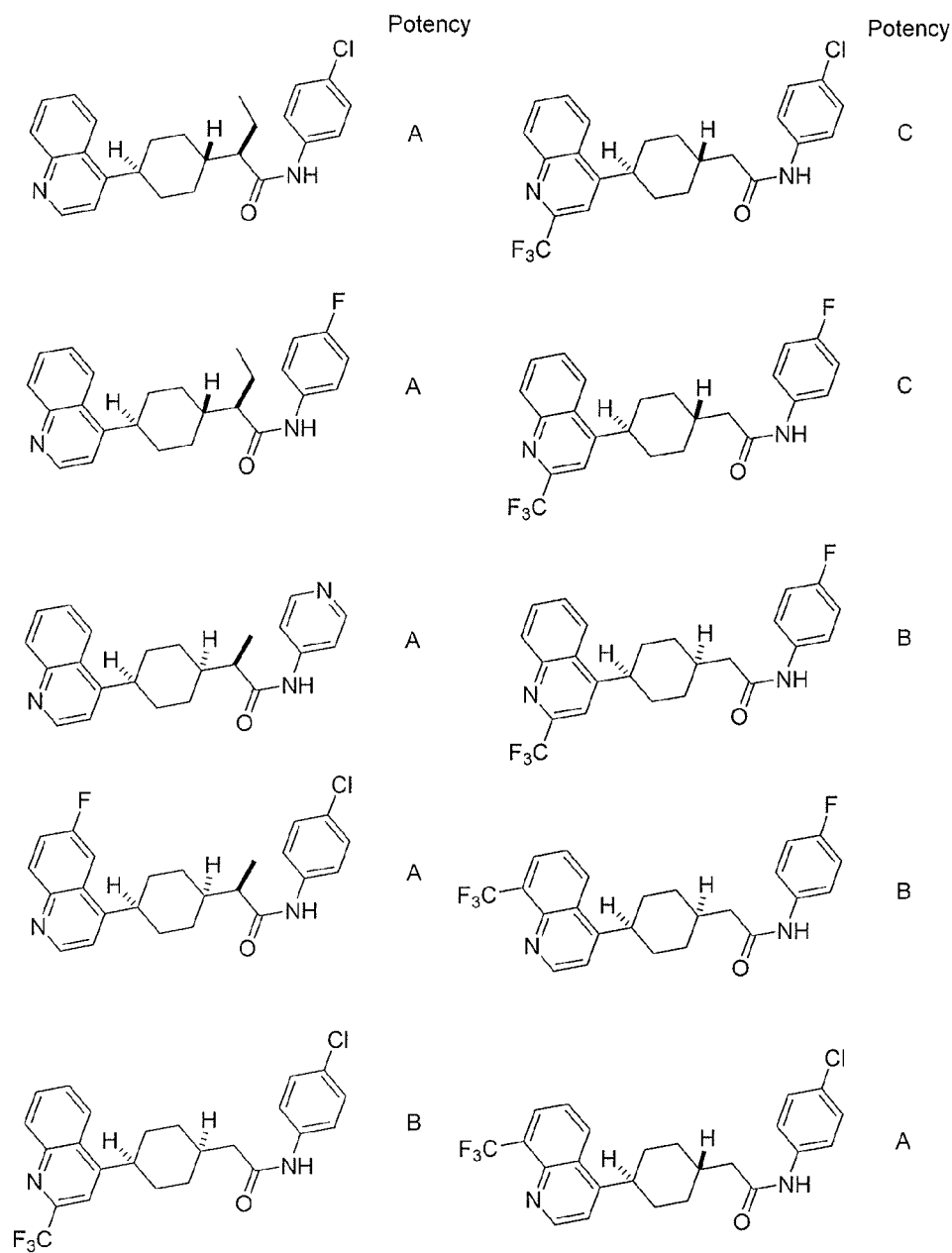
Figure 1G:
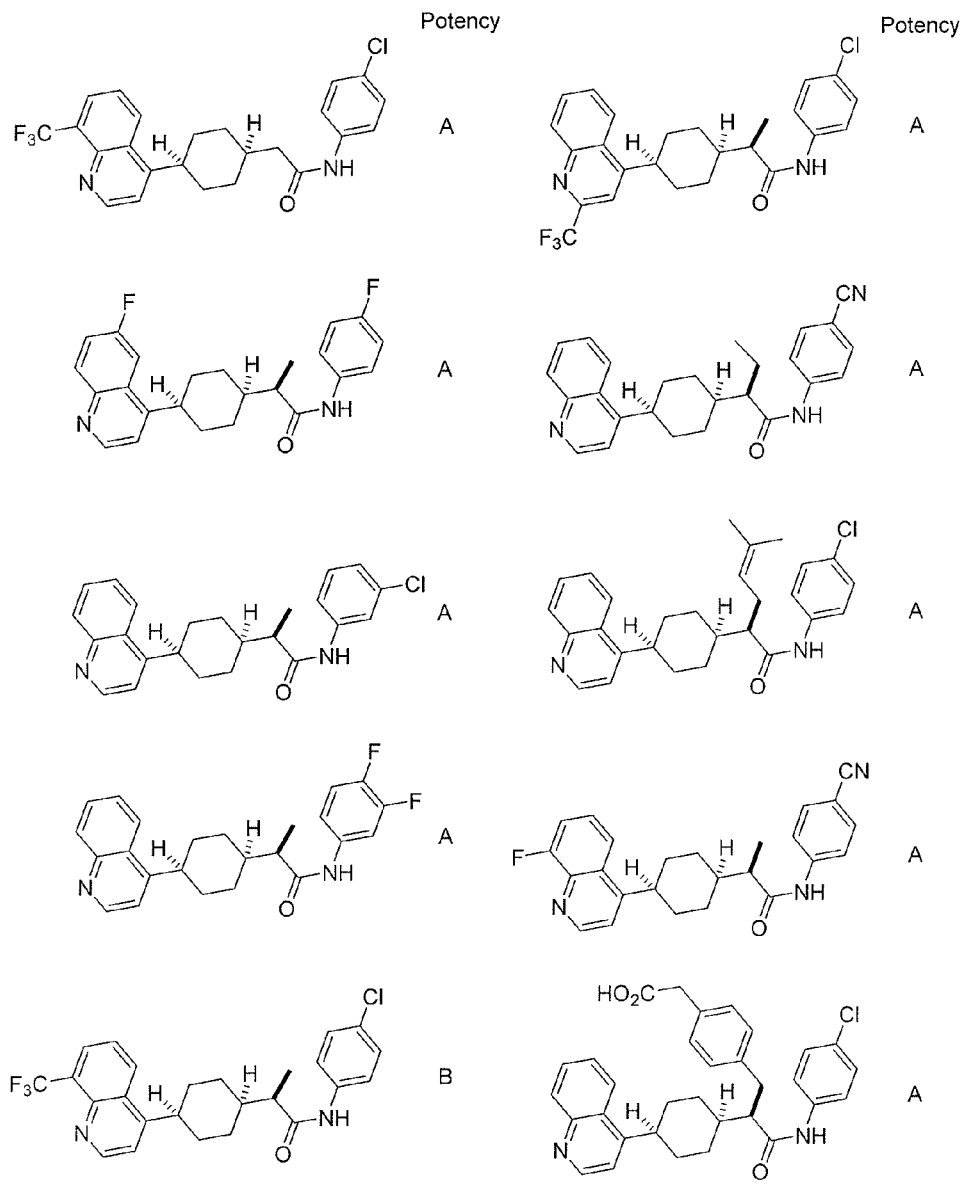
Figure 1H:
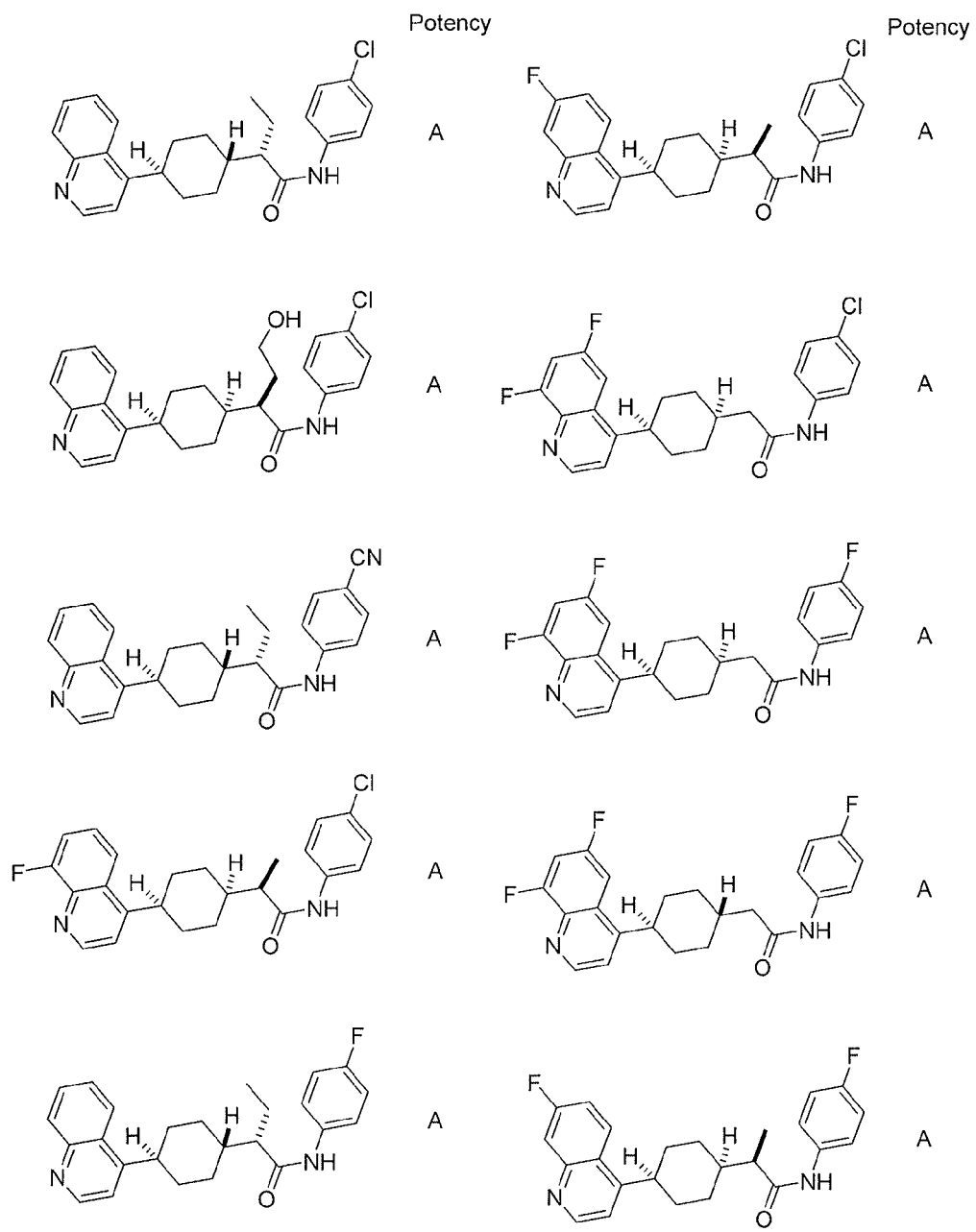
Figure 1I:
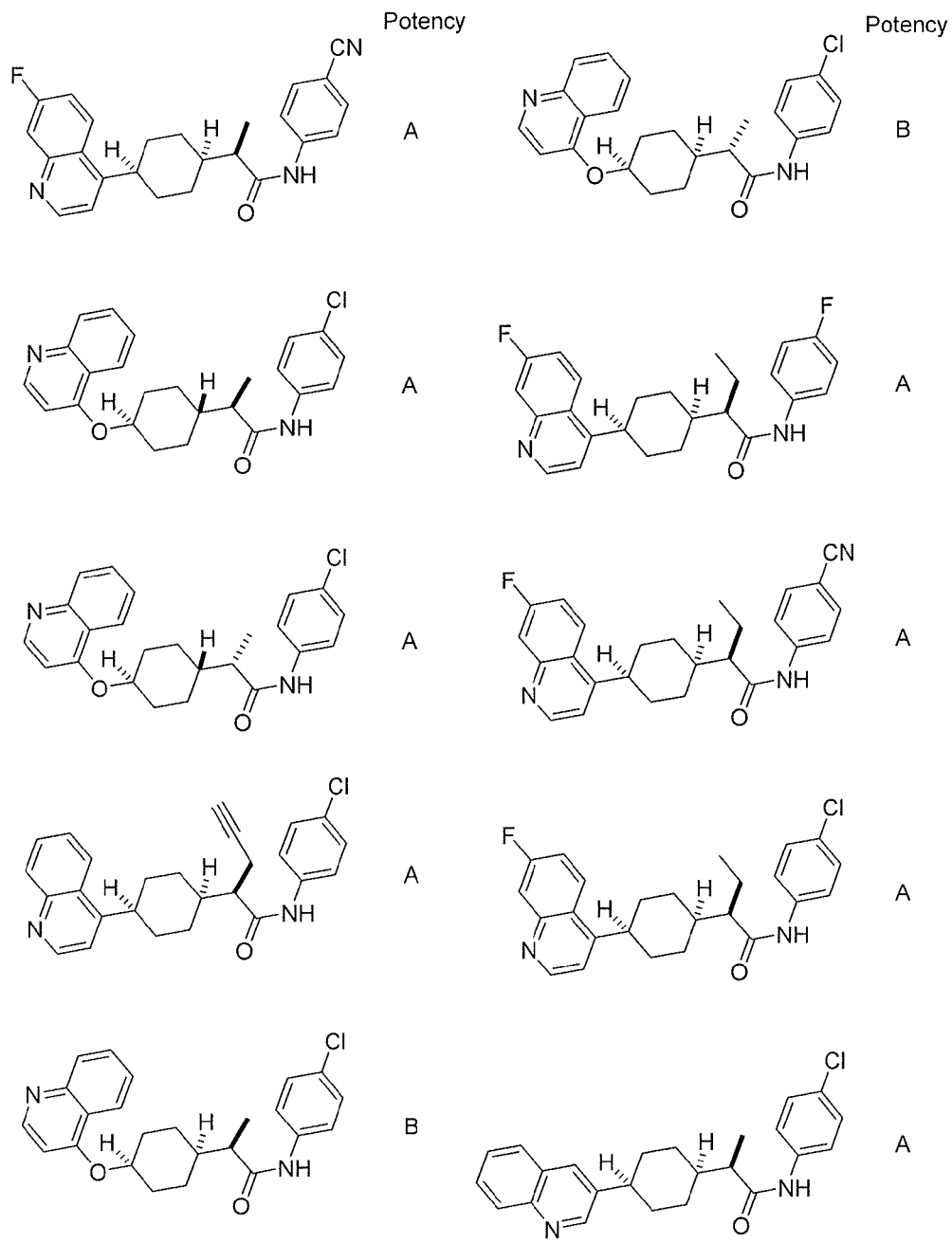
Figure 1J:
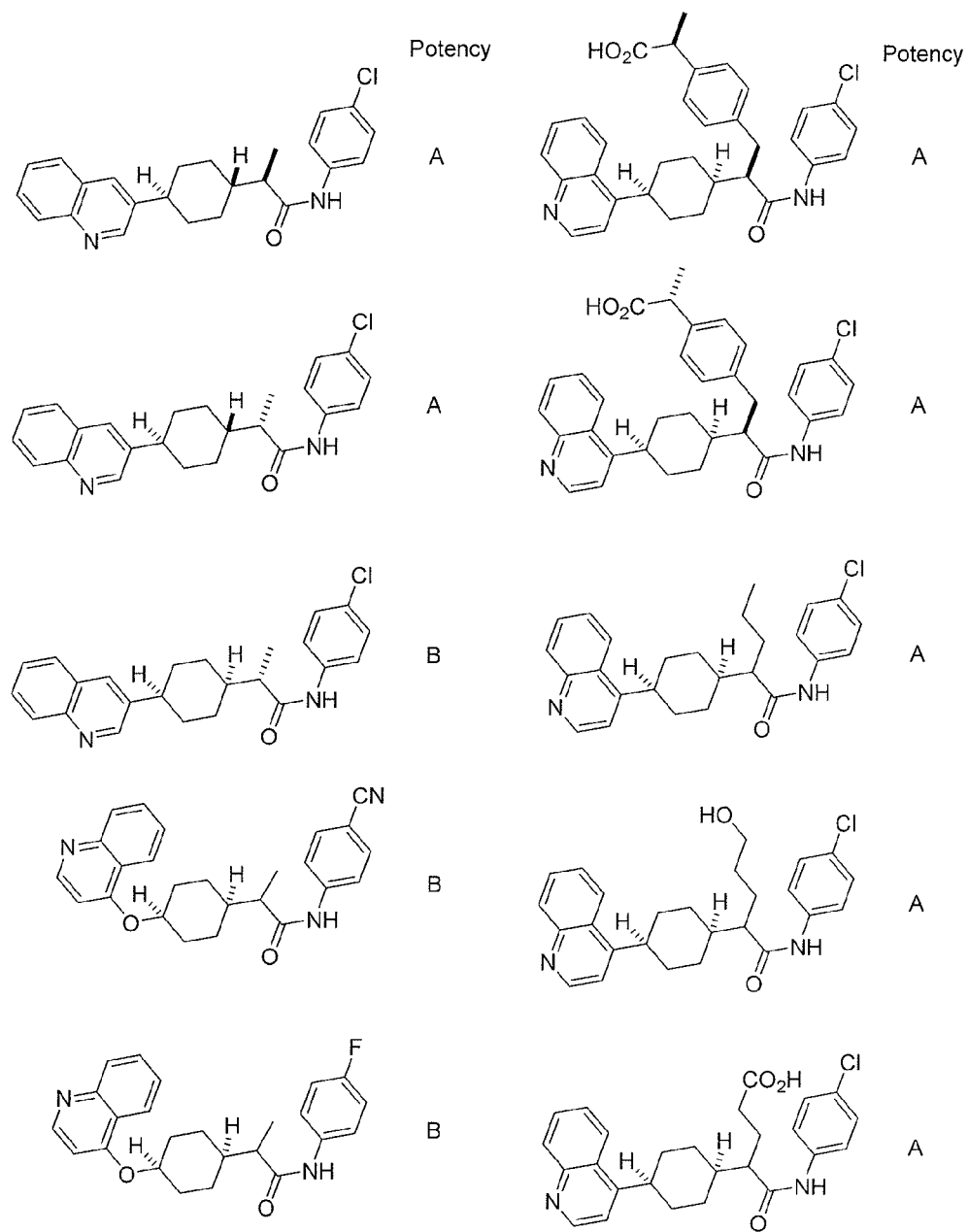
Figure 1K:
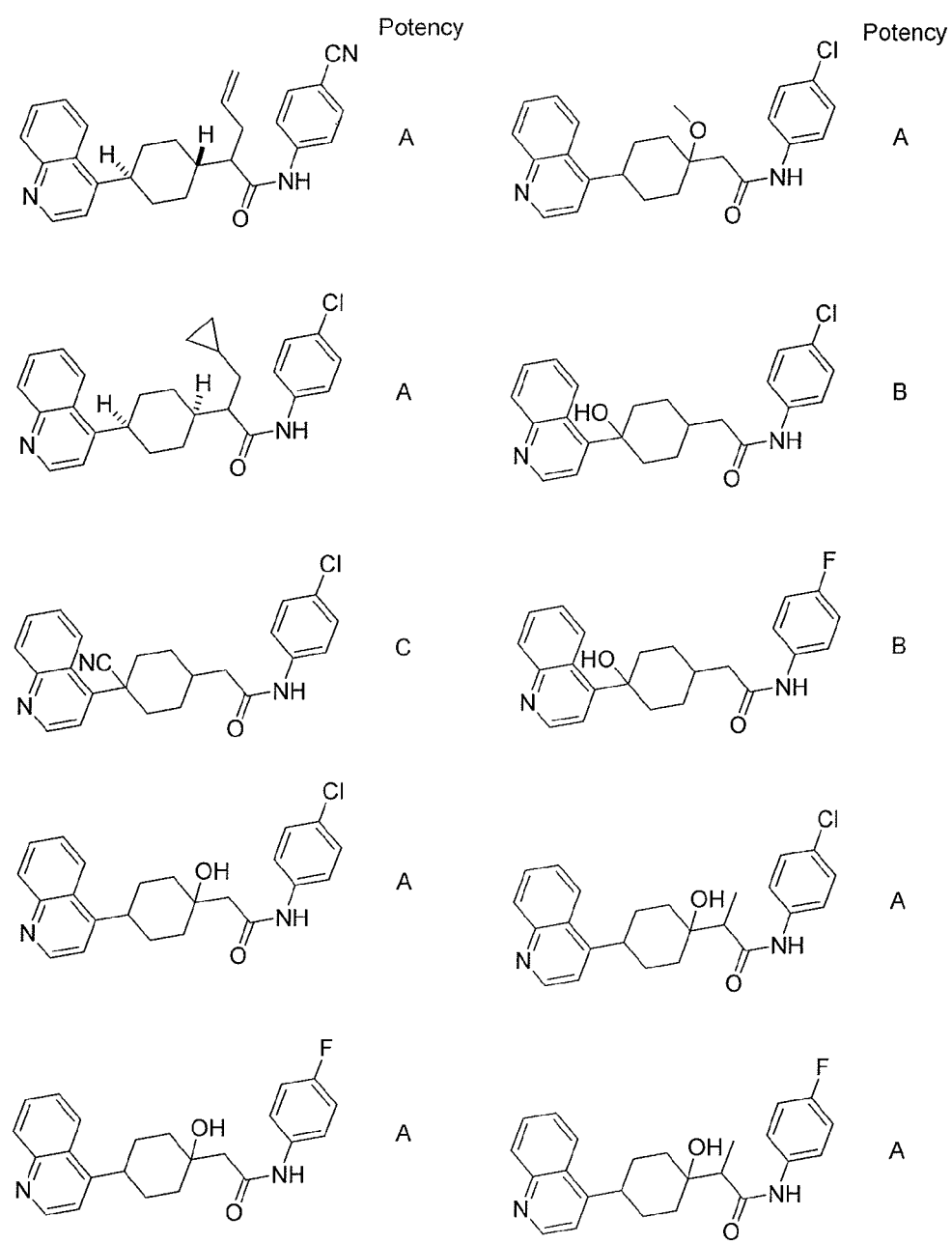
Figure 1L:
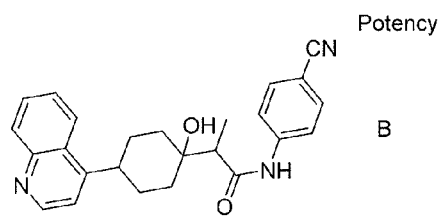
Figure 1M:
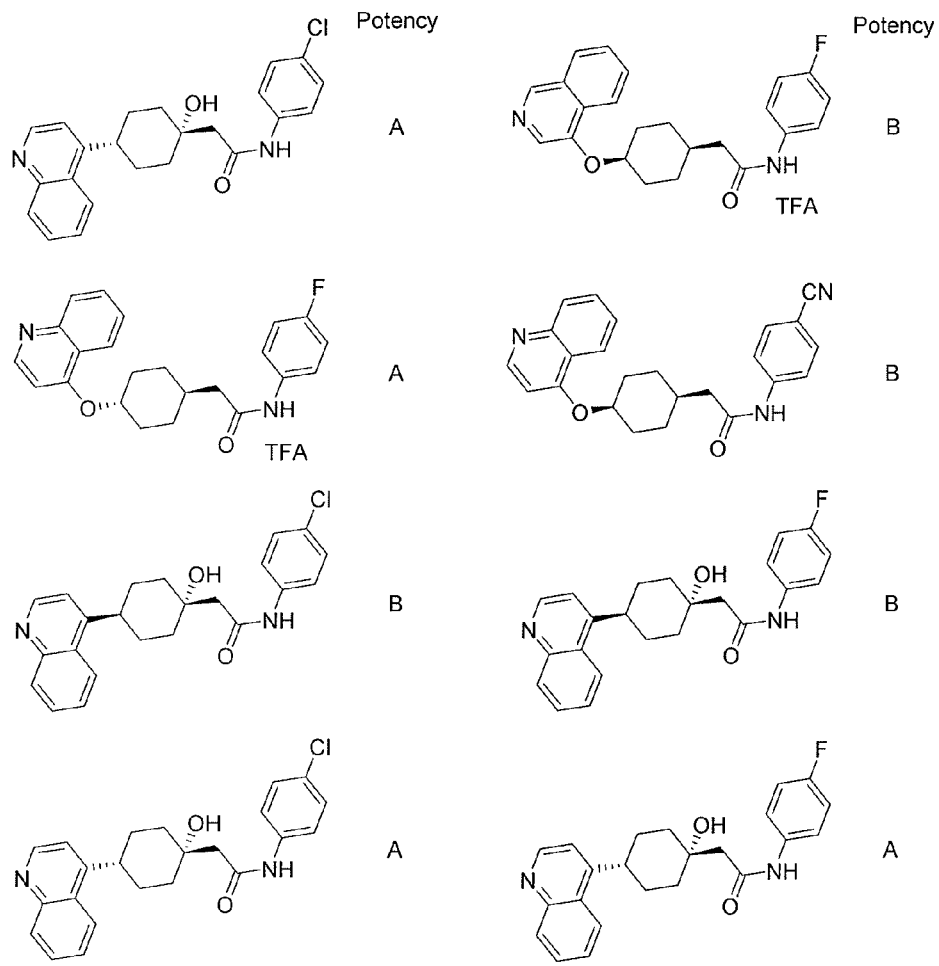
Figure 1N:
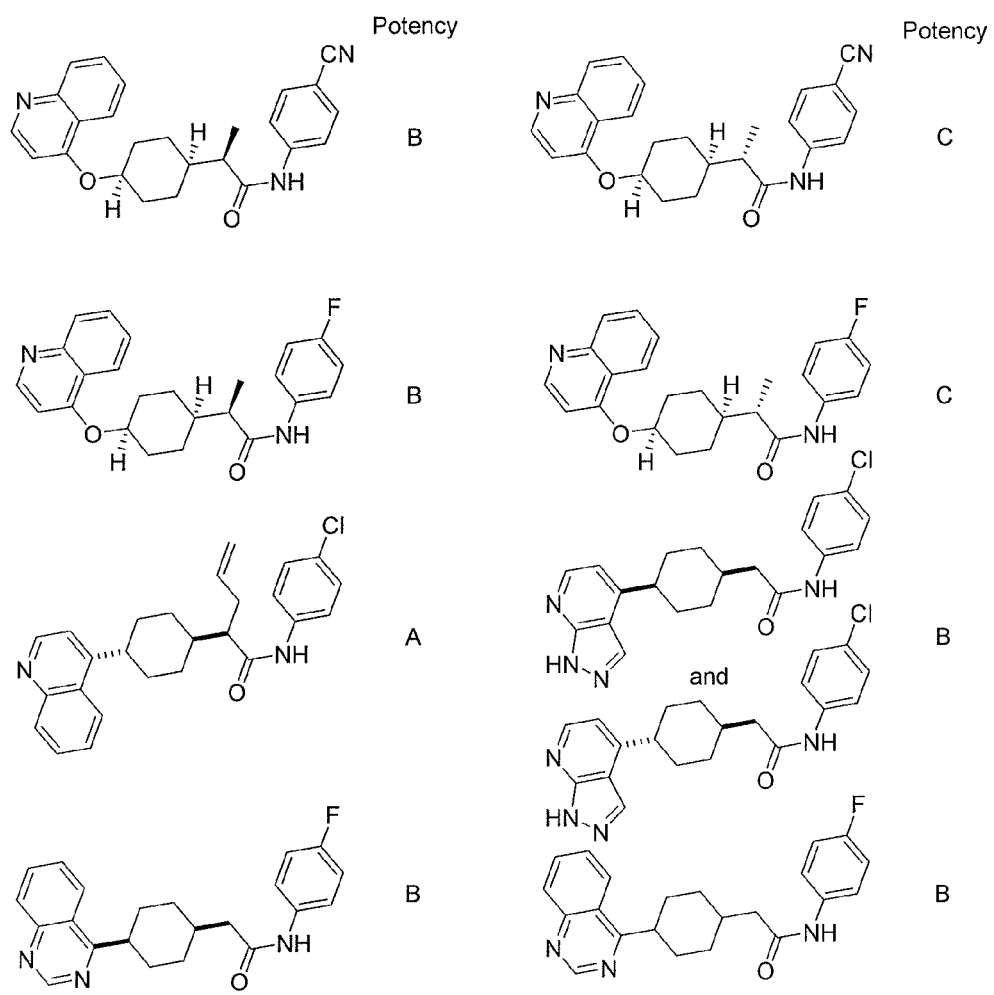
Figure 10:
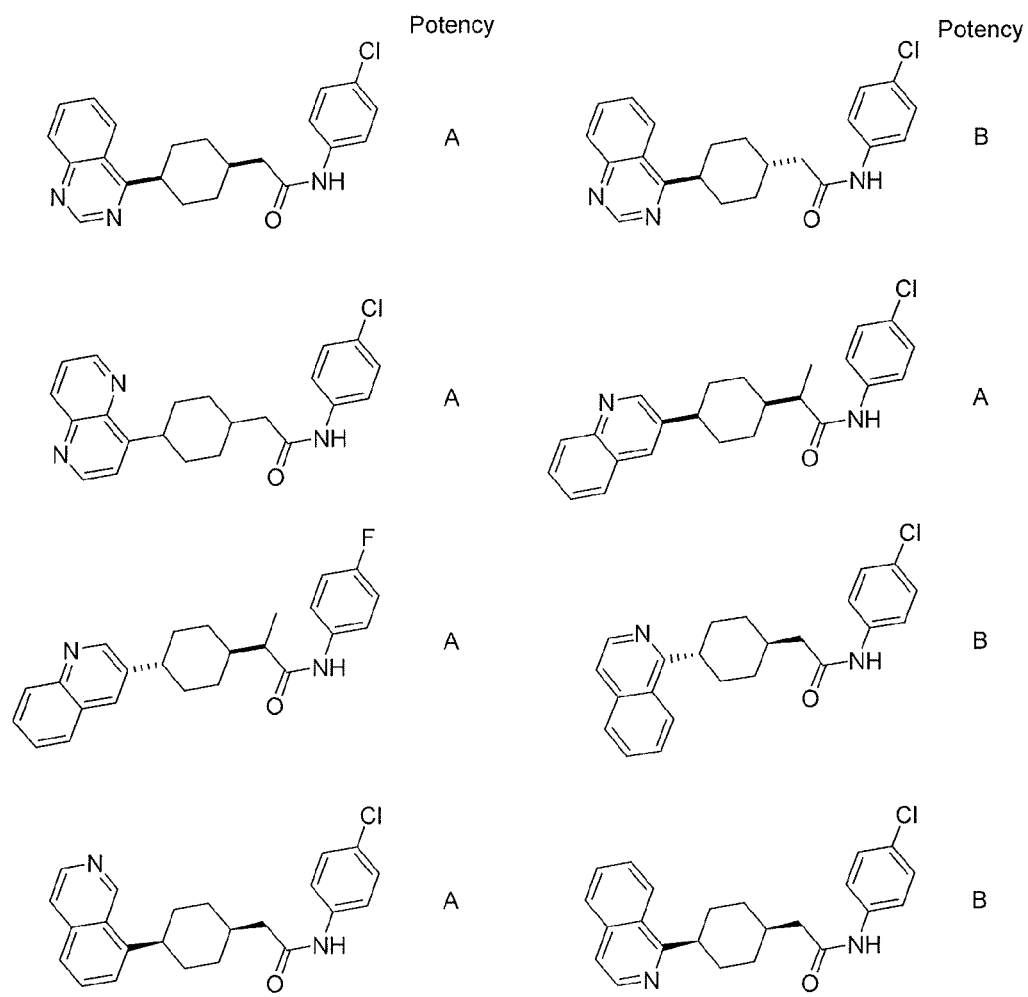

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology such as "solely", "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

Immune dysregulation is intimately associated with tumor evasion of the host immune system, resulting in tumor growth and progression. Traditional treatment approaches comprising chemotherapy and radiotherapy are generally difficult for the patient to tolerate and become less effective as tumors evolve to survive such treatments. By utilizing the patient's own immune system to identify and eliminate tumor cells, immunotherapy has the benefit of reduced toxicity. As upregulation of the immunoregulatory enzyme indoleamine 2,3-dioxygenase comprises one mechanism manipulated by tumors to promote growth, agents (e.g.,  small molecule compounds) that inhibit enzyme activity present a promising avenue for prophylaxis and/or treatment.

In addition, a large body of experimental data indicates a role for IDO inhibition in immunosuppression, tumor resistance and/or rejection, chronic infections, HIV-infection, and autoimmune diseases or disorders. Inhibition of IDO may also be an important treatment strategy for patients with neurological or neuropsychiatric diseases or disorders such as depression. The compounds, compositions and methods herein address the need for new classes of IDO modulators.

DEFINITIONS

Unless otherwise indicated, the following terms are intended to have the meaning set forth below. Other terms are defined elsewhere throughout the specification.

The term "alkyl", by itself or as part of another substituent, means, unless otherwise stated, a straight or branched chain hydrocarbon radical, having the number of carbon atoms designated (i.e., $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "cycloheteroalkyl" refers to a cycloalkyl ring having the indicated number of ring vertices (or members) and having from one to five heteroatoms selected from N, O, and S, which replace one to five of the carbon vertices, and wherein the nitrogen and sulfur atoms are optionally oxidized, and the nitrogen atom(s) are optionally quaternized. The cycloheteroalkyl may be a monocyclic, a bicyclic or a polycyclic ring system. Non limiting examples of cycloheteroalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A cycloheteroalkyl group can be attached to the remainder of the molecule through a ring carbon or a heteroatom.

As used herein, a wavy line, "〜", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)

NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy", "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3- to 7-membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen", by themselves or as part of another substituent, mean, unless otherwise stated, a fluorine, chlorine, bromine, or iodine atom. Additionally, terms such as "haloalkyl", are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for a heteroaryl ring can be selected from the group of acceptable substituents described below.

The above terms (e.g., "alkyl", "aryl" and "heteroaryl"), in some embodiments, will be optionally substituted. Selected substituents for each type of radical are provided below.

Optional substituents for the alkyl radicals (including those groups often referred to as alkylene, alkenyl, alkynyl and cycloalkyl) can be a variety of groups selected from: halogen, —OR', —NR'R", —SR', —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 m'+1), where m' is the total number of carbon atoms in such radical. R', R" and R''' each independently refer to hydrogen, unsubstituted $C_{1-8}$ alkyl, unsubstituted aryl, aryl substituted with 1-3 halogens, unsubstituted $C_{1-8}$ alkyl, $C_{1-8}$ alkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, optional substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{1-8}$ haloalkyl, $C_{3-6}$ cycloalkyl, $C_{2-8}$ alkenyl and $C_{2-8}$ alkynyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *J. Pharm. Sci.,* 66:1-19 (1977)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. "Substantially free of" another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as, for example, tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, an inhibitor of IDO, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", "treatment" and the like refer to a course of action (such as administering an inhibitor of IDO or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an IDO inhibitor or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of and IDO inhibitor (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

As used herein, the terms "IDO inhibitor", "IDO blocker" and terms similar thereto refer to agents capable of inhibiting the activity of IDO, thereby reversing IDO-mediated immunosuppression. An IDO inhibitor may be a competitive, noncompetitive, or irreversible IDO inhibitor. "A competitive IDO inhibitor" is a compound that reversibly inhibits IDO enzyme activity at the catalytic site; "a noncompetitive IDO Inhibitor" is a compound that reversibly inhibits IDO enzyme activity at a non-catalytic site; and "an irreversible IDO inhibitor" is a compound that irreversibly eliminates IDO enzyme activity by forming a covalent bond (or other stable means of inhibiting enzyme function) with the enzyme. A number of IDO inhibitors are commercially available (e.g., 5-Br-4-Cl-indoxyl 1,3-diacetate and 1-methyl-DL-tryptophan (1 MT); both available from Sigma-Aldrich, St. Louis, Mo.) and may be used as, for example, "tool" or "reference" compounds The term "ligand" refers to, for example, a peptide, a polypeptide, a membrane-associated or membrane-bound molecule, or a complex thereof, that can act as an agonist or antagonist of a receptor. A ligand encompasses natural and synthetic ligands, e.g., cytokines, cytokine variants, analogs, muteins, and binding compositions derived from antibodies, as well as small molecules. The term also encompasses an agent that is neither an agonist nor antagonist, but that can bind to a receptor without significantly influencing its biological properties, e.g., signaling or adhesion. Moreover, the term includes a membrane-bound ligand that has been changed by, e.g., chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex".

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of IDO, either directly or indirectly. A modulator may act alone, or it may use a cofactor, e.g., a protein, metal ion, or small molecule. Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently (though not always) means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

"Substantially pure" indicates that a component makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al., 1980 Analyt. Biochem. 107:220-239).

The term "response", for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide", "peptide", and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence, fusion proteins with heterologous and homologous leader sequences, with or without N-terminus methionine residues; immunologically tagged proteins; and the like.

As used herein, the terms "variants" and "homologs" are used interchangeably to refer to amino acid or DNA sequences that are similar to reference amino acid or nucleic acid sequences, respectively. The term encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Thus, variants and homologs encompass naturally occurring DNA sequences and proteins encoded thereby and their isoforms, as well as splice variants of a protein or gene. The terms also encompass nucleic acid sequences that vary in one or more bases from a naturally-occurring DNA sequence but still translate into an amino acid sequence that corresponds to the naturally-occurring protein due to degeneracy of the genetic code. Non-naturally-occurring variants and homologs include polypeptides and nucleic acids that comprise a change in amino acid or nucleotide sequence, respectively, where the change in sequence is artificially introduced (e.g., muteins); for example, the change is generated in the laboratory by human intervention ("hand of man"). Therefore, non-naturally occurring variants and homologs may also refer to those that differ from the naturally-occurring sequences by one or more conservative substitutions and/or tags and/or conjugates.

The term "muteins" as used herein refers broadly to mutated recombinant proteins. These proteins usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Indoleamine 2,3-Dioxygenase

As previously alluded to, IDO is an immune regulatory enzyme that is normally expressed in tumor cells and in activated immune cells. IDO is one of several immune response checkpoints that are involved in tumor immune escape; thus, IDO inhibitors disrupt mechanisms by which tumors evade the body's normal immune system.

IDO down-regulates the immune response mediated through oxidation of tryptophan. This results in inhibition of T-cell activation and induction of T-cell apoptosis, creating an environment in which tumor-specific cytotoxic T lymphocytes are rendered functionally inactive or are no longer able to attack a subject's cancer cells. Therefore, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

The expression of IDO is modulated by a complex array of signals, thus implicating a number of different mechanisms of actions. For example, IDO may be induced by inhibition of DNA methyl transferases or histone deacetylases. The NF-κB signaling pathway has also been implicated in IDO function. Inhibiting NF-kB activity blocks IDO expression and produces robust anti-tumor responses that are both T cell- and IDO-dependent; alternatively, NF-κB activation (which may be effected by various factors such as interferon-γR1/-γR2 signaling and toll-like-receptor activation) induces IDO gene expression.

Other mechanisms are involved with modulation of IDO function. By way of example, inhibitors of reactive oxidative species (ROS) may effect stabilization of IDO; IDO levels may be modulated by inhibition or activation of pathways that are both downstream and upstream of IDO; and activation of interferon-γ can activate an autocrine induction of IDO.

Studies indicate that the IDO pathway is active in many cancers, both within tumor cells as a direct defense against T cell attack, and also within antigen-presenting cells (APCs) in tumor-draining lymph nodes resulting in peripheral tolerance to tumor-associated antigens (TAAs). Cancers may use the IDO pathway to facilitate survival, growth, invasion, and metastasis of malignant cells expressing TAAs that might otherwise be recognized and attacked by the immune system.

As alluded to herein, tryptophan catabolism in tumor tissue by the rate-limiting enzyme IDO provides an opportunity for the use of IDO inhibitors as a therapeutic alternative to, or an additive with, conventional chemotherapy. However, certain cancers are capable of catabolizing tryptophan but are largely IDO-negative. Recent studies indicate that the alternative enzymatic pathway of tryptophan catabolism involving tryptophan-2,3-dioxygenase (TDO) is also relevant in cancer. TDO, which is considered responsible for regulating systemic tryptophan levels in the liver, is constitutively expressed in some cancers and is also capable of suppressing antitumor immune responses (See, e.g., Platten, M. et al., *Cancer Res.*, 72(21):5435-5440 (Nov. 1, 2012)).

IDO is expressed in a wide variety of human tumors and tumor cell lines as well as in host APCs, which correlates with a worse clinical prognosis. Therefore, inhibition of IDO may improve survival in cancer patients with IDO-mediated immunosuppression. In comparison, TDO is expressed in a wide variety of human tumors and tumor cell lines, and expression of TDO is evident in advanced human glioblastomas. The identification of tumors expressing high levels of IDO or TDO may allow more selective inhibition of the tryptophan-regulated immunosuppressive pathways. Alternatively, compounds inhibiting both IDO and TDO could provide the greatest coverage to prevent tumor escape by compensatory expression of the other tryptophan-degrading enzyme. Therefore, the use of dual IDO/TDO inhibitors or combinations of IDO- and TDO-specific inhibitors may prove to be a superior treatment alternative in immunotherapy of cancer to block immunosuppression mediated by tryptophan metabolism.

Although a precise understanding of the underlying mechanism of action by which the compounds of the present invention effect their activity is not required to practice the invention, the compounds (or a subset thereof) are believed to inhibit IDO function. Alternatively, the compounds (or a subset thereof) may inhibit TDO function. The compounds (or a subset thereof) may also have inhibitory activity on both IDO and TDO function. Although the compounds of the invention are generally referred to herein as IDO inhibitors, it is to be understood that the term "IDO inhibitors" encompasses compounds that act individually through inhibition of TDO or IDO, and/or compounds that act through inhibition of both IDO and TDO.

Identification of IDO Inhibitors Possessing Desirable Characteristics

The present invention is drawn, in part, to the identification of inhibitors of IDO with at least one property or characteristic that is of therapeutic relevance. Candidate inhibitors may be identified by using, for example, an art-accepted assay or model, examples of which are described herein.

After identification, candidate inhibitors can be further evaluated by using techniques that provide data regarding characteristics of the inhibitors (e.g., pharmacokinetic parameters, means of determining solubility or stability). Comparisons of the candidate inhibitors to a reference standard (which may the "best-of-class" of current inhibitors) are indicative of the potential viability of such candidates.

Compounds of the Invention

As noted above, the present invention provides compounds represented by formula (I):

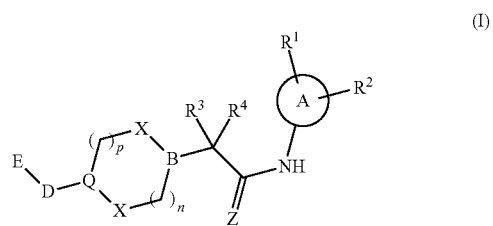

or a pharmaceutically acceptable salt, hydrate or solvate thereof, wherein, the subscript n is 1 or 0; the subscript p is 1 or 0; the ring designated as A is phenyl, 5- or 6-membered heteroaryl, or $C_{5-7}$ cycloalkyl; Z is O; B is N, $C(OR^{5a})$, or $C(R^{3a})$; each X is independently $NR^{5a}$, O, $CHR^5$, $C(O)$, or $CH(OR^{5a})$; Q is N, C(CN) or $CR^6$; D is a bond, O, $C(R^5)_2$, or $NR^{5a}$; E is an optionally substituted 9- or 10-membered fused bicyclic heteroaryl; $R^1$ and $R^2$ are independently hydrogen, halogen, $C_1$-$C_4$ haloalkyl, $C_3$-$C_6$ cycloalkyl, 3- to 6-membered cycloheteroalkyl, optionally substituted phenyl, optionally substituted heteroaryl, optionally substituted $C_1$-$C_4$ alkyl, $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl; $R^3$, $R^{3a}$ and $R^4$ are independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, optionally substituted $C_3$-$C_6$ cycloalkyl-$C_1$-$C_4$ alkyl, optionally substituted aryl-$C_1$-$C_6$ alkyl, fluorine, OH, CN, $CO_2H$, $C(O)NH_2$, $N(R^5)_2$, optionally substituted —O—$C_1$-$C_6$ alkyl, —$(CR^5R^5)_m$—OH, —$(CR^5R^5)_m$—$CO_2H$, —$(CR^5R^5)_m$—$C(O)NH_2$, —$(CR^5R^5)_m$—$C(O)NHR^5$, —$(CR^5R^5)_m N(R^5)_2$, —$NH(CR^5R^5)_m CO_2H$ or —$NH(CR^5R^5)_m$—$C(O)NH_2$; each $R^5$ is independently H, F, OH, or optionally substituted $C_1$-$C_6$ alkyl; each $R^{5a}$ is independently H, or optionally substituted $C_1$-$C_6$ alkyl; $R^6$ is H, OH, F, optionally substituted $C_1$-$C_6$ alkyl, optionally substituted —O—$C_1$-$C_6$ alkyl, or —$N(R^{5a})_2$; and each m is independently 1, 2, or 3.

In some embodiments, Q is C(CN) or $CR^6$.

In some embodiments, compounds are provided having formula (Ia) or (Ib):

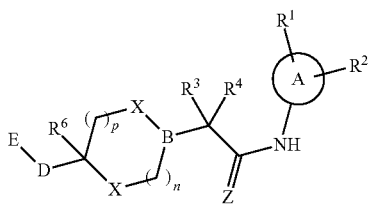

(Ia)

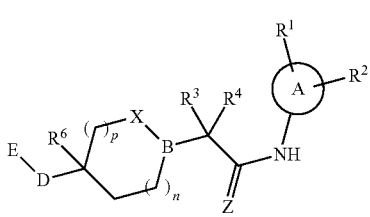

(Ib)

wherein each of the subscripts, letters, and $R^1$, $R^2$, $R^3$, $R^4$ and $R^6$ have the meanings provided with reference to the compounds of formula (I).

In other embodiments, compounds are provided having formula (Ic):

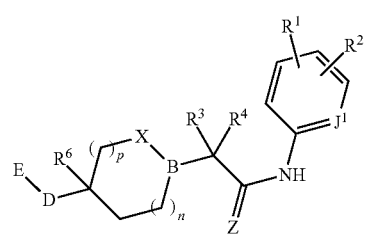

(Ic)

wherein $J^1$ is CH, N or optionally $C(R^2)$ when $R^2$ is attached to the ring vertex identified as $J^1$, and each of the subscripts, letters, and $R^1$, $R^2$, $R^3$, $R^4$ and $R^6$ have the meanings provided with reference to the compounds of formula (I).

In some selected embodiments, compounds are provided having a formula selected from (Ic1), (Ic2), (Ic3), (Ic4), (Ic5) and (Ic6):

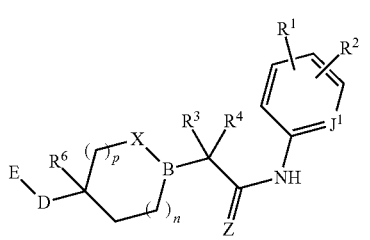

(Ic1)

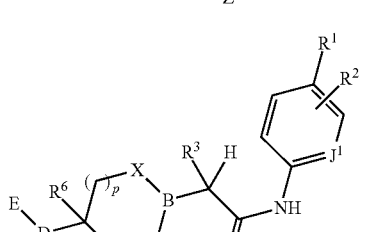

(Ic2)

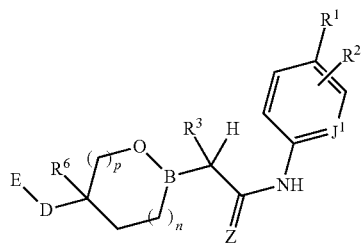

(Ic3)

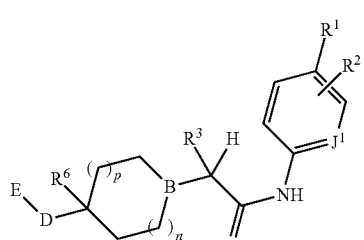

(Ic4)

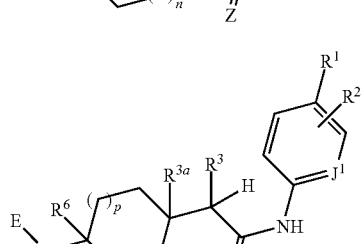

(Ic5)

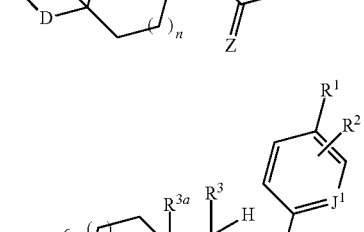

(Ic6)

wherein $J^1$ is CH, N or optionally $C(R^2)$ when $R^2$ is attached to the ring vertex identified as $J^1$, and each of the subscripts, letters, and $R^1$, $R^2$, $R^3$, $R^{3a}$, $R^4$ and $R^6$ have the meanings provided with reference to the compounds of formula (I).

In other embodiments, compounds are provided having formula (Id):

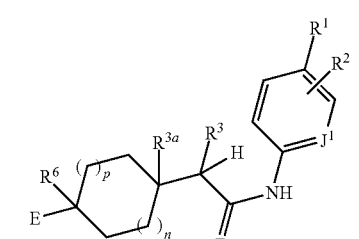

(Id)

wherein $J^1$ is CH, N or optionally $C(R^2)$ when $R^2$ is attached to the ring vertex identified as $J^1$, each of the subscripts, letters, and $R^1$, $R^2$, $R^3$, $R^{3a}$ and $R^6$ have the meanings provided with reference to the compounds of formula (I).

In some selected embodiments, compounds are provided having a formula selected from (Id1), (Id2), (Id3) and (Id4):

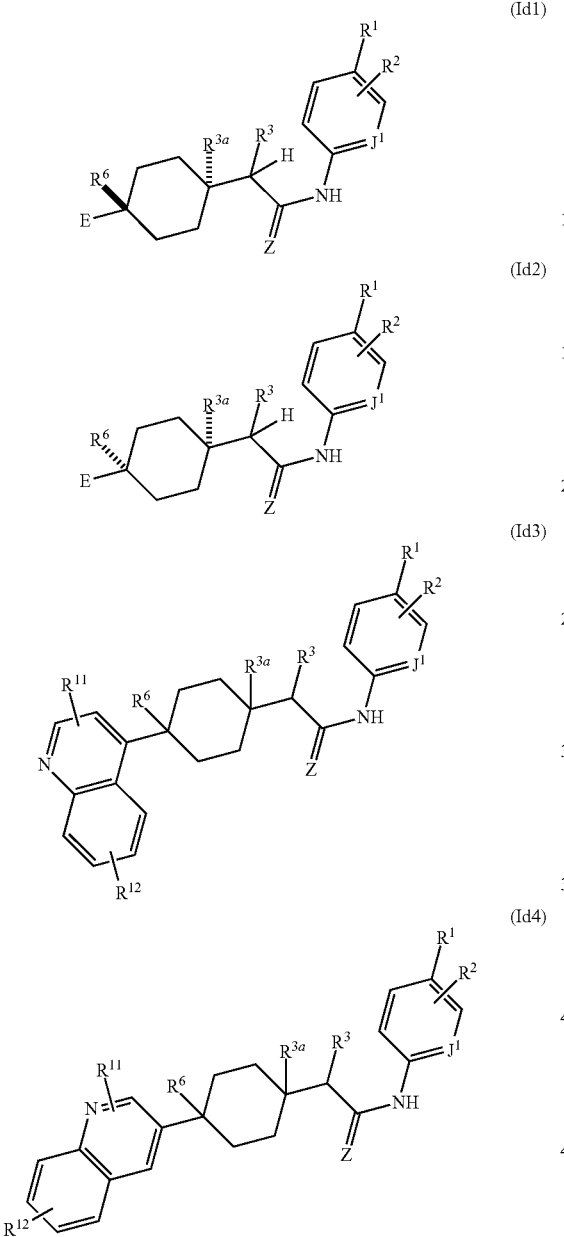

(Id1)

(Id2)

(Id3)

(Id4)

wherein for each of (Id1) and (Id2), the compounds are provided substantially free of other isomers at the stereocenters shown. For each of (Id3) and (Id4), $R^{11}$ and $R^{12}$ are independently hydrogen, halogen, $C_1$-$C_4$ haloalkyl, $C_3$-$C_6$ cycloalkyl, 3- to 6-membered cycloheteroalkyl, optionally substituted phenyl, optionally substituted heteroaryl, optionally substituted $C_1$-$C_4$ alkyl, $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl. For each of (Id1), (Id2), (Id3) and (Id4), the remaining letters, and $J^1$, $R^1$, $R^2$, $R^3$, $R^{3a}$ and $R^6$ have the meanings provided with reference to the compounds of formula (Id).

In other embodiments, compounds are provided having formula (Ie):

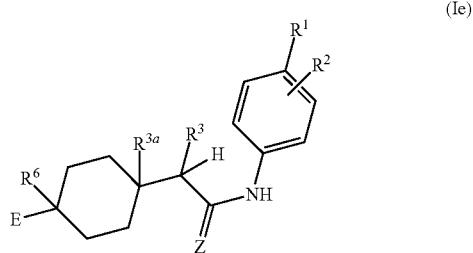

(Ie)

wherein the letters, and $R^1$, $R^2$, $R^3$, $R^{3a}$ and $R^6$ have the meanings provided with reference to the compounds of formula (I).

In some selected embodiments, compounds are provided having a formula selected from (Ie1), (Ie2), (Ie3), (Ie4), (Ie5), (Ie6) and (Ie7):

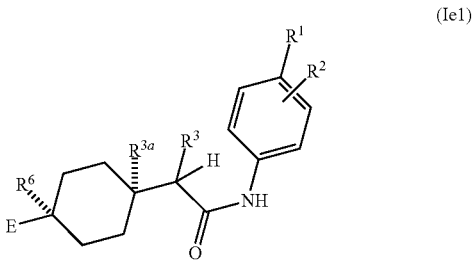

(Ie1)

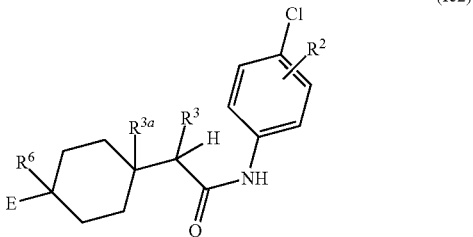

(Ie2)

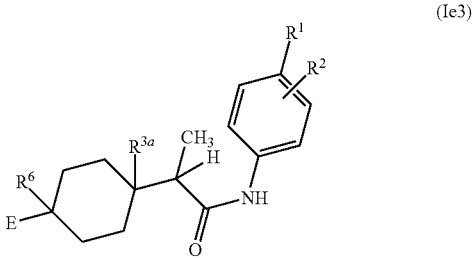

(Ie3)

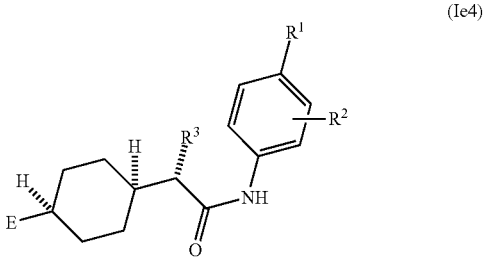

(Ie4)

-continued (Ie5)
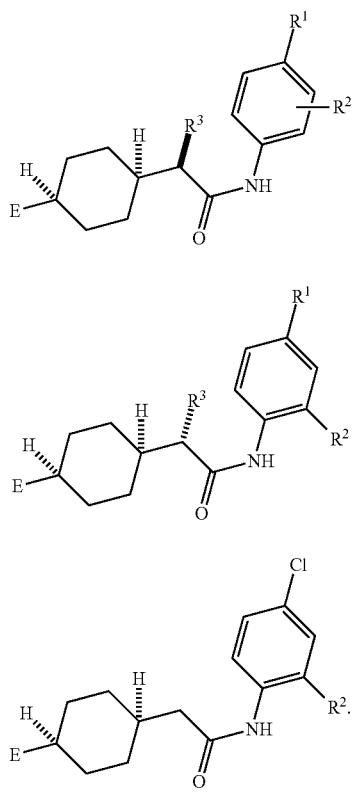
(Ie6)

(Ie7)

(Ig)
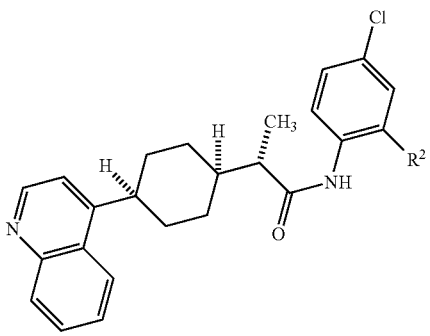

For each of formulae (Ie1), (Ie4), (Ie5), (Ie6) and (Ie7), the compounds are substantially free of other isomers at each of the stereocenters shown. In selected embodiments of formula (Ie4), compounds are provided wherein $R^1$ is Cl, F, optionally substituted phenyl, or CN. In selected embodiments of formula (Ie6), compounds are provided wherein $R^1$ is Cl, F, optionally substituted phenyl, or CN; and $R^2$ is H or F. In selected embodiments of formula (Ie6), compounds are provided wherein $R^1$ is Cl. In other selected embodiments of formula (Ie6), compounds are provided wherein $R^1$ is Cl; and $R^3$ is $CH_3$. When not specifically defined as noted here, the remaining letters, and $R^1$, $R^2$, $R^3$, $R^{3a}$ and $R^6$ have the meanings provided with reference to the compounds of formula (I).

In other embodiments, compounds are provided having formula (If) or (Ig):

(If)
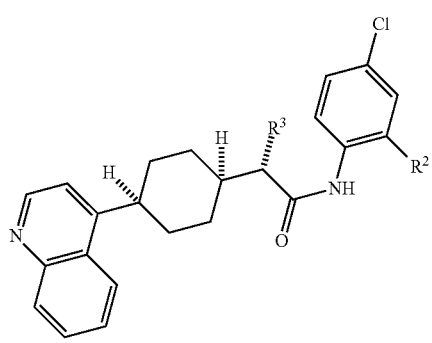

each of which is substantially free of other isomers at each of the three stereocenters shown, and wherein $R^2$ and $R^3$ have the meanings provided with reference to formula (I).

In one group of selected embodiments, any one compound of FIGS. 1A-1L is provided.

In another group of selected embodiments, any one compound of FIGS. 1A-1L is provided having an activity level identified as "A" or "B".

In another group of selected embodiments, any one compound of FIGS. 1A-1L is provided having an activity level identified as "A".

Methods of Synthesis

The compounds described herein can be prepared by a variety of methods.

Representative methods are provided in the Examples below.

Modifications to Enhance Inhibitor Characteristics

It is frequently beneficial, and sometimes imperative, to improve one of more physical properties of the treatment modalities disclosed herein and/or the manner in which they are administered. Improvements of physical properties include, for example, methods of increasing water solubility, bioavailability, serum half-life, and/or therapeutic half-life; and/or modulating biological activity.

Modifications known in the art include pegylation, Fc-fusion and albumin fusion. Although generally associated with large molecule agents (e.g., polypeptides), such modifications have recently been evaluated with particular small molecules. By way of example, Chiang, M. et al. (*J. Am. Chem. Soc.*, 136(9):3370-3373 (2014)) describe a small molecule agonist of the adenosine 2a receptor conjugated to the immunoglobulin Fc domain. The small molecule-Fc conjugate retained potent Fc receptor and adenosine 2a receptor interactions and showed superior properties compared to the unconjugated small molecule. Covalent attachment of PEG molecules to small molecule therapeutics has also been described (Li, W. et al., *Progress in Polymer Science*, 38:421-444 (2013)).

Therapeutic and Prophylactic Uses

The present invention contemplates the use of the IDO inhibitors described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an IDO inhibitor can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut et al., *Oncogene*, 22:3180-3187 (2003); and Sawaya et al., *New Engl. J. Med.*, 349:1501-1509 (2003)). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In some embodiments, the present invention provides methods for treating a proliferative condition, cancer, tumor, or precancerous condition with an IDO inhibitor and at least one additional therapeutic or diagnostic agent, examples of which are set forth elsewhere herein.

Immune- and Inflammatory-related Disorders. As used herein, terms such as "immune disease", "immune condition", "immune disorder", "inflammatory disease", "inflammatory condition", "inflammatory disorder" and the like are meant to broadly encompass any immune- or inflammatory-related condition (e.g., pathological inflammation and autoimmune diseases). Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

A non-limiting list of immune- and inflammatory-related diseases, disorders and conditions which may be treated or prevented with the compounds and compositions of the present invention include, arthritis (e.g., rheumatoid arthritis), kidney failure, lupus, asthma, psoriasis, colitis, pancreatitis, allergies, fibrosis, surgical complications (e.g., where inflammatory cytokines prevent healing), anemia, and fibromyalgia. Other diseases and disorders which may be associated with chronic inflammation include Alzheimer's disease, congestive heart failure, stroke, aortic valve stenosis, arteriosclerosis, osteoporosis, Parkinson's disease, infections, inflammatory bowel disease (e.g., Crohn's disease and ulcerative colitis), allergic contact dermatitis and other eczemas, systemic sclerosis, transplantation and multiple sclerosis.

Among other immune-related disorders, it is contemplated that inhibition of IDO function may also play a role in immunologic tolerance and prevention of fetal rejection in utero.

In some embodiments, an IDO inhibitor described herein can be combined with an immunosuppressive agent to reduce the number of immune effector cells.

Some of the aforementioned diseases, disorders and conditions for which an IDO inhibitor may be particularly efficacious (due to, for example, limitations of current therapies) are described in more detail hereafter.

Rheumatoid Arthritis (RA), which is generally characterized by chronic inflammation in the membrane lining (the synovium) of the joints, affects approximately 1% of the U.S. population (~2.1 million people). Further understanding of the role of cytokines, including TNF-α and IL-1, in the inflammatory process has enabled the development and introduction of a new class of disease-modifying antirheumatic drugs (DMARDs). Agents (some of which overlap with treatment modalities for RA) include ENBREL® (etanercept), REMICADE® (infliximab), HUMIRA® (adalimumab) and KINERET® (anakinra). Though some of these agents relieve symptoms, inhibit progression of structural damage, and improve physical function in particular patient populations, there is still a need for alternative agents with improved efficacy, complementary mechanisms of action, and fewer/less severe adverse effects.

Psoriasis, a constellation of common immune-mediated chronic skin diseases, affects more than 4.5 million people in the U.S., of which 1.5 million are considered to have a moderate-to severe form of the disease. Moreover, over 10% of patients with psoriasis develop psoriatic arthritis, which damages the bone and connective tissue around the joints. An improved understanding of the underlying physiology of psoriasis has resulted in the introduction of agents that, for example, target the activity of T lymphocytes and cytokines responsible for the inflammatory nature of the disease. Such agents include the TNF-α inhibitors (also used in the treatment of rheumatoid arthritis (RA)), including ENBREL® (etanercept), REMICADE® (infliximab) and HUMIRA® (adalimumab)), and T-cell inhibitors such as AMEVIVE® (alefacept) and RAPTIVA® (efalizumab). Though several of these agents are effective to some extent in certain patient populations, none have been shown to effectively treat all patients.

Subjects suffering from multiple sclerosis (MS), a seriously debilitating autoimmune disease comprising multiple areas of inflammation and scarring of the myelin in the brain and spinal cord, may be particularly helped by the IDO inhibitors described herein, as current treatments only alleviate symptoms or delay the progression of disability.

Similarly, the IDO inhibitors may be particularly advantageous for subjects afflicted with neurodegenerative disorders, such as Alzheimer's disease (AD), a brain disorder that seriously impairs patients' thought, memory, and language processes; and Parkinson's disease (PD), a progressive disorder of the CNS characterized by, for example, abnormal movement, rigidity and tremor. These disorders are progressive and debilitating, and no curative agents are available.

Viral-related Disorders. The present invention contemplates the use of the IDO inhibitors in the treatment and/or prevention of any viral disease, disorder or condition for which treatment with an IDO inhibitor may be beneficial. In particular embodiments, the viral disorder is a chronic viral disorder. Examples of viral diseases, disorders and conditions that are contemplated include, but are not limited to, hepatitis B virus (HBV), hepatitis C virus (HCV), human papilloma virus (HPV), HIV, AIDS (including its manifestations such as cachexia, dementia, and diarrhea), herpes simplex virus (HSV), Epstein-Barr virus (EBV), varicella zoster virus, coxsackie virus, and cytomegalovirus (CMV).

Bacterial- and Parasitic-related Disorders. Embodiments of the present invention contemplate the administration of the IDO inhibitors described herein to a subject for the treatment of a bacterial infection, for example, a *Mycobacterium* infection (e.g., *Mycobacterium leprae* or *Mycobacterium tuberculosis*) or an infection caused by *Listeria monocytogenes* or *Toxplasma gondii*. Other embodiments contemplate the treatment of a parasitic infection including, but not limited to, *Leishmania donovani, Leishmania tropica, Leishmania major, Leishmania aethiopica, Leishmania mexicana, Plasmodium falciparum, Plasmodium vivax, Plasmodium ovale,* or *Plasmodium malariae*. Frequently, anti-parasitic therapy is administered prophylactically (e.g., before a subject travels to an area with a high frequency of parasitic infection).

Pharmaceutical Compositions

The IDO inhibitors of the present invention may be in the form of compositions suitable for administration to a subject. In general, such compositions are "pharmaceutical compositions" comprising an IDO inhibitor(s) and one or more pharmaceutically acceptable or physiologically acceptable diluents, carriers or excipients. In certain embodiments, the IDO inhibitors are present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., an inhibitor of IDO function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly(methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example, peanut oil, liquid paraffin, or olive oil.

Aqueous suspensions contain the active materials in admixture with excipients suitable for the manufacture thereof. Such excipients can be suspending agents, for example, sodium carboxymethylcellulose, methylcellulose, hydroxy-propylmethylcellulose, sodium alginate, polyvinylpyrrolidone, gum tragacanth and gum acacia; dispersing or wetting agents, for example, a naturally-occurring phosphatide (e.g., lecithin), or condensation products of an alkylene oxide with fatty acids (e.g., polyoxyethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example, olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The pharmaceutical compositions typically comprise a therapeutically effective amount of an IDO inhibitor contemplated by the present invention and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EPIPEN®)), whereas a multi-use container (e.g., a multi-use vial) is provided in other embodiments. Any drug delivery apparatus may be used to deliver and IDO inhibitor, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, CREMOPHOR® EL (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the IDO inhibitors in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IDO inhibitors contemplated by the present invention may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present invention contemplates the administration of IDO inhibitors, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), sublingual and inhalation. Depot injections, which are generally administered subcutaneously or intramuscularly, may also be utilized to release the IDO inhibitors disclosed herein over a defined period of time.

Particular embodiments of the present invention contemplate oral administration.

Combination Therapy

The present invention contemplates the use of IDO inhibitors in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IDO inhibitors are administered or applied sequentially, e.g., where one agent is administered prior to one or more other agents. In other embodiments, the IDO inhibitors are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The IDO inhibitors of the present invention may be used in combination with at least one other (active) agent in any manner appropriate under the circumstances. In one embodiment, treatment with the at least one active agent and at least one IDO inhibitor of the present invention is maintained over a period of time. In another embodiment, treatment with the at least one active agent is reduced or discontinued (e.g., when the subject is stable), while treatment with an IDO inhibitor of the present invention is maintained at a constant dosing regimen. In a further embodiment, treatment with the at least one active agent is reduced or discontinued (e.g., when the subject is stable), while treatment with an IDO inhibitor of the present invention is reduced (e.g., lower dose, less frequent dosing or shorter treatment regimen). In yet another embodiment, treatment with the at least one active agent is reduced or discontinued (e.g., when the subject is stable), and treatment with the IDO inhibitor of the present invention is increased (e.g., higher dose, more frequent dosing or longer treatment regimen). In yet another embodiment, treatment with the at least one active agent is maintained and treatment with the IDO inhibitor of the present invention is reduced or discontinued (e.g., lower dose, less frequent dosing or shorter treatment regimen). In yet another embodiment, treatment with the at least one active agent and treatment with the IDO inhibitor of the present invention are reduced or discontinued (e.g., lower dose, less frequent dosing or shorter treatment regimen).

Oncology-Related Disorders.

The present invention provides methods for treating and/or preventing a proliferative condition, cancer, tumor, or precancerous disease, disorder or condition with an IDO inhibitor and at least one additional therapeutic agent, such as radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); and immune-stimulatory oligonucleotides.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC); (ii) epidermal growth factor (EGF)

receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

Additional treatment modalities that may be used in combination with an IDO inhibitor include a cytokine or cytokine antagonist, such as IL-12, IFN, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

Cardiovascular Diseases.

The present invention provides methods for treating and/or preventing certain cardiovascular- and/or metabolic-related diseases, disorders and conditions, as well as disorders associated therewith, with an IDO inhibitor and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IDO inhibitors described herein include various supplements and herbs (e.g., garlic, policosanol, and guggul). The present invention encompasses pharmaceutically acceptable salts, acids or derivatives of any of the above.

Immune- and Inflammatory-Related Disorders.

The present invention provides methods for treating and/or preventing immune- and/or inflammatory-related diseases, disorders and conditions, as well as disorders associated therewith, with an IDO inhibitor and at least one additional therapeutic or diagnostic agent.

Examples of therapeutic agents useful in combination therapy include, but are not limited to, the following: non-steroidal anti-inflammatory drug (NSAID) such as aspirin, ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone). Other combinations include cyclooxygenase-2 (COX-2) inhibitors.

Other active agents for combination include steroids such as prednisolone, prednisone, methylprednisolone, betamethasone, dexamethasone, or hydrocortisone. Such a combination may be especially advantageous since one or more adverse effects of the steroid can be reduced or even eliminated by tapering the steroid dose required.

Additional examples of active agents that may be used in combinations for treating, for example, rheumatoid arthritis, include cytokine suppressive anti-inflammatory drug(s) (CSAIDs); antibodies to, or antagonists of, other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists such as chimeric, humanized or human TNF antibodies, REMICADE, anti-TNF antibody fragments (e.g., CDP870), and soluble p55 or p75 TNF receptors, derivatives thereof, p75TNFRIgG (ENBREL.) or p55TNFRIgG (LENERCEPT), soluble IL-13 receptor (sIL-13), and also TNFα-converting enzyme (TACE) inhibitors; similarly, IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IDO inhibitors described herein include interferon-β1a (AVONEX); interferon-β1b (BETASERON); copaxone; hyperbaric oxygen; intravenous immunoglobulin; clabribine; and antibodies to, or antagonists of, other human cytokines or growth factors (e.g., antibodies to CD40 ligand and CD80).

Immune Checkpoint Inhibitors.

The present invention contemplates the use of the inhibitors of IDO function described herein in combination with additional immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

T cells have been the major focus of efforts to therapeutically manipulate endogenous antitumor immunity because of i) their capacity for the selective recognition of peptides derived from proteins in all cellular compartments; ii) their capacity to directly recognize and kill antigen-expressing cells (by CD8+ effector T cells; also known as cytotoxic T lymphocytes (CTLs)); and iii) their ability to orchestrate diverse immune responses by CD4+ helper T cells, which integrate adaptive and innate effector mechanisms. In the clinical setting, the blockade of immune checkpoints—which results in the amplification of antigen-specific T cell responses—has shown to be a promising approach in human cancer therapeutics.

T cell-mediated immunity includes multiple sequential steps, each of which is regulated by counterbalancing stimulatory and inhibitory signals in order to optimize the response. While nearly all inhibitory signals in the immune response ultimately modulate intracellular signaling pathways, many are initiated through membrane receptors, the ligands of which are either membrane-bound or soluble (cytokines). While co-stimulatory and inhibitory receptors and ligands that regulate T-cell activation are frequently not over-expressed in cancers relative to normal tissues, inhibitory ligands and receptors that regulate T cell effector functions in tissues are commonly overexpressed on tumor cells or on non-transformed cells associated with the tumor microenvironment. The functions of the soluble and membrane-bound receptor-ligand immune checkpoints can be modulated using agonist antibodies (for co-stimulatory pathways) or antagonist antibodies (for inhibitory pathways). Thus, in contrast to most antibodies currently approved for cancer therapy, antibodies that block immune checkpoints do not target tumor cells directly, but rather target lymphocyte receptors or their ligands in order to enhance endogenous antitumor activity. [See Pardoll, (April 2012) Nature Rev. Cancer 12:252-64].

Examples of immune checkpoints (ligands and receptors), some of which are selectively upregulated in various types of tumor cells, that are candidates for blockade include PD1 (programmed cell death protein 1); PDL1 (PD1 ligand); BTLA (B and T lymphocyte attenuator); CTLA4 (cytotoxic T-lymphocyte associated antigen 4); TIM3 (T-cell membrane protein 3); LAG3 (lymphocyte activation gene 3); A2aR (adenosine A2a receptor A2aR); and Killer Inhibitory Receptors, which can be divided into two classes based on their structural features: i) killer cell immunoglobulin-like receptors (KIRs), and ii) C-type lectin receptors (members of the type 11 transmembrane receptor family). Other less well-defined immune checkpoints have been described in the literature, including both receptors (e.g., the 2B4 (also known as CD244) receptor) and ligands (e.g., certain B7 family inhibitory ligands such B7-H3 (also known as CD276) and B7-H4 (also known as B7-S1, B7x and VCTN1)). [See Pardoll, (April 2012) Nature Rev. Cancer 12:252-64].

The present invention contemplates the use of the inhibitors of IDO function described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are also available for the treatment of cancer, including for example nivolumab (Bristol-Myers Squibb) and pembroluzimab (Merck), and anti-PDL1 antibodies are also being evaluated (e.g., MPDL3280A (Roche)). Nivolumab (Opdivo®) has shown promise in patients with melanoma, lung and kidney cancer, as well as multiple other malignancies.

In one aspect of the present invention, the claimed IDO inhibitors are combined with an immuno-oncology agent that is (i) an agonist of a stimulatory (including a co-stimulatory) receptor or (ii) an antagonist of an inhibitory (including a co-inhibitory) signal on T cells, both of which result in amplifying antigen-specific T cell responses. Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of the claimed IDO inhibitors and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and/or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD2. Other agents that can be combined with the IDO inhibitors of the present invention for the treatment of cancer include antagonists of inhibitory receptors on NK cells or agonists of activating receptors on NK cells. For example, compounds herein can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, the claimed IDO inhibitors can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The present invention encompasses pharmaceutically acceptable salts, acids or derivatives of any of the above.

Viral Diseases.

The present invention provides methods for treating and/or preventing viral diseases, disorders and conditions, as well as disorders associated therewith, with an IDO inhibitor and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an IDO inhibitor include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention encompasses pharmaceutically acceptable salts, acids or derivatives of any of the above.

Parasitic Disorders.

The present invention contemplates the use of the inhibitors of IDO function described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole.

The skilled artisan is aware of other agents that may find utility for the treatment of parasitic disorders.

The present invention encompasses pharmaceutically acceptable salts, acids or derivatives of any of the above.

Bacterial Infections.

Embodiments of the present invention contemplate the use of the IDO inhibitors described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

The present invention encompasses pharmaceutically acceptable salts, acids or derivatives of the agents (and members of the classes of agents) set forth above.

Dosing

The IDO inhibitors of the present invention may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IDO inhibitors of the present invention may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired IDO inhibitor is contained in a "unit dosage form". The phrase "unit dosage form" refers to physically discrete units, each unit containing a predetermined amount of the IDO inhibitor, either alone or in combination with one or more additional agents, sufficient to produce the desired effect. It will be appreciated that the parameters of a unit dosage form will depend on the particular agent and the effect to be achieved.

Kits

The present invention also contemplates kits comprising an IDO inhibitor, and pharmaceutical compositions thereof. The kits are generally in the form of a physical structure housing various components, as described below, and may be utilized, for example, in practicing the methods described above.

A kit can include one or more of the IDO inhibitors disclosed herein (provided in, e.g., a sterile container), which may be in the form of a pharmaceutical composition suitable for administration to a subject. The IDO inhibitors can be provided in a form that is ready for use (e.g., a tablet or capsule) or in a form requiring, for example, reconstitution or dilution (e.g., a powder) prior to administration. When the IDO inhibitors are in a form that needs to be reconstituted or diluted by a user, the kit may also include diluents (e.g., sterile water), buffers, pharmaceutically acceptable excipients, and the like, packaged with or separately from the IDO inhibitors. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: wt=wildtype; bp=base pair(s); kb=kilobase(s); nt=nucleotides(s); aa=amino acid(s); s or sec=second(s); min=minute(s); h or hr=hour(s); ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; IHC=immunohistochemistry; DMEM=Dulbecco's Modification of Eagle's Medium; EDTA=ethylenediaminetetraacetic acid.

Materials and Methods

The following general materials and methods were used, where indicated, or may be used in the Examples below:

Standard methods in molecular biology are described in the scientific literature (see, e.g., Sambrook et al., *Molecular Cloning*, Third Edition, Cold Spring Harbor Laboratory Press, Cold Spring Harbor, N.Y. (2001); and Ausubel et al., *Current Protocols in Molecular Biology*, Vols. 1-4, John Wiley and Sons, Inc. New York, N.Y. (2001), which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al., *Current Protocols in Protein Science*, Vols. 1-2, John Wiley and Sons, Inc., NY (2000)).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DECYPHER® (TimeLogic Corp., Crystal Bay, Nev.).

The literature is replete with assays and other experimental techniques that can serve as a basis for evaluation of the compounds described herein.

An IDO enzyme assay and cellular production of kynurenine (KYN) is described in Sarkar, S. A. et al., *Diabetes*, 56:72-79 (2007). Briefly, all chemicals can be purchased from Sigma-Aldrich (St. Louis, Mo.) unless specified otherwise. Groups of 1,000 human islets can be cultured for 24 h in 1 mL medium with cytokines, recovered by centrifugation for 5 min at 800×g and sonicated in 150 μL PBS containing a protease inhibitor cocktail (Set 2; Calbiochem, EMD Biosciences, San Diego, Calif.). The sonicate can be centrifuged for 10 min at 10,000×g, and the supernatant can be assayed in triplicate by incubating a 40 μl sample with an equal volume of 100 mmol/L potassium phosphate buffer, pH 6.5, containing 40 mmol/L ascorbic acid (neutralized to pH 7.0), 100 μmol/L methylene blue, 200 μg/mL catalase, and 400 μmol/l L-Trp for 30 min at 37° C. The assay can be terminated by the addition of 16 μL 30% (w/v) trichloroacetic acid (TCA) and further incubated at 60° C. for 15 min to hydrolyze N-formylkynurenine to KYN. The mixture can then be centrifuged at 12,000 rpm for 15 min, and KYN can be quantified by mixing equal volume of supernatant with 2% (w/v) Ehrlich's reagent in glacial acetic acid in 96-well microtiter plate and reading the absorbance at 480 nm using L-KYN as standard. Protein in the islet samples can be quantified by Bio-Rad Protein assay at 595 nm. For the detection of L-KYN in the islet culture supernatants, proteins can be precipitated with 5% (w/v) TCA and centrifuged at 12,000 rpm for 15 min, and determination of KYN in the supernatant with Ehrlich's reagent can be determined as described above. IL-4 (10 μg/mL; 500-2,000 units/mL) and 1-α-methyl Trp (1-MT; 40 μmol/L) can be added to the incubation media as indicated. This assay can also form the basis of a cell-based assay, and may be quantified via LCMS/MS as an alternative to UV/Vis detection.

Western Blot Analyses. Groups of 1,000-1,200 islets incubated for 24 h in Miami medium in the presence of cytokines can be harvested and sonicated in PBS as above, and 50 μg protein samples can be electrophoresed on 10% SDS-PAGE gels. COST cells ($0.6 \times 10^6$ cells/60 mm3 petri dish) transfected with human-IDO plasmid (3 μg) or empty vector cells can be used as positive and negative controls, respectively. Proteins can be transferred electrophoretically onto polyvinylidine fluoride membranes by semidry method and blocked for 1 h with 5% (w/v) nonfat dry milk in Tris-buffered saline and 0.1% Tween and then incubated overnight with anti-human mouse IDO antibody (1:500; Chemicon, Temecula, Calif.), phospho-$STAT_{1\alpha}$ p91, and $STAT_{1\alpha}$ p91 (1:500; Zymed, San Francisco, Calif.). Immunoreactive proteins can be visualized with ECL PLUS® Western blotting detection reagent (Amersham BioSciences, Buckinghamshire, U.K.) after incubation for 1 h with anti-mouse horseradish peroxidase-conjugated secondary antibody (Jackson Immunolabs, West Grove, Pa.).

Immunohistochemical Detection of IDO. Islets can be fixed in 4% paraformaldehyde in PBS (Invitrogen) for 1 h, immobilized in molten 10% porcine skin gelatin blocks (37° C.), and embedded in optimal cutting temperature compound. Immunofluorescent staining on islet tissue can be performed on 7 μm sections that were stained with antibodies raised against pancreatic duodenal homeobox 1 (PDX1) and IDO. Antigen retrieval can be performed in a water bath for 30 min in a buffer containing 10 mmol/l Tris and 1 mmol/l EDTA (pH 9.0) at 97° C. The sections can be blocked for 1 h with 5% normal goat serum in PBS. The tissues can then be reacted with mouse monoclonal anti-human IDO antibody (1:20; Chemicon) and goat polyclonal anti-human PDX1 antibody (1:2,000; which may be requested from Dr. Chris Wright, School of Medicine, Vanderbilt, Tenn.) overnight at room temperature in a humid chamber. Secondary antibodies anti-goat (labeled with Cy3) and anti-mouse (labeled with Cy2) can be purchased from Jackson Immunolabs and can be used at a concentration of 1:200. The nuclei can be stained with Hoechst 33258 (Molecular Probes, Eugene, Oreg.). Images can be acquired by Intelligent Imaging System software from an Olympus 1X81 inverted motorized microscope equipped with Olympus DSU (spinning disk confocal) and Hamamatsu ORCA IIER monochromatic CCD camera.

Alternative means for evaluating the IDO inhibitors of the present invention are described in WO 2010/0233166 and are summarized hereafter.

Biochemical Assay. cDNA clones for both human and mouse IDO have been isolated and verified by sequencing and are commercially available. In order to prepare IDO for biochemical studies, C-terminal His-tagged IDO protein can be produced in *E. coli* using the IPTG-inducible pET5a vector system and isolated over a nickel column. The yield of the partially purified protein can be verified by gel electrophoresis and the concentration estimated by comparison to protein standards. To assay IDO enzymatic activity, a 96-well plate spectrophotometric assay for kynurenine production can be run following published procedures (see, e.g., Littlejohn, T. K., et al., *Prot. Exp. Purif.,* 19:22-29 (2000)). To screen for IDO inhibitory activity, compounds can be evaluated at a single concentration of, for example, 200 μM against 50 ng of IDO enzyme in 100 μL reaction volumes with tryptophan added at increasing concentrations at, for example, 0, 2, 20, and 200 μM. Kynurenine production can be measured at 1 hour.

Cell-based Assay. COS-1 cells can be transiently transfected with a CMV promoter-driven plasmid expressing IDO cDNA using Lipofectamine 2000 (Invitrogen) as recommended by the manufacturer. A companion set of cells can be transiently transfected with TDO-expressing plasmid. Forty-eight hours post-transfection, the cells can be apportioned into a 96-well format at 6×10$^4$ cells per well. The following day, the wells can be washed and new media (phenol red free) containing 20 μg/mL tryptophan can be added together with inhibitor. The reaction can be stopped at 5 hours and the supernatant removed and spectrophotometrically-assayed for kynurenine as previously described for the enzyme assay. To obtain initial confirmation of IDO activity, compounds can be evaluated at a single concentration of, for example, 100 μM. More extensive dose-escalation profiles can be collected for select compounds.

Pharmacodynamic and Pharmacokinetic Evaluation. A pharmacodynamic assay can be based on measuring serum levels of both kynurenine and tryptophan, and calculating the kynurenine/tryptophan ratio provides an estimate of IDO activity that is independent of baseline tryptophan levels. Serum tryptophan and kynurenine levels can be determined by HPLC analysis, and serum compound levels can optionally also be determined in the same HPLC run.

Compounds can be initially evaluated by challenging mice with LPS and then subsequently administering a bolus dose of compound at the time that the serum kynurenine level plateaus. As the kynurenine pool is rapidly turned over with a half-life in serum of less than 10 minutes, pre-existing kynurenine is not expected to unduly mask the impact that an IDO inhibitor has on kynurenine production. Each experiment can include non-LPS-exposed mice (to determine baseline kynurenine levels against which to compare the other mice) and a set of LPS-exposed mice dosed with vehicle alone (to provide a positive control for IDO activation). Each compound can initially be evaluated in mice at a single high i.p. bolus dose in the range of at least 100 mg/kg. Blood can be collected at defined time intervals (for example, 50 μL sample at 5, 15, 30 min., 1, 2, 4, 6, 8, and 24 hr. following compound administration) for HPLC analysis of kynurenine and tryptophan levels (pharmacodynamic analysis) as well as for the level of compound (pharmacokinetic analysis). From the pharmacokinetic data the peak serum concentration of compound achieved can be determined as well as the estimated rate of clearance. By comparing the level of compound in serum relative to the kynurenine/tryptophan ratio at various time points, the effective IC$_{50}$ for IDO inhibition in vivo can be roughly estimated. Compounds exhibiting efficacy can be evaluated to determine a maximum dose that achieves 100% IDO inhibition at the peak concentration.

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute, minutes or min, "h" for hour, hours or h, "rt" for room temperature, "T$_r$" for retention time, "atm" for atmosphere, "psi" for pounds per square inch, "conc." For concentrate or concentrated, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| Hex | hexanes |
| MeOH | methanol |
| EtOH | ethanol |
| i-PrOH or IPA | isopropanol |
| AcOH or HOAc | acetic acid |
| BOP | (Benzotriazol-1-yloxy)tris(dimethylamino)phosphonium hexafluorophosphate |
| CDCl$_3$ | deutero-chloroform |
| CHCl$_3$ | chloroform |
| DCM | dichloromethane |
| cDNA | complimentary DNA |
| DMF | dimethyl formamide |
| DMSO | dimethyl sulfoxide |
| DIAD | Diisopropyl azodicarboxylate |
| DIPEA | N,N-diisopropylethylamine |
| EDC or EDCI | 1-Ethyl-3-(3-dimethylaminopropyl) carbodiimide |
| EDTA | ethylenediaminetetraacetic acid |
| EtOAc | ethyl acetate |
| Et$_2$O | diethyl ether |
| AlCl$_3$ | aluminum chloride |
| Boc | tert-butyloxycarbonyl |
| CH$_2$Cl$_2$ | dichloromethane |
| CH$_3$CN or ACN | acetonitrile |
| Cs$_2$CO$_3$ | cesium carbonate |
| HCl | hydrochloric acid |
| H$_2$SO$_4$ | sulfuric acid |
| HOBt | Hydroxybenzotriazole (and hydrate) |
| HATU | 1-[Bis(dimethylamino)methylene]-1H-1,2,3-triazolo[4,5-b]pyridinium 3-oxid hexafluorophosphate |
| Hunig's base, DIPEA | diisopropylethylamine |
| K$_2$CO$_3$ | potassium carbonate |
| mCPBA or m-CPBA | meta-chloroperbenzoic acid |
| Pd/C | palladium on carbon |
| PS | polystyrene |

| | |
|---|---|
| PyBOP | (Benzotriazol-1-yloxy)tripyrrolidinophosphonium hexafluorophosphate |
| SiO$_2$ | silica oxide |
| SnCl$_2$ | tin(II) chloride |
| TEA | triethylamine |
| TFA | trifluoroacetic acid |
| TFAA | trifluoroacetic anhydride |
| THF | tetrahydrofuran |
| TMSCHN$_2$ | trimethylsilyldiazomethane |
| KOAc | potassium acetate |
| LHMDS | Lithium hexamethyldisilazide |
| MgSO$_4$ | magnesium sulfate |
| NMP | N-Methylpyrrolidone |
| MsOH or MSA | methylsulfonic acid |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| LG | leaving group |
| RT, rt | Room temperature |
| RP | Reverse phase |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

METHODS OF PREPARATION

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Referring to Scheme I, treatment of the cyclohexanone II under standard Horner-Wadsworth Emmons conditions with the phosphonate III will afford the corresponding unsaturated ester. Catalytic hydrogenation with, for instance, Pd/C and hydrogen gas and subsequent ketal hydrolysis under acidic conditions gives the appended cycloalkanone of general structure IV. Treatment of compound IV with triflic anhydride and an organic base such as 2,6-lutidine will afford a vinyl triflate of general structure V. Coupling of V with arylboronic acids or esters E-B(OR)$_2$, preferably under the conditions of Suzuki (see Kotha, S. et al., *Tetrahedron*, 58:9633-9695 (2002)) affords cycloalkenes of general structure VI. Typically, this reaction is performed by heating the halide and the boronic acid or ester to from about 90 to about 98° C. with a base such as aqueous tribasic sodium or potassium phosphate or sodium or potassium carbonate in a solvent such as dioxane, DMF, THF, or NMP using a catalyst such as tetrakis(triphenylphosphine)palladium or Cl$_2$Pd (dppf). Many variations on this reaction involving the use of different temperatures, solvents, bases, anhydrous conditions, catalysts, boronate derivatives, and halide surrogates such as triflates are known to those skilled in the art of organic/medicinal chemistry. Mild conditions have been reported for the coupling of sensitive boronic acid derivatives. See Kinzel, T. et al., *J. Am. Chem. Soc.*, 132(40):14073-14075 (2010). Saturation of the olefin in VII can be accomplished by treatment with Pd/C in an atmosphere of hydrogen to give a compound of general structure VII as a mixture of cis and trans isomers about the carbocycle. Further substitution of the ester can be accomplished by treatment with a strong base, such as LDA or LiHMDS, followed by addition of an electrophile R$^4$—X where X is Br or I, to afford compounds of general structure VIII after basic hydrolysis with a base such as LiOH. Coupling of the acid VIII with amines of general structure IX under standard conditions, well-known to one skilled in the art, will afford compounds of general structure I.

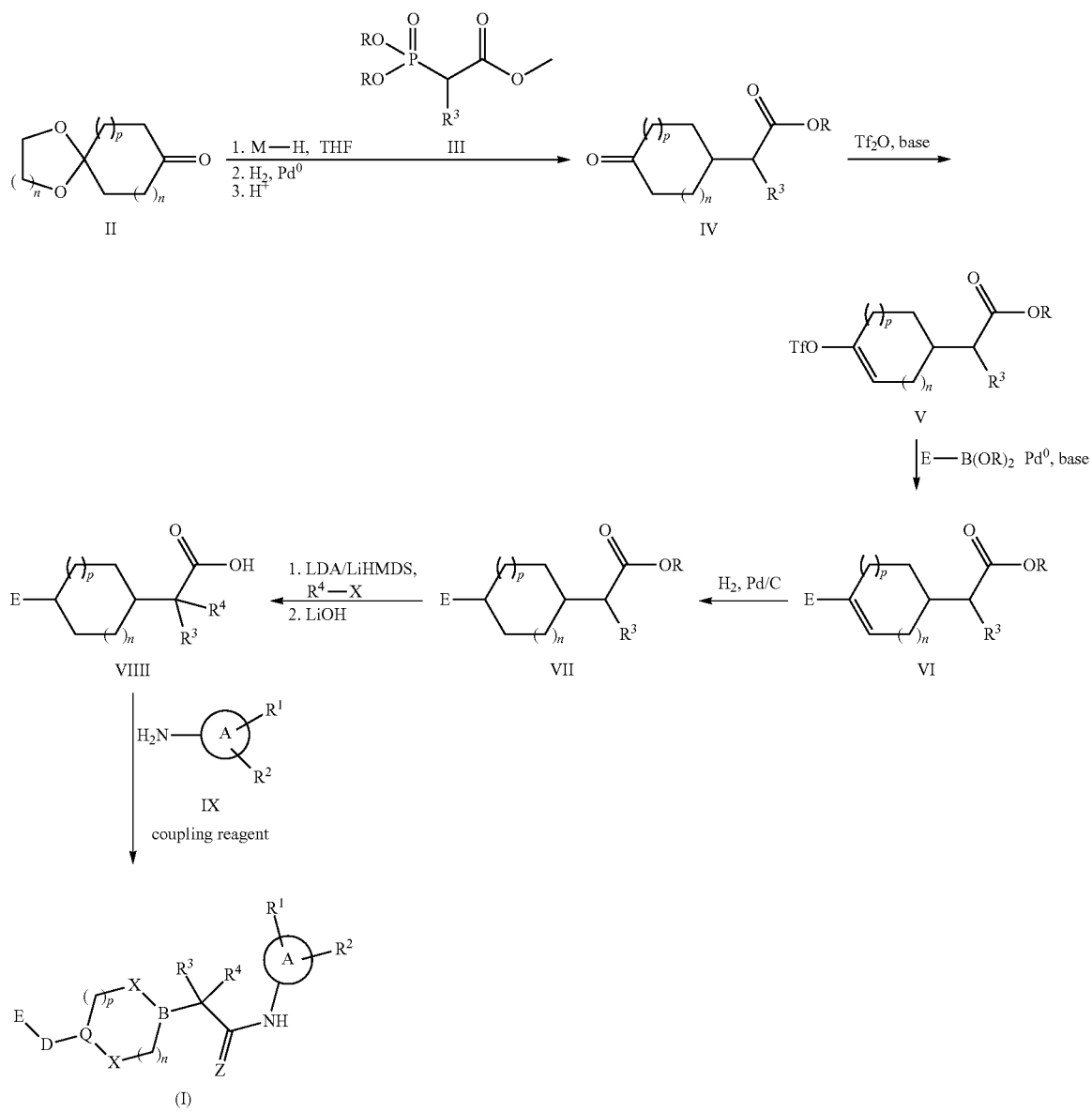

As represented in Scheme 2, the olefin VI can be hydroborated by treatment with a borane, such as catechol borane, followed by standard oxidative workup with hydrogen peroxide to afford a hydroxylated compound of general structure X, most likely as a mixture of isomers. Compound X can then be converted to a compound of general structure 1 by methods depicted in Scheme 1.

In Scheme 3 N-alkylation of a protected piperidinone of general structure XI can be accomplished by treatment with a haloacetate of general structure III (X=Br, Cl), subsequent acidic hydrolysis of the ketal will give a keto ester of general structure XII. Vinyl triflate formation, as previously described, will give a compound of general structure XIII. Treatment of the vinyl triflate with a diborane, such as bis-pinnacolatoborane, in the presence of a source of Pd(0), such as (PPh$_3$)$_4$Pd, will give a vinyl bornic ester of general structure XIV. Suzuki coupling of aryl halides, E-X, where X=Br, I, Cl, OTf, under standard conditions described previously, will afford an unsaturated compound of general structure XV. Compounds of general structure XV can be converted to compounds of general structure I by methods previously described herein. In another embodiment, compounds of general structure XV can first be treated with a borane, such as catechol borane, followed by oxidative workup with hydrogen peroxide, to afford compounds of general structure XVI, which can be converted to compounds of general structure I by methods already described.

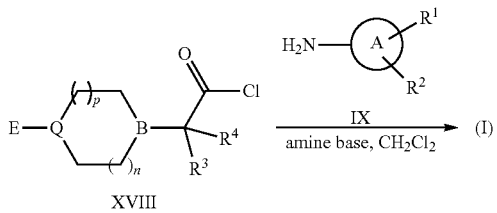

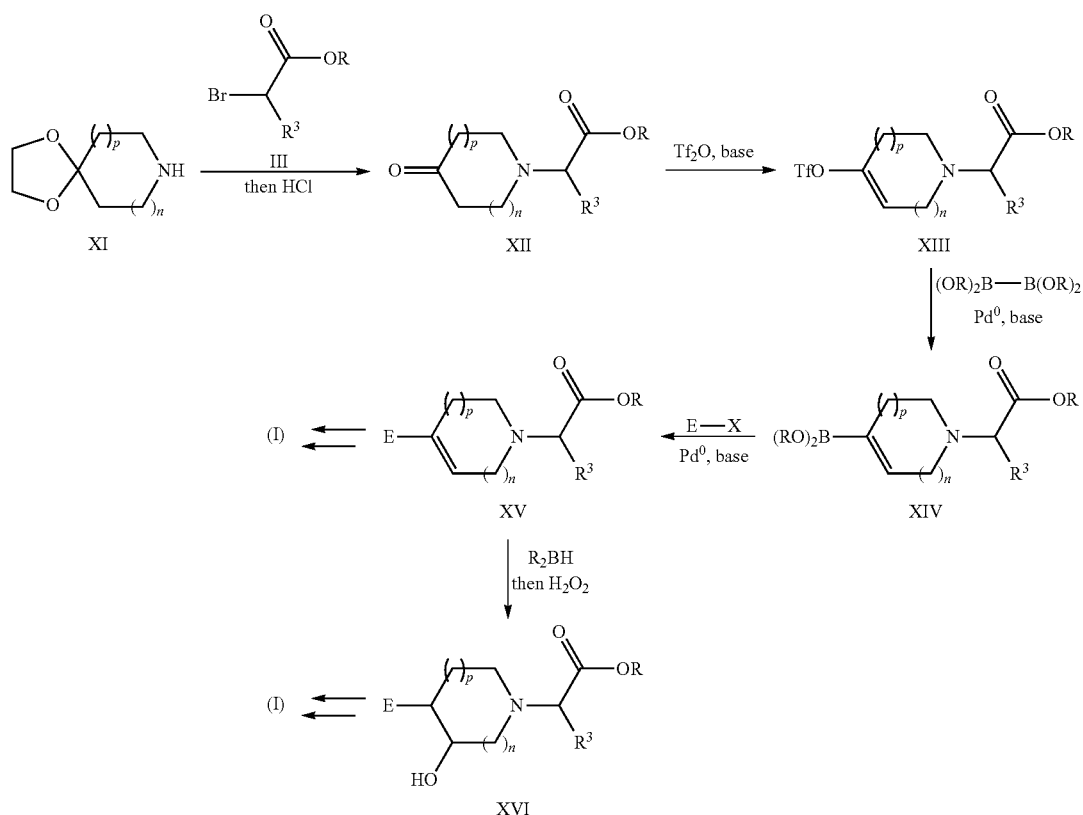

Scheme 4 depicts amide formation via an anhydride of general structure XVIII. Treatment of an acid of general structure XVII with chlorinating reagent, such as oxalyl chloride or thionyl chloride, will afford the desired acyl chloride of general structure XVIII. Compounds of general structure XVIII can be converted to amides of general structure I by treatment with an amine of general structure IX and an organic base, such as diisopropylethylamine.

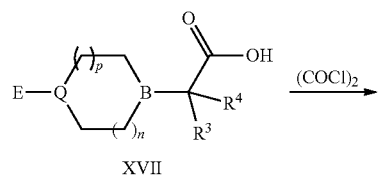

Scheme 5 depicts how a selective alkylation can be accomplished to install $R^3$ in the alpha position of amides that are of general structure I. Under standard conditions, mixed anhydrides of general structure XIX can be treated with a metalated oxazolidinone-derived chiral auxiliaries of general structure XX to afford an imide of general structure XXI. Evan's chiral auxiliaries are well-known to one skilled in the art. Selective alkylation of XXI is afforded by treatment with a strong base, such as NaHMDS, and an electrophile $R^3$—X to give a compound of general structure XXII with high diastereoselectivity for the incorporation of $R^3$. Hydrolysis of the imide XXII can be accomplished by standard methods such as a strong base and hydrogen peroxide (See Evans et al., *Tetrahedron Lett.*, 28:6141-6144 (1987)) to give a compound of general structure XXIII. The acid XXIII can converted to a compound of general structure I by methods already described herein.

Scheme 5

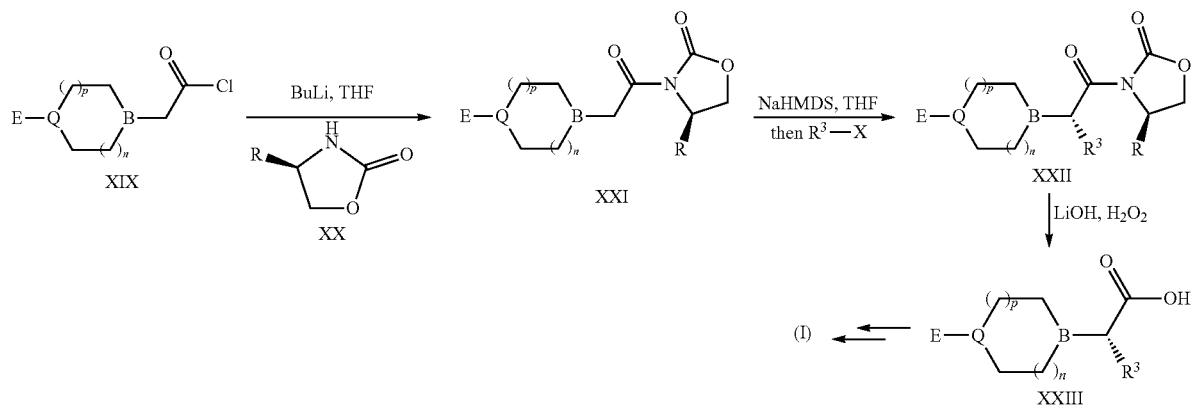

In Scheme 6, a ketone of general structure XXIV, which can be prepared by the methods described in Schemes 1 and 3, can be treated under strongly reducing conditions with a borohydride such as sodium borohydride, to give an alcohol of general structure XXV. The alcohol can be treated with a strong base in the presence of activated halo-substituted heteroaromatics to afford an ether of general structure XXVI. Alternatively, the alcohol XXV can be treated under standard Mitsunobu conditions of DIAD and triphenylphosphine to afford ethers of general structure XXVI, which can be converted to compounds of general structure I by methods already described herein.

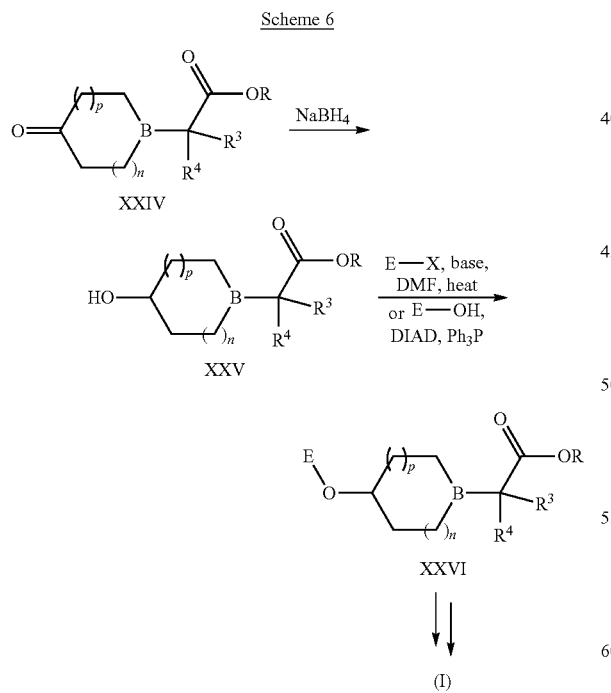

Scheme 7 demonstrates how a ketone of general structure XXIV can be converted to an amine of general structure XXVII via reductive amination. This can be accomplished first by sequential treatment with an amine followed by a reducing agent, such as sodium borohydride. The amine in XXVII can be appended by E-X where X=Cl, Br or I via thermal conditions, such as heat in a solvent such as DMF, or via palladium catalyzed coupling, such as a Buchwald coupling, to afford an amine of general structure XXVIII. The ester of general structure XXVIII can then be converted to a compound of general structure I via methods described herein.

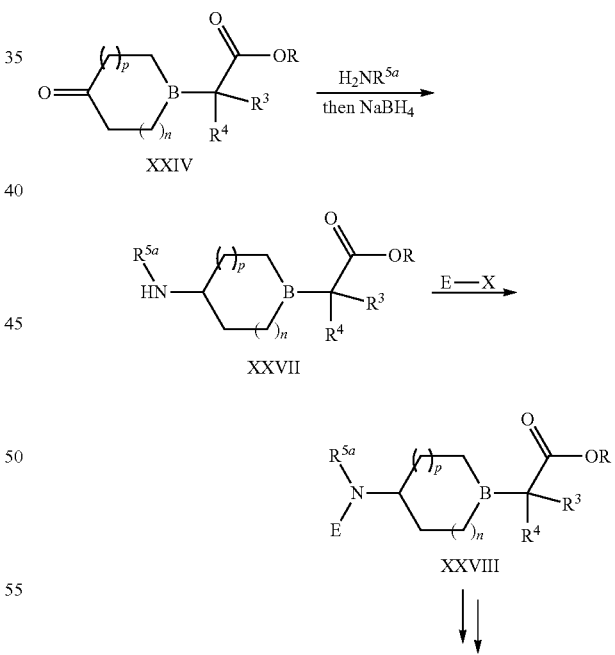

As shown in Scheme 8, a ketone of general structure XXIX can be treated with a haloacetate of general structure III in the presence of activated zinc metal to afford a tertiary alcohol of general structure XXX. The ester of general structure XXX can then be converted to a compound of general structure I via methods already described herein.

Scheme 8

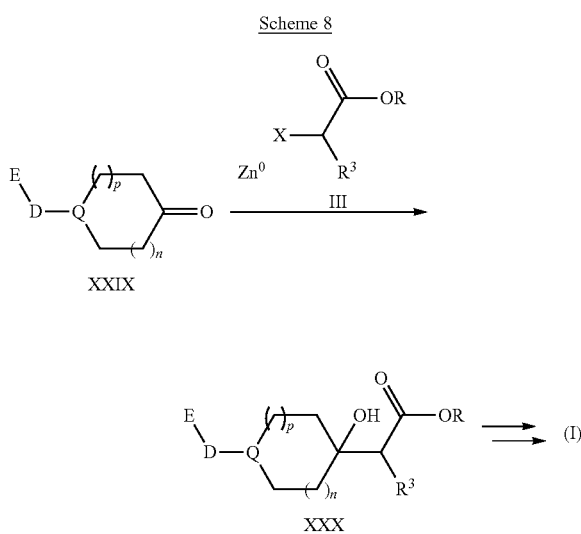

As shown in Scheme 9, a ketone of general structure XXIV can be treated with a metalated species E-M, where M=Li, Na or K, produced by treatment of an aryl halide with, for example an alkyl lithium, such as tert-butyllithium, to produce a tertiary alcohol of general structure XXXI. The ester of general structure XXXI can be converted to a compound of general structure I via methods already described herein.

Scheme 9

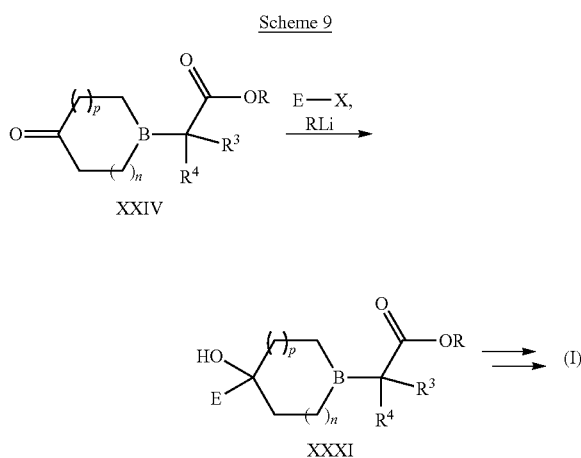

As shown in Scheme 10, a monoprotected diamine of general structure XXXII can be converted to a compound of general structure XXXIII by methods described in Scheme 3. Treatment of an amine of general structure XXXIII with E-X, where X=Cl, Br, I, and a palladium catalyst, such as Pd(Ph$_3$P)$_4$, will afford a compound of general structure XXXIV. Alternatively, an amine of general structure XXXIII can be treated with a compound ECH$_2$X under basic conditions sufficient for N-alkylation to afford a compound of general structure XXXIV. An ester of general structure XXXIV can then be converted to a compound of general structure I by methods already described herein.

Scheme 10

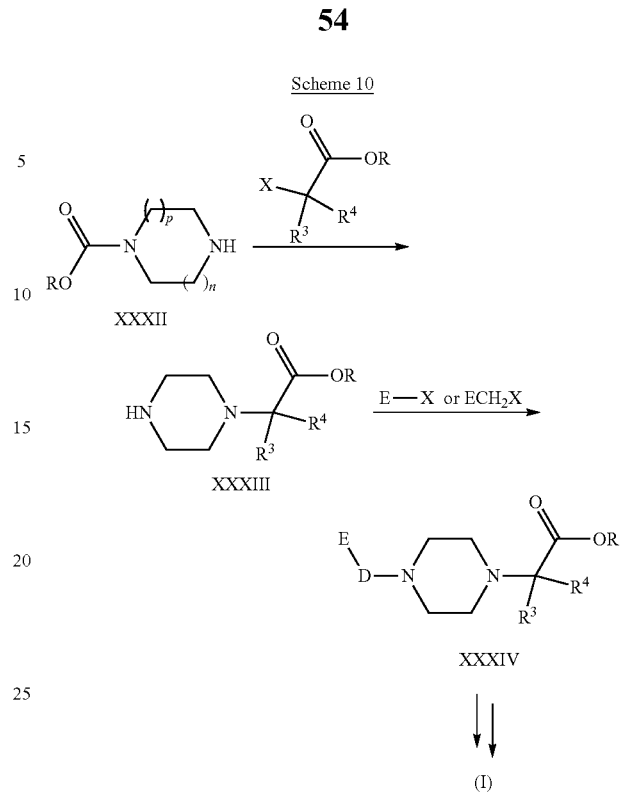

HPLC/Ms and Preparatory/Analytical HPLC Methods Employed in Characterization or Purification of Examples Analytical and Preparatory HPLC/MS was performed using the following methods:

Method A: Waters Acquity SDS using the following method: Linear Gradient of 2% to 98% Solvent B over 1.7 min; UV visualization at 220 nm; Column: BEH C18 2.1 mm×50 mm; 1.7 µm particle (Heated to Temp. 50° C.); Flow rate: 0.8 ml/min; Mobile Phase A: 100% water, 0.05% TFA; Mobile Phase B: 100% acetonitrile, 0.05% TFA.

Method B: Column: Waters Acquity UPLC BEH C18, 2.1×50 mm, particles; Mobile Phase A: 5:95 acetonitrile: water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.00 mL/min; Detection: UV at 220 nm.

Method C: Berger SFC MGII, Column: IC 25×3 cm ID, 5 µm Flow rate: 85.0 mL/min, Mobile Phase: 70/30 CO$_2$/MeOH, Detector Wavelength: 220 nm Method D: Berger analytical SFC, Column: Chiral IC 250×4.6 mm ID, 5 µm, Flow rate: 2.0 mL/min, Mobile Phase: 70/30 CO$_2$/MeOH Method E: Berger SFC MGM Column: Chiral OJ-H 25×3 cm ID, 5 µm Flow rate: 85.0 mL/min, Mobile Phase: 75/25 CO$_2$/MeOH, Detector Wavelength: 220 nm Method F: Aurora analytical SFC, Column: Chiral IC 250×4.6 mm ID, 5 µm, Flow rate: 2.0 mL/min, Mobile Phase: 70/30 CO$_2$/MeOH Method G: Berger SFC MGII, Column: Chiral AS 25×3 cm ID, 5 µm Flow rate: 85.0 mL/min, Mobile Phase: 87/13 CO$_2$/MeOH, Detector Wavelength: 220 nm Method H: Aurora analytical SFC, Column: Chiral AS 250×4.6 mm ID, 5 µm, Flow rate: 2.0 mL/min, Mobile Phase: 85/15 CO$_2$/MeOH Method I: Berger SFC MGII, Column: Chiral AS 25×3 cm ID, 5 μm Flow rate: 85.0 mL/min, Mobile Phase: 90/10 $CO_2$/MeOH w/0.1% DEA, Detector Wavelength: 220 nm Method J: Aurora analytical SFC, Column: Chiral AS 250×4.6 mm ID, 5 μm, Flow rate: 2.0 mL/min, Mobile Phase: 90/10 $CO_2$/MeOH w/0.1% DEA Method K: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method L: Chiral HPLC: IF-3 column, ID 4.6 mm×150 mm, Flow rate: 1 mL/min, Mobile Phase: 85% Heptanes/15% isopropanol.

Method M: Chiral HPLC: ID column CHIRALPAK®, Chiral Technologies, West Chester, Pa., 5 μm, ID 4.6 mm×250 mm, Flow rate: 20 mL/min Mobile Phase: 0.4% $Et_2NH$ in acetonitrile.

NMR Employed in Characterization of Examples $^1$H NMR spectra (unless otherwise noted) were obtained with JEOL® or Bruker FOURIER® transform spectrometers operating at 400 MHz or 500 MHz.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$). Abbreviations used in the description of NMR peaks: "a"=apparent, "br. s."=broad singlet General Procedures General Procedure A: Preparation of Aryl Cyclohexenes Via Suzuki Cross-Coupling Reaction

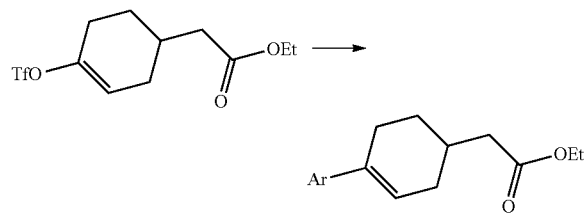

To ethyl 2-(4-(((trifluoromethyl)sulfonyl)oxy)cyclohex-3-en-1-yl)acetate* (1.0 eq.), boronic acid (1.2 equiv), $Na_2CO_3$ (2.5 eq.), KBr (1.1 eq.) in 1,4-dioxane/water (10:1 by volume, 0.25M) was added $Pd(PPh_3)_4$ (5 mol. %). The resulting reaction mixture was heated to 80-90° C. for 16 h, upon which the crude reaction mixture was concentrated. The resulting solids were diluted with EtOAc and water and the layers were separated. The aqueous layer was extracted with EtOAc thrice. The combined organic extracts were dried over anhydrous $MgSO_4$, filtered, and concentrated under reduced pressure. The crude reaction mixture was purified employing silica gel chromatography to afford the desired product.

*Ethyl 2-(4-(((trifluoromethyl)sulfonyl)oxy)cyclohex-3-en-1-yl)acetate is a known compound that can be prepared from commercially available 1,4-dioxaspiro[4.5]decan-8-one using the procedures outlined in 1) Stocks, P. A. et al., Angew. Chem. Int. Ed., 46:6278-6283 (2007); 2) Barlind, J. G. et al., J. Med. Chem., 55:10610-10629 (2012).

General Procedure B: Hydrogenation

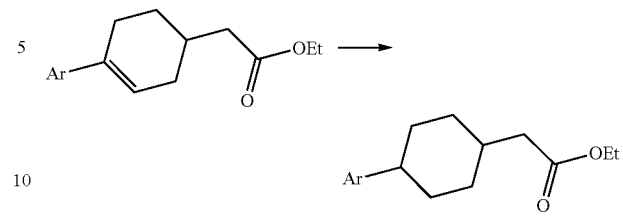

Unsaturated starting material was dissolved in a solvent of choice (e.g., methanol, ethyl acetate, or acetic acid) to form a 0.1-0.3 M solution. The resulting solution was purged with nitrogen and 20 wt. % of a catalyst (dry activated Pd/C 10 wt. %, or Degussa Pd/C 10 wt. %, or $Pd(OH)_2$/C 10 wt. %) was added to the solution to form a heterogeneous mixture. Hydrogen gas was bubbled through the solution until complete disappearance of the starting material determined by TLC, and/or LC-MS, and/or NMR. Upon completion, reaction mixture was purged with nitrogen, filtered through CELITE®, and concentrated under reduced pressure. Final product was purified by flash chromatography.

General Procedure E: Ester Hydrolysis

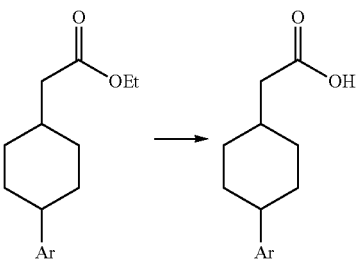

To a solution of ester (1.0 eq) in EtOH (1.0 M) was added an equal volume of aqueous LiOH solution (7.25 M). The reaction mixture was stirred vigorously, heated to 50° C. for 1 h and then diluted with 50 mL of water and further heated to 50° C. for 5 h. The reaction mixture was cooled with an ice bath and acidified (pH~1) by slow addition of 3 M HCl solution. EtOAc was added, the layers were separated, and the aqueous phase was extracted with EtOAc (3×). The combined organic extracts were dried over anhydrous $Na_2SO_4$, filtered and concentrated under reduced pressure to afford desired carboxylic acid which was used without further purification.

General Procedure G: Reaction Between Esters and Anilines

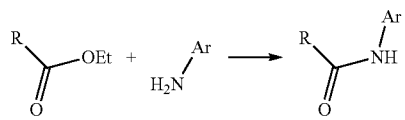

To a solution of the aniline (2.0 eq.) in THF (0.25 M) at 0° C. was added a solution of $^i$PrMgCl (2.0 eq., 2 M in THF). The resulting solution was warmed to room temperature and stirred for 5 minutes at which point the ester (1.0 eq.) was added. The resulting reaction mixture was stirred at room temperature for 8 hours and was poured into water. Ethyl acetate was added and the layers were separated. The aqueous layer was extracted three times with ethyl acetate.

The combined organic extracts were dried over anhydrous MgSO$_4$, filtered, and concentrated under reduced pressure. The crude reaction mixture was purified employing silica gel chromatography to afford the desired product.

General Procedure K: Preparation of Aryl Cyclohexenes Via Suzuki Cross-Coupling Reaction

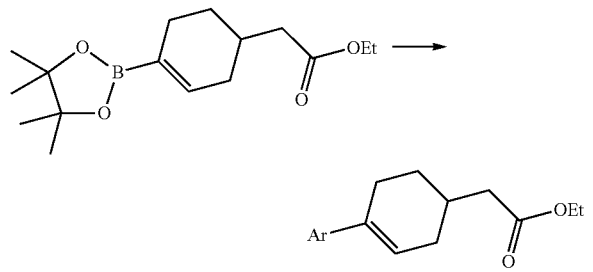

To ethyl 2-(4-(4,4,5,5-tetramethyl-1,3,2-dioxaborolan-2-yl)cyclohex-3-en-1-yl)acetate* (1.1 eq), aryl halide (1.0 eq), and Cs$_2$CO$_3$ (2.2 eq), in 1,4-dioxane/water (10:1 by volume, 0.25 M) was added catalytic amount of PEPPSI-IPr (2 mol. %). The resulting reaction mixture was heated to 100° C. for 2-12 hours, upon which the crude reaction mixture was concentrated and loaded on silica gel. The crude reaction mixture was purified employing silica gel chromatography.

*Ethyl 2-(4-(4,4,5,5-tetramethyl-1,3,2-dioxaborolan-2-yl)cyclohex-3-en-1-yl)acetate is a known compound that can be prepared from commercially available 1,4-dioxaspiro[4.5]decan-8-one using the procedures outlined in Barlind, J. G. et al., *J. Med. Chem.*, 55:10610-10629 (2012).

General Procedure L: Coupling of Carboxylic Acid with Chiral Auxiliary

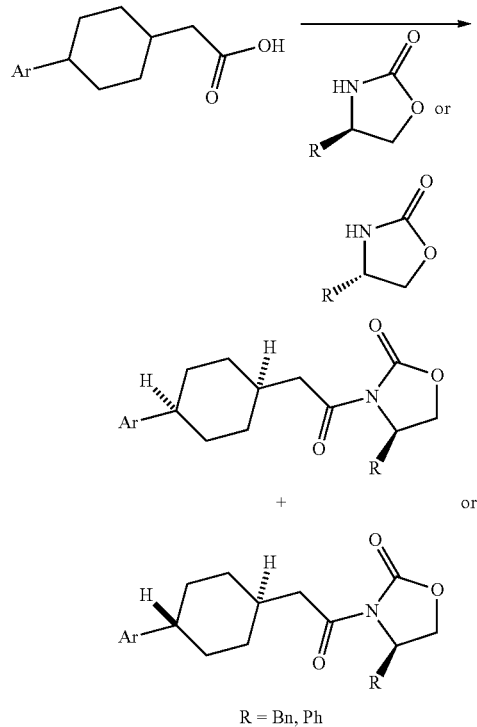

R = Bn, Ph

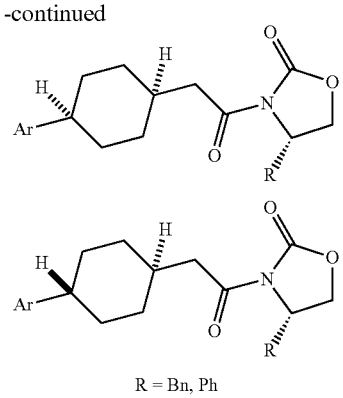

R = Bn, Ph

To an oven-dried round bottom flask (Flask #1) was added carboxylic acid (1.0 eq) as a mixture of diastereomers. The flask was evacuated and backfilled with nitrogen and subsequently charged with THF (0.25 M) and triethylamine (2.0 eq). The resulting solution was cooled to −78° C. before the slow addition of pivaloyl chloride (1.25 eq) over 15 min. The reaction mixture was then stirred at 0° C. for one hour.

To a separate oven-dried round bottomed flask (Flask #2) was added chiral (R)- or (S)-4-Benzyl- or 4-Phenyl-2-oxazolidinone (1.3 eq) and THF (0.25 M). This solution was cooled to −78° C. before the careful addition of n-BuLi (2.5M in hexanes, 1.3 eq). This reaction mixture was stirred at −78° C. for 15 minutes before being removed from the cold bath.

Flask #1 was then cooled back to −78° C. and the contents of Flask #2 were added to Flask #1 via cannula over the course of 15 minutes. After complete addition, the cold bath was removed and the reaction was stirred for 3 hours at room temperature. The reaction was quenched by addition of saturated ammonium chloride solution (100 mL) and subsequent extraction with ethyl acetate (100 mL×3). The combined organics were washed with brine, dried over sodium sulfate, filtered and concentrated. The crude residue was purified using silica gel chromatography.

General Procedure M: Alkylation of Oxazalidinone-Derived Imides

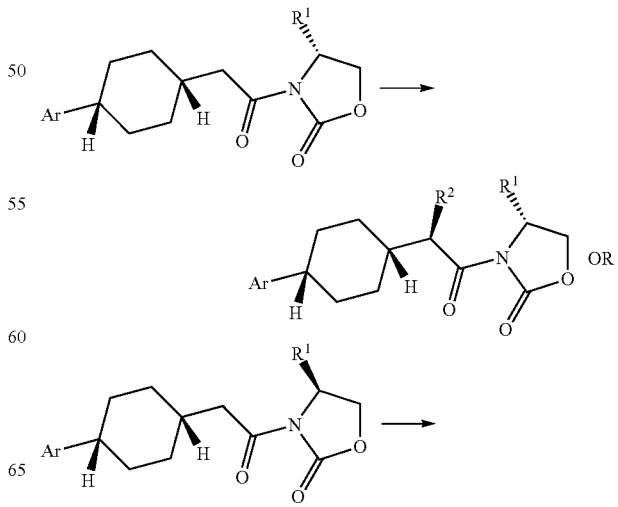

59

-continued

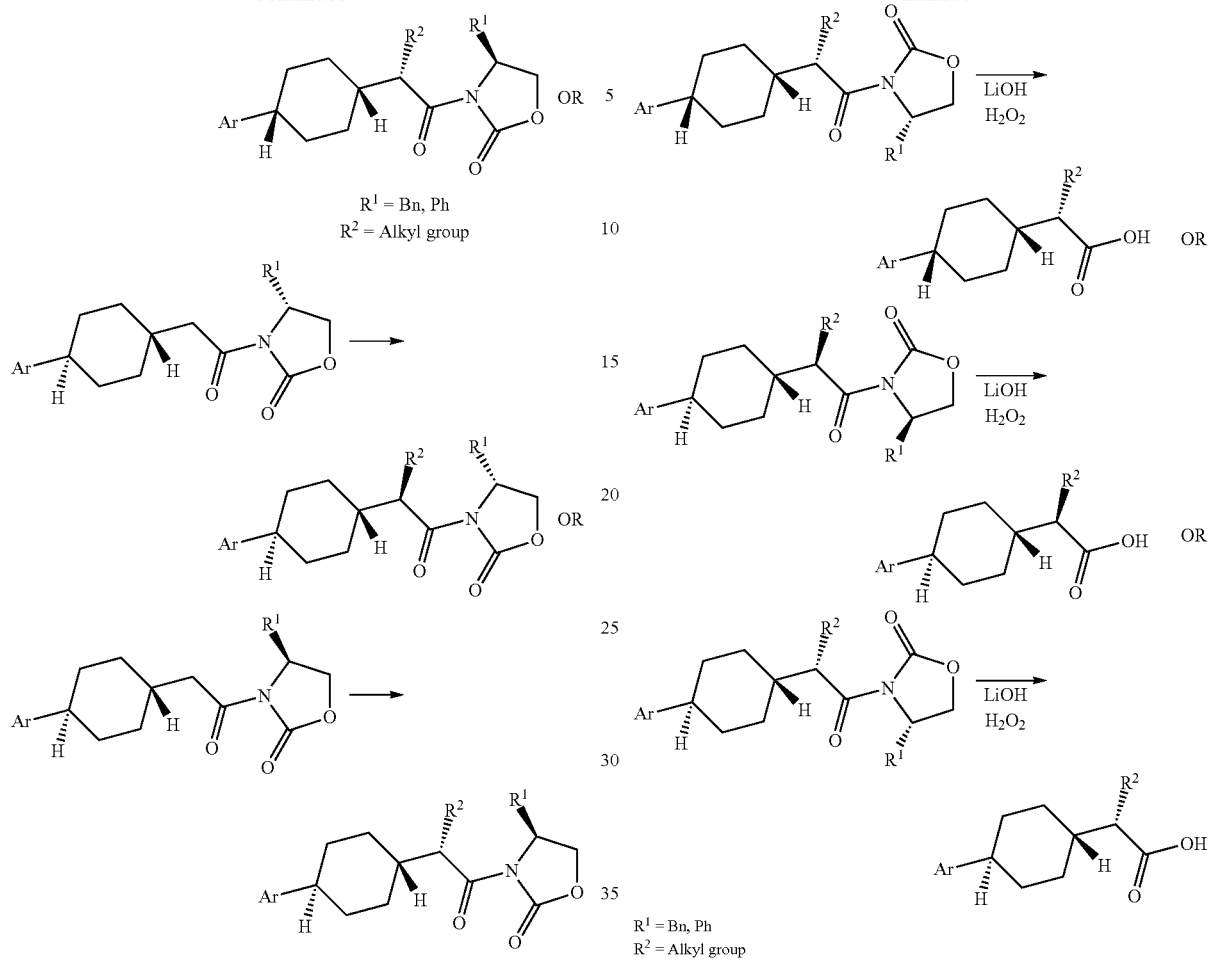

R¹ = Bn, Ph
R² = Alkyl group

60

-continued

R¹ = Bn, Ph
R² = Alkyl group

NaHMDS (2 M in THF, 1.2 eq) was added dropwise to 0.2 M solution of the imide (1.0 eq) in anhydrous tetrahydrofuran at −50° C. The solution was stirred for 10 min at −50° C. and then neat alkylhalide was added dropwise. Reaction mixture was stirred for additional 2 to 48 hours at −50 to −20° C. and then quenched by adding saturated solution of ammonium chloride while still cold. The reaction mixture was allowed to warm to ambient temperature and was extracted 3 times with ethyl acetate. The combined organic extracts were dried with MgSO₄, filtered, concentrated under reduced pressure, and subjected to flash chromatography on silica gel.

General Procedure N: Cleavage of Chiral Auxiliary

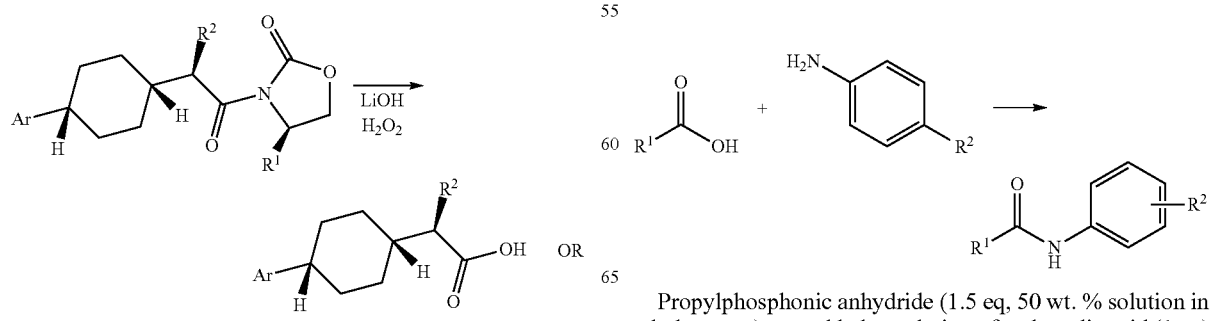

To a round bottom flask was added an oxazalidinone-derived imide (0.418 mmol, 1.0 eq), THF (0.25 M) and distilled water (1M). This solution was cooled to 0° C. before the slow addition of H₂O₂ (35 wt. % in water, 4 eq) followed by the addition of LiOH (2.7 M in water, 1.6 eq). The reaction solution was allowed to warm to rt. Progress was followed by LC/MS and the reaction solution was carefully quenched at 0° C. by the addition of saturated Na₂SO₃ once starting material had been consumed. The pH was adjusted to ~5-6 with 1N HCl and then the mixture was extracted with EtOAc and methylene chloride. The combined organics were dried over sodium sulfate, filtered, and concentrated. The crude product was purified using silica gel chromatography.

General Procedure O: Coupling of Carboxylic Acids and Anilines

Propylphosphonic anhydride (1.5 eq, 50 wt. % solution in ethyl acetate) was added to solution of carboxylic acid (1 eq)

and pyridine (3 eq) in ethyl acetate (0.1 M) at ambient temperature. Reaction mixture was stirred for 5 min and then aniline (1.5 eq) was added. The reaction was stirred at ambient temperature until complete consumption of the acid, which was determined by TLC and/or LC-MS. Reaction mixture was poured in water, 1M NaOH (10 eq) was added, and aqueous layer was extracted with ethyl acetate three times. The combined organic extracts were dried with MgSO$_4$ and concentrated in vacuo. The crude residue was purified via silica gel column chromatography.

Examples 1 and 2

N-(4-chlorophenyl)-2-(trans-4-(quinolin-4-yl)cyclohexyl)acetamide

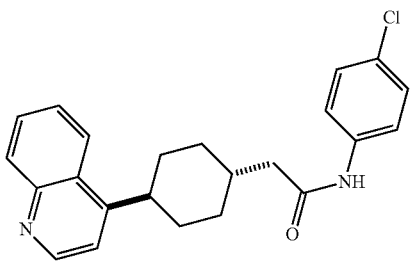

N-(4-chlorophenyl)-2-(4-(cis-quinolin-4-yl)cyclohexyl)acetamide

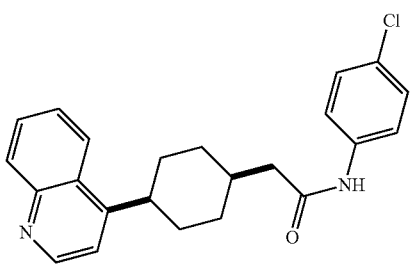

Examples 1 and 2

N-(4-chlorophenyl)-2-(trans-4-(quinolin-4-yl)cyclohexyl)acetamide and N-(4-chlorophenyl)-2-(cis-4-(quinolin-4-yl)cyclohexyl)acetamide Examples 1 and 2 were prepared using General Procedures A, B, and G. General Procedure A employed 7.91 g (25 mmol) of ethyl 2-(4-(((trifluoromethyl)sulfonyl)oxy)cyclohex-3-en-1-yl)acetate and 4.56 g (26 mmol) of quinoline-4-boronic acid. General Procedure B employed 20 wt. % of dry Pd/C (10 wt. %) and methanol as a solvent. General Procedure G employed 100 mg of ethyl 2-(4-(quinolin-4-yl)cyclohexyl)acetate (mixture of diastereomers) and 87 mg of 4-chloroaniline. Purified using silica gel chromatography (0% to 60% ethyl acetate in toluene) to afford Example 1 (trans-diastereomer) as the first eluting isomer. $^1$H NMR of trans-isomer (400 MHz; CDCl$_3$): δ 8.85 (d, J=4.6 Hz, 1H), 8.04-8.14 (m, 2H), 7.67-7.72 (m, 1H), 7.53-7.59 (m, 1H), 7.47-7.53 (m, 2H), 7.27-7.31 (m, 3H), 3.27-3.37 (m, 1H), 2.34 (d, J=6.6 Hz, 2H), 2.03-2.11 (m, 5H), 1.61-1.73 (m, 2H), 1.31-1.44 (m, 2H) ppm. m/z 379.2 (M+H$^+$).

Further elution from the column afforded Example 2 (cis-diastereomer) as the second eluting isomer. $^1$H NMR of cis-isomer (400 MHz; CDCl$_3$): δ 8.84 (d, J=4.6 Hz, 1H), 8.04-8.14 (m, 2H), 7.67-7.73 (m, 1H), 7.48-7.60 (m, 3H), 7.25-7.31 (m, 3H), 3.36-3.46 (m, 1H), 2.51-2.60 (m, 3H), 1.68-1.96 (m, 8H) ppm. m/z 379.2 (M+H$^+$).

Examples 3 and 4

N-(4-cyanophenyl)-2-(trans-4-(quinolin-4-yl)cyclohexyl)acetamide hydrochloride

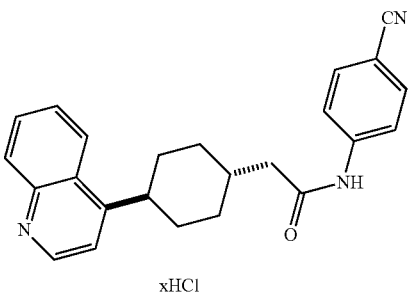

N-(4-cyanophenyl)-2-(cis-4-(quinolin-4-yl)cyclohexyl)acetamide hydrochloride

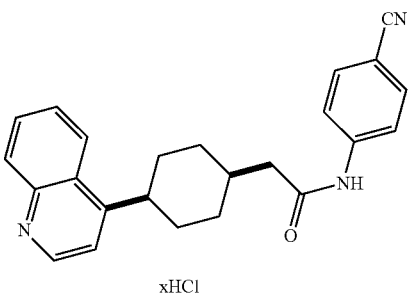

Examples 3 and 4

N-(4-cyanophenyl)-2-(trans-4-(quinolin-4-yl)cyclohexyl)acetamide hydrochloride and N-(4-cyanophenyl)-2-(cis-4-(quinolin-4-yl)cyclohexyl)acetamide hydrochloride Examples 3 and 4 were prepared using General Procedures A, B, and G. General Procedure A employed 7.91 g (25 mmol) of ethyl 2-(4-(((trifluoromethyl)sulfonyl)oxy)cyclohex-3-en-1-yl)acetate and 4.56 g (26 mmol) of quinoline-4-boronic acid. General Procedure B employed 20 wt. % of dry Pd/C (10 wt. %) and methanol as a solvent. General Procedure G employed 100 mg of ethyl 2-(4-(quinolin-4-yl)cyclohexyl)acetate (mixture of diastereomers) and 80 mg of 4-cyanoaniline. Purified using silica gel chromatography (0% to 60% ethyl acetate in toluene) to afford Example 3 (trans-diastereomer) as the first eluting isomer. Free base was converted to hydrochloride by mixing with excess of 2M HCl in diethyl ether, removing volatiles, and drying on high vacuum. ¹H NMR of trans-isomer (400 MHz; CDCl₃): δ 10.53 (s, 1H), 9.2 (d, J=5.7 Hz, 1H), 8.60 (d, J=8.4 Hz, 1H), 8.33 (d, J=8.6 Hz, 1H), 8.09-8.15 (m, 1H), 7.91-8.00 (m, 2H), 7.79-7.84 (m, 2H), 7.72-7.77 (m, 2H), 3.60-3.70 (m, 1H), 2.37 (d, J=6.7 Hz, 2H), 1.87-1.99 (m, 5H), 1.65-1.77 (m, 2H), 1.34-1.47 (m, 2H) ppm. m/z 370.2 (M+H⁺).

Further elution from the column afforded Example 4 (cis-diastereomer) as the second eluting isomer. Free base was converted to hydrochloride by mixing with excess of 2M HCl in diethyl ether, removing volatiles, and drying in high vacuum. ¹H NMR of cis-isomer (400 MHz; DMSO-d₆): δ 10.79 (s, 1H), 9.26 (d, J=5.7 Hz, 1H), 8.59 (d, J=8.4 Hz, 1H), 8.36 (d, J=8.2 Hz, 1H), 8.09-8.17 (m, 2H), 7.91-7.97 (m, 1H), 7.83-7.87 (m, 2H), 7.72-7.77 (m, 2H), 3.65-3.75 (m, 1H), 2.66 (d, J=7.8 Hz, 2H), 2.37-2.46 (m, 1H), 1.81-1.99 (m, 4H), 1.65-1.77 (m, 4H) ppm. m/z 370.2 (M+H⁺).

Examples 5 and 6

N-(4-fluorophenyl)-2-(trans-4-(quinolin-4-yl)cyclohexyl)acetamide

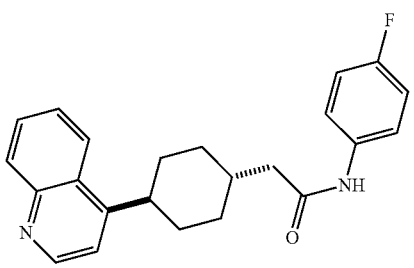

N-(4-fluorophenyl)-2-(cis-4-(quinolin-4-yl)cyclohexyl)acetamide

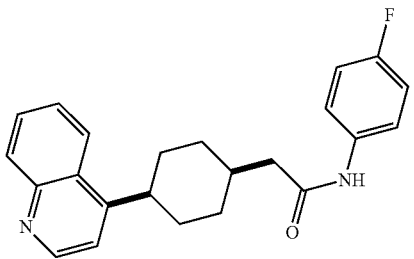

Examples 5 and 6

N-(4-fluorophenyl)-2-(trans-4-(quinolin-4-yl)cyclohexyl)acetamide and N-(4-fluorophenyl)-2-(cis-4-(quinolin-4-yl)cyclohexyl)acetamide Prepared using General Procedures A, B, and G. General Procedure A employed 7.91 g (25 mmol) of ethyl 2-(4-(((trifluoromethyl)sulfonyl)oxy)cyclohex-3-en-1-yl)acetate and 4.56 g (26 mmol) of quinoline-4-boronic acid. General Procedure B employed 20 wt. % of dry Pd/C (10 wt. %) and methanol as a solvent. General Procedure G employed 100 mg of ethyl 2-(4-(quinolin-4-yl)cyclohexyl)acetate (mixture of diastereomers) and 76 mg of 4-fluoroaniline. Purified using silica gel chromatography (0% to 60% ethyl acetate in toluene) to afford Example 5 (trans-diastereomer) as the first eluting isomer. ¹H NMR of trans-isomer (400 MHz; CDCl₃): δ 8.85 (d, J=4.5 Hz, 1H), 8.05-8.15 (m, 2H), 7.67-7.73 (m, 1H), 7.48-7.58 (m, 4H), 7.27 (d, J=4.7 Hz, 1H), 6.98-7.05 (m, 2H), 3.25-3.36 (m, 1H), 2.34 (d, J=6.6 Hz, 2H), 2.01-2.10 (m, 5H), 1.58-1.72 (m, 2H), 1.29-1.42 (m, 2H) ppm. m/z 363.2 (M+H⁺).

Further elution from the column afforded Example 6 (cis-diastereomer) as the second eluting isomer. ¹H NMR of cis-isomer (400 MHz; CDCl₃): δ 8.84 (d, J=4.6 Hz, 1H), 8.05-8.15 (m, 2H), 7.67-7.73 (m, 1H), 7.54-7.62 (m, 2H), 7.48-7.54 (m, 2H), 7.27 (d, J=4.6 Hz, 1H), 6.97-7.05 (m, 2H), 3.36-3.46 (m, 1H), 2.51-2.60 (m, 3H), 1.68-1.98 (m, 8H) ppm. m/z 379.2 (M+H⁺).

Examples 7 and 8

N-(4-fluorophenyl)-2-(cis-4-(quinolin-3-yl)cyclohexyl)acetamide

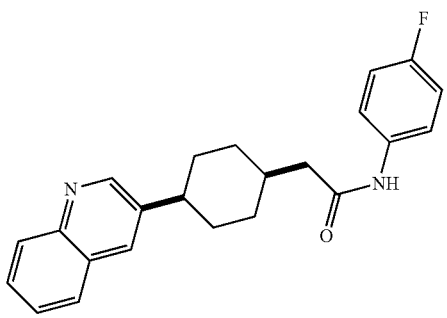

N-(4-fluorophenyl)-2-(trans-4-(quinolin-3-yl)cyclohexyl)acetamide hydrochloride

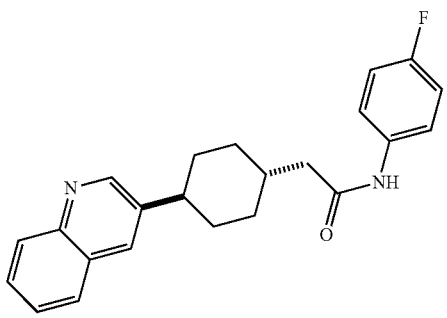

Examples 7 and 8

N-(4-fluorophenyl)-2-(cis-4-(quinolin-3-yl)cyclohexyl)acetamide and N-(4-fluorophenyl)-2-(trans-4-(quinolin-3-yl)cyclohexyl)acetamide hydrochloride Prepared using General Procedures A, B, and G. General Procedure A employed 10.0 g (32 mmol) of ethyl 2-(4-

(((trifluoromethyl)sulfonyl)oxy)cyclohex-3-en-1-yl)acetate and 6.02 g (35 mmol) of quinoline-3-boronic acid. General Procedure B employed 20 wt. % of dry Pd/C (10 wt. %) and methanol as a solvent. General Procedure G employed 95 mg of ethyl 2-(4-(quinolin-3-yl)cyclohexyl)acetate (mixture of diastereomers) and 71 mg of 4-fluoroaniline. Purified using silica gel chromatography (0% to 60% ethyl acetate in hexane) to afford Example 7 (cis-diastereomer) as the first eluting isomer. $^1$H NMR of cis-isomer (400 MHz; DMSO-$d_6$): δ 8.87-8.89 (d, J=2.2 Hz, 1H), 8.18 (d, J=1.8 Hz, 1H), 7.91-8.00 (m, 2H), 7.65-7.72 (m, 1H), 7.55-7.64 (m, 3H), 7.09-7.15 (m, 3H) 2.77-2.87 (m, 1H), 2.47 (m, J=8.0 Hz, 2H), 2.26-2.36 (m, 1H), 1.79-1.91 (m, 2H), 1.57-1.78 (m, 6H) ppm. m/z 379.2 (M+H$^+$).

Further elution from the column afforded Example 8 (trans-diastereomer) as the second eluting isomer. Free base was converted to hydrochloride by mixing with excess of 2M HCl in diethyl ether, removing volatiles, and drying in high vacuum. $^1$H NMR of trans-isomer (400 MHz; CDCl$_3$): δ 10.05 (s, 1H), 9.21 (d, J=1.8 Hz, 1H), 8.89 (s, 1H), 8.18-8.26 (m, 2H), 7.96-8.03 (m, 1H), 7.81-7.87 (m, 1H), 7.60-7.65 (m, 2H), 7.08-7.16 (m, 2H), 2.83-2.93 (m, 1H), 2.27 (d, J=6.6 Hz, 2H), 1.84-2.02 (m, 5H), 1.59-1.71 (m, 2H), 1.15-1.28 (m, 2H) ppm. m/z 379.2 (M+H$^+$).

Examples 9 and 10

N-(4-chlorophenyl)-2-(cis-4-(quinolin-3-yl)cyclohexyl)acetamide and N-(4-chlorophenyl)-2-(trans-4-(quinolin-3-yl)cyclohexyl)acetamide Prepared using General Procedures A, B, and G. General Procedure A employed 10.0 g (32 mmol) of ethyl 2-(4-(((trifluoromethyl)sulfonyl)oxy)cyclohex-3-en-1-yl)acetate and 6.02 g (35 mmol) of quinoline-3-boronic acid. General Procedure B employed 20 wt. % of dry Pd/C (10 wt. %) and methanol as a solvent. General Procedure G employed 95 mg of ethyl 2-(4-(quinolin-3-yl)cyclohexyl)acetate (mixture of diastereomers) and 82 mg of 4-chloroaniline. Purified using silica gel chromatography (0% to 60% ethyl acetate in hexane) to afford Example 9 (cis-diastereomer) as the first eluting isomer. $^1$H NMR of cis-isomer (400 MHz; CDCl$_3$): δ 8.80 (d, J=2.2 Hz, 1H), 8.06-8.11 (m, 1H), 7.74-7.82 (m, 3H), 7.66-7.72 (m, 1H), 7.51-7.59 (m, 3H), 7.26-7.30 (m, 2H), 2.79-2.89 (m, 1H), 2.43-2.47 (m, 3H), 1.60-1.90 (m, 8H) ppm. m/z 379.1 (M+H$^+$).

Further elution from the column afforded Example 10 (trans-diastereomer) as the second eluting isomer. $^1$H NMR of trans-isomer (400 MHz; CDCl$_3$): δ 8.81 (d, J=2.2 Hz, 1H), 8.04-8.09 (m, 1H), 7.90-7.93 (m, 1H), 7.76-7.80 (m, 1H), 7.63-7.68 (m, 1H), 7.47-7.55 (m, 3H), 7.26-7.32 (m, 2H), 7.24 (bs, 1H), 2.66-2.76 (m, 1H), 2.32 (d, J=6.7 Hz, 2H), 1.99-2.09 (m, 5H), 1.57-1.72 (m, 2H), 1.21-1.34 (m, 2H) ppm. m/z 379.1 (M+H$^+$).

Examples 11 and 12

N-(4-cyanophenyl)-2-(cis-4-(quinolin-3-yl)cyclohexyl)acetamide

N-(4-chlorophenyl)-2-(cis-4-(quinolin-3-yl)cyclohexyl)acetamide

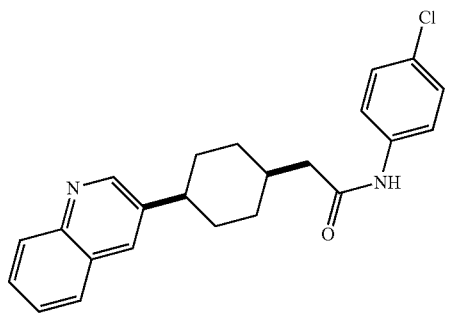

N-(4-chlorophenyl)-2-(trans-4-(quinolin-3-yl)cyclohexyl)acetamide

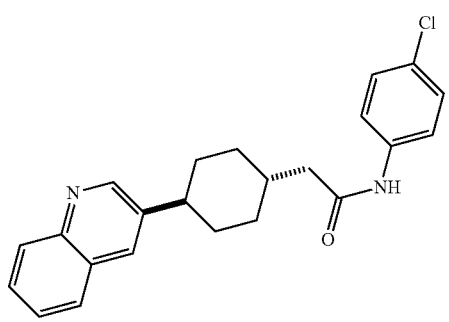

N-(4-cyanophenyl)-2-(trans-4-(quinolin-3-yl)cyclohexyl)acetamide

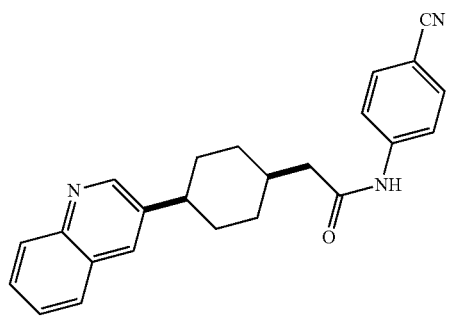

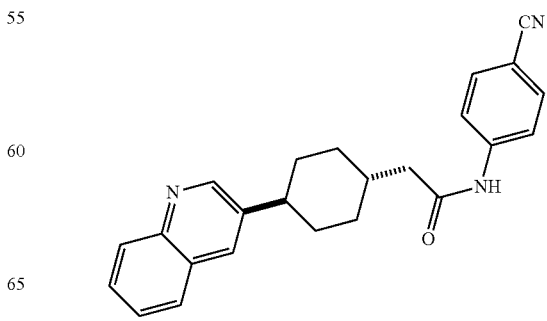

Examples 11 and 12

N-(4-cyanophenyl)-2-(cis-4-(quinolin-3-yl)cyclohexyl)acetamide and N-(4-cyanophenyl)-2-(trans-4-(quinolin-3-yl)cyclohexyl)acetamide Prepared using General Procedures A, B, and G. General Procedure A employed 10.0 g (32 mmol) of the triflate and 6.02 g (35 mmol) of quinoline-3-boronic acid. General Procedure B employed 20 wt. % of dry Pd/C (10 wt. %) and methanol as a solvent. General Procedure G employed 65 mg of ethyl 2-(4-(quinolin-3-yl)cyclohexyl)acetate (mixture of diastereomers) and 52 mg of 4-cyanoaniline. Purified using silica gel chromatography (0% to 60% ethyl acetate in hexane) to afford both Example 11 (cis-diastereomer) as the first eluting isomer. $^1$H NMR of cis-isomer (400 MHz; CDCl$_3$): δ 8.76 (d, J=2.3 Hz, 1H), 8.58 (bs, 1H), 8.07-8.11 (m, 1H), 7.69-7.79 (m, 4H), 7.64-7.67 (m, 1H), 7.57-7.63 (m, 3H), 2.75-2.85 (m, 1H), 2.45-2.50 (m, 3H), 1.45-1.85 (m, 8H) ppm. m/z 370.2 (M+H$^+$).

Further elution from the column afforded Example 12 (trans-diastereomer) as the second eluting isomer. $^1$H NMR of trans-isomer (400 MHz; CDCl$_3$): δ 8.80 (d, J=2.3 Hz, 1H), 8.05-8.09 (m, 1H), 7.90-7.93 (m, 1H), 7.76-7.80 (m, 1H), 7.60-7.73 (m, 5H), 7.50-7.56 (m, 1H), 7.45 (bs, 1H), 7.67-7.77 (m, 1H), 2.36 (d, J=6.7 Hz, 2H), 1.99-2.10 (m, 5H), 1.59-1.72 (m, 2H), 1.22-1.35 (m, 2H) ppm. m/z 370.2 (M+H$^+$).

Examples 13 (a) and (b)

2-(4-(cis-1H-Indazol-4-yl)cyclohexyl)-N-(4-cyanophenyl)acetamide

First Eluting Isomer, Relative Stereochemistry not Determined and Arbitrarily Assigned

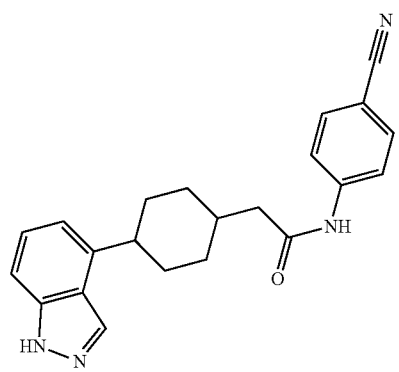 [SMILES: N#Cc1ccc(NC(=O)CC2CCC(c3cccc4[nH]ncc34)CC2)cc1]

2-(4-(trans-1H-Indazol-4-yl)cyclohexyl)-N-(4-cyanophenyl)acetamide

Second Eluting Isomer, Relative Stereochemistry not Determined and Arbitrarily Assigned

Example 13

2-(4-(1H-Indazol-4-yl)cyclohexyl)-N-(4-cyanophenyl)acetamide

Prepared by General Procedures A, B and G. General Procedure A utilized indazole-4-boronic acid and ethyl 2-(4-(((trifluoromethyl)sulfonyl)oxy)cyclohex-3-en-1-yl)acetate with dimethoxyethane as solvent, Pd(dppf)Cl$_2$ as catalyst, K$_2$CO$_3$ as base, and omitted KBr as an additive. General Procedure 13 used 10 wt. % Pd(OH)$_2$/C (10 wt. %) as catalyst and methanol as solvent. General Procedure G utilized 4-cyanoaniline (2 eq.) and ethyl 2-(4-(1H-indazol-4-yl)cyclohexyl)acetate (mixture of diastereomers) (1 eq). Purification of the reaction mixture by silica gel chromatography yielded both isomers of Example 13.

Example 13(a)

First Eluting Isomer, Relative Stereochemistry not Determined and Arbitrarily Assigned $^1$H NMR (400 MHz, CDCl$_3$) δ 8.15 (s, 1H), 7.55-7.40 (m, 2H), 7.40-7.20 (m, 4H), 7.14 (s, 1H), 7.08-7.01 (m, 1H), 3.21-3.00 (m, 1H), 2.59-2.44 (m, 3H), 1.98-1.72 (m, 8H) ppm.

Example 13(b)

Second Eluting Isomer, Relative Stereochemistry not Determined and Arbitrarily Assigned $^1$H NMR (400 MHz, CDCl$_3$) δ 8.13 (s, 1H), 7.69 (d, J=8.8 Hz, 2H), 7.63 (d, J=8.8 Hz, 2H), 7.37-7.20 (m, 3H), 6.99 (t, J=4.0 Hz, 1H), 3.06-2.88 (m, 14H), 2.37 (d, J=6.7 Hz, 2H), 2.13-1.97 (m, 5H), 1.83-1.65 (m, 2H), 1.39-1.27 (m, 2H) ppm.

Example 14

2-(4-(1H-Indazol-4-yl)cyclohexyl)-N-(4-chlorophenyl)acetamide

Mixture of Diastereomers

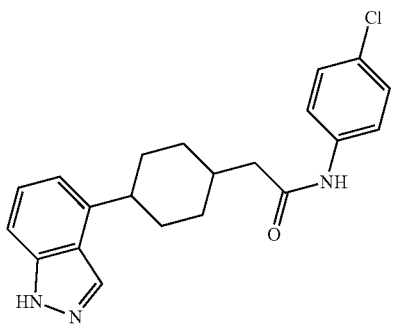 [SMILES: O=C(CC1CCC(c2cccc3[nH]ncc23)CC1)Nc1ccc(Cl)cc1]

Example 14

2-(4-(1H-Indazol-4-yl)cyclohexyl)-N-(4-chlorophenyl)acetamide

Prepared by General Procedures A, B and G. General Procedure A utilized indazole-4-boronic acid and ethyl 2-(4-(((trifluoromethyl)sulfonyl)oxy)cyclohex-3-en-1-yl)acetate with dimethoxyethane as solvent, Pd(dppf)Cl$_2$ as catalyst, K$_2$CO$_3$ as base, and omitted KBr as an additive. General Procedure B used 10 wt. % Pd(OH)$_2$/C (10 wt. %) as catalyst and methanol as solvent. General Procedure G utilized 4-chloroaniline (2 eq) and ethyl 2-(4-(1H-indazol-4-yl)cyclohexyl)acetate (1 eq). Purification of the reaction mixture by silica gel chromatography yielded Example 14 as a mixture of cis- and trans-diastereomers. $^1$H NMR (400 MHz, CDCl$_3$) δ 8.13 (s, 1H), 7.55-7.45 (m, 2H), 7.38-7.21 (m, 4H), 7.13 (s, 1H), 6.99 (t, J=3.9 Hz, 1H), 3.06-2.90 (m, 1H), 2.33 (d, J=6.7 Hz, 2H), 2.13-1.96 (m, 5H), 1.82-1.64 (m, 2H), 1.38-1.28 (m, 2H) ppm. m/z 368.2 (M+H$^+$).

Example 16

N-(4-fluorophenyl)-2-(cis-4-(quinolin-4-yl)cyclohexyl)propanamide

Single Diastereomer, Relative Stereochemistry not Determined and Arbitrarily Assigned

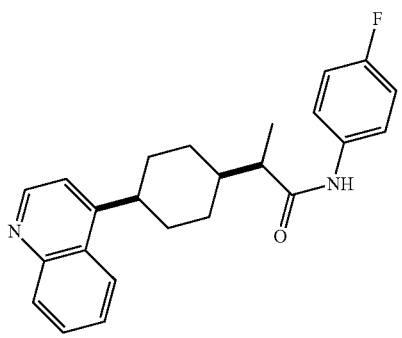

Intermediate 16A ethyl 2-(4-(quinolin-4-yl)cyclohexyl)acetate

Intermediate 16A was prepared with General procedures A and B. General procedure A utilized ethyl 2-(4-(((trifluoromethyl)sulfonyl)oxy)cyclohex-3-en-1-yl)acetate and quinoline-4-boronic acid. General Procedure B employed 20 wt. % of dry Pd/C (10 wt. %) and methanol as a solvent to afford desired product Intermediate 16A.

Intermediate 16B

Ethyl 2-(4-(quinolin-4-yl)cyclohexyl)propanoate

To a solution of Intermediate 16A (630 mg, 2.15 mmol) in THF (10 mL) at 0° C. was added NaHMDS solution (4.3 mL, 4.3 mmol, 1M in THF). The resulting yellow solution was stirred at 0° C. for 5 min and MeI (608 mg, 4.3 mmol) was added. The reaction mixture was stirred at 0° C. for 1 hour, upon which acetic acid (200 µL) was added along with Et$_2$O (10 mL). The reaction mixture was filtered through a plug of silica eluting with additional Et$_2$O (50 mL). The filtrate was concentrated and purified employing silica gel chromatography (15% to 30% EtOAc in hexanes) to afford Intermediate 16B as an oil and 2:1 mixture of cis:trans diastereomers.

Examples 16

N-(4-fluorophenyl)-2-(cis-4-(quinolin-4-yl)cyclohexyl)propanamide

Prepared with General Procedure G employing Intermediate 16B (78 mg, 0.25 mmol) and 4-fluoroaniline (56 mg, 0.5 mmol). Purified using silica gel chromatography (30% to 45% ethyl acetate in hexanes) to afford Example 16 as a white solid and single diastereomer (first eluting isomer, racemic, relative stereochemistry was not determined). $^1$H NMR (400 MHz; CDCl$_3$): δ 8.83 (d, J=4.6 Hz, 1H), 8.11 (dd, J=8.4, 0.8 Hz, 1H), 8.05 (dd, J=8.4, 0.5 Hz, 1H), 7.69 (ddd, J=8.4, 6.9, 1.4 Hz, 1H), 7.57-7.52 (m, 4H), 7.26 (s, 1H), 7.05-6.99 (m, 2H), 3.31-3.25 (m, 1H), 2.22-2.15 (m, 1H), 2.11-1.98 (m, 4H), 1.90 (s, 1H), 1.82-1.73 (m, 1H), 1.60 (qd, J=11.8, 2.6 Hz, 2H), 1.44-1.27 (m, 5H) ppm. m/z 377.3 (M+H$^+$).

Examples 17 and 18

N-(4-chlorophenyl)-2-(trans-4-(quinolin-4-yl)cyclohexyl)propanamide

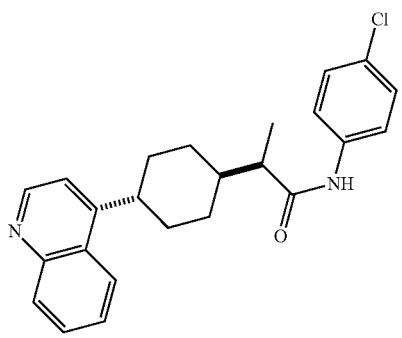

N-(4-chlorophenyl)-2-(cis-4-(quinolin-4-yl)cyclohexyl)propanamide

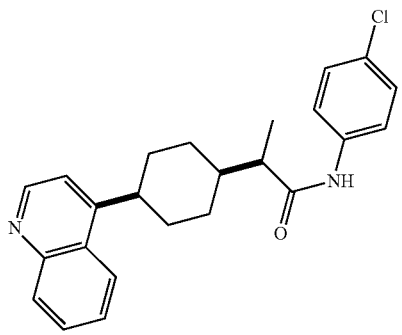

Examples 17 and 18

N-(4-chlorophenyl)-2-(trans-4-(quinolin-4-yl)cyclohexyl)propanamide and N-(4-chlorophenyl)-2-(cis-4-(quinolin-4-yl)cyclohexyl)propanamide Prepared with General Procedure G employing Intermediate 16B (44 mg, 0.14 mmol) and 4-chloroaniline (36 mg, 0.28 mmol). Purified using silica gel chromatography (30% to 45% EtOAc in hexanes) to afford Example 17 (trans-diastereomer, racemic) as a white solid and the first eluting isomer. $^1$H NMR (400 MHz; CDCl$_3$): δ 8.84 (d, J=4.6 Hz, 1H), 8.11 (dd, J=8.4, 1.0 Hz, 1H), 8.07-8.05 (m, 1H), 7.69 (ddd, J=8.4, 6.9, 1.4 Hz, 1H), 7.58-7.50 (m, 3H), 7.31-7.25 (m, 4H), 3.34-3.26 (m, 1H), 2.22-2.15 (m, 1H), 2.14-1.98

(m, 5H), 1.83-1.74 (m, 1H), 1.65-1.57 (m, 2H), 1.44-1.32 (m, 2H), 1.30 (d, J=6.9 Hz, 3H) ppm. m/z 393.2 (M+H⁺).

Further elution from the column in the previous example afforded Example 18 (cis-diastereomer, racemic) as a white solid and the second eluting isomer. ¹H NMR (400 MHz; CDCl₃): δ 8.79 (d, J=4.6 Hz, 1H), 8.11 (dd, J=8.4, 1.2 Hz, 1H), 8.07 (d, J=8.0 Hz, 1H), 8.03 (s, 1H), 7.71 (ddd, J=8.3, 6.9, 1.3 Hz, 1H), 7.58 (ddd, J=8.4, 6.9, 1.4 Hz, 1H), 7.55-7.52 (m, 2H), 7.28-7.23 (m, 3H), 3.50-3.42 (m, 1H), 2.68-2.60 (m, 1H), 2.18-2.12 (m, 1H), 1.95-1.67 (m, 8H), 1.29 (d, J=6.8 Hz, 3H) ppm. m/z 393.2 (M+H⁺).

Example 19

(R)—N-(4-chlorophenyl)-2-(cis-4-(6-fluoroquinolin-4-yl)cyclohexyl)propanamide

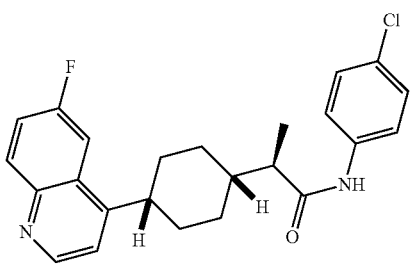 [SMILES: C[C@@H](C(=O)Nc1ccc(Cl)cc1)[C@H]1CC[C@@H](c2ccnc3ccc(F)cc32)CC1]

Example 19

(R)—N-(4-chlorophenyl)-2-(cis-4-(6-fluoroquinolin-4-yl)cyclohexyl)propanamide

Prepared using General Procedures K, B, E, L, M, N, and O. General Procedure L employed 2-(4-(6-fluoroquinolin-4-yl)-cyclohexyl)acetic acid (mixture of diastereomers), and (R)-2-phenyl-oxazolidinone. General Procedure M employed the cis product and iodomethane. The auxiliary was removed following General Procedure N and the desired product formed employing General Procedure O with 4-chloroaniline. Purified using silica gel chromatography (0% to 100% ethyl acetate in hexanes) to afford Example 19. ¹H NMR of cis-isomer (400 MHz; CDCl₃): δ 9.14 (s, 1H), 8.70 (d, J=4.6 Hz, 1H), 8.06 (dd, J=9.2 Hz, J=5.6 Hz, 1H), 7.58-7.64 (m, 3H), 7.45 (ddd, J=9.3 Hz, J=7.8 Hz, J=2.7 Hz, 1H), 7.19-7.24 (m, 2H), 7.15 (d, J=4.6 Hz, 1H), 3.16-3.26 (m, 1H), 2.59-2.69 (m, 1H), 2.08-2.16 (m, 1H), 1.66-1.86 (m, 7H), 1.31-1.42 (m, 1H), 1.21 (d, J=6.8 Hz, 3H) ppm. m/z 411.2 (M+H)⁺.

Example 20

(S)—N-(4-chlorophenyl)-2-(trans-4-(quinolin-3-yl)cyclohexyl)propanamide

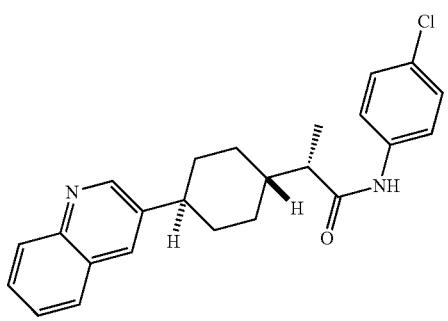 [SMILES: C[C@H](C(=O)Nc1ccc(Cl)cc1)[C@H]1CC[C@H](c2cnc3ccccc3c2)CC1]

Example 20

(S)—N-(4-chlorophenyl)-2-(trans-4-(quinolin-3-yl)cyclohexyl)propanamide

Prepared using General Procedures K, B, E, L, M, N, and O. General Procedure L employed 2-(4-(quinolin-3-yl)-cyclohexyl)acetic acid (mixture of diastereomers), and (S)-2-phenyl-oxazolidinone. General Procedure M employed the mixture of diastereomers and iodomethane. The auxiliary was removed following General Procedure N and the desired product formed employing General Procedure O with 4-chloroaniline. Purified using silica gel chromatography (0% to 10% isopropanol in hexanes) to afford Example 20 (trans-isomer) as a second eluting isomer. ¹H NMR of trans-isomer (400 MHz; MeOH): δ 9.21 (d, J=1.9 Hz, 1H), 9.10 (d, J=1.9 Hz, 1H), 8.30-8.34 (m, 1H), 8.19-8.23 (m, 1H), 8.10-8.16 (m, 1H), 7.94-8.00 (m, 1H), 7.57-7.63 (m, 2H), 7.29-7.34 (m, 2H), 3.00 (tt, J=12.0 Hz, J=3.1 Hz, 1H), 2.28-2.38 (m, 1H), 2.07-2.22 (m, 3H), 1.9302.01 (m, 1H), 1.65-1.82 (3H), 1.22-1.46 (m, 5H) ppm. m/z 393.2 (M+H)⁺.

Example 21

(R)—N-(4-cyanophenyl)-2-(cis-4-(7-fluoroquinolin-4-yl)cyclohexyl)butanamide

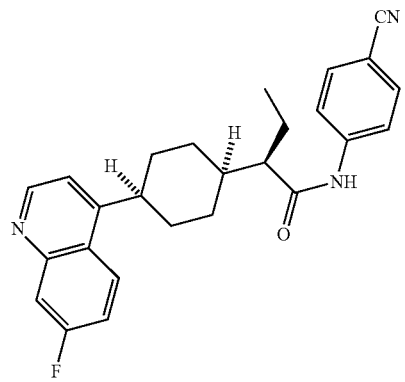 [SMILES: CC[C@@H](C(=O)Nc1ccc(C#N)cc1)[C@H]1CC[C@@H](c2ccnc3cc(F)ccc32)CC1]

Example 21

(R)—N-(4-cyanophenyl)-2-(cis-4-(7-fluoroquinolin-4-yl)cyclohexyl)butanamide

Prepared using General Procedures K, B, E, L, M, N, and O. General Procedure L employed 2-(4-(7-fluoroquinolin-4-yl)-cyclohexyl)acetic acid (mixture of diastereomers), and (R)-2-phenyl-oxazolidinone. General Procedure M employed the cis-product and iodoethane. The auxiliary was removed following General Procedure N and the desired product formed employing General Procedure O with 4-cyanoaniline. Purified using silica gel chromatography (10% to 25% EtOAc in CH₂Cl₂) to afford Example 21 (cis-isomer). ¹H NMR (400 MHz, CDCl₃) δ 8.78 (d, J=4.6 Hz, 1H), 8.55 (s, 1H), 8.07 (dd, J=9.4, 5.9 Hz, 1H), 7.80-7.67 (m, 3H), 7.60-7.53 (m, 2H), 7.37 (ddd, J=9.4, 7.9, 2.7 Hz, 1H), 7.26 (d, J=5.2 Hz, 1H), 3.44 (s, 1H), 2.51 (td, J=10.4, 3.7 Hz, 1H), 2.23-2.11 (m, 1H), 2.09-1.35 (m, 10H), 1.01 (t, J=7.4 Hz, 3H) ppm. m/z 416.2 (M+H)⁺.

Example 22

(R)—N-(4-chlorophenyl)-2-(cis-4-(7-fluoroquinolin-4-yl)cyclohexyl)butanamide

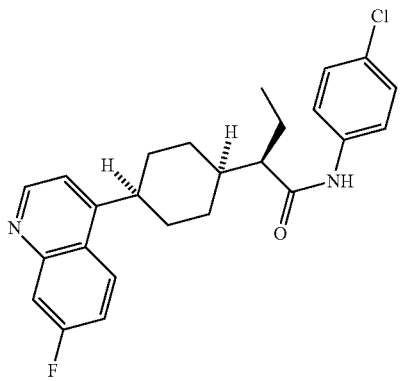 [SMILES: CC[C@@H](C(=O)Nc1ccc(Cl)cc1)[C@H]1CC[C@@H](c2ccnc3cc(F)ccc32)CC1]

Example 22

(R)—N-(4-chlorophenyl)-2-(cis-4-(7-fluoroquinolin-4-yl)cyclohexyl)butanamide

Prepared using General Procedures K, B, E, L, M, N, and O. General Procedure L employed 2-(4-(7-fluoroquinolin-4-yl)-cyclohexyl)acetic acid (mixture of diastereomers), and (R)-2-phenyl-oxazolidinone. General Procedure M employed the cis product and iodoethane. The auxiliary was removed following General Procedure N and the desired product formed employing General Procedure O with 4-chloroaniline. Purified using silica gel chromatography (20% to 50% EtOAc in hexanes). The residue was further purified using silica gel chromatography (25% EtOAc in $CH_2Cl_2$) to afford the desired product. $^1$H NMR (400 MHz, $CDCl_3$) δ 8.83 (d, J=4.6 Hz, 1H), 8.07 (dd, J=9.4, 5.9 Hz, 1H), 7.74 (dd, J=10.0, 2.7 Hz, 1H), 7.60-7.44 (m, 3H), 7.41-7.24 (m, 4H), 3.54-3.41 (m, 1H), 2.42 (td, J=10.7, 3.7 Hz, 1H), 2.19 (d, J=16.6 Hz, 1H), 2.17-1.37 (m, 10H), 1.02 (t, J=7.4 Hz, 3H) ppm. m/z 425.2 $(M+H)^+$.

Example 23

(R)—N-(4-chlorophenyl)-2-(cis-4-(quinolin-4-yl)cyclohexyl)propamide

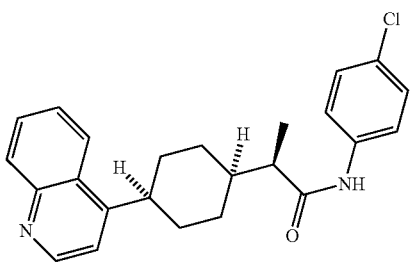 [SMILES: C[C@@H](C(=O)Nc1ccc(Cl)cc1)[C@H]1CC[C@@H](c2ccnc3ccccc32)CC1]

Example 23

(R)—N-(4-chlorophenyl)-2-(cis-4-(quinolin-4-yl)cyclohexyl)propamide

Prepared using General Procedures K, B, E, L, M, N, and O. General Procedure L employed 2-(4-(quinolin-4-yl)-cyclohexyl)acetic acid (mixture of diastereomers), and (R)-2-phenyl-oxazolidinone. General Procedure M employed the cis product and iodomethane. The auxiliary was removed following General Procedure N and the desired product formed employing General Procedure O with 4-chloroaniline to give Example 23. Minor, undesired enantiomer was removed via Method L: retention time of minor, undesired enantiomer=7.1 min, retention time of major, desired enantiomer=8.0 min. $^1$H NMR of desired enantiomer (400 MHz; $CDCl_3$): δ 8.84 (d, J=4.6 Hz, 1H), 8.29 (s, 1H), 8.14-8.02 (m, 2H), 7.70 (ddd, J=8.3, 6.8, 1.3 Hz, 1H), 7.62-7.54 (m, 2H), 7.32-7.20 (m, 2H), 3.60-3.26 (m, 1H), 2.71-2.48 (m, 1H), 2.16-2.08 (m, 1H), 1.96-1.66 (m, 9H), 1.63-1.45 (m, 1H), 1.24 (d, J=6.8 Hz, 3H) ppm. m/z 393.2 $(M+H)^+$.

Example 24

(R)—N-(4-cyanophenyl)-2-(cis-4-(quinolin-4-yl)cyclohexyl)propamide

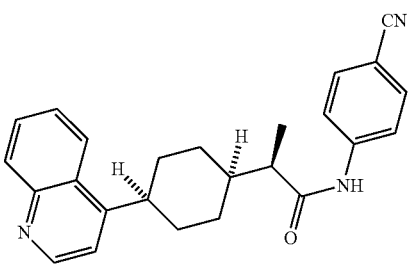 [SMILES: C[C@@H](C(=O)Nc1ccc(C#N)cc1)[C@H]1CC[C@@H](c2ccnc3ccccc32)CC1]

Example 24

(R)—N-(4-cyanophenyl)-2-(cis-4-(quinolin-4-yl)cyclohexyl)propamide

Prepared using General Procedures K, B, E, L, M, N, and O. General Procedure L employed 2-(4-(quinolin-4-yl)-cyclohexyl)acetic acid (mixture of diastereomers), and (R)-2-phenyl-oxazolidinone. General Procedure M employed the cis product and iodomethane. The auxiliary was removed following General Procedure N and General Procedure O with 4-cyanoaniline afforded Example 24. $^1$H NMR (400 MHz; $CDCl_3$): δ 8.89 (d, J=4.6 Hz, 1H), 8.41 (s, 1H), 8.11 (d, J=7.6 Hz, 1H), 8.06 (d, J=8.2 Hz, 1H), 7.78 (d, J=8.8 Hz, 2H), 7.74-7.67 (m, 1H), 7.64-7.54 (m, 3H), 7.33 (d, J=4.6 Hz, 1H), 3.54-3.37 (m, 1H), 2.67-2.53 (m, 1H), 2.16-2.09 (m, 1H), 2.00-1.72 (m, 7H), 1.57-1.45 (m, 1H), 1.26 (d, J=6.8 Hz, 3H) ppm. m/z 384.2 $(M+H)^+$.

Example 25

(R)—N-(4-chlorophenyl)-2-(cis-4-(quinolin-4-yl)cyclohexyl)butanamide

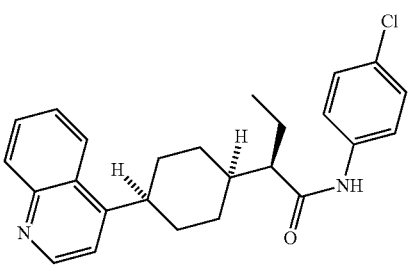 [SMILES: CC[C@@H](C(=O)Nc1ccc(Cl)cc1)[C@H]1CC[C@@H](c2ccnc3ccccc32)CC1]

Example 25

(R)—N-(4-chlorophenyl)-2-(cis-4-(quinolin-4-yl)cyclohexyl)butanamide

Prepared using General Procedures K, B, E, L, M, N, and O. General Procedure L employed 2-(4-(quinolin-4-yl)-cyclohexyl)acetic acid (mixture of diastereomers) and (R)-4-phenyl-2-oxazolidinone, General Procedure M employed the cis product of Procedure L and iodoethane. The auxiliary was removed following General Procedure N and the desired product formed employing General Procedure O with 4-chloroaniline. The compound was purified using silica gel chromatography (10% to 100% EtOAc in methylene chloride) to afford Example 25 as a white solid. $^1$H NMR (400 MHz; CDCl$_3$): δ 8.83 (d, J=4.6 Hz, 1H), 8.15-7.95 (m, 3H), 7.69 (dd, J=8.3, 7.0 Hz, 1H), 7.63-7.49 (m, 3H), 7.31-7.22 (m, 3H), 3.47 (s, 1H), 2.43 (td, J=10.4, 3.7 Hz, 1H), 2.16-2.13 (m, 1H), 1.98-1.52 (m, 11H), 1.01 (t, J=7.3 Hz, 3H) ppm. m/z 406.2 (M+H$^+$).

Example 26

(S)—N-(4-chlorophenyl)-2-(trans-4-(quinolin-4-yl)cyclohexyl)butanamide

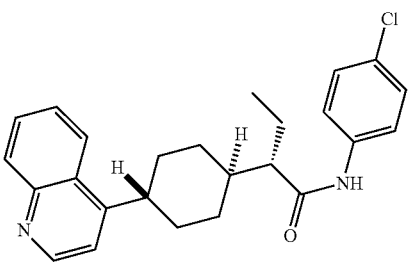 [SMILES: CC[C@H](C(=O)Nc1ccc(Cl)cc1)[C@H]1CC[C@H](c2ccnc3ccccc32)CC1]

Example 26

(S)—N-(4-chlorophenyl)-2-(trans-4-(quinolin-4-yl)cyclohexyl)butanamide

Prepared using General Procedures K, B, E, L, M, N, and O. General Procedure L employed 2-(4-(quinolin-4-yl)-cyclohexyl)acetic acid (mixture of diastereomers), and (S)-2-phenyl-oxazolidinone, General Procedure M employed iodoethane and the trans product of Procedure L. The auxiliary was removed following General Procedure N and the desired product formed employing General Procedure O with 4-chloroaniline. The compound was purified using silica gel chromatography (10% to 100% EtOAc in methylene chloride) to afford Example 26 as a white solid. $^1$H NMR (400 MHz; CDCl$_3$): δ 8.84 (d, J=4.6 Hz, 1H), 8.11 (dd, J=8.5, 1.1 Hz, 1H), 8.05 (dd, J=8.4, 0.6 Hz, 1H), 7.69 (ddd, J=8.4, 6.8, 1.4 Hz, 1H), 7.59-7.46 (m, 3H), 7.34-7.29 (m, 2H), 7.26-7.25 (m, 2H), 3.30 (t, J=11.7 Hz, 1H), 2.25-1.88 (m, 4H), 1.85-1.69 (m, 3H), 1.70-1.50 (m, 3H), 1.50-1.27 (m, 2H), 0.99 (t, J=7.4 Hz, 3H) ppm. m/z 406.2 (M+H$^+$).

Example 27

N-(4-chlorophenyl)-2-(cis-4-(quinolin-4-yloxy)cyclohexyl)propanamide

Enantiomerically Pure, Absolute Stereochemistry not Determined

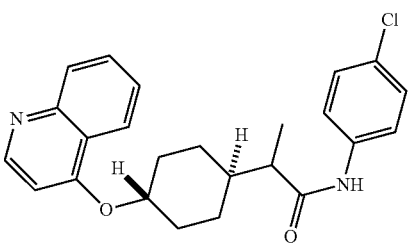 [SMILES: CC(C(=O)Nc1ccc(Cl)cc1)[C@H]1CC[C@H](Oc2ccnc3ccccc23)CC1]

Intermediate 27A

Ethyl 2-(1,4-dioxaspiro[4.5]decan-8-ylidene)propanoate

A suspension of 60% NaH (12.8 g, 385 mmol) in THF (500 mL) was cooled to 0° C. and triethyl-2-phosphono propionate (91.6 g, 385 mmol) was added over 30 min.

The reaction mixture was allowed to warm to room temperature and the cloudy suspension gradually became a yellow solution. After warming to room temperature, the reaction mixture was again cooled to 0° C. A solution of 1,4-cyclohexanedione monoethylene acetal (50 g, 320 mmol) was added dropwise via an addition funnel. After the addition was complete, the reaction mixture was allowed to warm to room temperature and stirred for 1 hour. The mixture was concentrated under reduced pressure and the yellow residue was diluted with saturated aqueous NaHCO$_3$ (500 mL) and EtOAc (1000 mL). The organic layer was separated and the aqueous layer was extracted with EtOAc (500 mL×2). The combined organic extracts were dried over anhydrous Na$_2$SO$_4$, filtered and concentrated under reduced pressure to afford Intermediate 27A (93.8 g), which was used in the next step without further purification.

Intermediate 27B racemic ethyl 2-(1,4-dioxaspiro[4.5]decan-8-yl)propanoate

Intermediate 27A (93.8 g, 390.3 mmol) was dissolved in EtOH (1000 mL) and 10% Palladium on Carbon (9.4 g) was added. A balloon of H₂ (g) with a needle was sparged through the black suspension, after which the balloon was re-filled and the vessel held under an atmosphere of H₂ (g) overnight. The mixture was filtered through CELITE®545 and the filtered cake was rinsed with EtOH. The filtrate was concentrated under reduced pressure to afford Intermediate 27B (92.5 g), which was used in the next step without further purification.

Intermediate 27C racemic ethyl 2-(4-oxocyclohexyl)propanoate

A racemic mixture of Intermediate 27B (17.1 g, 70.6 mmol) was dissolved in acetone (250 mL). Then 1 N aq. HCl (62 mL) was added and the mixture was stirred at room temperature for 24 hours. The mixture was concentrated under reduced pressure and extracted with EtOAc (200 mL×3). The combined organic extracts were washed with 1 N aq. NaOH (50 mL), dried over anhydrous MgSO₄, filtered and concentrated under reduced pressure. The residue was purified by silica gel column chromatography (0-20% EtOAc in petroleum ether) to afford Intermediate 27C (12.8 g, 91.5% yield).

Intermediate 27D ethyl-2-(trans-4-hydroxycyclohexyl)propanoate

To a solution of racemic Intermediate 27C (5.94 g, 30 mmol) in MeOH (100 mL) at 0° C. was added NaBH₄ (1.67 g, 45 mmol) portionwise. The mixture was warmed to room temperature and was monitored by TLC. When the starting material was consumed, the mixture was quenched with 1 M HCl and extracted with CH₂Cl₂ (2×100 mL). The combined organic extracts were dried over MgSO₄, filtered and concentrated under reduced pressure. The resulting light yellow oil was purified by silica gel chromatography (25% to 40% EtOAc in hexanes) to afford the trans-isomer, Intermediate 27D as the second eluting isomer.

Intermediate 27E ethyl-2-(cis-4-(quinolin-4-yloxy)cyclohexyl)propanoate

To a solution of racemic Intermediate 27D (690 mg, 3.45 mmol), quinolin-4-ol (600 mg, 4.13 mmol) and triphenylphosphine (2.69 g, 10.3 mmol) in THF (11.5 mL) at 0° C. was added DEAD (0.921 mL, 5.87 mmol) dropwise. The mixture was warmed to room temperature and stirred at room temperature for 18 hours. The mixture was diluted with 1 M NaOH and extracted with EtOAc (3×). The combined organic layers were washed with brine, dried over MgSO₄, filtered and concentrated under reduced pressure. The residue was purified using silica gel chromatography (10% to 100% EtOAc in hexanes) to afford Intermediate 27E.

Example 27

N-(4-chlorophenyl)-2-(cis-4-(quinolin-4-yloxy)cyclohexyl)propanamide

Example 27 was prepared with General Procedure G employing Intermediate 27E and 4-chloroaniline. The racemic mixture was resolved using Method M to afford Example 27 as a single enantiomer (absolute stereochemistry not determined, second eluting enantiomer). ¹H NMR (400 MHz, CDCl₃) δ 8.61 (d, J=5.3 Hz, 1H), 8.27 (s, 1H), 8.14 (d, J=8.4 Hz, 1H), 7.93 (d, J=8.4 Hz, 1H), 7.61 (t, J=7.6 Hz, 1H), 7.49 (d, J=8.7 Hz, 2H), 7.42 (t, J=7.6 Hz, 1H), 7.31-7.13 (m, 2H), 6.62 (d, J=5.3 Hz, 1H), 4.44-4.20 (m, 1H), 2.27-2.01 (m, 3H), 1.99-1.78 (m, 2H), 1.72-1.58 (m, 1H), 1.51 (dd, J=24.1, 12.8 Hz, 2H), 1.24-0.96 (m, 5H). m/z 409.2 (M+H)⁺.

Example 30

N-(4-Chlorophenyl)-2-(cis-1-hydroxy-4-(quinolin-4-yl)cyclohexyl)acetamide

Single Diastereomer, Relative Stereochemistry not Determined and Arbitrarily Assigned

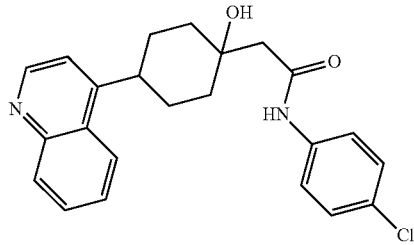 [SMILES: O=C(CC1(O)CCC(c2ccnc3ccccc23)CC1)Nc1ccc(Cl)cc1]

Intermediate 30A 4-(1,4-dioxaspiro[4.5]dec-7-en-8-yl)quinoline

To a 20 mL reaction vial containing 4,4,5,5-tetramethyl-2-(1,4-dioxaspiro[4.5]dec-7-en-8-yl)-1,3,2-dioxaborolane (See General Procedure K for reference to preparation) commercially available, CAS#[680596-79-6]) (1.0 g, 3.8 mmol, 1.0 equiv.), 4-bromoquinoline (0.86 g, 4.1 mmol, 1.1 equiv.), and Pd(dppf)Cl₂ (0.154 g, 0.188 mmol, 0.05 equiv.) was added dioxane (12 mL), water (1.2 mL), and NEt₃ (1.0 mL, 7.5 mmol, 2.0 equiv.). The flask was flushed with argon and placed in a pre-heated block at 100° C. for 15 hours. The crude residue was diluted with EtOAc (100 mL), filtered through a pad of CELITE®, and concentrated. The crude residue was purified by silica gel chromatography (0% to 50% EtOAc in hexanes) to afford Intermediate 30A (1.0 g, 99% yield).

Intermediate 30B 4-(quinolin-4-yl)cyclohexan-1-one

Intermediate 30A (3.25 g, 12.3 mmol, 1.0 equiv.) was dissolved in MeOH (100 mL) and sparged with argon for 1 hour before adding Pd/C (2.54 g, 2.4 mmol, 0.2 equiv.). The reaction solution was sparged with H₂ (g) and placed under positive pressure with a H₂ balloon. The reaction was stirred under H₂ for 14 h and filtered through CELITE®, rinsing with 100 mL MeOH. The solution was concentrated to afford a light yellow solid and oil mixture. The crude mixture was directly diluted with 3 M HCl (100 mL) and acetone (100 mL). The solution was stirred at room temperature for 2 hours and monitored by TLC. The reaction was basified with 1 N NaOH and extracted with EtOAc (2×100 mL), washed with brine, dried (MgSO₄), filtered, and concentrated. The crude residue was purified by silica gel chromatography (0% to 50% EtOAc in hexanes) to afford intermediate 30B (1.25 g, 45% yield over 2 steps).

Intermediate 30Ca ethyl 2-(cis-1-hydroxy-4-(quinolin-4-yl)cyclohexyl) acetate

Intermediate 30Cb ethyl 2-(trans-1-hydroxy-4-(quinolin-4-yl)cyclohexyl)acetate To a 20 mL reaction vial containing Intermediate 30B (0.99 g, 4.4 mmol, 1.0 equiv.) and $Zn^0$ (350 mg, 5.3 mol, 1.2 equiv.) under argon was added anhydrous THF (8 mL). A solution of ethyl bromoacetate (0.54 mL, 4.8 mol, 1.1 equiv.) in THF (4.0 mL) was added via syringe followed by a crystal of iodine. The reaction mixture was placed in a pre-heated block at 80° C. for 5 hours, after which time an additional 0.5 equiv. of ethyl bromoacetate (0.24 mL, 2.2 mmol) and $Zn^0$ (150 mg, 2.2 mmol) were added. The reaction continued to stir at 80° C. for an additional 2 hours. The mixture was diluted with EtOAc and filtered through a pad of CELITE®. The solution was concentrated and purified by silica gel chromatography (0% to 100% EtOAc in hexanes) to afford Intermediate 30Ca as the cis and Intermediate 30Cb trans isomers as yellow solids.

Example 30

N-(4-Chlorophenyl)-2-(cis-1-hydroxy-4-(quinolin-4-yl)cyclohexyl)acetamide

To a reaction vial containing 4-chloroaniline (56 mg, 0.44 mmol, 2.0 equiv.) was added iPrMgCl (2.0 M in THF, 0.22 mL, 2.0 equiv.). The reaction was stirred at rt for 15 min. In a separate vial, Intermediate 30C (70 mg, 0.22 mmol, 1.0 equiv.) was dissolved in 0.5 mL THF before adding 0.11 mL iPrMgCl (2.0 M in THF, 0.11 mmol, 1.0 equiv.). This solution was stirred for 5 min before syringing it into the anilide reaction vial. The mixture was stirred at room temperature for 14 hours and diluted with EtOAc (30 mL), washed with 3 M HCl (2×15 mL) and brine, dried ($MgSO_4$), filtered and concentrated. The crude residue was purified by silica gel chromatography (0% to 100% EtOAc in hexanes) to afford Example 30 (single diastereomer, relative stereochemistry not determined and arbitrarily assigned). $^1H$ NMR (400 MHz; $CD_3OD$): δ 8.89 (d, J=5.5 Hz, 1H) 8.31 (d, J=8.6 Hz, 1H) 8.14 (d, J=8.4 Hz, 1H) 7.94 (s, 1H) 7.77-7.85 (m, 2H) 7.50 (d, J=8.8 Hz, 2H) 7.19-7.28 (m, 2H) 3.50-3.64 (m, 1H) 2.75 (s, 2H) 1.93-2.10 (m, 4H) 1.73-1.89 (m, 4H). m/z 395.2 $(M+H)^+$.

Examples 31 and 32

Example 31

N-(4-Fluorophenyl)-2-(cis-4-(isoquinolin-4-yloxy) cyclohexyl)acetamide trifluoroacetate

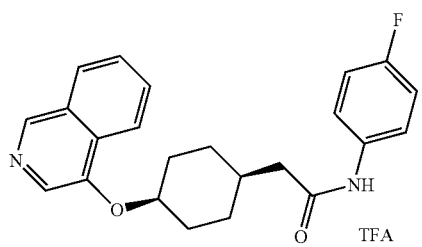 [SMILES: O=C(C[C@H]1CC[C@@H](Oc2cncc3ccccc23)CC1)Nc1ccc(F)cc1]

Example 32

N-(4-Fluorophenyl)-2-(trans-4-(isoquinolin-4-yloxy) cyclohexyl)acetamide trifluoroacetate

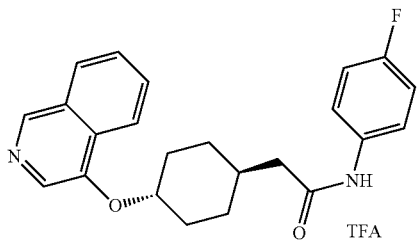 [SMILES: O=C(C[C@H]1CC[C@H](Oc2cncc3ccccc23)CC1)Nc1ccc(F)cc1]

Intermediate 31A

Ethyl 2-(4-hydroxycyclohexyl)acetate

To a solution of ethyl (2-(4-oxocyclohexyl)acetate (See References in General Procedure A for preparation) (1.0 g, 5.4 mmol) in methanol (40 mL) at rt was added $NaBH_4$ (0.60 g, 16 mmol). The resulting solution was stirred open to air for 13 h, after which it was diluted with $CH_2Cl_2$ (60 mL), washed with 1 M HCl (3×30 mL), dried over anhydrous $MgSO_4$, filtered, and concentrated under reduced pressure to afford Intermediate 31A as a 1:3 mixture of cis and trans isomers, as a clear colorless oil (1.0 g, 99% yield).

Intermediate 31B

N-(4-Fluorophenyl)-2-(4-hydroxycyclohexyl)acetamide

Prepared using General Procedure G employing intermediate 31A (1.0 g, 5.4 mmol) and 4-fluoroaniline (1.01 mL, 11 mmol). Purified using silica gel chromatography (50% to 100% EtOAc in hexanes) to afford Intermediate 31B as a 1:2 mixture of diastereomers (white solid, 772 mg, 57%).

Examples 31 and 32

N-(4-Fluorophenyl)-2-(cis-4-(isoquinolin-4-yloxy) cyclohexyl)acetamide trifluoroacetate and N-(4-Fluorophenyl)-2-(trans-4-(isoquinolin-4-yloxy)cyclohexyl)acetamide trifluoroacetate To a vial containing Intermediate 31B (200 mg, 0.80 mmol, 1.0 equiv.) and 4-isoquinolinol (170 mg, 1.2 mmol, 1.5 equiv.) was added toluene followed by cyanomethylenetributylphosphorane (0.31 mL, 1.2 mmol, 1.5 equiv.), dropwise. The reaction was stirred at 60° C. for 16 h before concentrating. The crude residue was purified by silica gel chromatography (0% to 100% EtOAc in hexanes) to afford a mixture containing Examples 31 and 32, which was further purified by preparative reverse-phase HPLC (PHENOMENEX® Gemini-NX, 10μ, C18, 110A, 250×30 mm, 20 mL/min, eluting with 0% to 100% acetonitrile in water with 0.1% TFA gradient over first 30 min of 40 min run) to afford Example 31 (cis-diastereomer, first eluting) as the TFA salt. ¹H NMR (400 MHz; CDCl₃): δ 8.87 (s, 1H) 8.22 (d, J=8.0 Hz, 1H) 8.07 (s, 1H) 7.94 (d, J=8.0 Hz, 1H) 7.56-7.73 (m, 2H) 7.42-7.52 (m, 2H) 7.39 (br. s., 1H) 6.95-7.06 (m, 2H) 4.85 (br. s., 1H) 2.33 (d, J=7.0 Hz, 2H) 2.22 (d, J=13.1 Hz, 2H) 2.11 (s, 1H) 1.66-1.79 (m, 4H) 1.51-1.66 (m, 2H). m/z 379.2 (M+H)⁺.

Further elution of the previous preparative reverse-phase HPLC afforded Example 32 (trans-diastereomer, second eluting) as the TFA salt. ¹H NMR (400 MHz; CDCl₃): δ 8.86 (s, 1H) 8.19-8.25 (m, 1H) 8.09 (s, 1H) 7.93 (d, J=8.0 Hz, 1H) 7.69 (ddd, J=8.3, 7.0, 1.3 Hz, 1H) 7.57-7.63 (m, 1H) 7.45-7.54 (m, 2H) 6.94-7.07 (m, 2H) 4.37-4.51 (m, 1H) 2.24-2.40 (m, 3H) 1.96-2.09 (m, 4H) 1.57-1.72 (m, 2H) 1.17-1.31 (m, 2H). m/z 379.2 (M+H)⁺.

Example 33

N-(4-Cyanophenyl)-2-(cis-4-(quinolin-4-yloxy)cyclohexyl)acetamide

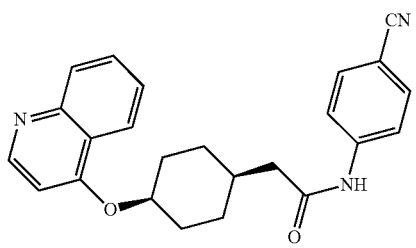 [SMILES: N#Cc1ccc(NC(=O)C[C@H]2CC[C@@H](Oc3ccnc4ccccc34)CC2)cc1]

Example 33

N-(4-Cyanophenyl)-2-(cis-4-(quinolin-4-yloxy)cyclohexyl)acetamide

To a mixture of N-(4-cyanophenyl)-2-(4-hydroxycyclohexyl)acetamide (prepared using General Procedure G from Intermediate 31A and 4-cyanoaniline) (200 mg, 0.775 mmol, 1.0 equiv.), 4-quinolinol (168 mg, 1.16 mmol, 1.5 equiv.), and PPh₃ (609 mg, 2.33 mmol 3.0 equiv.) cooled to 0° C. was added DEAD (0.182 mL, 1.16 mmol, 1.5 equiv.) dropwise. The ice bath was the removed, and the reaction mixture was allowed to warm to room temperature and stir for 16 hours. The mixture was then diluted with EtOAc, filtered through a pad of CELITE®, and concentrated under reduced pressure. The crude residue was purified using silica gel chromatography (0% to 100% EtOAc in hexanes) to afford Example 33 (cis-diastereomer), which was further purified by preparative reverse-phase HPLC (PHENOMENEX® Gemini-NX, 10μ, C18, 110A, 250×30 mm, 20 mL/min, eluting with 0% to 100% acetonitrile in water with 0.1% TFA gradient over first 30 min of 40 min run) to afford Example 33 as the TFA salt. ¹H NMR (400 MHz; CD₃OD): δ 8.96 (d, J=6.8 Hz, 1H) 8.48-8.56 (m, 1H) 8.06-8.17 (m, 2H) 7.90 (s, 1H) 7.76-7.83 (m, 2H) 7.62-7.69 (m, 2H) 7.52 (d, J=6.8 Hz, 1H) 5.33 (br. s., 1H) 2.65 (d, J=0.6 Hz, 1H) 2.43 (d, J=7.2 Hz, 2H) 2.25 (br. s., 2H) 2.05-2.19 (m, 1H) 1.93 (br. s., 2H) 1.79 (d, J=3.3 Hz, 2H) 1.64 (br. s., 2H). m/z 386.2 (M+H)⁺.

Example 34

N-(4-Chlorophenyl)-2-(trans-1-hydroxy-4-(quinolin-4-yl)cyclohexyl)acetamide

Single Diastereomer, Relative Stereochemistry not Determined and Arbitrarily Assigned

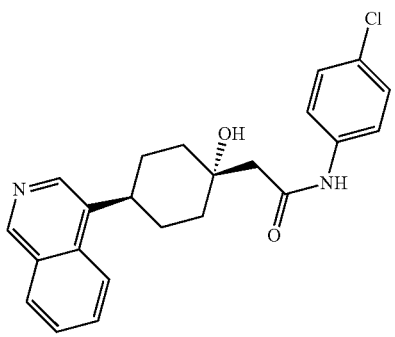 [SMILES: O=C(C[C@]1(O)CC[C@H](c2cncc3ccccc32)CC1)Nc1ccc(F)cc1]

Example 34

N-(4-Chlorophenyl)-2-(trans-1-hydroxy-4-(quinolin-4-yl)cyclohexyl)acetamide

Single Diastereomer, Relative Stereochemistry not Determined and Arbitrarily Assigned To a reaction vial containing 4-chloroaniline (33 mg, 0.25 mmol, 2.0 equiv.) was added iPrMgCl (2.0 M in THF, 0.13 mL, 0.25 mmol, 2.0 equiv.). The reaction was stirred at rt for 15 min. In a separate vial, a single diastereomer obtained from Intermediate 30Ca (40 mg, 0.13 mmol, 1.0 equiv.) was dissolved in 0.5 mL THF before adding 0.064 mL iPrMgCl (2.0 M in THF, 0.13 mmol, 1.0 equiv.). This solution was stirred for 5 min before syringing it into the anilide reaction vial. The mixture was stirred at room temperature for 14 hours and diluted with EtOAc (30 mL), washed with 3 M HCl (2×15 mL) and brine, dried (MgSO₄), filtered and concentrated under reduced pressure. The crude residue was purified by silica gel chromatography (0% to 100% EtOAc in hexanes) to afford Example 34 (single diastereomer, relative stereochemistry not determined and arbitrarily assigned). ¹H NMR (400 MHz; CD₃OD): δ 9.09 (d, J=5.9 Hz, 1H) 8.62 (d, J=8.6 Hz, 1H) 8.20-8.29 (m, 2H) 8.15 (ddd, J=8.4, 7.1, 1.1 Hz, 1H) 7.94-8.06 (m, 2H) 7.54-7.62 (m, 2H) 7.23-7.33 (m, 2H) 3.74 (t, J=12.1 Hz, 1H) 3.30 (dt, J=3.3, 1.6 Hz, 1H) 2.61 (s, 2H) 2.09-2.26 (m, 2H) 1.98-2.09 (m, 2H) 1.81-1.96 (m, 4H). m/z 395.2 (M+H)⁺.

Example 35

N-(4-Fluorophenyl)-2-(trans-1-hydroxy-4-(quinolin-4-yl)cyclohexyl)acetamide

Single Diastereomer, Relative Stereochemistry not Determined and Arbitrarily Assigned

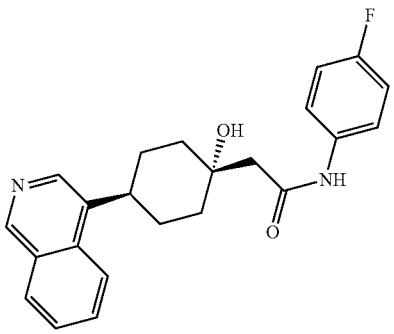

Example 35

N-(4-Fluorophenyl)-2-(trans-1-hydroxy-4-(quinolin-4-yl)cyclohexyl)acetamide

Single Diastereomer, Relative Stereochemistry not Determined and Arbitrarily Assigned To a reaction vial containing 4-fluoroaniline (28 mg, 0.25 mmol, 2.0 equiv.) was added iPrMgCl (2.0 M in THF, 0.13 mL, 0.26 mmol, 2.0 equiv.). The reaction was stirred at rt for 15 min. In a separate vial, a single diastereomer obtained from Intermediate 30Ca (40 mg, 0.13 mmol, 1.0 equiv.) was dissolved in 0.5 mL THF before adding 0.064 mL iPrMgCl (2.0 M in THF, 0.13 mmol, 1.0 equiv.). This solution was stirred for 5 min before syringing it into the anilide reaction vial. The mixture was stirred at room temperature for 14 hours and diluted with EtOAc (30 mL), washed with 3 M HCl (2×15 mL) and brine, dried (MgSO$_4$), filtered, and concentrated under reduced pressure. The crude residue was purified by silica gel chromatography (0% to 100% EtOAc in hexanes) to afford Example 35 (single diastereomer, relative stereochemistry not determined and arbitrarily assigned). $^1$H NMR (400 MHz; CDCl$_3$): δ 8.81 (d, J=4.7 Hz, 1H) 8.63-8.70 (m, 1H) 8.12 (dd, J=8.4, 1.0 Hz, 1H) 8.05 (d, J=8.2 Hz, 1H) 7.63-7.73 (m, 1H) 7.42-7.60 (m, 3H) 7.34 (d, J=4.7 Hz, 1H) 6.94-7.05 (m, 2H) 3.28 (t, J=12.0 Hz, 1H) 2.58 (s, 2H) 1.97-2.16 (m, 4H) 1.84 (d, J=10.9 Hz, 2H) 1.57-1.70 (m, 2H). m/z 379.2 (M+H)$^+$.

Example 36

N-(4-Chlorophenyl)-2-(trans-1-hydroxy-4-(quinolin-4-yl)cyclohexyl)acetamide

Single Diastereomer, Relative Stereochemistry not Determined and Arbitrarily Assigned

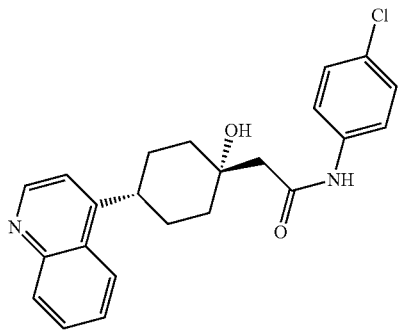 [SMILES: O=C(C[C@]1(O)CC[C@@H](c2ccnc3ccccc32)CC1)Nc1ccc(Cl)cc1]

Example 36

N-(4-Chlorophenyl)-2-(trans-1-hydroxy-4-(quinolin-4-yl)cyclohexyl)acetamide

Single Diastereomer, Relative Stereochemistry not Determined and Arbitrarily Assigned To a reaction vial containing 4-chloroaniline (51 mg, 0.40 mmol, 2.0 equiv.) was added iPrMgCl (2.0 M in THF, 0.20 mL, 0.40 mmol, 2.0 equiv.). The reaction was stirred at rt for 15 min. In a separate vial, the cis-diastereomer obtained from Intermediate 30C (63 mg, 0.20 mmol, 1.0 equiv.) was dissolved in 0.5 mL THF before adding 0.10 mL iPrMgCl (2.0 M in THF, 0.10 mmol, 1.0 equiv.). This solution was stirred for 5 min before syringing it into the anilide reaction vial. The mixture was stirred at room temperature for 14 hours and diluted with EtOAc (30 mL), washed with 3 M HCl (2×15 mL) and brine, dried (MgSO$_4$), filtered and concentrated under reduced pressure. The crude residue was purified by silica gel chromatography (0% to 100% EtOAc in hexanes) to afford Example 36 (single diastereomer, relative stereochemistry not determined and arbitrarily assigned). $^1$H NMR (400 MHz; CDCl$_3$): δ 9.73 (s, 1H) 8.75 (d, J=4.5 Hz, 1H) 8.10 (dd, J=8.4, 1.0 Hz, 1H) 8.03 (d, J=7.8 Hz, 1H) 7.70 (ddd, J=8.3, 7.0, 1.3 Hz, 1H) 7.50-7.62 (m, 3H) 7.21-7.29 (m, 2H) 7.14 (d, J=4.7 Hz, 1H) 3.30-3.45 (m, 1H) 2.75 (s, 2H) 2.03-2.12 (m, 2H) 1.93-2.02 (m, 2H) 1.82 (td, J=13.3, 3.3 Hz, 2H) 1.47-1.63 (m, 2H). m/z 395.2 (M+H)$^+$.

Example 37

N-(4-Fluorophenyl)-2-(trans-1-hydroxy-4-(quinolin-4-yl)cyclohexyl)acetamide

Single Diastereomer, Relative Stereochemistry not Determined and Arbitrarily Assigned

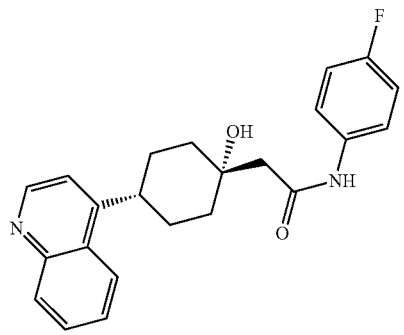 [SMILES: O=C(C[C@]1(O)CC[C@@H](c2ccnc3ccccc32)CC1)Nc1ccc(F)cc1]

Example 37

N-(4-Fluorophenyl)-2-(trans-1-hydroxy-4-(quinolin-4-yl)cyclohexyl)acetamide

Single Diastereomer, Relative Stereochemistry not Determined and Arbitrarily Assigned To a reaction vial containing 4-fluoroaniline (44 mg, 0.40 mmol, 2.0 equiv.) was added iPrMgCl (2.0 M in THF, 0.20 mL, 0.40 mmol, 2.0 equiv.). The reaction was stirred at rt for 15 min. In a separate vial, the cis-diastereomer obtained from Intermediate 30Cb (63 mg, 0.20 mmol, 1.0 equiv.) was dissolved in 0.5 mL THF before adding 0.064 mL iPrMgCl (2.0 M in THF, 0.10 mL, 0.20 mmol, 1.0 equiv.). This solution was stirred for 5 min before syringing it into the anilide reaction vial. The mixture was stirred at room temperature for 14 hours and diluted with EtOAc (30 mL), washed with 3 M HCl (2×15 mL) and brine, dried (MgSO$_4$), filtered, and concentrated under reduced pressure. The crude residue was purified by silica gel chromatography (0% to 100% EtOAc in hexanes) to afford Example 37 (single diastereomer, relative stereochemistry not determined and arbitrarily assigned). $^1$H NMR (400 MHz; CDCl$_3$): δ 9.60 (s, 1H) 8.76 (d, J=4.7 Hz, 1H) 8.10 (dd, J=8.4, 1.0 Hz, 1H) 8.04 (d, J=8.0 Hz, 1H) 7.71 (ddd, J=8.3, 6.9, 1.4 Hz, 1H) 7.52-7.65 (m, 2H) 7.15 (d, J=4.7 Hz, 1H) 6.93-7.07 (m, 2H) 3.30-3.45 (m, 1H) 2.75 (s, 2H) 2.07 (d, J=13.5 Hz, 2H) 1.92-2.02 (m, 2H) 1.83 (td, J=13.3, 3.4 Hz, 2H) 1.45-1.65 (m, 2H). m/z 379.2 (M+H)$^+$.

Examples 38 and 39

(R)—N-(4-Cyanophenyl)-2-(cis-4-(quinolin-4-yloxy)cyclohexyl)propanamide

Single Enantiomer, Absolute Stereochemistry not Determined and Arbitrarily Assigned

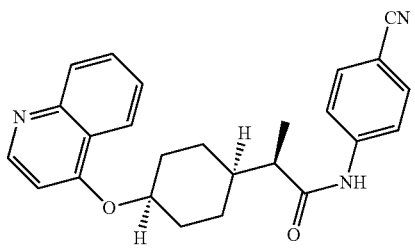 [SMILES: C[C@@H](C(=O)Nc1ccc(C#N)cc1)[C@H]1CC[C@@H](Oc2ccnc3ccccc23)CC1]

(S)—N-(4-Cyanophenyl)-2-(cis-4-(quinolin-4-yloxy)cyclohexyl)propanamide

Single Enantiomer, Absolute Stereochemistry not Determined and Arbitrarily Assigned

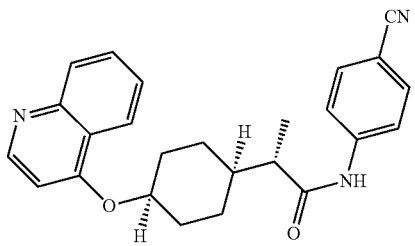 [SMILES: C[C@H](C(=O)Nc1ccc(C#N)cc1)[C@H]1CC[C@@H](Oc2ccnc3ccccc23)CC1]

Intermediate 38A ethyl 2-(4-((tert-butyldimethylsilyl)oxy)cyclohexyl)acetate

To a solution of ethyl 2-(4-hydroxycyclohexyl)acetate (17.4 g, 93.4 mmol, 1.0 equiv.) in DMF (100 mL) under argon was added imidazole (9.54 g, 140 mmol, 1.5 equiv.) and tert-butyldimethylsilyl chloride (15.5 g, 103 mmol, 1.1 equiv.). The reaction became cloudy and was stirred overnight. The reaction mixture was diluted with water (100 mL) and extracted with EtOAc (150 mL and 2×60 mL). The combined organic layers were dried (MgSO$_4$) and concentrated to afford Intermediate 38A as a clear, colorless oil.

Intermediate 38B ethyl 2-(4-((tert-butyldimethylsilyl)oxy)cyclohexyl)propanoate

Intermediate 38A (5.0 g, 17 mmol, 1.0 equiv.) was diluted with Et$_2$O and cooled to −78° C. Sodium hexamethyldisilazide (2.0 M in THF, 9.2 mL, 18 mmol, 1.1 equiv.) was added via syringe, and the reaction turned light yellow and was stirred for 5 min. Methyl iodide (5.1 mL, 83 mmol, 5.0 equiv.) was added, and the reaction was allowed to warm to room temperature overnight. The reaction was diluted with EtOAc (100 mL) and brine (100 mL) and sat. aq. NH$_4$Cl (100 mL). The layers were separated, and the aqueous layer was extracted with EtOAc (2×60 mL). The combined organic layers were dried (MgSO$_4$), filtered, concentrated under reduced pressure, and purified by silica gel chromatography (0% to 10% EtOAc in hexanes) to afford Intermediate 38B as a faint yellow oil (4.56 g, 86%).

Intermediate 38C ethyl 2-(4-hydroxycyclohexyl)propanoate

Intermediate 38B (4.54 g, 14.5 mmol, 1.0 equiv.) was diluted in THF (48 mL), and the solution was treated with tetrabutylammonium fluoride solution (1.0 M in THF, 22 mL, 21.7 mmol, 1.5 equiv.). The reaction solution was allowed to stir overnight. The reaction solution was concentrated and then diluted with EtOAc (200 mL), washed with water and brine, dried (MgSO$_4$), filtered, and concentrated under reduced pressure. The crude residue was purified by silica gel chromatography (0% to 30% EtOAc in hexanes) to afford Intermediate 38C as a 7:3 trans to cis ratio (2.78 g, 96% yield).

Intermediate 38D ethyl 2-(cis-4-(quinolin-4-yloxy)cyclohexyl)propanoate

To a solution of Intermediate 38C (1.07 g, 5.35 mmol, 1.0 equiv.), 4-quinolinol (0.931 g, 6.42 mmol, 1.2 equiv.), and PPh$_3$ (4.22 g, 16.1 mmol, 3.0 equiv.) in THF (18 mL, 0.3 M) at 0° C. was added DEAD (1.27 mL, 8.03 mmol, 1.5 equiv.). The reaction was allowed to warm to room temperature overnight. The reaction was concentrated and then diluted with EtOAc (100 mL). The solution was washed with 1 M NaOH and brine, dried (MgSO$_4$), filtered, concentrated under reduced pressure, and purified by silica gel chromatography (0% to 100% EtOAc in hexanes) to afford Intermediate 38D.

Examples 38 and 39

(R)—N-(4-Cyanophenyl)-2-(cis-4-(quinolin-4-yloxy)cyclohexyl)propanamide and (S)—N-(4-Cyanophenyl)-2-(cis-4-(quinolin-4-yloxy)cyclohexyl)propanamide Both as Single Enantiomers, Absolute Stereochemistry not Determined and Arbitrarily Assigned To a solution of 4-chloroaniline (340 mg, 2.9 mmol, 2.0 equiv.) in THF (2.5 mL) was added iPrMgCl (2.0 M in THF, 1.45 mL, 2.9 mmol, 2.0 equiv.). The solution turned orange/brown and was stirred for 15 min. A solution of Intermediate 38D (502 mg, 1.45 mmol, 1.0 equiv.) in THF (0.5 mL) was added, and the reaction was allowed to stir overnight. The reaction mixture was diluted with EtOAc (30 mL) and washed with 3 M HCl (2×15 mL) and brine. The combined organics were dried (MgSO$_4$), filtered, concentrated under reduced pressure, and purified by silica gel chromatography (0% to 100% EtOAc) to afford Examples 38 and 39 as a mixture of enantiomers. Chiral semipreparative normal phase HPLC (Diacel CHIRALPAK® ID, 5μ, 250×20 mm, 15 mL/min, eluting with 95% 1:1 hexane:CH$_2$Cl$_2$ and 5% acetonitrile with 0.4% diethylamine isocratic over 40 min) to afford Example 38 as the first eluting isomer. $^1$H NMR (400 MHz; CDCl$_3$): δ 8.71 (d, J=5.3 Hz, 1H) 8.19 (dd, J=8.4, 1.4 Hz, 1H) 8.02 (d, J=8.4 Hz, 1H) 7.78 (s, 1H) 7.64-7.73 (m, 2H) 7.54-7.61 (m, 21-1) 7.44 (ddd, J=8.2, 7.0, 1.2 Hz, 1H) 6.70 (d, J=5.5 Hz, 1H) 4.86 (br. s., 1H) 2.14-2.32 (m, 2H) 1.47-1.86 (m, 7H), 1.27 (d, J=7.0 Hz, 2H). m/z 400.2 (M+H)$^+$.

Further elution of the previous semipreparative chiral HPLC column afforded Example 39 as the second eluting isomer. $^1$H NMR (400 MHz; CDCl$_3$): δ 8.71 (d, J=5.3 Hz, 1H) 8.19 (dd, J=8.4, 1.4 Hz, 1H) 8.02 (d, J=8.4 Hz, 1H) 7.78 (s, 1H) 7.64-7.73 (m, 2H) 7.54-7.61 (m, 2H) 7.44 (ddd, J=8.2, 7.0, 1.2 Hz, 1H) 6.70 (d, J=5.5 Hz, 1H) 4.86 (br. s., 1H) 2.14-2.32 (m, 2H) 1.47-1.86 (m, 7H), 1.27 (d, J=7.0 Hz, 2H). m/z 400.2 (M+H)$^+$.

Examples 40 and 41

(R)—N-(4-Fluorophenyl)-2-(cis-4-(quinolin-4-yloxy)cyclohexyl)propanamide

Single Enantiomer, Absolute Stereochemistry not Determined and Arbitrarily Assigned

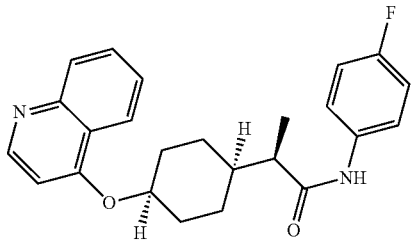 [SMILES: C[C@@H](C(=O)Nc1ccc(F)cc1)[C@H]1CC[C@@H](Oc2ccnc3ccccc23)CC1]

(S)—N-(4-Fluorophenyl)-2-(cis-4-(quinolin-4-yloxy)cyclohexyl)propanamide

Single Enantiomer, Absolute Stereochemistry not Determined and Arbitrarily Assigned

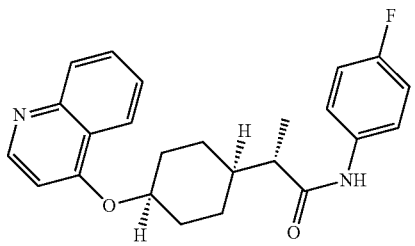 [SMILES: C[C@H](C(=O)Nc1ccc(F)cc1)[C@H]1CC[C@@H](Oc2ccnc3ccccc23)CC1]

Examples 40 and 41

(R)—N-(4-Fluorophenyl)-2-(cis-4-(quinolin-4-yloxy)cyclohexyl)propanamide and (S)—N-(4-Fluorophenyl)-2-(cis-4-(quinolin-4-yloxy)cyclohexyl)propanamide Both Obtained as a Single Enantiomer, Absolute Stereochemistry not Determined and Arbitrarily Assigned To a solution of 4-fluoroaniline (0.275 mL, 2.9 mmol, 2.0 equiv.) in THF (2.5 mL) was added iPrMgCl (2.0 M in THF, 1.45 mL, 2.9 mmol, 2.0 equiv.). The solution turned orange/brown and was stirred for 15 min. A solution of Intermediate 38D (502 mg, 1.45 mmol, 1.0 equiv.) in THF (0.5 mL) was added, and the reaction was allowed to stir overnight. The reaction mixture was diluted with EtOAc (30 mL) and washed with 3 M HCl (2×15 mL) and brine. The solution was dried (MgSO$_4$), concentrated, and purified by silica gel chromatography (0% to 100% EtOAc) to afford Examples 40 and 41 as a mixture of enantiomers. Chiral semipreparative normal phase HPLC (Diacel CHIRALPAK® ID, 5μ, 250×20 mm, 15 mL/min, eluting with 95% 1:1 hexane:CH$_2$Cl$_2$ and 5% acetonitrile with 0.4% diethylamine isocratic over 40 min) to afford Example 40 as the first eluting isomer. $^1$H NMR (400 MHz; CDCl$_3$): δ 8.72 (d, J=5.3 Hz, 1H) 8.22 (dd, J=8.3, 1.1 Hz, 1H) 8.03 (d, J=8.6 Hz, 1H) 7.69 (ddd, J=8.4, 6.9, 1.5 Hz, 1H) 7.42-7.53 (m, 2H) 7.21 (s, 1H) 6.94-7.05 (m, 2H) 6.71 (d, J=5.5 Hz, 1H) 4.87 (br. s., 1H) 2.06-2.31 (m, 4H) 1.47-1.88 (m, 5H) 1.22-1.29 (m, 4H). m/z 393.2 (M+H)$^+$.

Further elution of the previous semipreparative chiral HPLC column afforded Example 41 as the second eluting isomer. $^1$H NMR (400 MHz; CDCl$_3$): δ 8.72 (d, J=5.3 Hz, 1H) 8.22 (dd, J=8.3, 1.1 Hz, 1H) 8.03 (d, J=8.6 Hz, 1H) 7.69 (ddd, J=8.4, 6.9, 1.5 Hz, 1H) 7.42-7.53 (m, 2H) 7.21 (s, 1H) 6.94-7.05 (m, 2H) 6.71 (d, J=5.5 Hz, 1H) 4.87 (br. s., 1H) 2.06-2.31 (m, 4H) 1.47-1.88 (m, 5H) 1.22-1.29 (m, 4H). m/z 393.2 (M+H)$^+$.

Example 42

(±)-N-(4-chlorophenyl)-2-(trans-4-(quinolin-4-yl)cyclohexyl)pent-4-enamide

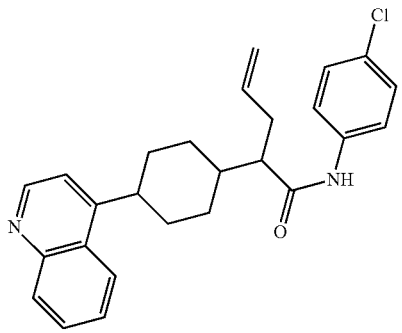 [SMILES: C=CCC(C(=O)Nc1ccc(Cl)cc1)C1CCC(c2ccnc3ccccc23)CC1]

Intermediate 42A ethyl-2-4-(quinolin-4-yl)cyclohexyl)pent-4-enoate

To a solution of ethyl 2-(4-(quinolin-4-yl)cyclohexyl) acetate (which can be prepared using General Procedures A and B) in THF (0.2 M) at 0° C. was added NaHMDS solution (2 equivalents). The resulting yellow solution was stirred at 0° C. for 5 min and allyl bromide (2 equivalents) was added. The reaction mixture was warmed to room temperature and stirred for 1 hour, upon which AcOH was added along with Et$_2$O. The reaction mixture was filtered through a plug of silica eluting with additional Et$_2$O. The filtrate was concentrated and purified employing silica gel chromatography to afford Intermediate 42A as mixture of cis/trans diastereomers.

Example 42

N-(4-chlorophenyl)-2-(trans-4-(quinolin-4-yl)cyclohexyl)pent-4-enamide

Intermediate 42A was subjected to General Procedure G using 4-chloroaniline and Example 42 was isolated as a white solid. $^1$H NMR (400 MHz, CDCl$_3$): δ 9.53 (s, 1H), 8.58 (d, J=4.6 Hz, 1H), 8.10 (dd, J=11.5, 8.5 Hz, 2H), 7.70 (t, J=7.2 Hz, 1H), 7.60 (t, J=7.2 Hz, 1H), 7.54 (d, J=8.8 Hz, 2H), 7.25 (ddd, J=8.9, 5.8, 2.3 Hz, 1H), 7.20-7.15 (m, 2H), 6.00-5.87 (m, 1H), 5.21-5.09 (m, 2H), 3.46 (s, 1H), 2.71 (td, J=10.1, 4.9 Hz, 1H), 2.45 (q, J=9.7 Hz, 2H), 2.28-1.62 (m, 9H).

Example 43

2-(4-(1H-pyrazolo[3,4-b]pyridin-4-yl)cyclohexyl)-N-(4-chlorophenyl)acetamide

Mixture of Cis-/Trans-Diastereomers

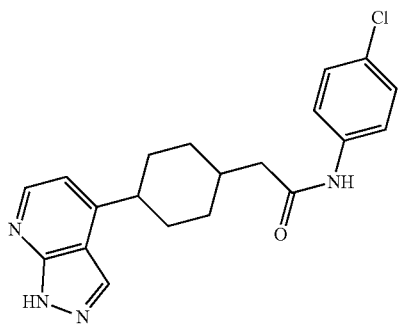 [SMILES: O=C(CC1CCC(c2ccnc3[nH]ncc23)CC1)Nc1ccc(Cl)cc1]

Example 43

2-(4-(1H-pyrazolo[3,4-b]pyridin-4-yl)cyclohexyl)-N-(4-chlorophenyl)acetamide

Mixture of Cis-/Trans-Diastereomers

Prepared using General Procedures K, B, and G. In General Procedure K, 4-bromo-1H-pyrazolo[3,4-b]pyridine was used as coupling partner and dimethoxyethane was used as solvent. In General Procedure G, 4-chloroaniline was used. Example 43 was isolated as a white solid and ~1:1 mixture of diastereomers. $^1$H NMR (400 MHz, CDCl$_3$): δ 8.52-8.45 (m, 1H), 8.20-8.11 (m, 1H), 7.52-7.46 (m, 2H), 7.34-7.27 (m, 2H), 7.08-6.96 (m, 1H), 3.20-2.90 (m, 1H), 2.50 (s, 1H), 2.33 (d, J=6.7 Hz, 1H), 2.14-1.64 (m, 8H), 1.39-1.25 (m, 2H). LC/MS, m/z 369 (M+H)$^+$.

Examples 44 and 45

N-(4-fluorophenyl)-2-(cis-4-(quinazolin-4-yl)cyclohexyl)acetamide

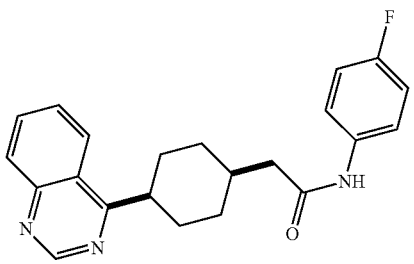

N-(4-Fluorophenyl)-2-(4-(quinazolin-4-yl)cyclohexyl)acetamide

Mixture of Diastereomers

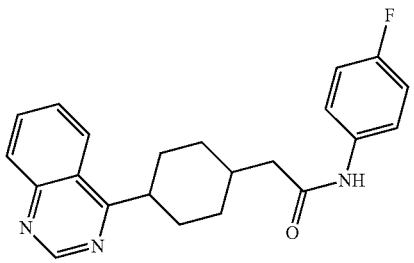 [SMILES: O=C(CC1CCC(c2ncnc3ccccc23)CC1)Nc1ccc(F)cc1]

Examples 44 and 45

N-(4-fluorophenyl)-2-(cis-4-(quinazolin-4-yl)cyclohexyl)acetamide and N-(4-fluorophenyl)-2-(4-(quinazolin-4-yl)cyclohexyl)acetamide Mixture of Diastereomers Prepared using General Procedures K, B, and G. 4-Chloroquinazoline and Pd(PPh$_3$)$_4$ were employed in Procedure K. 4-Fluoroaniline was employed in Procedure G. Purified using silica gel chromatography (50% EtOAc in hexanes) to give Example 44 (cis-diastereomer) as the first eluting isomer. $^1$H NMR (400 MHz, CD$_3$OD) δ 9.15 (s, 1H), 8.37 (d, J=8.5 Hz, 1H), 8.08-7.93 (m, 2H), 7.75 (ddd, J=8.4, 6.0, 2.2 Hz, 1H), 7.56 (ddd, J=7.0, 5.3, 2.8 Hz, 2H), 7.08-6.97 (m, 2H), 3.82 (t, J=10.0 Hz, 1H), 2.56 (d, J=7.9 Hz, 2H), 2.43 (s, 1H), 2.20-2.02 (m, 2H), 2.00 (s, 1H), 2.00-1.74 (m, 6H) ppm. m/z 364.2 (M+H)$^+$.

Further elution from the column afforded Example 45 as a 1:1 mixture of cis:trans isomers. m/z 364.2 (M+H)$^+$.

Examples 46 and 47

Example 46

N-(4-chlorophenyl)-2-(cis-4-(quinazolin-4-yl)cyclohexyl)acetamide

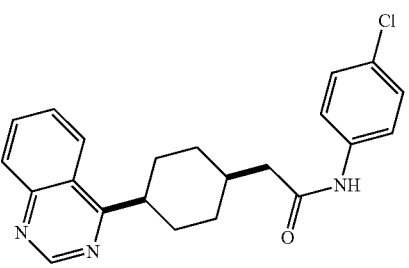

Example 47

N-(4-chlorophenyl)-2-(trans-4-(quinazolin-4-yl)cyclohexyl)acetamide

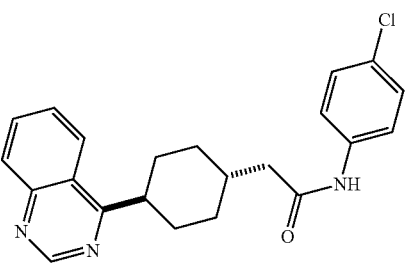

Examples 46 and 47

N-(4-chlorophenyl)-2-(cis-4-(quinazolin-4-yl)cyclohexyl)acetamide and N-(4-chlorophenyl)-2-(trans-4-(quinazolin-4-yl)cyclohexyl)acetamide Prepared using General Procedures K, B, and G. 4-Chloroquinazoline and Pd(PPh$_3$)$_4$ was employed in Procedure K. 4-Chloroaniline was employed in Procedure G. Purified using silica gel chromatography (50% EtOAc in hexanes) to give Example 46 (cis-diastereomer) as the first eluting isomer. $^1$H NMR (400 MHz, CDCl$_3$) δ 9.28 (s, 1H), 8.19 (d, J=8.2 Hz, 1H), 8.06 (d, J=8.3 Hz, 1H), 7.90 (ddd, J=8.4, 6.9, 1.3 Hz, 1H), 7.67 (ddd, J=8.3, 6.9, 1.2 Hz, 2H), 7.53 (d, J=8.8 Hz, 2H), 7.32-7.24 (m, 2H), 3.69 (dd, J=12.0, 8.6 Hz, 1H), 2.57 (s, 3H), 2.05 (dt, J=19.0, 8.4 Hz, 2H), 1.86-1.72 (m, J=30.7, 27.2 Hz, 6H) ppm. m/z 380 (M+H)$^+$.

Further elution from the column afforded Example 47 (trans-diastereomer) as the second eluting isomer. $^1$H NMR (400 MHz, CDCl$_3$) δ 9.25 (s, 1H), 8.17 (d, J=8.6 Hz, 1H), 8.05 (d, J=8.3 Hz, 1H), 7.89 (t, J=7.7 Hz, 1H), 7.65 (t, J=7.7 Hz, 1H), 7.51 (d, J=8.7 Hz, 2H), 7.35-7.15 (m, 3H), 3.54 (t, J=11.5 Hz, 1H), 2.36 (d, J=6.5 Hz, 2H), 2.15-1.81 (m, 5H), 1.48-1.30 (m, 2H), 0.87 (d, J=11.4 Hz, 2H) ppm. m/z 380 (M+H)$^+$.

Example 48

N-(4-chlorophenyl)-2-(4-(1,5-naphthyridin-4-yl)cyclohexyl)acetamide

Mixture of Diastereomers

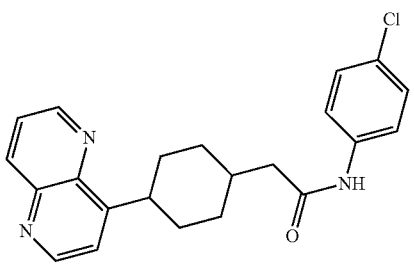 [SMILES: O=C(CC1CCC(c2ccnc3cccnc23)CC1)Nc1ccc(Cl)cc1]

Example 48

N-(4-chlorophenyl)-2-(4-(1,5-naphthyridin-4-yl)cyclohexyl)acetamide

Mixture of Diastereomers

Prepared using General Procedures K, B, and G. 4-Chloro-1,5-naphthyridine was employed in Procedure K and 4-chloroaniline was employed in Procedure G. Purified using silica gel chromatography (25-75% EtOAc in hexanes) to give a residue. The residue was further purified using silica gel chromatography (25-75% EtOAc in toluene) to give the desired product as a 2:1 mixture of diastereomers. m/z 380.2 (M+H)$^+$.

Example 49

N-(4-chlorophenyl)-2-(cis-4-(quinolin-3-yl)cyclohexyl)propanamide

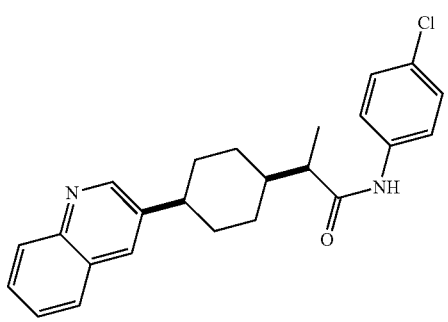

Example 49

N-(4-chlorophenyl)-2-(cis-4-(quinolin-3-yl)cyclohexyl)propanamide

Prepared with General Procedure G employing ethyl 2-(4-(quinolin-3-yl)cyclohexyl)propanoate and 4-chloroaniline. Purified using silica gel chromatography (0% to 10% 2-propanol in hexanes) to afford Example 49 as a white solid and the first eluting isomer. $^1$H NMR (400 MHz, CDCl$_3$): δ 8.74 (d, J=2.2 Hz. 1H), 8.64 (s, 1H), 8.05-8.11 (m, 1H), 7.68-7.75 (m, 2H), 7.55-7.64 (m, 3H), 7.23-7.28 (m, 3H), 2.74-2.84 (m, 1H), 2.44-2.54 (m, 1H), 1.99-2.09 (m, 1H), 1.36-1.80 (m, 8H), 1.26 (d, J=6.9 Hz, 3H) ppm. m/z 393.3 (M+H)$^+$.

Example 50

N-(4-fluorophenyl)-2-(trans-4-(quinolin-3-yl)cyclohexyl)propanamide

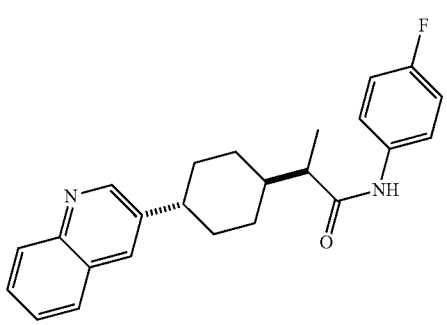

Example 50

N-(4-fluorophenyl)-2-(trans-4-(quinolin-3-yl)cyclohexyl)propanamide

Prepared with General Procedure G employing ethyl 2-(4-(quinolin-3-yl)cyclohexyl)propanoate and 4-fluoroaniline. Purified using silica gel chromatography (0% to 10% 2-propanol in hexanes) to afford Example 50 as a white solid and the second eluting isomer. $^1$H NMR (400 MHz, CDCl$_3$): δ 8.80 (d, J=2.2 Hz, 1H), 8.04-8.09 (m, 1H), 7.89-7.91 (m, 1H), 7.75-7.80 (m, 1H), 7.52-7.69 (m, 1H), 7.48-7.56 (m, 3H), 7.27 (s, 1H), 6.98-7.06 (2H), 2.69 (tt, 1H, J=3.1 Hz, J=12.6 Hz), 1.95-2.20 (m, 5H), 1.54-1.90 (m, 5H), 1.28 (d, J=6.9 Hz, 3H) ppm. m/z 377.3 (M+H)$^+$.

Examples 51 and 52

N-(4-Chlorophenyl)-2-((trans)-4-(isoquinolin-1-yl)cyclohexyl)acetamide

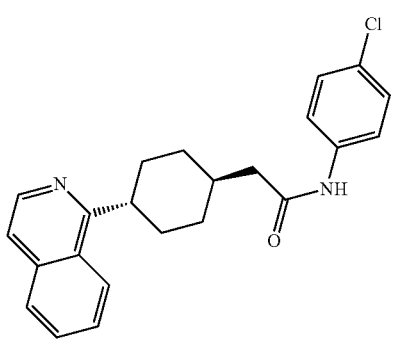 [SMILES: O=C(C[C@H]1CC[C@H](c2nccc3ccccc32)CC1)Nc1ccc(Cl)cc1]

N-(4-Chlorophenyl)-2-((cis)-4-(isoquinolin-1-yl)cyclohexyl)acetamide

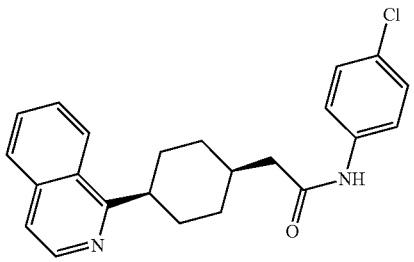 [SMILES: O=C(C[C@H]1CC[C@@H](c2nccc3ccccc32)CC1)Nc1ccc(Cl)cc1]

Examples 51 and 52

N-(4-Chlorophenyl)-2-((trans)-4-(isoquinolin-1-yl)cyclohexyl)acetamide and N-(4-Chlorophenyl)-2-((cis)-4-(isoquinolin-1-yl)cyclohexyl)acetamide Prepared using General Procedures K, B, and G. For General Procedure K, 1-chloroisoquinoline was employed. For General Procedure B, ethanol was employed as the solvent, and the reaction was run at 50° C. For General Procedure G, 4-chloroaniline was employed, and trimethylaluminum was used in place of $^i$PrMgCl. The desired compound was purified via preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes.) to give examples 51 and 52 as a mixture of diastereomers. The residue was further purified via preparative TLC (33% EtOAc in hexanes) to give Example 51 (trans-diastereomer, higher retention factor). $^1$H NMR (400 MHz; CDCl$_3$): δ 8.49-8.43 (m, 1H), 8.24-8.20 (m, 1H), 7.85-7.82 (m, 2H), 7.65-7.50 (m, 4H), 7.28-7.25 (m, 2H), 3.70-3.62 (m, 1H), 2.62-2.56 (m, 2H), 2.41-2.36 (m, 2H), 2.09-2.02 (m, 2H), 1.86-1.82 (m, 3H), 1.28-1.24 (m, 2H) ppm. m/z 379.2 (M+H)$^+$.

Preparative TLC also afforded Example 52 (cis-diastereomer, lower retention factor). $^1$H NMR (400 MHz; CDCl$_3$): δ 8.50-8.46 (m, 1H), 8.24-8.20 (m, 1H), 7.86-7.82 (m, 1H), 7.72-7.50 (m, 4H), 7.30-7.26 (m, 2H), 3.59-3.54 (m, 1H), 2.38-2.33 (m, 2H), 2.20-1.95 (m, 6H), 1.40-1.22 (m, 3H) ppm. m/z 379.1 (M+H)$^+$.

Examples 53 and 54

N-(4-Chlorophenyl)-2-((cis)-4-(isoquinolin-8-yl)cyclohexyl)acetamide

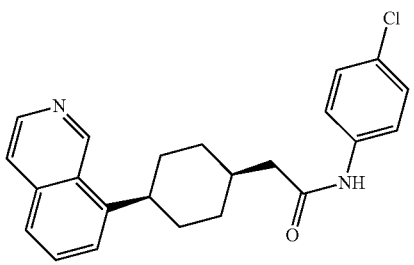 [SMILES: O=C(C[C@H]1CC[C@@H](c2cccc3ccncc32)CC1)Nc1ccc(Cl)cc1]

N-(4-Chlorophenyl)-2-((trans)-4-isoquinolin-8-yl)cyclohexyl)acetamide

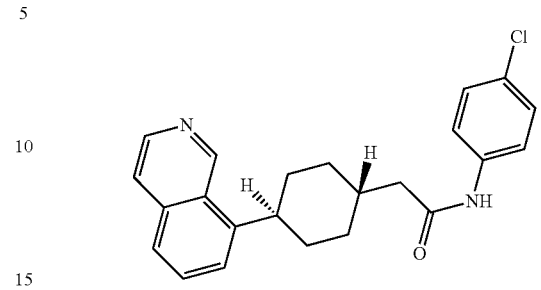

Examples 53 and 54

N-(4-Chlorophenyl)-2-((cis)-4-(isoquinolin-8-yl)cyclohexyl)acetamide and N-(4-Chlorophenyl)-2-((trans)-4-(isoquinolin-8-yl)cyclohexyl)acetamide Prepared using General Procedures K, B, and G. For General Procedure K, 8-bromoisoquinoline was employed. For General Procedure B, ethanol was employed as the solvent and the reaction was run at 50° C. For General Procedure G, 4-chloroaniline was employed and trimethylaluminum was used in place of $^i$PrMgCl. The residue was purified via preparative HPLC (Varian ProStar using Hamilton C18 PRP-1 column (15×250 mm) with flow rate of 20 mL/min, Mobile Phase A: 0.5% formic acid in water; Mobile Phase B: 0.5% formic acid in acetonitrile; 0% to 100% B gradient elution during 30 minutes) to afford Example 53 (cis-diastereomer) as the first eluting isomer. $^1$H NMR (400 MHz; CDCl$_3$): δ 9.25 (s, 1H), 8.56-8.53 (m, 1H), 7.85-7.82 (m, 2H), 7.62-7.47 (m, 4H), 7.31-7.26 (m, 2H), 3.38-3.27 (m, 1H), 2.57-2.53 (m, 3H), 2.04-1.25 (m, 8H) ppm. m/z 379 (M+H)$^+$.

Further elution afforded Example 54 (trans-diastereomer) as the second eluting isomer. $^1$H NMR (400 MHz; CDCl$_3$): δ 9.24 (s, 1H), 8.56-8.52 (m, 1H), 7.86-7.81 (m, 2H), 7.69-7.49 (m, 4H), 7.32-7.26 (m, 2H), 3.26-3.18 (m, 1H), 2.35-2.23 (m, 3H), 1.67-1.59 (m, 4H), 1.40-1.27 (m, 4H) ppm. m/z 379 (M+H)$^+$.

Example 55

N-(4-Chlorophenyl)-2-((trans)-4-(isoquinolin-5-yl)cyclohexyl)acetamide

Single Diastereomer, Relative Stereochemistry not Determined and Arbitrarily Assigned

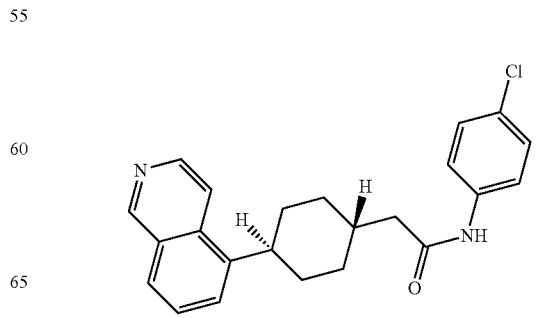

Example 55

N-(4-Chlorophenyl)-2-((trans)-4-(isoquinolin-5-yl)cyclohexyl)acetamide

Prepared using General Procedures K, B, and G. For General Procedure K, 5-bromoisoquinoline was employed. For General Procedure B, ethanol was employed as the solvent, and the reaction was run at 50° C. For General Procedure G, 4-chloroaniline was employed, and trimethylaluminum was used in place of $^i$PrMgCl. The residue was purified via preparative HPLC (Varian ProStar using Hamilton C18 PRP-1 column (15×250 mm) with flow rate of 20 mL/min. Mobile Phase A: 0.5% formic acid in water; Mobile Phase B: 0.5% formic acid in acetonitrile; 0% to 100% B gradient elution during 30 minutes.) to give Example 55 (single diastereomer, relative stereochemistry not determined and arbitrarily assigned). $^1$H NMR (400 MHz; CDCl$_3$): δ 9.24 (s, 1H), 8.55-8.52 (m, 1H), 7.85-7.81 (m, 2H), 7.60-7.48 (m, 4H), 7.32-7.26 (m, 2H), 3.27-3.20 (m, 1H), 2.38-2.32 (m, 1H), 2.09-2.02 (m, 3H), 1.70-1.57 (m, 3H), 1.41-1.24 (m, 4H). m/z 379 (M+H)$^+$.

Example 56

N-(4-fluorophenyl)-2-(cis-4-(quinolin-3-yl)cyclohexyl)propanamide

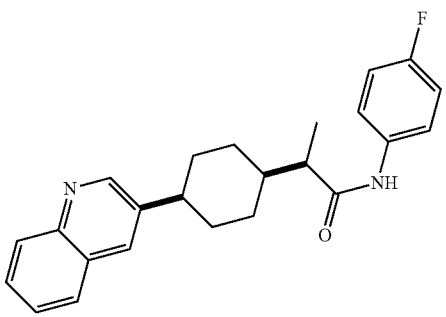

Example 56

N-(4-fluorophenyl)-2-(cis-4-(quinolin-3-yl)cyclohexyl)propanamide

Prepared with General Procedure G employing ethyl 2-(4-(quinolin-3-yl)cyclohexyl)propanoate and 4-fluoroaniline. Purified using silica gel chromatography (0% to 10% 2-propanol in hexanes) to afford Example 56 (cis-diastereomer) as a white solid and the first eluting isomer. $^1$H NMR (400 MHz, CDCl$_3$): δ 8.76-8.79 (m, 1H), 8.19 (bs, 1H), 8.06-8.11 (m, 1H), 7.65-7.77 (m, 3H), 7.53-7.62 (m, 3H), 6.96-7.04 (m, 2H), 2.79-2.89 (m, 1H), 2.43-2.53 (m, 1H), 1.99-2.08 (m, 1H), 1.50-1.85 (m, 8H), 1.27 (d, J=6.8 Hz, 3H) ppm. m/z 377.3 (M+H)$^+$.

Example 57

(±)-N-(4-Cyanophenyl)-2-((cis)-4-(quinolin-4-yl)cyclohexyl)pent-4-enamide

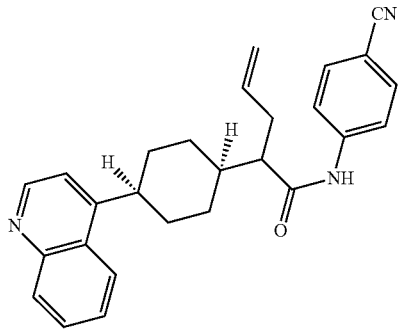 [SMILES: C=CCC(C(=O)Nc1ccc(C#N)cc1)[C@H]1CC[C@@H](c2ccnc3ccccc32)CC1]

Intermediate 57A

Ethyl 2-(cis-4-(quinolin-4-yl)cyclohexyl)pent-4-enoate

To a solution of ethyl 2-(4-(quinolin-4-yl)cyclohexyl)acetate (which can be prepared using General procedures A and B) (740 mg, 2.5 mmol) in THF (5 mL) at −78° C. was added NaHMDS (2 M in THF, 3.0 mL, 6.0 mmol). The resulting reaction mixture was stirred at −78° C. for 5 min, and allyl bromide (333 mg, 2.75 mmol) was added. The reaction was warmed to 0° C. and stirred for 10 min. The reaction was diluted with Et$_2$O and filtered through a 2×2 cm pad of silica gel, washing with an additional 50 mL of Et$_2$O. The filtrate was concentrated and used directly in the next step.

Example 57

(±)-N-(4-Cyanophenyl)-2-((cis)-4-(quinolin-4-yl)cyclohexyl)pent-4-enamide

Intermediate 57A was hydrolyzed to the carboxylic acid employing General Procedure E. The acid product was coupled with 4-cyanoaniline employing General Procedure O. Example 57 was obtained as a white solid after column chromatography (10% to 30% 2-propanol in hexanes). $^1$H NMR (400 MHz; CDCl$_3$): δ 9.16 (s, 1H), 8.67 (d, J=4.6 Hz, 1H), 8.13-8.08 (m, 2H), 7.72 (dtd, J=8.7, 3.4, 1.7 Hz, 3H), 7.61 (ddd, J=8.4, 6.9, 1.4 Hz, 1H), 7.55-7.51 (m, 2H), 7.14 (d, J=4.6 Hz, 1H), 5.95-5.84 (m, 1H), 5.18 (dt, J=16.3, 1.1 Hz, 1H), 5.13-5.10 (m, 1H), 3.50-3.49 (m, 1H), 2.69-2.68 (m, 1H), 2.48-2.41 (m, 2H), 2.23 (dt, J=10.4, 0.3 Hz, 1H), 2.01-1.65 (m, 8H).

Example 58

(R)-2-((cis)-4-(6-fluoroquinolin-4-yl)cyclohexyl)-N-phenylpropanamide

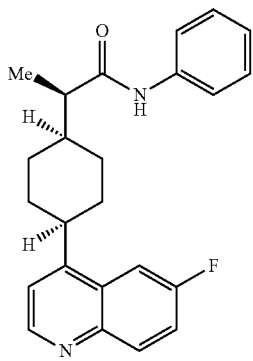 [SMILES: C[C@@H](C(=O)Nc1ccccc1)[C@H]1CC[C@@H](c2ccnc3ccc(F)cc32)CC1]

Intermediate 58A

(R)-2-((cis)-4-(6-fluoroquinolin-4-yl)cyclohexyl) propanoic acid

Intermediate 58A can be prepared from General Procedures K, B, E, L, M, and N. General Procedure L employed 2-(4-(6-fluoroquinolin-4-yl)-cyclohexyl)acetic acid (mixture of diastereomers), and (R)-2-phenyl-oxazolidinone. General Procedure M employed the cis product and iodomethane. The auxiliary was removed following General Procedure N. LC-MS Anal: m/z [M+H]$^+$ 302.2. $^1$H-NMR (400 MHz; DMSO, d6): δ 12.10 (s, 1H), 8.70 (d, J=4.5 Hz, 1H), 8.07 (dd, J=9.2, 5.9 Hz, 1H), 7.97-7.94 (m, 1H), 7.67-7.62 (m, 1H), 7.49 (d, J=4.5 Hz, 1H), 3.41-3.36 (m, 1H), 2.73-2.65 (m, 1H), 1.83-1.61 (m, 9H), 1.08 (d, J=6.8 Hz, 3H).

Example 58

(R)-2-((cis)-4-(6-fluoroquinolin-4-yl)cyclohexyl)-N-phenylpropanamide

Intermediate 58A (R)-2-((1s,4S)-4-(6-fluoroquinolin-4-yl)cyclohexyl)propanoic acid (10 mg, 0.033 mmol) was added to a vial and taken up in DMF (350 μl). Aniline (4.64 mg, 0.050 mmol) and HATU (18.93 mg, 0.050 mmol) were added followed with DIPEA (17.39 μl, 0.100 mmol). The reaction was stirred at room temperature for 3 hours. The reaction mixture was diluted with DMF to reach a total volume of 2 mL and filtered. The crude sample was purified via preparative HPLC/MS to give Example 58 (9.7 mg, 0.026 mmol, 78%). LC-MS Anal. Calc'd for $C_{24}H_{25}FN_2O$ 376.20. found [M+H] 377.0 $T_r$=1.969 min (Method B). $^1$H NMR (500 MHz, DMSO-$d_6$) δ: 9.96 (s, 1H), 8.82 (d, J=4.5 Hz, 1H), 8.05 (dd, J=9.2, 5.8 Hz, 1H), 7.93 (dd, J=10.9, 2.5 Hz, 1H), 7.62 (td, J=8.7, 2.6 Hz, 1H), 7.57 (d, J=7.9 Hz, 2H), 7.53 (d, J=4.5 Hz, 1H), 7.25 (t, J=7.8 Hz, 2H), 6.99 (t, J=7.4 Hz, 1H), 2.83 (dd, J=10.8, 6.7 Hz, 1H), 1.64-1.97 (m, 7H), 1.51-1.64 (m, 3H), 1.08 (d, J=6.6 Hz, 3H)

Examples 59 to 81

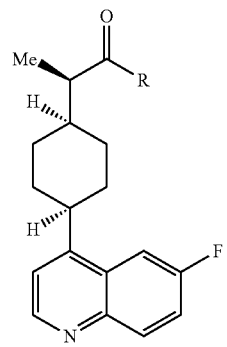

Examples 59-81 were prepared from Intermediate 58A following the procedure for Example 58 using the corresponding anilines or aryl amines.

TABLE 1

| Ex. No. | Name | R | Tr (min)$^{(Method\ B)}$ | [M + H]$^+$ |
|---|---|---|---|---|
| 59 | (R)-N-(4-fluoro-2-methylphenyl)-2-((cis)-4-(6-fluoroquinolin-4-yl)cyclohexyl)propanamide | 2-methyl-4-fluorophenyl-NH- | 1.985 | 409.2 |
| 60 | (R)-2-((cis)-4-(6-fluoroquinolin-4-yl)cyclohexyl)-N-(4-(trifluoromethyl)phenyl)propanamide | 4-CF$_3$-phenyl-NH- | 2.294 | 445.0 |
| 61 | (R)-N-(2,2-difluorobenzo[d][1,3]dioxol-5-yl)-2-((cis)-4-(6-fluoroquinolin-4-yl)cyclohexyl)propanmide | 2,2-difluorobenzo[d][1,3]dioxol-5-yl-NH- | 2.268 | 457.1 |

TABLE 1-continued

| Ex. No. | Name | R | Tr (min)$^{(Method\ B)}$ | [M + H]$^+$ |
|---|---|---|---|---|
| 62 | (R)-N-(2-ethoxyphenyl)-2-((cis)-4-(6-fluoroquinolin-4-yl)cyclohexyl)propanamide | 2-ethoxyphenyl-NH- | 2.162 | 421.1 |
| 63 | (R)-N-(3-(difluoromethyl)phenyl)-2-((cis)-4-(6-fluoroquinolin-4-yl)cyclohexyl)propanamide | 3-(CF$_2$H)phenyl-NH- | 2.082 | 427.3 |
| 64 | (R)-N-(4-chloro-2-methylphenyl)-2-((cis)-4-(6-fluoroquinolin-4-yl)cyclohexyl)propanamide | 4-Cl-2-Me-phenyl-NH- | 2.145 | 425.1 |
| 65 | (R)-N-(3-chlorophenyl)-2-((cis)-4-(6-fluoroquinolin-4-yl)cyclohexyl)propanamide | 3-Cl-phenyl-NH- | 2.203 | 411.0 |
| 66 | (R)-N-(3,4-dichlorophenyl)-2-((cis)-4-(6-fluoroquinolin-4-yl)cyclohexyl)propanamide | 3,4-diCl-phenyl-NH- | 2.385 | 445.2 |
| 67 | methyl 3-((R)-2-((cis)-4-(6-fluoroquinolin-4-yl)cyclohexyl)propanamido)benzoate | 3-(CO$_2$Me)phenyl-NH- | 2.025 | 435.1 |
| 68 | methyl 4-((R)-2-((cis)-4-(6-fluoroquinolin-4-yl)cyclohexyl)propanamido)benzoate | 4-(CO$_2$Me)phenyl-NH- | 2.042 | 435.1 |
| 69 | (R)-2-((cis)-4-(6-fluoroquinolin-4-yl)cyclohexyl)-N-methyl-N-phenylpropanamide | phenyl-N(Me)- | 1.964 | 391.1 |
| 70 | (R)-2-((cis)-4-(6-fluoroquinolin-4-yl)cyclohexyl)-N-(3-(trifluoromethyl)phenyl)propanamide | 3-(CF$_3$)phenyl-NH- | 2.278 | 445.0 |
| 71 | (R)-2-((cis)-4-(6-fluoroquinolin-4-yl)cyclohexyl)-N-(4-phenoxyphenyl)propanamide | 4-(PhO)phenyl-NH- | 2.324 | 469.3 |

TABLE 1-continued

| Ex. No. | Name | R | Tr (min)(Method B) | [M + H]+ |
|---|---|---|---|---|
| 72 | (R)-2-((cis)-4-(6-fluoroquinolin-4-yl)cyclohexyl)-N-(m-tolyl)propanamide | *–NH–(3-methylphenyl)* | 2.082 | 391.1 |
| 73 | (R)-2-((cis)-4-(6-fluoroquinolin-4-yl)cyclohexyl)-N-(3-phenoxyphenyl)propanamide | *–NH–(3-phenoxyphenyl)* | 2.355 | 469.1 |
| 73(a) | (R)-2-((cis)-4-(6-fluoroquinolin-4-yl)cyclohexyl)-N-(2-phenoxyphenyl)propanamide | *–NH–(2-phenoxyphenyl)* | 2.337 | 469.1 |
| 74 | (R)-2-((cis)-4-(6-fluoroquinolin-4-yl)cyclohexyl)-N-(pyridin-4-yl)propanamide | *–NH–(pyridin-4-yl)* | 1.669 | 378.3 |
| 75 | (R)-2-((cis)-4-(6-fluoroquinolin-4-yl)cyclohexyl)-N-(thiazol-2-yl)propanamide | *–NH–(thiazol-2-yl)* | 1.852 | 384.2 |
| 76 | (R)-2-((cis)-4-(6-fluoroquinolin-4-yl)cyclohexyl)-N-(pyridin-3-yl)propanamide | *–NH–(pyridin-3-yl)* | 1.654 | 378.0 |
| 77 | (R)-N-(2-fluorophenyl)-2-((cis)-4-(6-fluoroquinolin-4-yl)cyclohexyl)propanamide | *–NH–(2-fluorophenyl)* | 1.998 | 395.0 |
| 78 | (R)-N-(4-ethoxyphenyl)-2-((cis)-4-(6-fluoroquinolin-4-yl)cyclohexyl)propanamide | *–NH–(4-ethoxyphenyl)* | 2.030 | 421.1 |
| 79 | (R)-N-(3-cyanophenyl)-2-((cis)-4-(6-fluoroquinolin-4-yl)cyclohexyl)propanamide | *–NH–(3-cyanophenyl)* | 1.992 | 402.1 |

TABLE 1-continued

| Ex. No. | Name | R | Tr (min)(Method B) | [M + H]+ |
|---|---|---|---|---|
| 80 | (R)-N-(3-chloro-4-methylphenyl)-2-((cis)-4-(6-fluoroquinolin-4-yl)cyclohexyl)propanamide | ![structure] | 2.302 | 425.1 |
| 81 | (R)-N-(3-fluorophenyl)-2-((cis)-4-(6-fluoroquinolin-4-yl)cyclohexyl)propanamide | ![structure] | 2.094 | 395.1 |

Example 82

(R)—N-(3-Cyano-4-(trifluoromethyl)phenyl)-2-((cis)-4-(6-fluoroquinolin-4-yl)cyclohexyl)propanamide

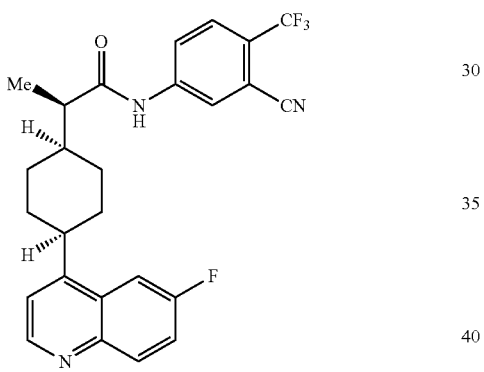

Intermediate 58A (15 mg, 0.050 mmol) was taken up in tetrahydrofuran (249 µl) and triethylamine (13.88 µl, 0.100 mmol) was added. The solution was cooled to 0° C. Isobutyl carbonochloridate (10.20 mg, 0.075 mmol) was added and the reaction stirred at 0° C. for 10 minutes prior to the addition of 5-amino-2-(trifluoromethyl)benzonitrile (12.97 mg, 0.070 mmol). After addition of the aniline, the reaction was allowed to warm to room temperature and stir at room temperature overnight. After 16 hours, 5-amino-2-(trifluoromethyl)benzonitrile (12.97 mg, 0.070 mmol) was added and the reaction was heated to 50° C. for 24 hours. The reaction was then concentrated in vacuo, diluted with DMF (~2 mL) filtered and purified via preparative HPLC to give Example 82 (5.8 mg, 0.012 mmol, 25%). LC-MS Anal. Calc'd for $C_{26}H_{23}F_4N_3O$ 469.18. found [M+H] 470.1 $T_r$=2.219 min (Method B). $^1$H NMR (500 MHz, DMSO-$d_6$) δ: 10.69 (br. s., 1H), 8.79 (br. s., 1H), 8.38 (br. s., 1H), 8.05 (d, J=8.2 Hz, 2H), 7.95 (d, J=8.0 Hz, 2H), 7.60-7.71 (m, 1H), 7.44 (br. s., 1H), 2.39 (br. s., 1H), 1.83-2.00 (m, 3H), 1.60-1.83 (m, 3H), 1.27-1.60 (m, 4H), 1.15 (d, J=6.2 Hz, 3H)

Example 83

(±)-N-(4-Chlorophenyl)-2-((trans)-4-((7-(trifluoromethyl)quinolin-4-yl)oxy)cyclohexyl)butanamide

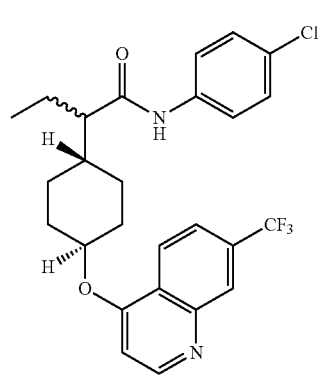 [SMILES: CCC(C(=O)Nc1ccc(Cl)cc1)[C@H]1CC[C@H](Oc2ccnc3cc(C(F)(F)F)ccc23)CC1]

Intermediate 83A

Ethyl 2-(1,4-dioxaspiro[4.5]decan-8-ylidene)acetate

Triethyl phosphonoacetate (21.79 ml, 109 mmol) was added to a suspension of sodium hydride (3.84 g, 96 mmol) in THF (64.0 ml) and 0° C. Reaction was stirred at room temperature for 30 minutes. After 30 minutes, the reaction was retooled to 0° C. and a solution of 1,4-dioxaspiro[4.5]decan-8-one (10 g, 64.0 mmol) in 5 mL THF was added. The reaction was then stirred at room temperature for 30 minutes prior to quenching with water. The mixture was extracted with DCM three times. Combined organic extracts were dried with sodium sulfate, filtered, and concentrated in vacuo. Crude residue was purified via silica gel chromatography to give Intermediate 83A (13.88 g, 61.3 mmol, 96% yield). TLC: product stains as purple spot in anisaldehyde (Rf=0.75 in 1:1 Hex/EtOAc). NMR (400 MHz, chloroform-d) δ: 5.65 (s, 1H), 4.13 (q, J=7.2 Hz, 2H), 3.92-3.99 (m, 4H), 2.94-3.02 (m, 2H), 2.31-2.40 (m, 2H), 1.71-1.79 (m, 4H), 1.26 (t, J=7.2 Hz, 3H)

Intermediate 83B

Ethyl 2-(1,4-dioxaspiro[4.5]decan-8-yl)acetate

Intermediate 83A (13.88 g, 61.3 mmol) was taken up in EtOAc (61.3 ml) and was added to a Parr hydrogenation bottle containing wet 10% palladium on carbon (1.306 g, 12.27 mmol) (54% w/w water) under an atmosphere of nitrogen. The reaction bottle was purged and back-filled with nitrogen three times, and then purged and backfilled three times with hydrogen. After filling the bottle with hydrogen to 50 psi, the bottle was placed in a Parr shaker and shaken. After 4 hours, the reaction was filtered over pressed CELITE® and concentrated in vacuo to give Intermediate 83B (13.78 g, 60.4 mmol, 98% yield). LC-MS Anal. Calc'd for $C_{12}H_{20}O_4$ 228.14. found [M+H] 299.1 $T_r$=0.83 min (Method A). $^1$H NMR (400 MHz, chloroform-d) δ: 4.11 (q, J=7.2 Hz, 2H), 3.88-3.95 (m, 4H), 2.21 (d, J=7.0 Hz, 2H), 1.83 (dqd, J=11.0, 7.5, 3.5 Hz, 1H), 1.68-1.78 (m, 4H), 1.50-1.61 (m, 2H), 1.27-1.35 (m, 2H), 1.24 (t, J=7.2 Hz, 3H).

Intermediate 83C

Ethyl 2-(1,4-dioxaspiro[4.5]decan-8-yl)butanoate

Diisopropylamine (2.347 ml, 16.63 mmol) taken up in dry THF (15.99 ml) (under $N_2$ atmosphere) and cooled to −78° C. n-BuLi (6.14 ml, 15.35 mmol) (2.5 M in hexanes) was added over ~5 minutes at −78° C. After stirring for 45 minutes, reaction was warmed to room temperature for 10 minutes and returned to −78° C. Then, 1,3-dimethyltetrahydropyrimidin-2(1H)-one (1.541 ml, 12.79 mmol) was added followed by a solution of Intermediate 83B (2.92 g, 12.79 mmol) in THF (15.99 ml) (dropwise over ~5 minutes). After 1 hour, iodoethane (1.125 ml, 14.07 mmol) (neat) was added dropwise over ~5 minutes. Reaction stirred another 2 hours at −78° C. before slowly warming to room temperature. The reaction was then stirred over night at room temperature. The reaction was quenched by pouring into 1:1 water/brine and extracting with EtOAc. The Combined organics washed with brine, dried with sodium sulfate, filtered and concentrated in vacuo. Crude residue was purified via silica gel column chromatography to give Intermediate 83C (2.27 g, 8.86 mmol, 69% yield). TLC: product stains as purple spot in anisaldehyde (Rf=0.80 in 1:1 Hex/EtOAc). $^1$H NMR (400 MHz, chloroform-d) δ: 4.14 (q, J=7.5 Hz, 2H), 3.88-3.95 (m, 4H), 2.09 (td, J=8.4, 5.6 Hz, 1H), 1.69-1.83 (m, 4H), 1.45-1.64 (m, 6H), 1.33-1.42 (m, 1H), 1.25 (t, J=7.1 Hz, 3H), 0.86 (t, J=7.5 Hz, 3H)

Intermediate 83D

Ethyl 2-(4-oxocyclohexyl)butanoate

Intermediate 83C (2.00 g, 7.80 mmol) was taken up in THF (39.0 ml) and Hydrochloric Acid, 1M (39.0 ml) was added. Reaction stirred at room temperature for 2 hours. The reaction was concentrated in vacuo, diluted with water and extracted with EtOAc. The combined organic extracts were dried with sodium sulfate, filtered and concentrated in vacuo. The crude material was purified on silica gel column chromatography to give Intermediate 83D (1.47 g, 6.92 mmol, 89% yield). TLC: product stains faintly pink in anisaldehyde (Rf=0.65 in 1:1 Hex/EtOAc). $^1$H NMR (400 MHz, chloroform-d) δ: 4.15 (q, J=7.1 Hz, 2H), 2.25-2.42 (m, 4H), 2.18 (ddd, J=9.3, 7.8, 5.2 Hz, 1H), 2.10 (ddt, J=13.1, 6.2, 3.3 Hz, 1H), 1.90-2.03 (m, 2H), 1.56-1.70 (m, 2H), 1.38-1.56 (m, 2H), 1.25 (t, J=7.2 Hz, 3H), 0.89 (t, J=7.4 Hz, 3H)

Intermediate 83E

Ethyl-2-((trans)-4-hydroxycyclohexyl)butanoate

Intermediate 83D (1.47 g, 6.92 mmol) was dissolved in EtOH (13.85 ml) and cooled to 0° C. $NaBH_4$ (0.314 g, 8.31 mmol) was added and the reaction was then allowed to stir at 0° C. for 1 hour. The reaction was quenched with saturated aqueous $NH_4Cl$ and extracted with EtOAc. Combined organic extracts were dried with sodium sulfate, filtered, and concentrated in vacuo. The crude material was purified via silica gel column chromatography to give Intermediate 83E (1.22 g, 5.69 mmol, 82% yield) along with (138 mg, 0.644 mmol, 9.30% yield) of the cis-isomer. $^1$H NMR (400 MHz, chloroform-d) δ: 4.14 (q, J=7.1 Hz, 2H), 3.53 (t, J=10.5 Hz, 1H), 1.92-2.08 (m, 2H), 1.80-1.89 (m, 1H), 1.63-1.70 (m, 1H), 1.52-1.62 (m, 4H), 1.37-1.52 (m, 2H), 1.26 (t, J=7.2 Hz, 3H), 0.95-1.17 (m, 2H), 0.87 (t, J=7.4 Hz, 3H).

Intermediate 83F

Ethyl 2-((trans)-4-((7-(trifluoromethyl)quinolin-4-yl)oxy)cyclohexyl)butanoate Intermediate 83E (100 mg, 0.467 mmol) was taken up in DMSO (933 µl) and NaH (22.40 mg, 0.933 mmol) as added slowly, portionwise at room temperature. After 1 hour, 4-chloro-7-(trifluoromethyl)quinoline (130 mg, 0.560 mmol) was added and the reaction was heated to 80° C. After 16 hours, the reaction was quenched with ammonium chloride and extracted with EtOAc. The combined organic extracts were dried with sodium sulfate, filtered, concentrated in vacuo. The crude residue was purified via silica gel column chromatography to give Intermediate 83F (91 mg, 0.222 mmol, 47.6% yield). LC-MS Anal. Calc'd for $C_{22}H_{26}F_3NO_3$ 409.19. found [M+H] 410.2 $T_r$=0.91 min (Method A).

Intermediate 83G

2-((trans)-4-((7-(Trifluoromethyl)quinolin-4-yl)oxy)cyclohexyl)butanoic acid Intermediate 83F (91 mg, 0.222 mmol) was taken up in THF (889 µl), water (889 µl), and MeOH (445 µl). Lithium hydroxide (53.2 mg, 2.223 mmol) added and reaction stirred at 60° C. for 40 hours. The reaction was concentrated in vacuo, diluted with water, acetic acid added (precipitate forms), the aqueous was extracted with EtOAc. Organics were combined, dried with sodium sulfate, filtered and concentrated in vacuo to give Intermediate 83G (85 mg, 0.223 mmol, 100% yield). LC-MS Anal. Calc'd for $C_{20}H_{22}F_3NO_3$ 381.16. found [M+H] 382.2 $T_r$=0.78 min (Method A).

Example 83

N-(4-Chlorophenyl)-2-((trans)-4-((7-(trifluoromethyl)quinolin-4-yl)oxy)cyclohexyl)butanamide Intermediate 83G (41 mg, 0.108 mmol) was placed under a nitrogen atmosphere and taken up in $SOCl_2$ (78 µl, 1.075 mmol). 1 drop of anhydrous DMF was added and the mixture was stirred for 1 h at room temperature. The mixture was then concentrated in vacuo and co-evaporation with toluene, in vacuo, was used to remove the remaining thionyl chloride. The crude acyl chloride was dissolved in DCM (1075 µl) under a nitrogen atmosphere and TEA (74.9 µl, 0.538 mmol) was added followed by 4-chloroaniline (20.57 mg, 0.161 mmol). The mixture was stirred at room temperature for 30 minutes. The reaction was concentrated in vacuo, taken up in DMF, filtered, and purified via preparative HPLC to give Example 83 (14.4 mg, 0.029 mmol, 27% yield). LC-MS Anal. Calc'd for $C_{26}H_{26}ClF_3N_2O_2$ 490.16. found [M+H] 491.2 $T_r$=0.94 min (Method A). $^1$H NMR (500 MHz, DMSO-$d_6$) δ: 10.07 (s, 1H), 8.82 (d, J=5.1 Hz, 1H), 8.32 (d, J=8.6 Hz, 1H), 8.25 (s, 1H), 7.80 (d, J=8.7 Hz, 1H), 7.67 (d, J=8.5 Hz, 2H), 7.35 (d, J=8.5 Hz, 2H), 7.29 (d, J=5.0 Hz, 1H), 4.66 (t, J=10.1 Hz, 1H), 2.10-2.27 (m, 3H), 1.97 (d, J=11.4 Hz, 1H), 1.73 (d, J=13.2 Hz, 1H), 1.41-1.65 (m, 5H), 1.28-1.41 (m, 1H), 1.21 (d, J=10.4 Hz, 1H), 0.85 (t, J=7.1 Hz, 3H).

Enantiomer 1 and Enantiomer 2

Enantiomer 1

Example 83 (a)

N-(4-Chlorophenyl)-2-((trans)-4-((7-(trifluoromethyl)quinolin-4-yl)oxy)cyclohexyl)-2-butanamide Homochiral, Absolute Stereochemistry not Determined

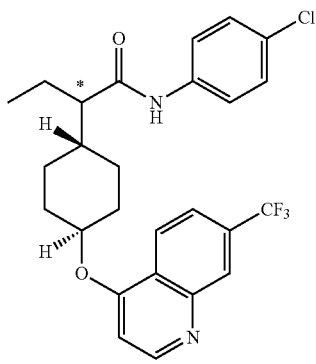 [SMILES: CCC(C(=O)Nc1ccc(Cl)cc1)[C@H]1CC[C@H](Oc2ccnc3cc(C(F)(F)F)ccc23)CC1]

Enantiomer 2

Example 83 (b)

N-(4-Chlorophenyl)-2-((trans)-4-((7-(trifluoromethyl)quinolin-4-yl)oxy)cyclohexyl)-2-butanamide Homochiral, Absolute Stereochemistry not Determined

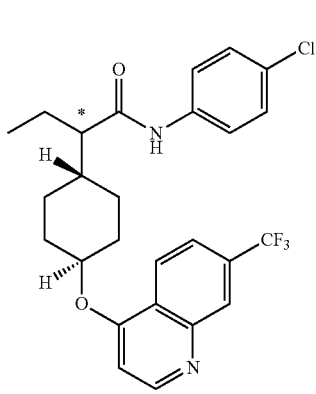 [SMILES: CCC(C(=O)Nc1ccc(Cl)cc1)[C@H]1CC[C@H](Oc2ccnc3cc(C(F)(F)F)ccc23)CC1]

Example 83(a), Enantiomer 1, and Example 83(b), Enantiomer 2

Chiral separation of the racemic sample (Method C) gave Enantiomer 1 $T_r$=3.611 min (Method D) and Enantiomer 2 $T_r$=5.106 min (Method D) Absolute stereochemistry was not determined.

Example 83(a)

Enantiomer 1

MS (ES): m/z=491.1 [M+H]$^+$. $T_r$=2.529 min (Method B). $^1$H NMR (500 MHz, DMSO-$d_6$) δ: 10.14 (s, 1H), 8.78 (d, J=5.0 Hz, 1H), 8.32 (d, J=8.6 Hz, 1H), 8.23 (s, 1H), 7.79 (d, J=8.8 Hz, 1H), 7.61 (d, J=8.8 Hz, 2H), 7.33 (d, J=8.7 Hz, 2H), 7.21 (d, J=5.3 Hz, 1H), 4.61 (br. s., 1H), 2.06-2.23 (m, 3H), 1.94 (d, J=13.0 Hz, 1H), 1.69 (d, J=12.0 Hz, 1H), 1.36-1.62 (m, 5H), 1.30 (d, J=13.2 Hz, 1H), 1.11-1.26 (m, 1H), 0.81 (t, J=7.1 Hz, 3H)

Example 83(b)

Enantiomer 2

MS (ES): m/z=491.1 [M+H]$^+$. $T_r$=2.545 min (Method B). $^1$H NMR (500 MHz, DMSO-$d_6$) δ: 10.13 (s, 1H), 8.78 (d, J=5.1 Hz, 1H), 8.32 (d, J=8.7 Hz, 1H), 8.23 (s, 1H), 7.79 (d, J=8.7 Hz, 1H), 7.62 (d, J=8.8 Hz, 2H), 7.33 (d, J=8.8 Hz, 2H), 7.22 (d, J=5.2 Hz, 1H), 4.62 (br. s., 1H), 2.08-2.25 (m, 3H), 1.95 (d, J=13.4 Hz, 1H), 1.70 (d, J=11.6 Hz, 1H), 1.39-1.62 (m, 5H), 1.30 (d, J=12.3 Hz, 1H), 1.18 (d, J=11.4 Hz, 1H), 0.81 (t, J=7.1 Hz, 3H)

Example 84

(±)-N-(4-Chlorophenyl)-2-((trans)-4-((2-(trifluoromethyl)quinolin-4-yl)oxy)cyclohexyl)butanamide

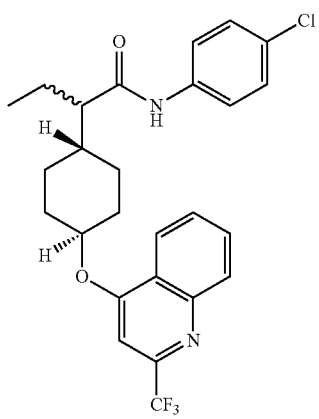 [SMILES: CCC(C(=O)Nc1ccc(Cl)cc1)[C@H]1CC[C@H](Oc2cc(C(F)(F)F)nc3ccccc23)CC1]

Example 84

(±)-N-(4-Chlorophenyl)-2-((trans)-4-((2-(trifluoromethyl)quinolin-4-yl)oxy)cyclohexyl)butanamide Example 84 was prepared from Intermediate 83E and the analogous procedures outlined to make 83F, 83G, and Example 83 except that 4-chloro-2-(trifluoromethyl)quinoline was used in part F. LC-MS Anal. Calc'd for $C_{26}H_{26}ClF_3N_2O_2$ 490.16. found [M+H] 491.2 $T_r$=1.20 min (Method A). $^1$H NMR (500 MHz, DMSO-$d_6$) δ: 10.07 (s, 1H), 8.20 (d, J=8.2 Hz, 1H), 8.05 (d, J=8.7 Hz, 1H), 7.84-7.91 (m, 1H), 7.63-7.74 (m, 3H), 7.48 (s, 1H), 7.35 (d, J=8.7 Hz, 2H), 4.79-4.90 (m, 1H), 2.10-2.27 (m, 3H), 1.96 (d, J=13.1 Hz, 1H), 1.72 (d, J=12.0 Hz, 1H), 1.44-1.63 (m, J=7.6 Hz, 5H), 1.32-1.42 (m, 1H), 1.20-1.32 (m, 1H), 0.85 (t, J=7.1 Hz, 3H).

Example 85

(±)-N-(4-Chlorophenyl)-2-((trans)-4-(quinolin-4-yloxy)cyclohexyl)butanamide

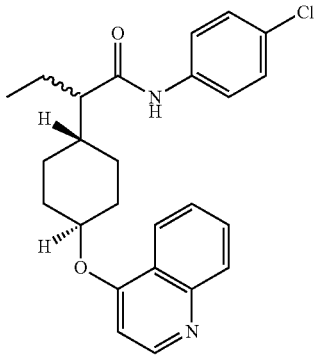 [SMILES: CCC(C(=O)Nc1ccc(Cl)cc1)[C@H]1CC[C@H](Oc2ccnc3ccccc23)CC1]

Example 85

(±)-N-(4-Chlorophenyl)-2-((trans)-4-(quinolin-4-yloxy)cyclohexyl)butanamide

Example 85 was prepared from Intermediate 83E and the analogous procedures outlined to make 83F, 83G, and Example 83 except that 4-bromo-quinoline was used in part F. LC-MS Anal. Calc'd for $C_{25}H_{27}ClN_2O_2$ 422.18. found [M+H] 423.2 $T_r$=0.87 min (Method A). $^1$H NMR (500 MHz, DMSO-$d_6$) δ: 10.14 (s, 1H), 8.65 (d, J=5.2 Hz, 1H), 8.11 (d, J=8.2 Hz, 1H), 7.91 (d, J=8.4 Hz, 1H), 7.72 (t, J=7.6 Hz, 1H), 7.63 (d, J=8.7 Hz, 2H), 7.54 (t, J=7.5 Hz, 1H), 7.34 (d, J=8.6 Hz, 2H), 7.06 (d, J=5.2 Hz, 1H), 4.58 (t, J=10.1 Hz, 1H), 2.08-2.26 (m, 3H), 1.95 (d, J=12.6 Hz, 1H), 1.70 (d, J=12.9 Hz, 1H), 1.39-1.66 (m, 5H), 1.31 (q, J=11.9 Hz, 1H), 1.10-1.25 (m, J=12.4 Hz, 1H), 0.82 (t, J=7.2 Hz, 3H).

Example 86

N-(4-Chlorophenyl)-2-((trans)-4-((8-(trifluoromethyl)quinolin-4-yl)oxy)cyclohexyl)butanamide

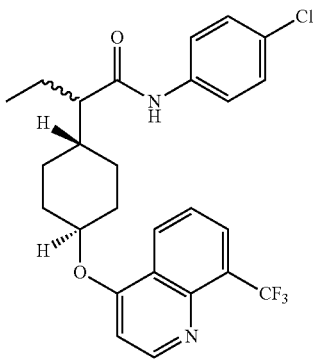 [SMILES: CCC(C(=O)Nc1ccc(Cl)cc1)[C@H]1CC[C@H](Oc2ccnc3c(C(F)(F)F)cccc23)CC1]

Example 86 was prepared from Intermediate 83E and the analogous procedures outlined to make 83F, 83G, and Example 83 except that that 4-chloro-8-(trifluoromethyl)quinoline was used in part F. LC-MS Anal. Calc'd for $C_{26}H_{26}ClF_3N_2O_2$ 490.16. found [M+H] 491.2 $T_r$=1.03 min (Method A). $^1$H NMR (500 MHz, DMSO-$d_6$) δ: 10.13 (s, 1H), 8.77 (d, J=5.2 Hz, 1H), 8.39 (d, J=8.4 Hz, 1H), 8.12 (d, J=7.2 Hz, 1H), 7.58-7.67 (m, 3H), 7.33 (d, J=8.7 Hz, 2H), 7.19 (d, J=5.4 Hz, 1H), 4.61 (t, J=10.4 Hz, 1H), 2.08-2.24 (m, 3H), 1.94 (d, J=12.0 Hz, 1H), 1.69 (d, J=13.8 Hz, 1H), 1.37-1.63 (m, 5H), 1.24-1.37 (m, J=12.5 Hz, 1H), 1.11-1.24 (m, J=11.1 Hz, 1H), 0.81 (t, J=7.2 Hz, 3H)

Example 87

2-(4-((R)-3-((4-Chlorophenyl)amino)-2-((cis)-4-(6-fluoroquinolin-4-yl)cyclohexyl)-3-oxopropyl)phenyl)propanoic acid

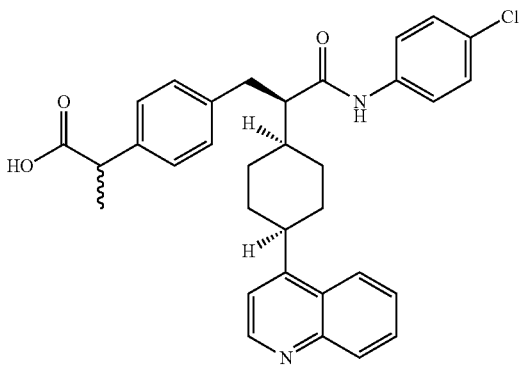 [SMILES: CC(C(=O)O)c1ccc(C[C@@H](C(=O)Nc2ccc(Cl)cc2)[C@H]2CC[C@@H](c3ccnc4ccccc43)CC2)cc1]

Example 87

2-(4-((R)-3-((4-Chlorophenyl)amino)-2-((cis)-4-(6-fluoroquinolin-4-yl)cyclohexyl)-3-oxopropyl)phenyl)propanoic acid Racemic Example 87 can be made utilizing General procedures K with 4-chloroquiline, B, E, and L followed by alkylation with Intermediate 137A using the procedure to make 137B followed by the analogous procedures for intermediates 137C, D, and Example 137.

Enantiomer 1 and Enantiomer 2

Enantiomer 1

Example 87(a)

2-(4-((R)-3-((4-Chlorophenyl)amino)-2-((cis)-4-(6-fluoroquinolin-4-yl)cyclohexyl)-3-oxopropyl)phenyl)-2-propanoic acid Homochiral, Stereochemistry not Determined

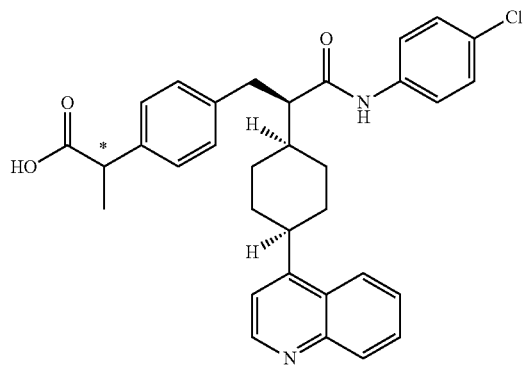 [SMILES: CC(C(=O)O)c1ccc(C[C@@H](C(=O)Nc2ccc(Cl)cc2)[C@H]2CC[C@@H](c3ccnc4ccccc43)CC2)cc1]

Enantiomer 2

Example 87(b)

2-(4-((R)-3-((4-Chlorophenyl)amino)-2-((cis)-4-(6-fluoroquinolin-4-yl)cyclohexyl)-3-oxopropyl)phenyl)-2-propanoic acid Homochiral, Stereochemistry not Determined

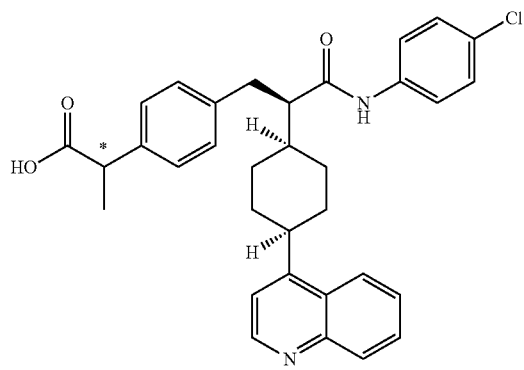 [SMILES: CC(C(=O)O)c1ccc(C[C@@H](C(=O)Nc2ccc(Cl)cc2)[C@H]2CC[C@@H](c3ccnc4ccccc43)CC2)cc1]

Example 87 (a) Enantiomer 1 and Example 87(b) Enantiomer 2

Chiral separation of the racemic sample (Method E) gave Enantiomer 1 $T_r$=10.161 min (Method F) and Enantiomer 2 $T_r$=13.160 min (Method F) Absolute stereochemistry was not determined.

Example 87 (a)

Enantiomer 1

MS (ES): m/z=541.3 [M+H]$^+$. $T_r$=0.84 min (Method A). $^1$H NMR (400 MHz, chloroform-d) δ: 8.78 (d, J=4.6 Hz, 1H), 8.09 (m, 2H), 7.69 (ddd, J=8.4, 7.0, 1.2 Hz, 1H), 7.58 (ddd, J=8.4, 7.0, 1.1 Hz, 1H), 7.30 (d, J=4.5 Hz, 1H), 7.11-7.20 (m, 8H), 6.91 (s, 1H), 3.72-3.78 (m, 1H), 3.02 (dd, J=13.2, 3.4 Hz, 1H), 2.79-2.89 (m, J=13.0 Hz, 1H), 2.62 (td, J=10.8, 3.5 Hz, 1H), 2.28-2.37 (m, 1H), 1.71-2.15 (m, 9H), 1.40 (d, J=7.1 Hz, 3H)

Example 87(b)

Enantiomer 2

MS (ES): m/z=541.3 [M+H]$^+$. $T_r$=0.84 min (Method A). $^1$H NMR (400 MHz, chloroform-d) δ: 8.82 (d, J=4.6 Hz, 1H), 8.05-8.14 (m, 2H), 7.70 (ddd, J=8.3, 7.0, 1.2 Hz, 1H), 7.58 (ddd, J=8.3, 6.9, 1.2 Hz, 1H), 7.33 (d, J=4.6 Hz, 1H), 7.09-7.20 (m, 8H), 6.78 (s, 1H), 3.72-3.77 (m, 1H), 3.02 (dd, J=13.1, 3.5 Hz, 1H), 2.83 (t, J=12.2 Hz, 1H), 2.61 (td, J=10.9, 3.5 Hz, 1H), 2.29-2.37 (m, 1H), 1.72-2.16 (m, 9H), 1.40 (d, J=7.2 Hz, 3H)

Example 88

(±)-N-(4-Chlorophenyl)-2-((cis)-4-((2-(trifluoromethyl)quinolin-4-yl)oxy)cyclohexyl)butanamide

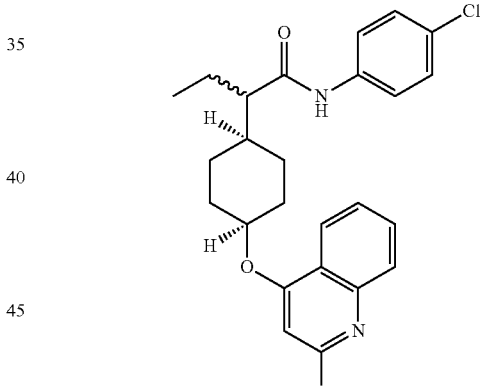

Intermediate 88A

Ethyl 2-((cis)-4-((2-(trifluoromethyl)quinolin-4-yl)oxy)cyclohexyl)butanoate

Intermediate 83E (300 mg, 1.400 mmol) was dissolved in THF (5600 μl) and 2-(trifluoromethyl)quinolin-4-ol (656 mg, 3.08 mmol) and triphenylphosphine (808 mg, 3.08 mmol) were added. Solution was cooled to 0° C. in an ice bath. Diisopropyl azodicarboxylate (599 μl, 3.08 mmol) was added and the reaction was allowed to stir at room temperature once addition was complete. Stirred at room temperature overnight. Then, the reaction was concentrated in vacuo and purified via silica gel column chromatography to give Intermediate 88A (383 mg, 0.935 mmol, 66.8% yield). LC-MS Anal. Calc'd for $C_{22}H_{26}F_3NO_3$ 409.19. found [M+H] 410.2 $T_r$=1.22 min (Method A).

Intermediate 88B

2-((cis)-4-((2-(Trifluoromethyl)quinolin-4-yl)oxy)cyclohexyl)butanoic acid

Intermediate 88A (383 mg, 0.935 mmol) was taken up in THF (748 μl), Water (748 μl), and MeOH (374 μl). Lithium hydroxide (224 mg, 9.35 mmol) added and reaction stirred at 60° C. overnight. After 16 hours, more Lithium hydroxide (224 mg, 9.35 mmol) was added and reaction heated another 24 hours. The reaction was concentrated in vacuo, diluted with water, acidified with AcOH and extracted with EtOAc. The aqueous layer was extracted again with 7:3 chloroform:propanol. The combined organic extracts were dried with sodium sulfate, filtered, and concentrated in vacuo to give Intermediate 88B (348 mg, 0.912 mmol, 98% yield). LC-MS Anal. Calc'd for $C_{20}H_{22}F_3NO_3$ 381.16. found [M+H] 382.3 $T_r$=1.04 min (Method A).

Example 88

N-(4-Chlorophenyl)-2-((cis)-4-((2-(trifluoromethyl)quinolin-4-yl)oxy)cyclohexyl)butanamide Intermediate 88B (50 mg, 0.131 mmol) was placed under a nitrogen atmosphere and taken up in $SOCl_2$ (96 μl, 1.311 mmol). 1 drop of anhydrous DMF was added and the mixture was stirred for 1 hour at room temperature. The mixture was then concentrated in vacuo and co-evaporation with toluene, in vacuo, was used to remove the remaining thionyl chloride. The crude acyl chloride was dissolved in DCM (1311 μl) under a nitrogen atmosphere and TEA (91 μl, 0.655 mmol) was added followed by 4-chloroaniline (25.09 mg, 0.197 mmol). The mixture was stirred at room temperature for 30 minutes. The reaction was concentrated in vacuo, taken up in DMF, filtered, and purified via preparative HPLC to give Example 88 (38.0 mg, 0.077 mmol, 59%). LC-MS Anal. Calc'd for $C_{26}H_{26}ClF_3N_2O_2$ 490.16. found [M+H] 491.2 $T_r$=1.18 min (Method A). $^1H$ NMR (500 MHz, DMSO-$d_6$) δ: 10.09 (s, 1H), 8.21 (d, J=8.2 Hz, 1H), 8.05 (d, J=8.5 Hz, 1H), 7.87 (t, J=7.5 Hz, 1H), 7.66 (t, J=7.6 Hz, 1H), 7.61 (d, J=8.8 Hz, 2H), 7.36 (s, 1H), 7.32 (d, J=8.7 Hz, 2H), 5.13 (br. s., 1H), 2.17 (br. s., 1H), 2.03 (br. s., 2H), 1.60-1.78 (m, 4H), 1.46-1.60 (m, 4H), 1.34-1.46 (m, 1H), 0.81 (t, J=7.2 Hz, 3H)

Enantiomer 1 and Enantiomer 2

Enantiomer 1

Example 88 (a)

N-(4-Chlorophenyl)-2-((cis)-4-((2-(trifluoromethyl)quinolin-4-yl)oxy)cyclohexyl)butanamide Homochiral, Absolute Stereochemistry not Determined

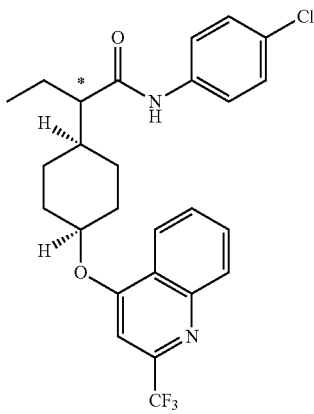 [SMILES: CCC(C(=O)Nc1ccc(Cl)cc1)[C@H]1CC[C@@H](Oc2cc(C(F)(F)F)nc3ccccc23)CC1]

Enantiomer 2

Example 88(b)

N-(4-Chlorophenyl)-2-((cis)-4-((2-(trifluoromethyl)quinolin-4-yl)oxy)cyclohexyl)butanamide Homochiral, Absolute Stereochemistry not Determined

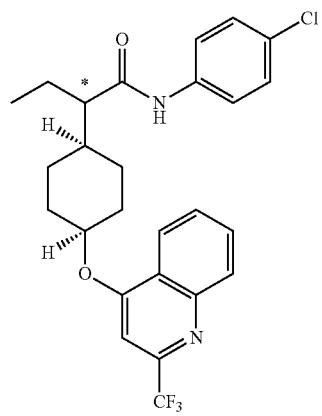 [SMILES: CCC(C(=O)Nc1ccc(Cl)cc1)[C@H]1CC[C@@H](Oc2cc(C(F)(F)F)nc3ccccc23)CC1]

Example 88(a) Enantiomer 1 and Example 88(b) Enantiomer 2

Chiral separation of the racemic sample (Method G) gave Enantiomer 1 $T_r$=3.911 min (Method H) and Enantiomer 2 $T_r$=4.551 min (Method H) Absolute stereochemistry was not determined.

Example 88(a)

Enantiomer 1

MS (ES): m/z=491.3 [M+H]$^+$. $T_r$=2.549 min (Method B). $^1H$ NMR (500 MHz, DMSO-$d_6$) δ: 10.05 (s, 1H), 8.22 (d, J=8.2 Hz, 1H), 8.06 (d, J=8.4 Hz, 1H), 7.88 (t, J=7.5 Hz, 1H), 7.68 (t, J=7.5 Hz, 1H), 7.63 (d, J=8.7 Hz, 2H), 7.38 (s, 1H), 7.33 (d, J=8.7 Hz, 2H), 5.15 (br. s., 1H), 2.19 (br. s., 1H), 2.04 (d, J=7.1 Hz, 2H), 1.35-1.78 (m, 9H), 0.83 (t, J=7.2 Hz, 3H)

Example 88(b)

Enantiomer 2

MS (ES): m/z=491.3 [M+H]$^+$. $T_r$=2.541 min (Method B). $^1H$ NMR (500 MHz, DMSO-$d_6$) δ: 10.05 (s, 1H), 8.21 (d, J=8.2 Hz, 1H), 8.06 (d, J=8.5 Hz, 1H), 7.87 (t, J=7.5 Hz, 1H), 7.67 (t, J=7.6 Hz, 1H), 7.63 (d, J=8.7 Hz, 2H), 7.37 (s, 1H), 7.33 (d, J=8.7 Hz, 2H), 5.15 (br. s., 1H), 2.18 (br. s., 1H), 1.98-2.10 (m, J=5.0 Hz, 2H), 1.36-1.80 (m, 9H), 0.83 (t, J=7.2 Hz, 3H)

Example 89

(±)-N-(4-Chlorophenyl)-2-((cis)-4-((6-(trifluoromethyl)quinolin-4-yl)oxy)cyclohexyl)butanamide

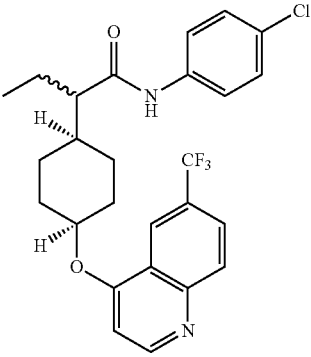 [SMILES: CCC(C(=O)Nc1ccc(Cl)cc1)[C@H]1CC[C@@H](Oc2ccnc3ccc(C(F)(F)F)cc23)CC1]

Example 89

(±)-N-(4-Chlorophenyl)-2-((cis)-4-((6-(trifluoromethyl)quinolin-4-yl)oxy)cyclohexyl)butanamide Example 89 was prepared from Intermediate 83E and the analogous procedures outlined to make 88F, 88G, and Example 88 except that 4-hydroxy-6-(trifluoromethyl)quinoline was used in part F. LC-MS Anal. Calc'd for $C_{26}H_{26}ClF_3N_2O_2$ 490.16. found [M+H] 491.3 $T_r$=0.90 min (Method A). $^1$H NMR (500 MHz, DMSO-$d_6$) δ: 10.06 (s, 1H), 8.83 (d, J=5.2 Hz, 1H), 8.43 (s, 1H), 8.14 (d, J=8.8 Hz, 1H), 8.00 (d, J=8.2 Hz, 1H), 7.62 (d, J=8.7 Hz, 2H), 7.30 (d, J=8.7 Hz, 2H), 7.17 (d, J=5.3 Hz, 1H), 4.98 (br. s., 1H), 2.22 (br. s., 1H), 2.05 (br. s., 2H), 1.72 (d, J=13.1 Hz, 4H), 1.46-1.62 (m, 4H), 1.41 (d, J=11.5 Hz, 1H), 0.83 (t, J=7.2 Hz, 3H)

Enantiomer 1 and Enantiomer 2

Enantiomer 1

Example 89(a)

N-(4-Chlorophenyl)-2-((cis)-4-((6-(trifluoromethyl)quinolin-4-yl)oxy)cyclohexyl)butanamide Homochiral, Absolute Stereochemistry not Determined

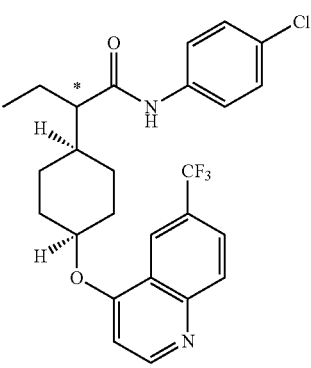 [SMILES: CCC(C(=O)Nc1ccc(Cl)cc1)[C@H]1CC[C@@H](Oc2ccnc3ccc(C(F)(F)F)cc23)CC1]

Enantiomer 2

Example 89(b)

N-(4-Chlorophenyl)-2-((cis)-4-((6-(trifluoromethyl)quinolin-4-yl)oxy)cyclohexyl)butanamide Homochiral, Absolute Stereochemistry not Determined

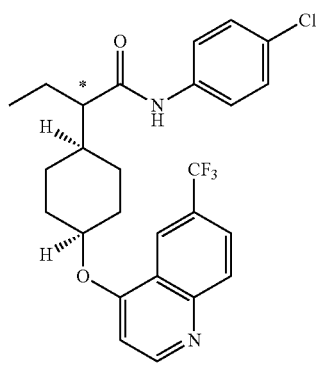 [SMILES: CCC(C(=O)Nc1ccc(Cl)cc1)[C@H]1CC[C@@H](Oc2ccnc3ccc(C(F)(F)F)cc23)CC1]

Example 89(a) Enantiomer 1 and Example 89(b) Enantiomer 2

Chiral separation of the racemic sample (Method I) gave Enantiomer 1 $T_r$=6.320 min (Method J) and Enantiomer 2 $T_r$=7.500 min (Method J) Absolute stereochemistry was not determined.

Example 89(a)

Enantiomer 1

MS (ES): m/z=491.3 [M+H]$^+$. $T_r$=2.418 min (Method B). $^1$H NMR (500 MHz, DMSO-$d_6$) δ: 10.05 (s, 1H), 8.82 (d, J=5.3 Hz, 1H), 8.43 (s, 1H), 8.13 (d, J=8.8 Hz, 1H), 7.99 (d, J=8.8 Hz, 1H), 7.61 (d, J=8.8 Hz, 2H), 7.29 (d, J=8.8 Hz, 2H), 7.16 (d, J=5.4 Hz, 1H), 4.97 (br. s., 1H), 2.22 (br. s., 1H), 2.04 (br. s., 2H), 1.34-1.79 (m, 9H), 0.83 (t, J=7.2 Hz, 3H)

Example 89(b)

Enantiomer 2

MS (ES): m/z=491.3 [M+H]$^+$. $T_r$=2.418 min (Method B). $^1$H NMR (500 MHz, DMSO-$d_6$) δ: 10.06 (s, 1H), 8.84 (d, J=5.2 Hz, 1H), 8.44 (s, 1H), 8.14 (d, J=8.8 Hz, 1H), 7.99 (d, J=7.6 Hz, 1H), 7.63 (d, J=8.8 Hz, 2H), 7.30 (d, J=8.8 Hz, 2H), 7.17 (d, J=5.3 Hz, 1H), 4.98 (br. s., 1H), 2.23 (br. s., 1H), 2.01-2.11 (m, J=5.4 Hz, 2H), 1.37-1.79 (m, 9H), 0.84 (t, J=7.2 Hz, 3H).

Example 90

N-(4-Chlorophenyl)-2-(4-((4-chloroquinolin-6-yl)oxy)piperidin-1-yl)acetamide

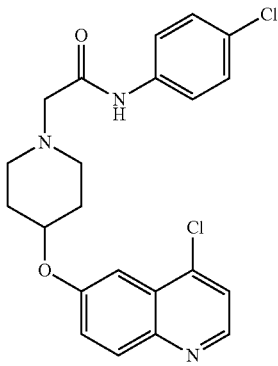 [SMILES: O=C(CN1CCC(Oc2ccc3nccc(Cl)c3c2)CC1)Nc1ccc(Cl)cc1]

Intermediate 90A tert-Butyl 4-((4-chloroquinolin-6-yl)oxy)piperidine-1-carboxylate, and Intermediate 90B. tert-Butyl 4-((6-fluoroquinolin-4-yl)oxy)piperidine-1-carboxylate A solution of tert-butyl 4-hydroxypiperidine-1-carboxylate (0.242 g, 1.200 mmol) in 1 mL of dioxane was treated with potassium hexamethyldisilazide (1.200 ml, 1.200 mmol) in THF. The resulting hazy solution was stirred 5 min. at room temperature then treated with 4-chloro-6-fluoroquinoline (0.182 g, 1 mmol) in 1 mL of dioxane. The reaction was brought to 60° C. and stirred for 30 min. then overnight at room temperature. The reaction was quenched with 0.1 mL of glacial HOAc and chromatographed on silica gel (3:1 dichloromethane-EtOAc then EtOAc then 95:5 EtOAc-EtOH). Concentration of the appropriate (high $R_f$) fractions afforded Intermediate 90A: tert-butyl 4-((4-chloroquinolin-6-yl)oxy)piperidine-1-carboxylate (0.11 g, 30% yield) as a colorless oil. MS (ES): m/z=363 [M+H]$^+$. $t_R$=0.93 min (Method A). Concentration of the low $R_f$ fractions afforded Intermediate 90B: tert-butyl 4-((6-fluoroquinolin-4-yl)oxy)piperidine-1-carboxylate (0.09 g, 26% yield) as a pale yellow oil. MS (ES): m/z=347 [M+H]$^+$. $t_R$=0.77 min (Method A).

Intermediate 90C

4-Chloro-6-(piperidin-4-yloxy)quinoline

A mixture of Intermediate 90A (0.1 g, 0.276 mmol) in HCl/dioxane (1.033 ml, 4.13 mmol) was stirred at RT. The starting material oiled out onto the glass after addition of HCl. It did not dissolve even after sonication, so ~0.5 mL of dichloromethane was added, and this mixture was stirred for 3 hours. During this time, dissolution of the oil appears to have occurred, and a white precipitate formed. The reaction was pumped to dryness to afford 0.08 g (97%) of Intermediate 90C, HCl as an off-white powder. MS (ES): m/z=263 [M+H]$^+$. $t_R$=0.50 min (Method A).

Intermediate 90D

Ethyl 2-(4-((4-chloroquinolin-6-yl)oxy)piperidin-1-yl)acetate

A suspension of 4-chloro-6-(piperidin-4-yloxy)quinoline, HCl (0.06 g, 0.201 mmol) and potassium carbonate (0.097 g, 0.702 mmol) in DMF (0.5 mL) was treated with ethyl bromoacetate (0.045 mL, 0.401 mmol), and the resulting mixture was stirred 4 hours at room temperature. This mixture was neutralized with glacial HOAc, and the residue was purified by flash chromatography (1:1 EtOAc—CH$_2$Cl$_2$ up to EtOAc). Concentration of the appropriate fractions Intermediate 90D as a colorless oil. MS (ES): m/z=349 [M+H]$^+$. $t_R$=0.56 min (Method A).

Intermediate 90E 2-(4-((4-Chloroquinolin-6-yl)oxy)piperidin-1-yl)acetic acid, 2 HCl A solution of 0.04 g of Intermediate 90D in THF (2 mL) was treated with lithium hydroxide (0.04 g, 1.670 mmol) in water (1 mL). Methanol, ~1 mL, was added to give a single phase, and the reaction was stirred 2 hours at room temperature. Solvent was removed under a stream of nitrogen, and the resulting slurry was treated with ~3 mL of water to dissolve. Aq. HCl was added slowly, eventually bringing the solution pH down to ~4, but product did not precipitate at any point. The pH was brought back up to ~7.5 with aq. sodium bicarbonate. Brine was added, but still no precipitate. This solution was ext. six times with 3:1 chloroform-IPA, and the comb. org. exts. were stripped to afford an oil. This was treated with 5 eq. of HCl/dioxane, and a drop of water was added to dissolve. This solution was then lyophilized to afford Intermediate 90E (0.04 g, 92%) as a greenish-brown solid. MS (ES): m/z=321 [M+H]$^+$. $t_R$=0.48 min (Method A).

Example 90

N-(4-Chlorophenyl)-2-(4-((4-chloroquinolin-6-yl)oxy)piperidin-1-yl)acetamide

A solution of Intermediate 90E (0.04 g, 0.102 mmol) and 4-chloroaniline (0.014 g, 0.112 mmol) and triethylamine (0.057 mL, 0.406 mmol) in DMF (1 mL) was treated with BOP (0.067 g, 0.152 mmol). This solution was stirred 2 h at RT then purified by prep. HPLC. Concentration of the appropriate fraction afforded material with a purity of ~90%. This material was further purified by flash chromatography. Concentration of the appropriate fractions then lyophilization afforded Example 90 (0.016 g, 36% yield) as a white powder. MS (ES): m/z=430 [M+H]+. $t_R$=0.73 min (Method A). $^1$H NMR (400 MHz, DMSO-d$_6$) δ 9.88 (s, 1H), 8.69 (d, 1H, J=4.7 Hz), 8.04 (d, 1H, J=9.2 Hz), 7.69-7.74 (m, 3H), 7.57 (dd, 1H, J=9.2, 2.8 Hz), 7.50 (d, 1H, J=2.7 Hz), 7.36-7.39 (m, 2H), 4.69-4.76 (m, 1H), 3.19 (s, 2H), 2.78-2.86 (m, 2H), 2.06-2.13 (m, 2H), 1.81-1.89 (m, 2H). Note: one signal at ~2.55 ppm is largely obscured by solvent.

Example 91

(±)-N-(4-Chlorophenyl)-2-(4-((4-chloroquinolin-6-yl)oxy)piperidin-1-yl)propanamide

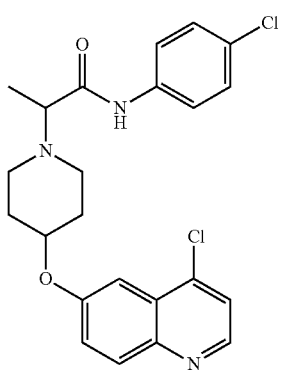 [SMILES: CC(C(=O)Nc1ccc(Cl)cc1)N1CCC(Oc2ccc3nccc(Cl)c3c2)CC1]

Intermediate 91A (±)-Ethyl 2-(4-((4-chloroquinolin-6-yl)oxy)piperidin-1-yl)propanoate (±)-Ethyl 2-(4-((4-chloroquinolin-6-yl)oxy)piperidin-1-yl)propanoate was prepared as a pale yellow oil in 97% yield from 90C and ethyl 2-bromopropionate using the procedure for the conversion of 90C to 90D except that the reaction was performed at 60° C. and no chromatography was performed. MS (ES): m/z=363 [M+H]$^+$. $t_R$=0.58 min (Method A).

Intermediate 91B (±)-2-(4-((4-Chloroquinolin-6-yl)oxy)piperidin-1-yl)propanoic acid (±)-2-(4-((4-Chloroquinolin-6-yl)oxy)piperidin-1-yl)propanoic acid was prepared as an off-white foam in 93% yield from 91A using the procedure for the conversion of 90D to 90E except that the isolated material was not converted to the HCl salt. MS (ES): m/z=335 [M+H]$^+$. $t_R$=0.49 min (Method A).

Example 91

(±)-N-(4-Chlorophenyl)-2-(4-((4-chloroquinolin-6-yl)oxy)piperidin-1-yl)propanamide (±)-N-(4-Chlorophenyl)-2-(4-((4-chloroquinolin-6-yl)oxy)piperidin-1-yl)propanamide was prepared as the trifluoroacetate salt in 57% yield after preparative HPLC purification from 91B using the procedure for the conversion of 90E to Example 90. MS (ES): m/z=444 [M+H]+. $t_R$=0.73 min (Method A). $^1$H NMR (400 MHz, DMSO-d$_6$) δ 10.83 (s, 1H), 8.69 (d, 1H, J=4.4 Hz), 8.07 (d, 1H, J=9.1 Hz), 7.73 (d, 1H, J=4.2 Hz), 7.59-7.65 (m, 3H), 7.56 (s, 1H), 7.49 (d, 2H, J=8.1 Hz), 4.63-4.67 (m, 1H), 3.10-3.70 (m, 5H), 2.01-2.39 (m, 4H), 1.66 (d, 3H, J=6.7 Hz).

Example 92

(±)-2-(4-((4-Chloroquinolin-6-yl)oxy)piperidin-1-yl)-N-(p-tolyl)propanamide

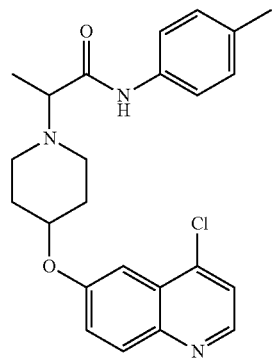 [SMILES: Cc1ccc(NC(=O)C(C)N2CCC(Oc3ccc4nccc(Cl)c4c3)CC2)cc1]

Example 92

(±)-2-(4-((4-Chloroquinolin-6-yl)oxy)piperidin-1-yl)-N-(p-tolyl)propanamide (±)-2-(4-((4-chloroquinolin-6-yl)oxy)piperidin-1-yl)-N-(p-tolyl)propanamide was prepared as the HCl salt in 77% yield after preparative HPLC purification and salt exchange from 91B and p-toluidine using the procedure for the conversion of 90E to Example 90. MS (ES): m/z=424 [M+H]+. $t_R$=0.71 min (Method A). $^1$H NMR (400 MHz, DMSO-d$_6$) δ 11.02 (s, not integrated), 10.91 (s, not integrated), 10.72 (br. s, not integrated), 10.57 (br. s, not integrated), 8.78 (s, 1H), 8.13 (t, 1H, J=9.8 Hz), 7.83 (s, 1H), 7.52-7.70 (m, 4H), 7.19 (d, 2H, J=7.2 Hz), 4.27-4.35 (m, 1H), 3.25-3.77 (m, 5H), 1.96-2.41 (m, 7H), 1.62 (d, 3H, J=5.1 Hz).

Enantiomer 1 and Enantiomer 2 of Racemic Example 91

Enantiomer 1

Example 93

N-(4-Chlorophenyl)-2-(4-((4-chloroquinolin-6-yl)oxy)piperidin-1-yl)propanamide

Homochiral, Absolute Stereochemistry was not Determined

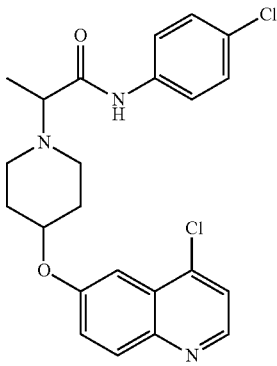 [SMILES: CC(C(=O)Nc1ccc(Cl)cc1)N1CCC(Oc2ccc3nccc(Cl)c3c2)CC1]

Example 94

Enantiomer 2

N-(4-Chlorophenyl)-2-(4-((4-chloroquinolin-6-yl)oxy)piperidin-1-yl)propanamide

Homochiral, Absolute Stereochemistry was not Determined

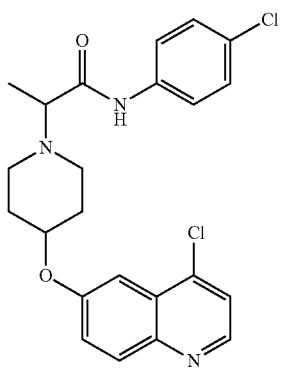 [SMILES: CC(C(=O)Nc1ccc(Cl)cc1)N1CCC(Oc2ccc3nccc(Cl)c3c2)CC1]

Examples 93 and 94

N-(4-Chlorophenyl)-2-(4-((4-chloroquinolin-6-yl)oxy)piperidin-1-yl)propanamide

Both Enantiomers, Absolute Stereochemistry not Assigned

Racemic Example 91 material (0.038 g) was purified by chiral SFC (27% MeOH in $CO_2$, 0.1% (v/v) each of diethylamine and ammonium formate) CHIRALPAK® AD column, 85 ml/min.) Concentration of the appropriate (earlier eluting) fraction afforded:

Example 93

Enantiomer 1, First Eluting, Absolute Stereochemistry was not Determined (0.007 g, 23%) MS(ESI): m/z=444 [M+H]$^+$. $t_R$=1.28 min (SCP TFA). $^1$H NMR (400 MHz, DMSO-d$_6$) δ 8.65 (d, 1H, J=4.5 Hz), 8.02 (d, 1H, J=9.2 Hz), 7.69 (d, 1H, J=4.5 Hz), 7.64 (d, 2H, J=8.6 Hz), 7.54 (br. d, 1H, J=9.3 Hz), 7.47 (br. s, 1H), 7.37 (d, 2H, J=8.5 Hz), 4.68-4.75 (m, 1H), 3.56-3.0 (m, 5H), 2.06-2.15 (m, 2H), 1.80-1.90 (m, 2H), 1.24-1.32 (m, 3H).

Example 94

Enantiomer 2

Second Eluting, Absolute Stereochemistry was not Determined (0.027 g) MS(ESI): m/z=444 [M+H]$^+$. $t_R$=1.27 min (Method K). $^1$H NMR (400 MHz, DMSO-d$_6$): essentially the same as racemate NMR (Some diethylammonium formate is present.).

Example 95

N-(4-Chlorophenyl)-2-(4-((6-fluoroquinolin-4-yl)oxy)piperidin-1-yl)acetamide

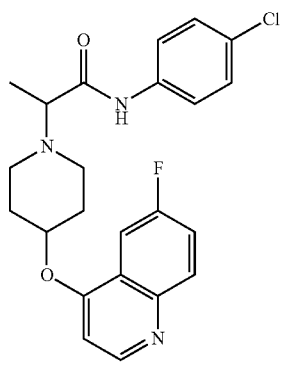 [SMILES: CC(C(=O)Nc1ccc(Cl)cc1)N1CCC(Oc2ccnc3ccc(F)cc23)CC1]

Intermediate 95A

6-Fluoro-4-(piperidin-4-yloxy)quinoline, 2 HCl

6-Fluoro-4-(piperidin-4-yloxy)quinoline, 2 HCl was prepared from 90B in quantitative yield as a tan solid using the conditions for the conversion of 90A to 90C. MS (ES): m/z=247 [M+H]$^+$. $t_R$=0.42 min (Method A).

Intermediate 95B

Ethyl 2-(4-((6-fluoroquinolin-4-yl)oxy)piperidin-1-yl)acetate

Ethyl 2-(4-((6-fluoroquinolin-4-yl)oxy)piperidin-1-yl)acetate was prepared in 63% yield as a pale yellow oil from 95A using the conditions for the conversion of 90C to 90D. MS (ES): m/z=333 [M+H]$^+$. $t_R$=0.48 min (Method A).

Intermediate 95C 2-(4-((6-Fluoroquinolin-4-yl)oxy)piperidin-1-yl)acetic acid 2-(4-((6-Fluoroquinolin-4-yl)oxy)piperidin-1-yl)acetic acid was prepared in 75% yield as a yellow glass from 95B using the conditions for the conversion of 90D to 90E except that the isolated material was not converted into the HCl salt. MS (ES): m/z=305 [M+H]$^+$. $t_R$=0.42 min (Method A).

Example 95

N-(4-Chlorophenyl)-2-(4-((6-fluoroquinolin-4-yl)oxy)piperidin-1-yl)acetamide

N-(4-chlorophenyl)-2-(4-((6-fluoroquinolin-4-yl)oxy)piperidin-1-yl)acetamide was prepared in 38% yield from 95C using the conditions for the conversion of 90E to Example 90. MS (ES): m/z=414 [M+H]+. $t_R$=0.66 min (Method A). $^1$H NMR (400 MHz, DMSO-d$_6$) δ 8.68 (d, 1H, J=5.1 Hz), 8.04 (dd, 1H, J=9.0, 5.2 Hz), 7.81 (d, 1H, J=9.3 Hz), 7.63-7.68 (m, 3H), 7.36 (d, 2H, J=8.4 Hz), 7.13 (d, 1H, J=5.0 Hz), 4.81-4.87 (m, 1H), 3.69 (s, 2H), 2.80-2.88 (m, 2H), 2.58-2.67 (m, 2H), 2.07-2.14 (m, 2H), 1.89-1.98 (m, 2H).

Example 96

(±)-N-(4-Chlorophenyl)-2-(4-((6-fluoroquinolin-4-yl)oxy)piperidin-1-yl)propanamide

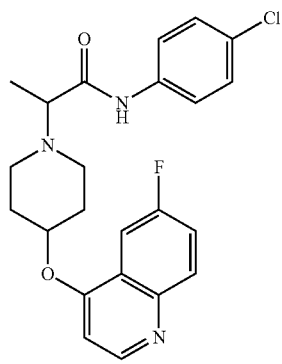 [SMILES: CC(C(=O)Nc1ccc(Cl)cc1)N1CCC(Oc2ccnc3ccc(F)cc23)CC1]

Intermediate 96A (±)-Ethyl 2-(4-((6-fluoroquinolin-4-yl)oxy)piperidin-1-yl)propanoate (±)-Ethyl 2-(4-((6-fluoroquinolin-4-yl)oxy)piperidin-1-yl)propanoate was prepared as a colorless oil in 83% yield from 95A and ethyl 2-bromopropionate using the procedure for the conversion of 90C to 90D. MS (ES): m/z=347 [M+H]$^+$. $t_R$=0.51 min. (Method A).

Intermediate 96B (±)-2-(4-((6-Fluoroquinolin-4-yl)oxy)piperidin-1-yl)propanoic acid (±)-2-(4-((6-Fluoroquinolin-4-yl)oxy)piperidin-1-yl)propanoic acid was prepared as a glass in 68% yield from 96A using the procedure for the conversion of 90D to 90E except that the isolated material was not converted to the HCl salt. MS (ES): m/z=319 [M+H]$^+$. $t_R$=0.42 min. (Method A).

Example 96

(±)-N-(4-Chlorophenyl)-2-(4-((6-fluoroquinolin-4-yl)oxy)piperidin-1-yl)propanamide (±)-N-(4-chlorophenyl)-2-(4-((6-fluoroquinolin-4-yl)oxy)piperidin-1-yl)propanamide was prepared in 58% yield after preparative HPLC purification from 96B using the procedure for the conversion of 90E to Example 90. MS (ES): m/z=428 [M+H]+. $t_R$=0.72 min (Method A). $^1$H NMR (400 MHz, DMSO-$d_6$) δ 9.97 (s, 1H), 8.69 (d, 1H, J=5.4 Hz), 8.02 (dd, 1H, J=9.8, 5.4 Hz), 7.77 (dd, 1H, J=9.7, 2.8 Hz), 7.71 (d, 2H, J=8.1 Hz), 7.64-7.68 (m, 1H), 7.37 (d, 2H, J=8.8 Hz), 7.15 (d, 1H, J=5.2 Hz), 4.78-4.85 (m, 1H), 2.77-2.87 (m, 2H), 2.57-2.63 (m, 1H), 2.06-2.14 (m, 2H), 1.85-1.94 (m, 2H), 1.22 (d, 3H, J=6.8 Hz). Note: One signal is largely obscured by solvent.

Examples 97 to 101

Intermediate 97A (±)-Ethyl 2-(4-((6-fluoroquinolin-4-yl)oxy)piperidin-1-yl)butanoate (±)-Ethyl 2-(4-((6-fluoroquinolin-4-yl)oxy)piperidin-1-yl)butanoate was prepared as a colorless oil in 71% yield from 95A and ethyl 2-bromobutyrate using the procedure for the conversion of 90C to 90D except that the reaction was run at 50° C. MS (ES): m/z=361 [M+H]$^+$. $t_R$=0.54 min. (Method A).

Intermediate 97B (±)-2-(4-((6-Fluoroquinolin-4-yl)oxy)piperidin-1-yl)butanoic acid (±)-2-(4-((6-Fluoroquinolin-4-yl)oxy)piperidin-1-yl)butanoic acid was prepared as a straw-colored foam in 74% yield from 97A using the procedure for the conversion of 90D to 90E except that the isolated material was not converted to the HCl salt. MS (ES): m/z=333 [M+H]$^+$. $t_R$=0.44 min. (Method A).

Examples 97 to 101

Bop coupling (Scheme 1, below) of carboxylic acids x (Intermediates 96B and 97B prepared in the preceding examples) with the appropriate anilines under the conditions described for the conversion of 90E to Example 90 affords compounds of the invention 1 shown in Table 2 below. (All entries are racemic.)

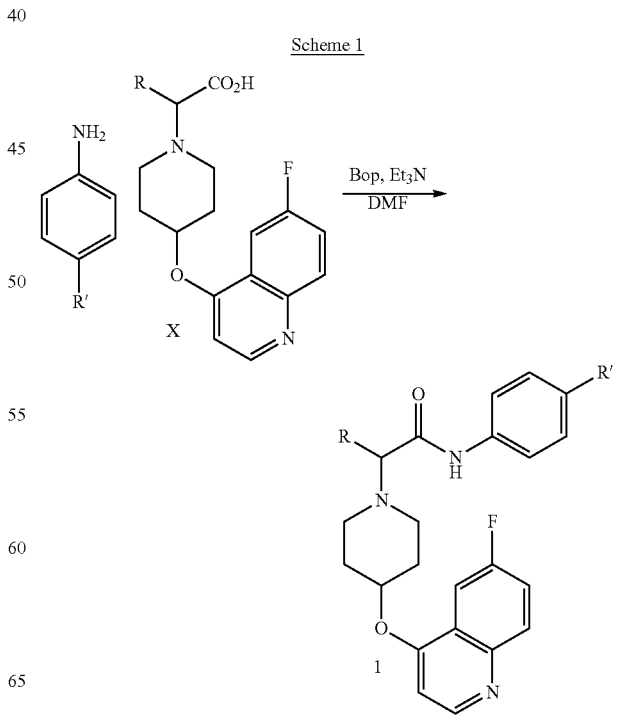

Scheme 1

127

TABLE 2

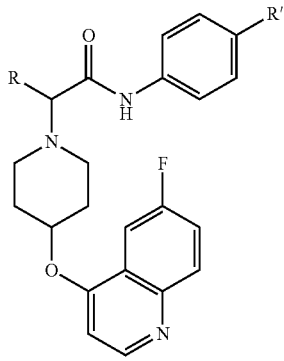

| Ex. No. | R | R' | (M + H)⁺ | $t_R$ (min.)$^{Method}$ |
|---|---|---|---|---|
| 97 | Et | Me | 422 | 1.13$^K$ |
| 98 | Et | Cl | 442 | 1.15$^K$ |
| 99 | Me | F | 412 | 0.94$^K$ |
| 100 | Me | EtO | 438 | 1.03$^K$ |
| 101 | Me | Me | 408 | 1.02$^K$ |

Example 102

(±)-N-(4-Chlorophenyl)-2-(4-((6-fluoroquinolin-4-yl)oxy)piperidin-1-yl)-3-methylbutanamide

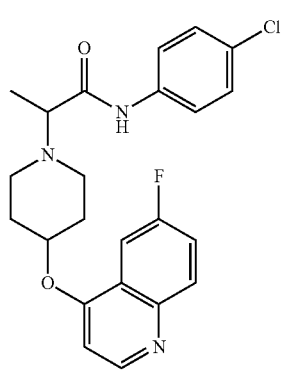 [SMILES: CC(C(=O)Nc1ccc(Cl)cc1)N1CCC(Oc2ccnc3ccc(F)cc23)CC1]

102A. (±)-Ethyl 2-(4-((6-fluoroquinolin-4-yl)oxy)piperidin-1-yl)-3-methylbutanoate (±)-ethyl 2-(4-((6-fluoroquinolin-4-yl)oxy)piperidin-1-yl)-3-methylbutanoate was prepared as a pale yellow oil in 59% yield from 95A and ethyl 2-bromo-3-methylbutyrate using the procedure for the conversion of 90C to 90D except that the reaction was run at 90° C. MS (ES): m/z=375 [M+H]⁺. $t_R$=0.60 min. (Method A).

102B. (±)-2-(4-((6-Fluoroquinolin-4-yl)oxy)piperidin-1-yl)-3-methylbutanoic acid (±)-2-(4-((6-Fluoroquinolin-4-yl)oxy)piperidin-1-yl)-3-methylbutanoic acid was prepared as an off-white solid in 77% yield from 102A using the procedure for the conversion of 90D to 90E except that reaction was run over several days at 75° C. and the isolated material was not converted to the HCl salt. MS (ES): m/z=347 [M+H]⁺. $t_R$=0.47 min. (Method A).

128

Example 102

(±)-N-(4-Chlorophenyl)-2-(4-((6-fluoroquinolin-4-yl)oxy)piperidin-1-yl)-3-methylbutanamide A solution of 2-(4-((6-fluoroquinolin-4-yl)oxy)piperidin-1-yl)-3-methylbutanoic acid (0.02 g, 0.058 mmol) and N-methylmorpholine (0.013 mL, 0.115 mmol) in THF (0.2 mL) was cooled to 0° C. and treated with isobutyl chloroformate (9.10 µl, 0.069 mmol). This mixture was stirred 15 min. then treated with 4-chloroaniline (8.84 mg, 0.069 mmol) and warmed to RT and stirred 1 h. The reaction was quenched by the addition of 1 drop of water, diluted with DMF, and purified by prep. HPLC. Concentration of the appropriate fraction afforded Example 102, 2 TFA (0.005 g, 13% yield) as a white powder. MS (ES): m/z=456 [M+H]⁺. $t_R$=0.82 min (Method A). ¹H NMR (400 MHz, DMSO-d₆) δ 10.94 (br. s, 1H), 9.96 (br. s, 1H), 8.02-8.19 (m, 3H), 7.82-7.91 (m, 1H), 7.67 (d, 2H, J=8.7 Hz), 7.44 (d, 2H, J=8.2 Hz), 2.01-2.37 (m, 5H), 1.10 (d, 6H, J=5.3 Hz). Note: Several signals obscured by large water peak.

Examples 103 to 112

Chiral SFC (Scheme 2, below) of racemic materials (prepared in the preceding examples) with the indicated columns under the conditions (MeOH—CO₂) described for the resolution of Example 91 into its component enantiomers Example 93 and Example 94 affords homochiral compounds of the invention 1 shown in Table 2 below. (All entries are homochiral, absolute stereochemistry not determined)

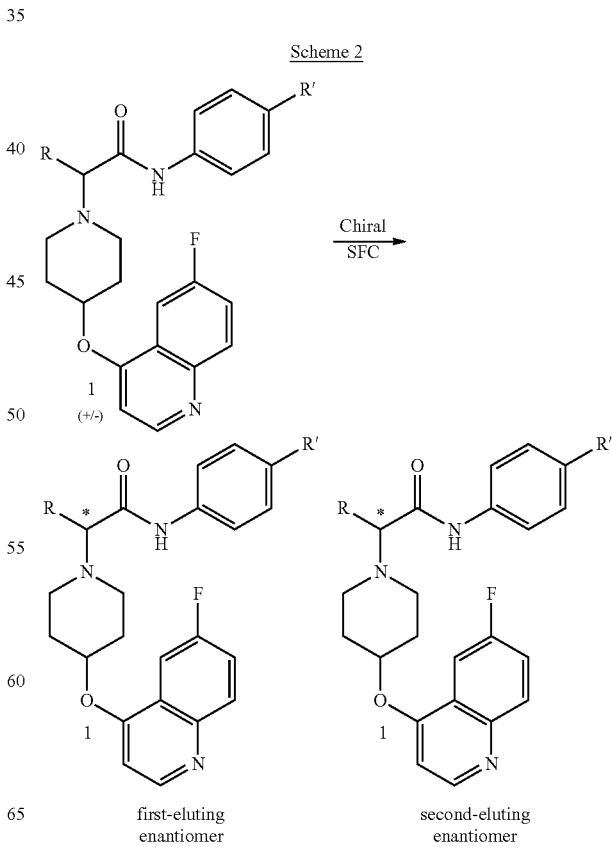

Scheme 2

TABLE 3

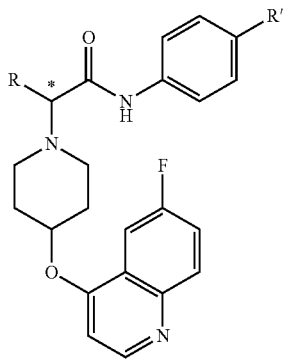

| Ex. No. | R | R' | Column, eluant | Elution Order | (M + H)+ | $t_R$ (min.)$^{Method}$ |
|---|---|---|---|---|---|---|
| 103 | Me | Cl | Chiraltech AD, 30% MeOH | First | 428 | 1.08$^K$ |
| 104 | Me | Cl | Chiraltech AD, 30% MeOH | Second | 428 | 1.07$^K$ |
| 105 | Me | F | Chiraltech AD, 40% MeOH + 0.1% EtNH$_2$ | First | 412 | 1.00$^K$ |
| 106 | Me | F | Chiraltech AD, 40% MeOH + 0.1% EtNH$_2$ | Second | 412 | 0.97$^K$ |
| 107 | Me | EtO | Chiraltech AD, 40% MeOH + 0.1% EtNH$_2$ | First | 438 | 1.01$^K$ |
| 108 | Me | EtO | Chiraltech AD, 40% MeOH + 0.1% EtNH$_2$ | Second | 438 | 1.01$^K$ |
| 109 | Me | Me | Chiraltech, AD, 40% MeOH + 0.1% EtNH$_2$ | First | 408 | 1.07$^K$ |
| 110 | Me | Me | Chiraltech AD, 40% MeOH + 0.1% EtNH$_2$ | Second | 408 | 1.04$^K$ |
| 111 | Et | Cl | Chiraltech AD, 40% MeOH + 0.1% EtNH$_2$ | First | 442 | 1.16$^K$ |
| 112 | Et | Cl | Chiraltech AD, 40% MeOH + 0.1% EtNH$_2$ | Second | 442 | 1.20$^K$ |

Example 113

N-(4-Chlorophenyl)-2-(1-(quinolin-4-ylmethyl)piperidin-4-yl)acetamide

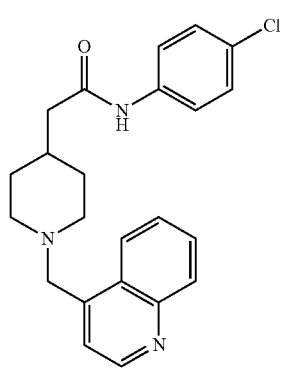 [SMILES: O=C(CC1CCN(Cc2ccnc3ccccc23)CC1)Nc1ccc(Cl)cc1]

Intermediate 113A

Methyl 2-(1-(quinolin-4-ylmethyl)piperidin-4-yl)acetate

A solution of methyl 2-(piperidin-4-yl)acetate, HCl (0.465 g, 2.400 mmol) and triethylamine (0.892 ml, 6.40 mmol) in 1 mL of DMF was treated with 4-(chloromethyl) quinoline, HCl (0.428 g, 2 mmol). The resulting solution was stirred at room temperature for 3 hours then diluted with EtOAc. The organic extracts were then washed with water, dried, filtered, and stripped to afford methyl 2-(1-(quinolin-4-ylmethyl)piperidin-4-yl)acetate (0.54 g, 86% yield) as an amber oil. MS (ES): m/z=299 [M+H]$^+$. $t_R$=0.48 min (Method A).

Intermediate 113B 2-(1-(Quinolin-4-ylmethyl)piperidin-4-yl)acetic acid

A solution of Intermediate 113A (0.1 g, 0.335 mmol) in THF (1 mL) was treated with aq. lithium hydroxide (0.268 mL, 0.670 mmol) followed by 0.2 mL of water. Methanol, ~0.5 mL, was added to give a single phase, and the reaction was stirred 18 h at RT. Most of the organic solvent was removed under a stream of nitrogen, and the residue was quenched with 0.08 mL of glacial HOAc. The pH was brought to ~7 with sat. aq. sodium bicarbonate, and the resulting solution was ext. three times with 3:1 chloroform-isopropanol. The combined organic extracts were dried, filtered, and stripped to afford 2-(1-(quinolin-4-ylmethyl) piperidin-4-yl)acetic acid (0.095 g, 95% yield) as a tan solid. MS (ES): m/z=285 [M+H]$^+$. $t_R$=0.43 min (Method A).

Example 113

N-(4-Chlorophenyl)-2-(1-(quinolin-4-ylmethyl)piperidin-4-yl)acetamide

N-(4-Chlorophenyl)-2-(1-(quinolin-4-ylmethyl)piperidin-4-yl)acetamide was prepared in 51% yield from 113B using the conditions for the conversion of 90E to Example 90. MS (ES): m/z=394 [M+H]+. $t_R$=1.07 min (Method K). $^1$H NMR (400 MHz, DMSO-d$_6$) δ 10.08 (s, 1H), 8.82 (d, 1H, J=3.9 Hz), 8.27 (d, 1H, J=8.3 Hz), 8.02 (d, 1H, J=8.3 Hz), 7.75 (t, 1H, J=7.5 Hz), 7.55-7.64 (m, 3H), 7.49 (d, 1H, J=3.4 Hz), 7.33 (d, 2H, J=8.4 Hz), 3.76 (s, 2H), 2.81-2.88 (m, 2H), 2.22 (d, 2H, J=6.7 Hz), 2.03-2.13 (m, 2H), 1.73-1.82 (m, 1H), 1.59-1.65 (m, 2H), 1.19-1.28 (m, 2H).

Example 114

N-(4-Fluorophenyl)-2-(1-(quinolin-4-ylmethyl)piperidin-4-yl)acetamide

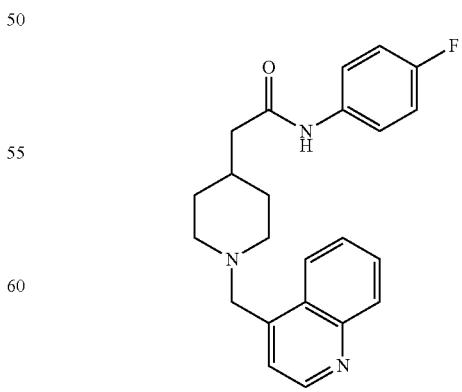

N-(4-Fluorophenyl)-2-(1-(quinolin-4-ylmethyl)piperidin-4-yl)acetamide was prepared in 76% yield from 113E and 4-fluoroaniline using the conditions for the conversion of 90E to Example 90. MS (ES): m/z=378 [M+H]+. $t_R$=0.88 min (Method K). $^1$H NMR (400 MHz, DMSO-d$_6$) δ 10.03 (s, 1H), 8.79 (d, 1H, J=4.0 Hz), 8.25 (d, 1H, J=8.3 Hz), 8.01 (d, 1H, J=8.4 Hz), 7.75 (t, 1H, J=7.5 Hz), 7.61 (t, 1H, J=7.5 Hz), 7.47-7.55 (m, 3H), 7.09 (t, 2H, J=8.7 Hz), 3.90 (s, 2H), 2.80-2.86 (m, 2H), 2.20 (d, 2H, J=6.9 Hz), 2.03-2.11 (m, 2H), 1.71-1.79 (m, 1H), 1.58-1.64 (m, 2H), 1.18-1.27 (m, 2H).

Example 115

N-(4-Fluorophenyl)-2-(1-(6-fluoroquinolin-4-yl)piperidin-4-yl)acetamide

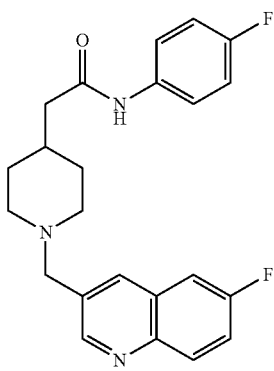 [SMILES: O=C(CC1CCN(Cc2cnc3ccc(F)cc3c2)CC1)Nc1ccc(F)cc1]

Intermediate 115A

Methyl 2-(1-(6-fluoroquinolin-4-yl)piperidin-4-yl)acetate

To a mixture of 4-chloro-6-fluoroquinoline (200.0 mg, 1.1 mmol) in anhydrous NMP (4 mL), in a sealable vial, was added methyl 2-(piperidin-4-yl)acetate (260.0 mg, 1.7 mmol) followed by DIPEA (0.8 mL, 4.6 mmol). The vial was capped and the mixture was stirred at ambient temperature for two hours, then at 120° C. for 66 hours. The reaction mixture was cooled to room temperature before being partitioned between water and Et$_2$O. The layers were separated and the aqueous layer was extracted twice more with Et$_2$O. These organic extracts were combined with the original organic layer and were washed with brine, dried (Na$_2$SO$_4$), filtered and concentrated in vacuo to afford the crude product. Purification by Isco chromatography afforded methyl 2-(1-(6-fluoroquinolin-4-yl)piperidin-4-yl)acetate as a gold oil (304.3 mg; 91% yield). MS (ES): m/z=303 [M+H]$^+$. $t_R$=0.64 min (Method A). $^1$H NMR (400 MHz, DMSO-d$_6$) δ 8.67 (d, J=5.0 Hz, 1H), 8.04-7.97 (m, 1H), 7.67-7.53 (m, 2H), 7.02 (d, J=5.0 Hz, 1H), 3.63 (s, 3H), 3.51-3.43 (m, 2H), 2.87-2.76 (m, 2H), 2.39 (d, J=7.0 Hz, 2H), 1.94-1.89 (m, 1H), 1.87-1.81 (m, 2H), 1.62-1.49 (m, 2H).

Intermediate 115B 2-(1-(6-Fluoroquinolin-4-yl)piperidin-4-yl)acetic acid

To a homogeneous mixture of Intermediate 115A (304.3 mg, 1.0 mmol) in EtOH (10 mL), at room temperature under nitrogen atmosphere, was added dropwise 2M NaOH (aq) (1 mL, 2.0 mmol). The mixture was stirred at ambient temperature for 22 hours before being quenched with 4M HCl in dioxane (0.5 mL, 2.0 mmol). After stirring for 5 minutes, the mixture was concentrated in vacuo to afford a pale gold solid, which was used in the next step without further purification. MS (ES): m/z=289 [M+H]$^+$. $t_R$=0.55 min (Method A).

Example 115

N-(4-Fluorophenyl)-2-(1-(6-fluoroquinolin-4-yl)piperidin-4-yl)acetamide

To a mixture of Intermediate 115B (20.0 mg, 0.07 mmol) and 4-fluoroaniline (9.3 mg, 0.08 mmol) in anhydrous DMF (1 mL), at room temperature under nitrogen, was added DIPEA (0.04 mL, 0.23 mmol) followed by PyBOP (36.1 mg, 0.07 mmol). The resulting mixture was stirred at ambient temperature for 4 hours before being concentrated in vacuo to remove volatiles, diluted with DMSO, filtered through a syringe filter, then purified via preparative HPLC/MS to afford the title compound (14.4 mg; 54% yield). MS (ES): m/z=382 [M+H]$^+$. $t_R$=1.25 min (Method K). $^1$H NMR (500 MHz, DMSO-d$_6$) δ 10.04 (s, 1H), 8.66 (d, J=4.9 Hz, 1H), 8.03-7.99 (m, 1H), 7.64-7.58 (m, 4H), 7.16-7.11 (m, 2H), 7.03 (d, J=4.9 Hz, 1H), 3.59-3.15 (m, 2H), 2.86-2.78 (m, 2H), 2.36 (d, J=7.1 Hz, 2H), 2.07-1.98 (m, 1H), 1.89-1.84 (m, 2H), 1.62-1.53 (m, 2H).

Examples 116 to 119

Reaction of Intermediate 115B with an appropriate amine, under the conditions described for Example 115 (Scheme 3, below), affords compounds of the invention shown in Table 3 below.

Scheme 3

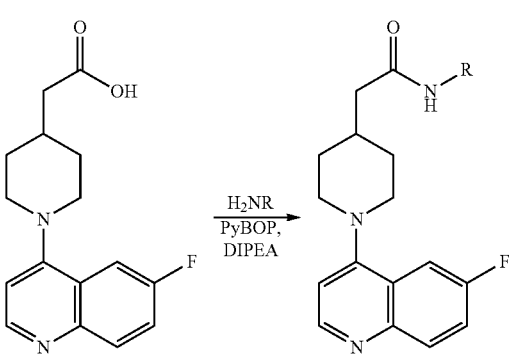

TABLE 4

| Ex. No. | R | (M + H)$^+$ | $t_R$ (min.)$^{Method}$ |
|---|---|---|---|
| 116 | ~~⟨⟩~~Cl | 398 | 1.43$^K$ |

TABLE 4-continued

| Ex. No. | R | (M + H)+ | $t_R$ (min.)$^{Method}$ |
|---|---|---|---|
| 117 | 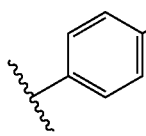 | 442 | 1.48$^K$ |
| 118 | 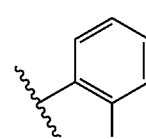 | 396 | 1.35$^K$ |
| 119 | 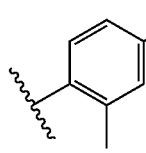 | 412 | 1.42$^K$ |

Example 120

N-(4-Fluorophenyl)-2-(1-(6-fluoroquinolin-4-yl)-4-methylpiperidin-4-yl)acetamide

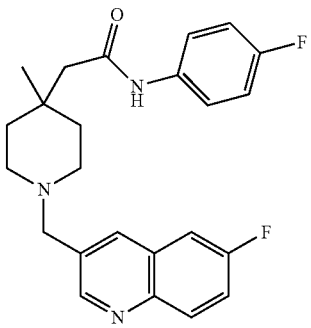 [SMILES: CC1(CC(=O)Nc2ccc(F)cc2)CCN(Cc2cnc3ccc(F)cc3c2)CC1]

Intermediate 120A

Methyl 2-(4-methylpiperidin-4-yl)acetate, HCl

To a flask charged with MeOH (7.5 mL), at 0° C. under nitrogen atmosphere, was slowly added acetyl chloride (1.1 mL, 15.2 mmol). After the addition was complete, the mixture was stirred at 0° C. for 5 minutes before a homogeneous mixture of 2-(4-methylpiperidin-4-yl)acetic acid, HCl (675.0 mg, 3.5 mmol) in MeOH (1.5 mL) was added slowly dropwise. The resultant homogeneous mixture was stirred at 0° C. for 5 minutes then at 60° C. for 8 hours, before being concentrated in vacuo to afford the HCl salt of Intermediate 120A as a white solid (718.0 mg, 99% yield) which was used without further purification. $^1$H NMR (400 MHz, DMSO-d$_6$) δ 9.41-9.12 (m, 1H), 3.60 (s, 3H), 3.25-3.15 (m, 2H), 2.93-2.82 (m, 2H), 2.39-2.30 (m, 2H), 1.74-1.64 (m, 4H), 1.02 (s, 3H).

Intermediate 120B

Methyl 2-(1-(6-fluoroquinolin-4-yl)-4-methylpiperidin-4-yl)acetate

To a homogeneous mixture of 4-chloro-6-fluoroquinoline (350.0 mg, 1.9 mmol) in anhydrous NMP (5 mL), in a sealable vial, was added the HCl salt of methyl 2-(4-methylpiperidin-4-yl)acetate (120A, 480.0 mg, 2.3 mmol) followed by DIPEA (1.6 mL, 9.2 mmol). The vial was sealed and the mixture was stirred at 120° C. After 26 hours, the reaction mixture was cooled to room temperature then partitioned between water and EtOAc. The layers were separated and the aqueous layer was extracted once more with EtOAc. The organic layers were combined, washed with brine, then concentrated in vacuo to afford the crude product. Purification by Isco chromatography afforded Intermediate 120B as an oil (565.8 mg; 93% yield). MS (ES): m/z=317 [M+H]$^+$. $t_R$=0.66 min (Method A). NMR (400 MHz, DMSO-d$_6$) δ 8.38 (d, J=5.4 Hz, 1H), 7.96 (dd, J=11.7, 2.8 Hz, 1H), 7.89-7.84 (m, 1H), 7.55-7.49 (m, 1H), 6.54 (d, J=5.5 Hz, 1H), 3.82-3.63 (m, 2H), 3.59 (s, 3H), 3.54-3.34 (m, 2H), 2.45-2.38 (m, 2H), 1.87-1.72 (m, 4H), 1.05 (s, 3H).

Intermediate 120C 2-(1-(6-Fluoroquinolin-4-yl)-4-methylpiperidin-4-yl)acetic acid To a homogeneous mixture of methyl 2-(1-(6-fluoroquinolin-4-yl)-4-methylpiperidin-4-yl)acetate (321.0 mg, 1.0 mmol) in MeOH (5 mL), under nitrogen atmosphere, was added dropwise 2M NaOH aqueous solution (1 mL, 2.0 mmol). The reaction was then stirred at ambient temperature for 20 hours before being treated with 1N HCl (aq) until pH 6 to pH test strips. The mixture was then partitioned between water and EtOAc, the layers were separated and the aqueous layer was twice extracted with EtOAc. The aqueous layer from the extraction was lyophilized to afford the crude Example 120C as an off-white solid (302.1 mg, 98% yield) which was used without further purification. MS (ES): m/z=303 [M+H]$^+$. $t_R$=0.59 min (Method A). $^1$H NMR (400 MHz, DMSO-d$_6$) δ 12.12 (br. s, 1H), 8.41 (d, J=6.1 Hz, 1H), 8.12 (dd, J=11.5, 2.7 Hz, 1H), 8.00 (dd, J=9.3, 5.7 Hz, 1H), 7.75-7.64 (m, 1H), 6.64 (d, J=6.2 Hz, 1H), 3.98-3.87 (m, 1H), 3.87-3.78 (m, 1H), 3.69-3.49 (m, 2H), 2.38-2.29 (m, 2H), 1.92-1.70 (m, 4H), 1.06 (s, 3H).

Example 120

N-(4-Fluorophenyl)-2-(1-(6-fluoroquinolin-4-yl)-4-methylpiperidin-4-yl)acetamide To a mixture of 2-(1-(6-fluoroquinolin-4-yl)-4-methylpiperidin-4-yl)acetic acid (25.6 mg, 0.09 mmol) and 4-fluoroaniline (11.3 mg, 0.1 mmol) in anhydrous DMF (1 mL), under nitrogen atmosphere, was added DIPEA (0.05 mL, 0.3 mmol) followed by PyBOP (44.1 mg, 0.09 mmol). The resulting mixture was stirred at ambient temperature for 156 hours, before being diluted with DMF, filtered through a syringe filter, then purified via preparative HPLC/MS to afford the title compound (17.2 mg; 51% yield). MS (ES): m/z=396 [M+H]$^+$. $t_R$=1.32 min (Method K). $^1$HKNMR (500 MHz, DMSO-d$_6$) δ 10.05 (s, 1H), 8.33 (d, J=5.5 Hz, 1H), 7.99-7.93 (m, 1H), 7.89-7.83 (m, 1H), 7.57-7.50 (m, 3H), 7.13-7.08 (m, 2H), 6.54 (d, J=5.5 Hz, 1H), 3.85-3.61 (m, 2H), 3.59-3.36 (m, 2H), 2.41-2.31 (m, 2H), 1.86-1.75 (m, 4H), 1.07 (s, 3H).

Examples 121 to 125

Reaction of 2-(1-(6-fluoroquinolin-4-yl)-4-methylpiperidin-4-yl)acetic acid with an appropriate amine, under the conditions described for Example 120 (Scheme 4, below), affords compounds of the invention shown in Table 4 below.

Scheme 4

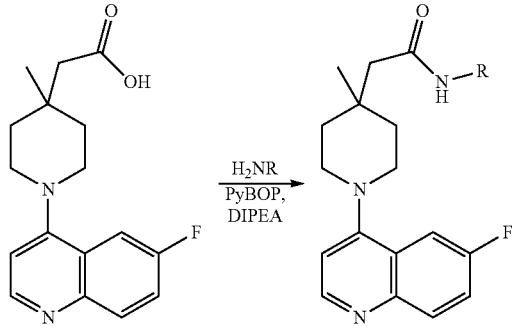

TABLE 5

| Ex. No. | R | (M + H)$^+$ | $t_R$ (min.)$^{Method}$ |
|---|---|---|---|
| 121 | (4-methylphenyl) | 392 | 1.39$^K$ |
| 122 | (pyrimidin-5-yl) | 380 | 0.91$^K$ |
| 123 | (4-chlorophenyl) | 412 | 1.78$^K$ |
| 124 | (2-methoxypyrimidin-5-yl) | 410 | 1.04$^K$ |
| 125 | (4-ethoxyphenyl) | 422 | 1.40$^K$ |

Example 126

(±)-N-(4-Chlorophenyl)-2-(4-(6-fluoroquinolin-4-yl)piperazin-1-yl)propanamide

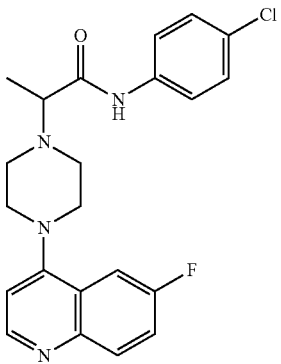 [SMILES: CC(C(=O)Nc1ccc(Cl)cc1)N1CCN(c2ccnc3ccc(F)cc23)CC1]

Intermediate 126A tert-Butyl 4-(6-fluoroquinolin-4-yl)piperazine-1-carboxylate

To a mixture of 4-chloro-6-fluoroquinoline (200.0 mg, 1.1 mmol) in anhydrous NMP (4 mL), in a sealable vial, was added 1-Boc-piperizine (308.0 mg, 1.7 mmol) followed by DIPEA (0.8 mL, 4.6 mmol). The vial was capped and the mixture was stirred at ambient temperature for two hours, then at 120° C. for 66 hours. The reaction mixture was cooled to room temperature before being partitioned between water and Et$_2$O. The layers were separated and the aqueous layer was extracted twice more with Et$_2$O. These organic extracts were combined with the original organic layer and were washed with brine, dried (Na$_2$SO$_4$), filtered and concentrated in vacuo to afford the crude product. Purification by Isco chromatography afforded tert-butyl 4-(6-fluoroquinolin-4-yl)piperazine-1-carboxylate as an oil (362.8 mg; 98% yield). MS (ES): m/z=332 [M+H]$^+$. $t_R$=0.70 min (Method A). $^1$H NMR (400 MHz, DMSO-d$_6$) δ 8.70 (d, J=4.9 Hz, 1H), 8.09-8.00 (m, 1H), 7.77-7.67 (m, 1H), 7.67-7.62 (m, 1H), 7.07 (d, J=4.9 Hz, 1H), 3.67-3.57 (m, 4H), 3.15-3.06 (m, 4H), 1.44 (s, 9H).

Intermediate 126B

6-Fluoro-4-(piperazin-1-yl)quinoline

To a flask charged with tert-butyl 4-(6-fluoroquinolin-4-yl)piperazine-1-carboxylate (362.8 mg, 1.1 mmol), under nitrogen atmosphere, was added 4M HCl in dioxane (10 mL, 40.0 mmol). The resultant mixture was stirred at ambient temperature for 5.5 hours, during which time a precipitate formed. The heterogeneous mixture was concentrated to approximately ½ of its original volume. Vacuum filtration afforded the HCl salt of the title compound as an off-white solid (259.0 mg; 88% yield) which was used without further purification. MS (ES): m/z=232 [M+H]$^+$. $t_R$=0.34 min (Method A).

Intermediate 126C

Ethyl 2-(4-(6-fluoroquinolin-4-yl)piperazin-1-yl)propanoate

To a heterogeneous mixture of the HCl salt of 6-fluoro-4-(piperazin-1-yl)quinoline (126B, 80.0 mg, 0.3 mmol) in anhydrous NMP (2 mL), in a sealable reaction vial, was added K$_2$CO$_3$ (60.0 mg, 0.4 mmol) followed by ethyl 2-bromopropanoate (65.0 mg, 0.4 mmol). The flask was then sealed and the mixture was stirred at 60° C. After 67.5 hours, the reaction was cooled to room temperature then partitioned between water and DCM. The layers were separated and the aqueous layer was extracted once more with DCM. The organic layers were combined and concentrated in vacuo to afford the product as an oil (92.7 mg, 94%), which was used without further purification. MS (ES): m/z=332 [M+H]$^+$. t$_R$=0.51 min (Method A).

Intermediate 126D 2-(4-(6-Fluoroquinolin-4-yl)piperazin-1-yl)propanoic acid

To a homogeneous mixture of ethyl 2-(4-(6-fluoroquinolin-4-yl)piperazin-1-yl)propanoate (92.7 mg, 0.3 mmol) in EtOH (3 mL), under nitrogen atmosphere, was added dropwise 2M NaOH (aq) (0.3 mL, 0.6 mmol). The resultant mixture was stirred at ambient temperature for 21 hours before being quenched with 4M HCl in dioxane (0.15 mL, 0.6 mmol). After stirring at ambient temperature for 30 minutes, the mixture was concentrated in vacuo to afford the product as a light tan sold, which was used without further purification, based on 100%, in the next step. MS (ES): m/z=304 [M+H]$^+$. t$_R$=0.39 min (Method A).

Example 126

(±)-N-(4-Chlorophenyl)-2-(4-(6-fluoroquinolin-4-yl)piperazin-1-yl)propanamide

To a mixture of 2-(4-(6-fluoroquinolin-4-yl)piperazin-1-yl)propanoic acid (30 mg, 0.1 mmol) and 4-chloroaniline (15.1 mg, 0.1 mmol) in anhydrous DMF (1.5 mL), under nitrogen atmosphere, was added DIPEA (0.06 mL, 0.3 mmol) followed by PyBOP (51.5 mg, 0.1 mmol). The resulting mixture was stirred at ambient temperature for 17.5 hours, before being diluted with DMF, filtered through a syringe filter, then purified via preparative HPLC/MS to afford the title compound as a racemate (11.0 mg; 27% yield). MS (ES): m/z=413 [M+H]$^+$. t$_R$=1.01 min (Method K). $^1$H NMR (500 MHz, DMSO-d$_6$) δ 10.05 (s, 1H), 8.71-8.62 (m, 1H), 8.06-7.96 (m, 1H), 7.66 (d, J=8.7 Hz, 2H), 7.64-7.57 (m, 2H), 7.35 (d, J=8.7 Hz, 2H), 7.04 (d, J=4.9 Hz, 1H), 3.36 (q, J=6.8 Hz, 1H), 3.27-3.13 (m, 4H), 2.90-2.73 (m, 4H), 1.25 (d, J=6.8 Hz, 3H).

Example 127

(±)-N-(4-Bromophenyl)-2-(4-(6-fluoroquinolin-4-yl)piperazin-1-yl)propanamide

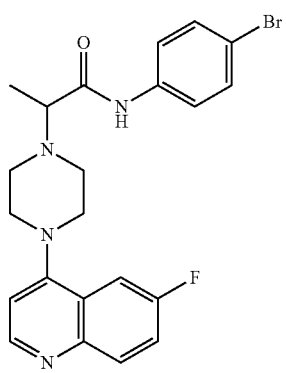 [SMILES: CC(C(=O)Nc1ccc(Br)cc1)N1CCN(c2ccnc3ccc(F)cc23)CC1]

Example 127 (17.1 mg; 37% yield) was prepared following a procedure analogous to that for the synthesis of Example 126, except that 4-bromoaniline (20.4 mg, 0.12 mmol) was used instead of 4-chloroaniline. MS (ES): m/z=457 [M+H]$^+$. T$_r$=1.04 min (Method K). $^1$H NMR (500 MHz, DMSO-d$_6$) δ 10.58 (br. s., 1H), 8.65 (d, J=6.0 Hz, 1H), 8.09-7.98 (m, 1H), 7.85-7.76 (m, 2H), 7.61-7.48 (m, 4H), 7.20 (d, J=6.1 Hz, 1H), 3.76-3.66 (m, 2H), 3.39-3.27 (m, 2H), 3.27-3.16 (m, 2H), 2.95-2.82 (m, 1H), 2.58-2.54 (m, 2H), 1.46 (d, J=6.6 Hz, 3H).

Example 128

(±)-2-(4-(6-Fluoroquinolin-4-yl)piperazin-1-yl)-N-phenylpropanamide

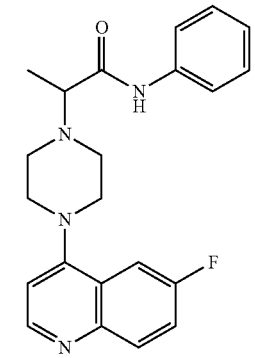 [SMILES: CC(C(=O)Nc1ccccc1)N1CCN(c2ccnc3ccc(F)cc23)CC1]

Example 128 (10.9 mg; 29% yield) was prepared following a procedure analogous to that for the synthesis of Example 126, except that aniline (11.1 mg, 0.12 mmol) was used instead of 4-chloroaniline. MS (ES): m/z=379 [M+H]$^+$. T$_r$=0.81 min (Method K). $^1$H NMR (500 MHz, DMSO-d$_6$) δ 9.92 (s, 1H), 8.65 (d, J=4.9 Hz, 1H), 8.08-7.96 (m, 1H), 7.67-7.54 (m, 4H), 7.30 (t, J=7.7 Hz, 2H), 7.12-7.00 (m, 2H), 3.36 (q, J=6.7 Hz, 1H), 3.28-3.11 (m, 4H), 2.93-2.74 (m, 4H), 1.25 (d, J=6.8 Hz, 3H).

Enantiomer 1 and Enantiomer 2 of Racemic Example 126

Enantiomer 1

Example 129

N-(4-Chlorophenyl)-2-(4-(6-fluoroquinolin-4-yl)piperazin-1-yl)propanamide

Homochiral, Absolute Stereochemistry not Determined

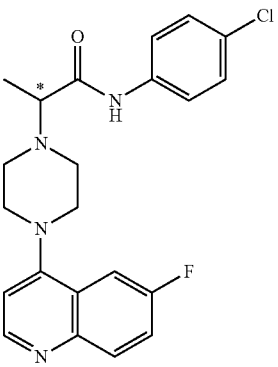 [SMILES: CC(C(=O)Nc1ccc(Cl)cc1)N1CCN(c2ccnc3ccc(F)cc23)CC1]

Enantiomer 2

Example 130

N-(4-Chlorophenyl)-2-(4-(6-fluoroquinolin-4-yl)piperazin-1-yl)propanamide

Homochiral, Absolute Stereochemistry not Determined

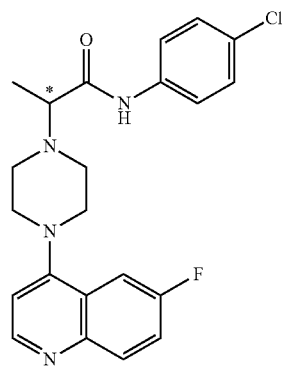 [SMILES: CC(C(=O)Nc1ccc(Cl)cc1)N1CCN(c2ccnc3ccc(F)cc23)CC1]

Racemic Example 126 (11.0 mg) was purified by chiral SFC (70/30 CO$_2$/MeOH Mobile Phase, Chiral AD 25×3 cm, 5 µm column, 85 ml/min, detector wavelength=220 nm). Concentration of the appropriate fractions afforded:

Example 129

Enantiomer 1, First Eluting (4.2 mg) MS (ES): m/z=413 [M+H]$^+$. T$_r$=1.04 min (Method K). $^1$H NMR (500 MHz, DMSO-d$_6$): superimposable upon racemate NMR.

Example 130

Enantiomer 2

Second Eluting (4.1 mg) MS (ES): m/z=413 [M+H]$^+$. T$_r$=1.04 min (Method K). $^1$H NMR (500 MHz, DMSO-d$_6$): superimposable upon racemate NMR.

Example 131

(±)-N-(4-Chlorophenyl)-2-(4-(6-fluoroquinolin-4-yl)piperazin-1-yl)butanamide

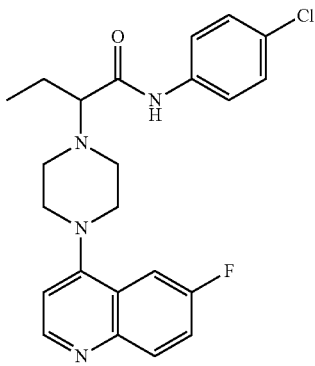

Example 131 (5.6 mg; 14% yield) was prepared following a procedure analogous to that for the synthesis of Example 126, except that ethyl 2-bromobutanoate was used instead of ethyl 2-bromopropanoate. MS (ES): m/z=427 [M+H]$^+$. T$_r$=1.09 min (Method K). $^1$H NMR (500 MHz, DMSO-d$_6$) δ 10.17 (s, 1H), 8.65 (d, J=5.0 Hz, 1H), 8.01 (dd, J=9.0, 5.6 Hz, 1H), 7.68 (d, J=8.8 Hz, 2H), 7.64-7.57 (m, 2H), 7.37 (d, J=8.8 Hz, 2H), 7.03 (d, J=5.0 Hz, 1H), 3.58-3.54 (m, 1H), 3.25-3.11 (m, 4H), 2.95-2.76 (m, 4H), 1.85-1.60 (m, 2H), 0.89 (t, J=7.3 Hz, 3H).

Example 132

(±)-2-(4-(6-Fluoroquinolin-4-yl)piperazin-1-yl)-N-phenylbutanamide

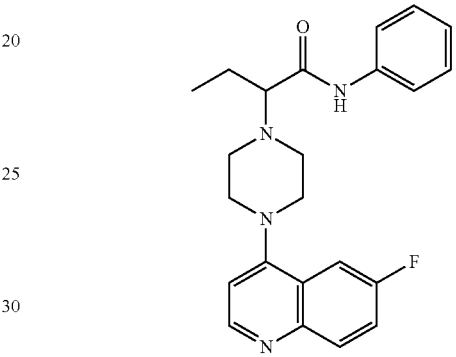

Example 132 (6.6 mg; 17% yield) was prepared following a procedure analogous to that for the synthesis of Example 131, except that aniline was used instead of 4-chloroaniline. MS (ES): m/z=393 [M+H]$^+$. T$_r$=0.91 min (Method K). $^1$H NMR (500 MHz, DMSO-d$_6$) δ 10.08 (s, 1H), 8.61 (d, J=4.0 Hz, 1H), 7.98 (dd, J=8.8, 5.6 Hz, 1H), 7.65-7.52 (m, 4H), 7.31 (t, J=7.8 Hz, 2H), 7.13-6.98 (m, 2H), 3.24-3.09 (m, 5H), 2.96-2.76 (m, 4H), 1.83-1.60 (m, 2H), 0.87 (t, J=7.3 Hz, 3H).

Example 133

(±)-N-(4-Chlorophenyl)-2-(4-(6-fluoroquinolin-4-yl)piperazin-1-yl)-3-methoxypropanamide

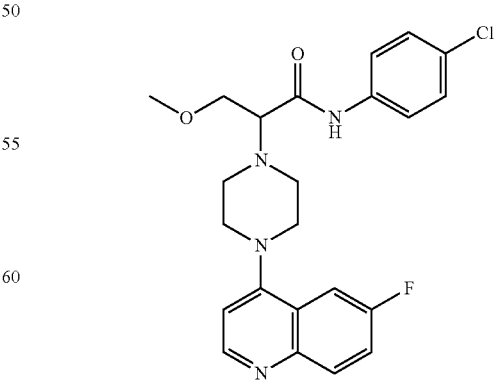

Example 133 (12.0 mg; 29% yield) was prepared following a procedure analogous to that for the synthesis of Example 126, except that methyl 2-bromo-3-methoxypropanoate was used instead of ethyl 2-bromopropanoate. MS (ES): m/z=443 [M+H]$^+$. T$_r$=1.14 min (Method K). $^1$H NMR (500 MHz, DMSO-d$_6$) δ 10.15 (s, 1H), 8.68 (d, J=4.4 Hz, 1H), 8.06-7.96 (m, 1H), 7.71 (d, J=8.3 Hz, 2H), 7.65-7.56 (m, 2H), 7.38 (d, J=8.3 Hz, 2H), 7.04 (d, J=4.3 Hz, 1H), 3.83-3.64 (m, 2H), 3.62-3.36 (m, 1H), 3.18 (s, 3H), 3.01-2.93 (m, 2H), 2.89-2.81 (m, 2H), 2.57-2.53 (m, 4H).

Example 134

(±)-N-(4-Fluorophenyl)-2-(4-(6-fluoroquinolin-4-yl)piperazin-1-yl)-3-methoxypropanamide

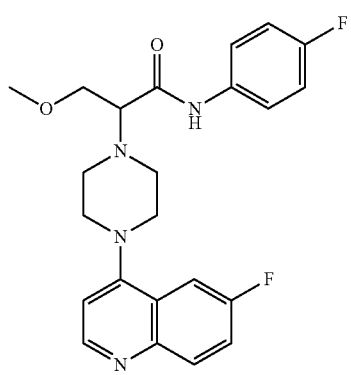 [SMILES: COCC(C(=O)Nc1ccc(F)cc1)N1CCN(c2ccnc3ccc(F)cc23)CC1]

Example 134 (11.3 mg; 35% yield) was prepared following a procedure analogous to that for the synthesis of Example 133, except that 4-fluoroaniline was used instead of 4-chloroaniline. MS (ES): m/z=427 [M+H]$^+$. T$_r$=1.05 min (Method K). $^1$H NMR (500 MHz, DMSO-d$_6$) δ 10.07 (s, 1H), 8.67 (d, J=4.5 Hz, 1H), 8.09-7.98 (m, 1H), 7.73-7.65 (m, 2H), 7.63-7.58 (m, 2H), 7.20-7.11 (m, 2H), 7.04 (d, J=4.5 Hz, 1H), 3.88-3.62 (m, 2H), 3.60-3.34 (m, 1H), 3.19 (s, 3H), 3.01-2.94 (m, 2H), 2.89-2.82 (m, 2H), 2.56-2.52 (m, 4H).

Examples 135 and 136

Enantiomer 1

N-(4-Chlorophenyl)-2-(4-(6-fluoroquinolin-4-yl)piperazin-1-yl)-3-methoxypropanamide Homochiral, Absolute Stereochemistry not Determined

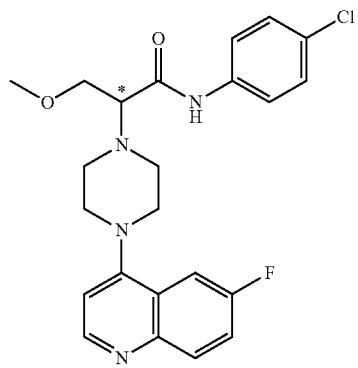 [SMILES: COCC(C(=O)Nc1ccc(Cl)cc1)N1CCN(c2ccnc3ccc(F)cc23)CC1]

Enantiomer 2

N-(4-Chlorophenyl)-2-(4-(6-fluoroquinolin-4-yl)piperazin-1-yl)-3-methoxypropanamide Homochiral, Absolute Stereochemistry not Determined

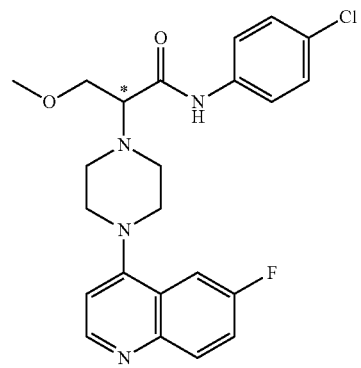 [SMILES: COCC(C(=O)Nc1ccc(Cl)cc1)N1CCN(c2ccnc3ccc(F)cc23)CC1]

Racemic Example 133 (9.8 mg) was purified by chiral SFC (70/30 CO$_2$/MeOH Mobile Phase, Chiral Lux-4 25×3 cm, 5 µm column, 85 ml/min, detector wavelength=220 nm). Concentration of the appropriate (earlier eluting) fractions afforded:

Example 135 (first eluting) (3.2 mg) assigned as N-(4-chlorophenyl)-2-(4-(6-fluoroquinolin-4-yl)piperazin-1-yl)-3-methoxypropanamide (Enantiomer 1). MS (ES): m/z=443 [M+H]$^+$. T$_r$=1.19 min (Method K). $^1$H NMR (500 MHz, DMSO-d$_6$): superimposable upon racemate NMR.

Example 136 (second eluting) (3.3 mg) assigned as N-(4-chlorophenyl)-2-(4-(6-fluoroquinolin-4-yl)piperazin-1-yl)-3-methoxypropanamide (Enantiomer 2). MS (ES): m/z=443 [M+H]$^+$. T$_r$=1.19 min (Method K). $^1$H NMR (500 MHz, DMSO-d$_6$): superimposable upon racemate NMR.

Example 137

2-(4-((R)-3-((4-Chlorophenyl)amino)-2-((cis)-4-(6-fluoroquinolin-4-yl)cyclohexyl)-3-oxopropyl)phenyl)propanoic acid Mixture of Two Diastereomers

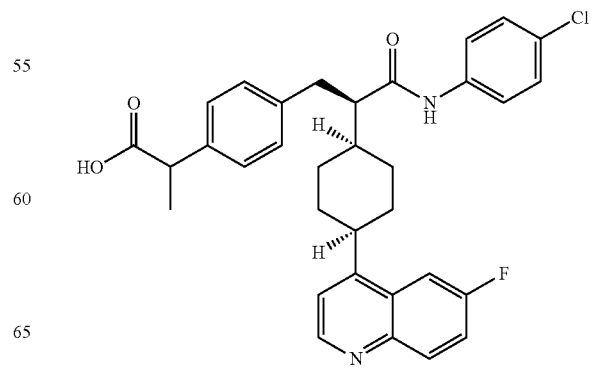

Intermediate 137A tert-Butyl 2-(4-(bromomethyl)phenyl)propanoate

To a solution of 2-(4-(bromomethyl)phenyl)propanoic acid (3 g, 12.34 mmol) in $CH_2Cl_2$ (100 mL) at RT was added oxalyl chloride (1.400 mL, 16.04 mmol) and 1 drop of DMF. The reaction was stirred at RT for 1 h. Then the mixture was concentrated to dryness. To above reaction was added $CH_2Cl_2$ (2 mL) followed by t-BuOH (100 mL). The mixture was stirred at RT for 16 h. The mixture was diluted with $CH_2Cl_2$ and washed with saturated $NaHCO_3$, brine, dried over $MgSO_4$, filtered and concentrated to give Intermediate 137A (1.8 g, 6.02 mmol, 48.7% yield) as light yellow liquid. $^1$H NMR (400 MHz, chloroform-d) δ 7.36 (d, J=8.3 Hz, 2H), 7.33-7.23 (m, 2H), 4.60 (s, 1H), 4.51 (s, 1H), 3.64 (dd, J=7.2, 2.8 Hz, 1H), 1.47 (dd, J=7.2, 1.2 Hz, 3H), 1.42 (s, 9H)

Intermediate 137B tert-Butyl 2-(4-((R)2-((cis)-4-(6-fluoroquinolin-4-yl)cyclohexyl)-3-oxo-3-((R)-2-oxo-4-phenyloxazolidin-3-yl)propyl)phenyl)propanoate

Mixture of Diastereomers

To a solution of (R)-3-(2-((cis)-4-(6-fluoroquinolin-4-yl)cyclohexyl)acetyl)-4-phenyloxazolidin-2-one (prepared from general procedures K, B, E, and L) (200 mg, 0.462 mmol) in THF (4 mL) at −40° C. was added NaHMDS (1M in THF) (0.555 mL, 0.555 mmol) dropwise. The mixture was stirred at −40° C. to −30° C. for 20 min. Then tert-butyl 2-(4-(bromomethyl)phenyl)propanoate (304 mg, 1.017 mmol) in THF (0.5 mL) was added. The reaction was stirred at −20° C. for 16 h. The reaction was quenched with saturated $NH_4Cl$ and EtOAc at −20° C. organic was separated and washed with brine, dried over $MgSO_4$, filtered and concentrated to dryness. This crude material was dissolved in DMF and purified with prep HPLC (PHENOMENEX® Luna 5μ 30×100 mm), 40 mL/min flow rate with gradient of 20% B-100% B over 10 minutes. Hold at 100% B for 5 min. (A: 0.1% TFA in water/MeOH (90:10), B: 0.1% TFA in water/MeOH (10:90) monitoring at 254 nm. Combined fractions (tr=11.06 min) containing the product. After concentration, 134 mg of Intermediate 137B (0.204 mmol, 44.1%) was obtained as mixture of diastereomers. $^1$H NMR (400 MHz, chloroform-d) δ 9.15 (d, J=5.1 Hz, 1H), 8.65 (dd, J=9.2, 4.9 Hz, 1H), 8.02 (d, J=3.5 Hz, 1H), 7.94 (dd, J=9.3, 2.2 Hz, 1H), 7.89-7.73 (m, 1H), 7.36-7.24 (m, 4H), 7.13 (d, J=8.1 Hz, 1H), 7.17 (d, J=8.1 Hz, 1H), 6.99 (d, J=7.9 Hz, 2H), 6.84-6.64 (m, 2H), 5.44-5.35 (m, 1H), 4.98 (br. s., 1H), 4.63-4.46 (m, 1H), 4.10 (ddd, J=8.9, 6.5, 4.3 Hz, 1H), 3.69-3.60 (m, 1H), 3.52 (d, J=11.7 Hz, 1H), 3.03 (dt, J=13.6, 4.2 Hz, 1H), 2.74 (ddd, J=13.6, 10.6, 6.8 Hz, 1H), 2.37-2.23 (m, 1H), 2.16 (d, J=12.8 Hz, 1H), 2.10-2.00 (m, 1H), 2.00-1.74 (m, 7H), 1.50 (dd, J=8.6, 7.2 Hz, 3H), 1.45-1.29 (m, 9H) MS: Anal. Calc'd for $C_{40}H_{43}FN_2O_5$ 650.316. found [M+H] 651.3 LC: tr=1.03 min (Method B).

Intermediate 137C

(2R)-3-(4-(1-tert-Butoxy)-1-oxopropan-2-yl)phenyl)-2-((cis)-4-(6-fluoroquinolin-4-yl)cyclohexyl)propanoic acid

Mixture of Diastereomers

To a solution of Intermediate 137B (0.206 mmol, 134 mg) in THF (1.3 mL) at 0° C. was added 30% $H_2O_2$ (0.093 mL, 0.824 mmol) dropwise, followed by the addition of 2.7 M LiOH in $H_2O$ (0.122 mL, 0.329 mmol). The reaction was allowed to warm to RT and stirred at RT for 16 h. The reaction was carefully quenched at 0° C. by addition of saturated $Na_2SO_3$. The pH was adjusted to 5-6 with 1N HCl and the mixture was extracted with EtOAc. The combined organics were dried over $MgSO_4$, filtered and concentrated. The crude material was purified with ISCO 12 g column, 30 mL/min. 0-100% EtOAc/Hexane in 35 min. The desired product was eluted with 22% EtOAc/Hexane. After concentration, 35 mg (0.069 mmol, 33%) of 137C was obtained as white solid. $^1$H NMR (400 MHz, chloroform-d) δ 8.82 (d, J=4.6 Hz, 1H), 8.15 (dd, J=9.2, 5.7 Hz, 1H), 7.68 (dd, J=10.5, 2.7 Hz, 1H), 7.49 (ddd, J=9.2, 7.9, 2.7 Hz, 1H), 7.41 (d, J=4.5 Hz, 1H), 7.27-7.06 (m, 4H), 3.60 (d, J=7.0 Hz, 1H), 3.37 (br. s., 1H), 3.04-2.96 (m, 2H), 2.95-2.81 (m, 1H), 2.12 (d, J=19.2 Hz, 1H), 2.00-1.76 (m, 8H), 1.45 (d, J=7.2 Hz, 3H), 1.42-1.34 (m, 9H) MS: Anal. Calc'd for $C_{31}H_{36}FNO_4$ 505.263. found [M+H] 506.1 LC: tr=0.92 min (Method B).

Intermediate 137D tert-Butyl 2-(4-((R)-3-((4-chlorophenyl)amino)-2-((cis)-4-(6-fluoroquinolin-4-yl)cyclohexyl)-3-oxo-propyl)phenyl)propanoate

Mixture of Diastereomers

To a solution of 137C (35 mg, 0.069 mmol) in $CH_2Cl_2$ (3 mL) at RT was added oxalyl chloride (8.90 μl, 0.104 mmol) dropwise followed by 1 drop of DMF. The reaction was stirred at RT for 2 h. Then the mixture was concentrated to dryness. To this mixture in THF (1 mL) at RT was added 4-chloroaniline (8.76 mg, 0.069 mmol), followed by Hunig's Base (0.018 mL, 0.103 mmol). The reaction was stirred at RT for 3 h. The mixture was diluted with MeOH and purified with prep HPLC (PHENOMENEX® Luna 5μ 30×100 mm), 40 mL/min flow rate with gradient of 20% B-100% B over 10 minutes Hold at 100% B for 5 min. (A: 0.1% TFA in water/MeOH (90:10), B: 0.1% TFA in water/MeOH (10:90) monitoring at 254 nm. Intermediate 137D (10 mg, 0.016 mmol, 46.4% yield) was obtained as white solid. $^1$H NMR (400 MHz, chloroform-d) δ 9.06 (br. s., 1H), 8.57 (br. s., 1H), 7.95-7.84 (m, 2H), 7.84-7.63 (m, 1H), 7.26-7.10 (m, 8H), 3.66-3.49 (m, 4H), 3.06 (dd, J=13.6, 3.4 Hz, 2H), 2.87 (t, J=12.3 Hz, 1H), 2.70 (br. s., 1H), 2.40 (br. s., 1H), 2.15 (br. s., 1H), 2.10-1.80 (m, 7H), 1.41 (d, J=7.1 Hz, 3H), 1.37-1.30 (m, 9H) MS: Anal. Calc'd for $C_{37}H_{40}ClFN_2O_3$ 614.271. found [M+H] 615.3 LC: tr=1.06 min (Method B).

Example 137

2-(4-((R)-3-((4-Chlorophenyl)amino)-2-((cis)-4-(6-fluoroquinolin-4-yl)cyclohexyl)-3-oxopropyl)phenyl)propanoic acid To Intermediate 137D (10 mg, 0.016 mmol) in a 2 dram vial was added 50% TFA/$CH_2Cl_2$ (0.3 mL, 0.016 mmol) The reaction was stirred at RT for 2 h. The reaction was concentrated to dryness and freeze dried for 2 days. Example 137 (9.5 mg, 0.014 mmol, 83% yield) was obtained as white solid. ¹H NMR (400 MHz, chloroform-d) δ 8.74-8.52 (m, 1H), 8.34 (br. s., 1H), 7.90-7.78 (m, 2H), 7.72 (t, J=7.9 Hz, 1H), 7.32-7.19 (m, 6H), 7.15 (d, J=8.7 Hz, 2H), 6.92 (d, J=8.6 Hz, 1H), 6.95 (d, J=8.3 Hz, 1H), 3.67 (d, J=6.7 Hz, 1H), 3.42 (br. s., 1H), 3.13-2.83 (m, 3H), 2.30 (br. s., 1H), 2.15 (br. s., 1H), 2.02 (br. s., 1H), 1.97-1.87 (m, 3H), 1.84 (br. s., 3H), 1.41 (t, J=6.1 Hz, 3H) MS: Anal. Calc'd for $C_{33}H_{32}ClFN_2O_3$ 558.209. found [M+H] 559.3 LC: tr=0.87 min (Method B).

Enantiomer 1 and 2 from Racemic Example 137

Enantiomer 1

Example 138

2-(4-((R)-3-((4-chlorophenyl)amino)-2-((cis)-4-(6-fluoroquinolin-4-yl)cyclohexyl)-3-oxopropyl)phenyl)propanoic acid Homochiral, Stereochemistry not Determined

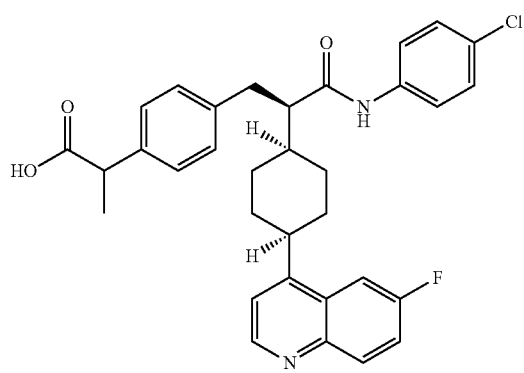 [SMILES: CC(C(=O)O)c1ccc(C[C@@H](C(=O)Nc2ccc(Cl)cc2)[C@H]2CC[C@@H](c3ccnc4ccc(F)cc43)CC2)cc1]

Enantiomer 2

Example 139

2-(4-((R)-3-((4-chlorophenyl)amino)-2-((cis)-4-(6-fluoroquinolin-4-yl)cyclohexyl)-3-oxopropyl)phenyl)propanoic acid Homochiral, Stereochemistry not Determined

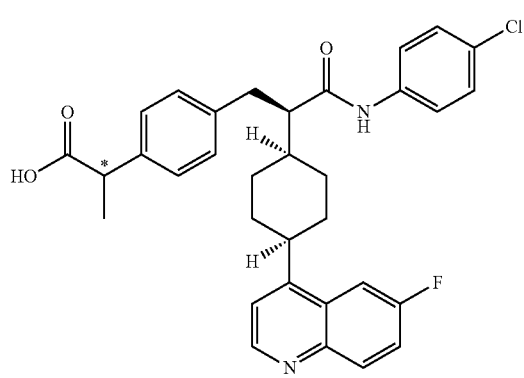 [SMILES: CC(C(=O)O)c1ccc(C[C@@H](C(=O)Nc2ccc(Cl)cc2)[C@H]2CC[C@@H](c3ccnc4ccc(F)cc43)CC2)cc1]

The diastereomers of Example 137 were purified via preparative SFC with the following conditions: Column: Chiral WHELK-O® KROMASIL® 25×3 cm ID, 5-μm particles; Mobile Phase A: 70/30 $CO_2$/MeOH; Detector Wavelength: 220 nm; Flow: 85 mL/min. The appropriate fractions (Enantiomer 1 "Peak-1" tr=15.2 min (Example 138) and Enantiomer 2 "Peak-2" tr=17.2 min (Example 139) to afford:

Example 138

Enantiomer 1, First Eluting

¹H NMR (400 MHz, chloroform-d) δ 8.67 (br. s., 1H), 8.18-7.97 (m, 1H), 7.67 (d, J=10.5 Hz, 1H), 7.47 (t, J=7.2 Hz, 1H), 7.33-7.23 (m, 6H), 7.17 (d, J=7.8 Hz, 2H), 7.08 (s, 4H), 7.02 (br. s., 1H), 3.76 (d, J=6.7 Hz, 1H), 3.36 (br. s., 1H), 3.03 (d, J=10.1 Hz, 1H), 2.87 (t, J=12.2 Hz, 1H), 2.63 (t, J=10.0 Hz, 2H), 2.32 (br. s., 2H), 2.12 (br. s., 2H), 2.02-1.79 (m, 2H), 1.73 (d, J=10.0 Hz, 2H), 1.53 (d, J=7.1 Hz, 3H) MS: Anal. Calc'd for $C_{33}H_{32}ClFN_2O_3$ 558.209. found [M+H] 559.3 LC: tr=0.86 min (Method B).

Example 139

Enantiomer 2

First Eluting

¹H NMR (400 MHz, chloroform-d) δ 8.64 (br. s., 1H), 8.16-8.03 (m, 1H), 7.66 (d, J=8.8 Hz, 1H), 7.45 (t, J=7.3 Hz, 1H), 7.30 (br. s., 7H), 7.20-7.01 (m, 7H), 3.74 (br. s., 1H), 3.35 (br. s., 1H), 3.00 (d, J=11.1 Hz, 1H), 2.96-2.80 (m, 1H), 2.71-2.55 (m, 1H), 2.31 (d, J=8.7 Hz, 1H), 2.25-2.13 (m, 1H), 2.09 (br. s., 3H), 2.00-1.86 (m, 2H), 1.83 (br. s., 2H), 1.58-1.33 (m, 2H), 1.30-1.25 (m, 2H), 1.00-0.71 (m, 1H) MS: Anal. Calc'd for $C_{33}H_{32}ClFN_2O_3$ 558.209. found [M+H] 559.3 LC: tr=0.86 min (Method B).

Example 140

2-(4-((R)-3-((4-Cyanophenyl)amino)-2-((cis)-4-(6-fluoroquinolin-4-yl)cyclohexyl)-3-oxopropyl)phenyl)propanoic acid

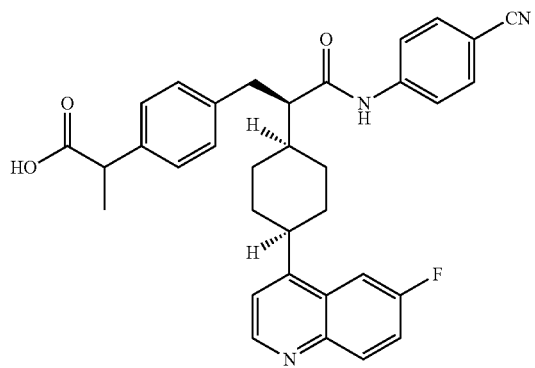 [SMILES: CC(C(=O)O)c1ccc(C[C@@H](C(=O)Nc2ccc(C#N)cc2)[C@H]2CC[C@@H](c3ccnc4ccc(F)cc43)CC2)cc1]

Example 140 was obtained following the procedures in Example 137 using the corresponding 4-cyanoaniline. ¹H NMR (400 MHz, chloroform-d) δ 8.99 (br. s., 1H), 8.42 (br.

s., 1H), 8.06 (br. s., 1H), 7.95 (d, J=9.3 Hz, 1H), 7.83 (t, J=8.2 Hz, 1H), 7.50-7.35 (m, 3H), 7.25-7.10 (m, 4H), 3.78-3.54 (m, 1H), 3.53 (s, 1H), 3.18-2.92 (m, 2H), 2.92-2.65 (m, 1H), 2.38 (br. s., 1H), 2.27-2.16 (m, 1H), 2.03 (s, 2H), 2.00-1.93 (m, 3H), 1.91 (br. s., 3H), 1.80 (br. s., 1H), 1.52-1.36 (m, 3H), 0.94-0.69 (m, 1H) MS: Anal. Calc'd for $C_{34}H_{32}FN_3O_3$ 549.243. found [M+H] 550.3 LC: tr=0.83 min (Method B).

Examples 141 and 142

These compounds were obtained following the procedures in Example 137 using the corresponding carboxylic acids (which can be made either by using General Procedures K, B, E or 58A) and cyclohexylamine.

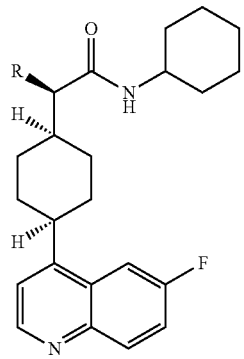

Example 143

(±)-N-(4-chlorophenyl)-2-(cis- and trans-4-(pyrazolo[1,5-a]pyrimidin-7-yl)cyclohexyl)propanamide Mixture of Four Isomers

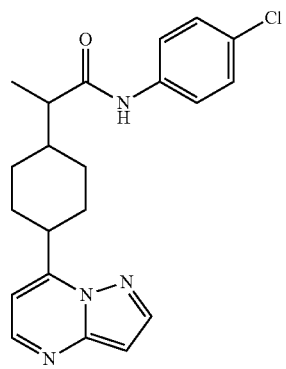 [SMILES: CC(C(=O)Nc1ccc(Cl)cc1)C1CCC(c2ccnc3ccnn23)CC1]

Intermediate 143A ethyl 2-(1,4-dioxaspiro[4.5]decan-8-ylidene)propanoate

To a suspension of NaH (0.307 g, 7.68 mmol) in THF (8 mL) cooled at 0° C. was added ethyl 2-(diethoxyphosphoryl)

TABLE 6

| Ex. No. | Name | R | Tr (min) | [M + H]⁺ |
|---|---|---|---|---|
| 141 | (R)-N-cyclohexyl-2-((cis)-4-(6-fluoroquinolin-4-yl)cyclohexyl)propanamide | | 0.77 | 383.1 |
| 142 | N-cyclohexyl-2-((cis)-4-(6-fluoroquinolin-4-yl)cyclohexyl)acetamide | | 0.74 | 369.1 | propanoate (1.830 g, 7.68 mmol) slowly. After 30 min, 1,4-dioxaspiro[4.5]decan-8-one (1 g, 6.40 mmol) was added. The resulting mixture was stirred at 0° C. for 2 hours, then warmed up to room temperature for overnight. The mixture was quenched with water, THF was removed under reduced pressure. The residue was dissolved in EtOAc, washed with water, brine, dried over $Na_2SO_4$ and concentrated. The crude was purified by ISCO (EtOAc/Hex 0-30%). Fractions containing the product were concentrated to yield Intermediate 143A (1.2 g, 78% yield) a light yellow oil. NMR (400 MHz, CHLOROFORM-d) δ 4.19 (q, J=7.1 Hz, 2H), 4.03-3.89 (m, 4H), 2.68-2.53 (m, 2H), 2.46-2.28 (m, 2H), 1.89 (s, 3H), 1.78-1.66 (m, 4H), 1.30 (t, J=7.1 Hz, 3H)

Intermediate 143B ethyl 2-(1,4-dioxaspiro[4.5]decan-8-yl)propanoate

A suspension of Intermediate 143A (500 mg, 2.081 mmol) (1A) and 10% palladium on carbon (25 mg, 0.024 mmol) in EtOAc (5 mL) was hydrogenated in a Parr shaker at 45 psi for 6 h. The catalyst was filtered, and the filtrate was concentrated to yield Intermediate 143B (450 mg, 89% yield) as a light oil. $^1$H NMR (400 MHz, CHLOROFORM-d) δ 4.12 (dtt, J=10.7, 7.1, 3.6 Hz, 2H), 3.98-3.81 (m, 4H), 2.35-2.17 (m, 1H), 1.83-1.68 (m, 3H), 1.66-1.45 (m, 4H), 1.43-1.28 (m, 2H), 1.27-1.22 (m, 3H), 1.14-1.07 (m, 3H)

Intermediate 143C ethyl 2-(4-oxocyclohexyl)propanoate

To a solution of ethyl 2-(1,4-dioxaspiro[4.5]decan-8-yl) propanoate (450 mg, 1.857 mmol)(1B) in THF (5 mL) was added 1M hydrogen chloride(aqueous) (0.929 mL, 3.71 mmol). The mixture was heated to 50° C. for 6 h. The reaction mixture was concentrated. The residue was dissolved in EtOAc, washed with water (2×), brine, dried over $Na_2SO_4$ and concentrated. The crude was purified with ISCO (EtOAc/Hex 0-30%). Fractions containing product were concentrated to yield Intermediate 143C (290 mg, 79% yield) as a clear oil. $^1$H NMR (400 MHz, CHLOROFORM-d) δ 4.22-4.06 (m, 2H), 2.46-2.30 (m, 5H), 2.13-1.91 (m, 3H), 1.56-1.42 (m, 2H), 1.31-1.24 (m, 3H), 1.18 (d, J=7.1 Hz, 3H)

Intermediate 143D ethyl 2-(4-(((trifluoromethyl)sulfonyl)oxy)cyclohex-3-en-1-yl)propanoate Intermediate 143C (200 mg, 1.01 mmol)(1 C) and 2,6-di-tert-butyl-4-methylpyridine (238 mg, 1.16 mmol) were dissolved in dry DCM (10 ml). To the reaction mixture trifluoromethanesulfonic anhydride (0.186 mL, 1.11 mmol) was added dropwise and stirred for 2 h. The suspension was filtered and the filtrate was diluted with DCM, washed with 1N HCl (2×), satd. sodium bicarb solution, water, brine and dried over $Na_2SO_4$ and concentrated to yield Intermediate 143D (320 mg, 96% yield) as a brown oil. $^1$H NMR (400 MHz, CHLOROFORM-d) δ 5.73 (t, J=6.1 Hz, 1H), 4.28-4.05 (m, 2H), 2.52-2.17 (m, 4H), 2.08-1.79 (m, 3H), 1.49 (dt, J=11.1, 6.6 Hz, 1H), 1.31-1.20 (m, 3H), 1.19-1.04 (m, 3H)

Intermediate 143E ethyl 2-(4-(4,4,5,5-tetramethyl-1,3,2-dioxaborolan-2-yl)cyclohex-3-en-1-yl)propanoate To a solution of Intermediate 143D (300 mg, 0.908 mmol)(1D) in DMSO (5 mL) was added 4,4,4',4',5,5,5',5'-octamethyl-2,2'-bi(1,3,2-dioxaborolane) (230 mg, 0.908 mmol) and potassium acetate (267 mg, 2.72 mmol). After the mixture was degassed with $N_2$ for 10 min, $PdCl_2$(dppf) (19.9 mg, 0.027 mmol) was added. The mixture was heated to 80° C. for overnight. The mixture was partitioned between EtOAc and water. The organic phase was concentrated and purified by ISCO. Fractions containing product were concentrated to yield Intermediate 143E (168 mg, 60% yield) as a brown oil. $^1$H NMR (400 MHz, CHLOROFORM-d) δ 6.66-6.40 (m, 1H), 4.31-4.00 (m, 2H), 2.34-2.26 (m, 1H), 2.25-2.19 (m, 1H), 2.19-2.04 (m, 2H), 1.95-1.75 (m, 3H), 1.73-1.60 (m, 1H), 1.29-1.24 (m, 15H), 1.13 (dd, J=11.6, 7.0 Hz, 3H)

Intermediate 143F

Ethyl 2-(4-(pyrazolo[1,5-a]pyrimidin-7-yl)cyclohex-3-en-1-yl)propanoate

A mixture of 7-chloropyrazolo[1,5-a]pyrimidine (0.193 g, 1.260 mmol), Intermediate 143E (0.400 g, 1.298 mmol), $Na_2CO_3$ (0.534 g, 5.04 mmol), and $Pd(Ph_3P)_4$ (0.073 g, 0.063 mmol) in dioxane (11.67 ml) and water (3.89 ml) was heated at 100° C. overnight. The reaction was quenched with water and diluted with EtOAc. Layers were separated. The aqueous phase was extracted with EtOAc (3×). The organics were combined, dried over $Na_2SO_4$, filtered, and concentrated to afford a brown residue. Purification of the crude material by silica gel chromatography using an ISCO machine (40 g column, 40 mL/min, 0-70% EtOAc in hexanes over 16 min, $t_r$=10.5 min) gave 143F (0.224 g, 0.748 mmol, 59.4% yield) as a yellow residue. ESI MS (M+H)$^+$=300.2. HPLC Peak $t_r$=0.95 minutes. HPLC conditions: method A.

Intermediate 143G

Ethyl 2-(4-(pyrazolo[1,5-a]pyrimidin-7-yl)cyclohexyl)propanoate

To a solution of 143F (0.224 g, 0.748 mmol) in MeOH (3.74 ml) was added ammonium formate (0.236 g, 3.74 mmol) followed by Pd/C (0.021 g, 0.202 mmol). The reaction was heated at 70° C. for 1 h. The reaction was filtered through CELITE® and the filter cake washed with $CH_2Cl_2$. The filtrate was concentrated. The crude material was taken up in EtOAc and washed with a sat. aq. solution of $NaHCO_3$ (1×). The organic phase was dried over $Na_2SO_4$, filtered, and concentrated to afford 143G (220 mg, 98%) as a yellow residue. ESI MS (M+H)$^+$=302.2. HPLC Peak $t_r$=0.94 minutes. HPLC conditions: method A.

Example 143

(±)-N-(4-chlorophenyl)-2-(cis- and trans-4-(pyrazolo[1,5-a]pyrimidin-7-yl)cyclohexyl)propanamide Mixture of Four Isomers To a solution of 4-chloroaniline (92 mg, 0.720 mmol) in THF (0.9 mL) at 0° C. was added a solution of isopropylmagnesium chloride (360 μl, 0.720 mmol). The resulting solution was warmed to rt and stirred for 5 min, then 143G (108.5 mg, 0.360 mmol) in THF (0.9 mL) was added dropwise. The reaction was heated at 70° C. for 2.5 h, then allowed to cool to rt. Additional 4-chloroaniline (42 mg) and isopropylmagnesium chloride (360 μl, 0.720 mmol) were added. The reaction was quenched with a sat. aq. soln. of NH₄Cl and diluted with EtOAc. Layers were separated. The aqueous phase was extracted with EtOAc (3×). The combined organic phases were dried over Na₂SO₄, filtered, and concentrated to afford a residue. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-80% B over 20 minutes, then a 5-minute hold at 100% B; Flow: 20 mL/min. Fractions containing the desired product were combined and dried via centrifugal evaporation to afford the title compound as a mixture of 4 isomers (43.4 mg, 31%). ESI MS (M+H)⁺=383.1. HPLC Peak t$_r$=0.96 minutes. Purity=99%. HPLC conditions: method A.

Examples 144 (a), (b), (c), and (d)

(S)—N-(4-chlorophenyl)-2-((cis)-4-(pyrazolo[1,5-a]pyrimidin-7-yl)cyclohexyl)propanamide and (R)—N-(4-chlorophenyl)-2-((cis)-4-(pyrazolo[1,5-a]pyrimidin-7-yl)cyclohexyl)propanamide and (S)—N-(4-chlorophenyl)-2-((trans)-4-(pyrazolo[1,5-a]pyrimidin-7-yl)cyclohexyl)propanamide and (R)—N-(4-chlorophenyl)-2-((trans)-4-(pyrazolo[1,5-a]pyrimidin-7-yl)cyclohexyl)propanamide Homochiral, Absolute and Relative Stereochemistry was not Determined and Arbitrarily Assigned

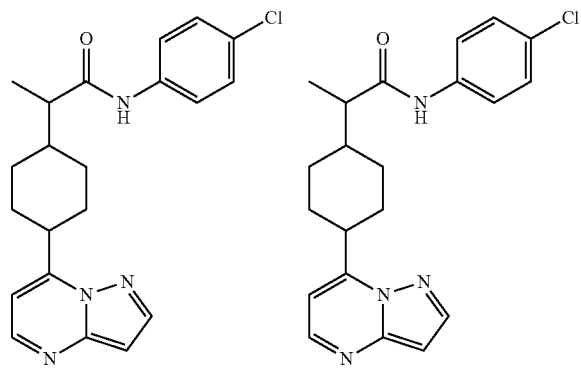

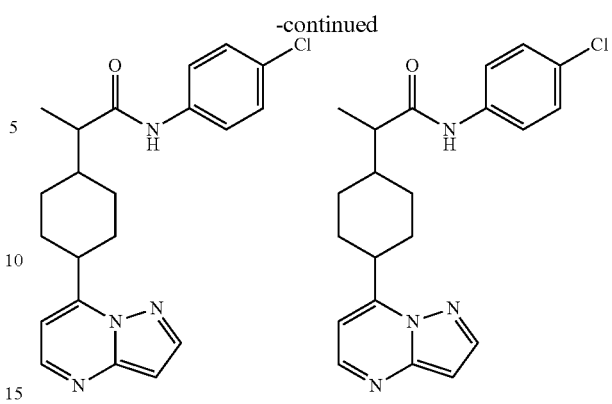

Approximately 43.4 mg of diastereomeric and racemic Example 143 was resolved. The isomeric mixture was purified via preparative SFC with the following conditions: Column: Chiral IE, 25×3 cm ID, 5-μm particles; Mobile Phase A: 80/20 CO₂/MeOH; Detector Wavelength: 220 nm; Flow: 85 mL/min. The fractions (144(a) "Peak-1" t$_r$=13.272, 144(b) "Peak-2" t$_r$=14.097, 144(c) "Peak-3" t$_r$=19.986, 144 (d) "Peak-4" t$_r$=27.958; analytical conditions: Column: Chiral IE, 250×4.6 mm ID, 5-μm particles; Mobile Phase A: 80/20 CO₂/MeOH; Flow: 2.0 mL/min) were collected in MeOH. The stereoisomeric purity of peak 2 and peak 3 was estimated to be greater than 99% based on the prep-SFC chromatograms. Peak 1 (23.8 mg) was re-purified via preparative SFC with the following conditions: Column: Chiral OJ, 25×3 cm ID, 5-μm particles; Mobile Phase A: 80/20 CO₂/MeOH; Detector Wavelength: 220 nm; Flow: 85 mL/min. The fractions ("Peak-1" t$_r$=4.558 and "Peak-2" t$_r$=5.622; analytical conditions: Column: Chiral OJ, 250×4.6 mm ID, 5-μm particles; Mobile Phase A: 80/20 CO₂/MeOH; Flow: 2.0 mL/min) was collected in MeOH. The stereoisomeric purity of the fractions was estimated to be greater than 99% based on the prep-SFC chromatogram. Each diastereomer or enantiomer was further purified via preparative LC/MS:

Example 144(a)

First Eluting Isomer

The crude material was purified via preparative LC/MS with the following conditions: Column: Waters XBridge c-18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 10-minute hold at 100% B; Flow: 20 mL/min. Fractions containing the desired product were combined and dried via centrifugal evaporation to afford Isomer 1 (11.3 mg, 8.2%). ESI MS (M+H)⁺=383.2. HPLC Peak t$_r$=1.833 minutes. Purity=100%. HPLC conditions: B. Absolute stereochemistry not determined.

Example 144(b)

Second Eluting Isomer

The crude material was purified via preparative LC/MS with the following conditions: Column: Waters XBridge c-18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 10-minute hold at 100% B; Flow: 20 mL/min. Fractions containing the desired product were combined and dried via centrifugal evaporation to afford Isomer 2 (11.1 mg, 8.1%). ESI MS (M+H)$^+$=382.9. HPLC Peak $t_r$=1.829 minutes. Purity=100%. HPLC conditions: B. Absolute stereochemistry not determined.

Example 144(c)

Third Eluting Isomer

The crude material was purified via preparative LC/MS with the following conditions: Column: Waters XBridge c-18, 19×200 mm, 5-gin particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 10-minute hold at 100% B; Flow: 20 mL/min. Fractions containing the desired product were combined and dried via centrifugal evaporation to afford Isomer 3 (7.2 mg, 5.0%). ESI MS (M+H)$^+$=383.2. HPLC Peak $t_r$=1.874 minutes. Purity=96%. HPLC conditions: B. Absolute stereochemistry not determined.

Example 144(d)

Fourth Eluting Isomer

The crude material was purified via preparative LC/MS with the following conditions: Column: Waters XBridge c-18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 40-100% B over 20 minutes, then a 10-minute hold at 100% B; Flow: 20 mL/min. Fractions containing the desired product were combined and dried via centrifugal evaporation to afford Isomer 4 (7.6 mg, 5.1%). ESI MS (M+H)$^+$=383.3. HPLC Peak $t_r$=1.874 minutes. Purity=93%. HPLC conditions: B. Absolute stereochemistry not determined.

Example 147

(±)-2-(Cis- and trans-4-(1,8-naphthyridin-4-yl)cyclohexyl)-N-(4-chlorophenyl)propanamide Mixture of Four Isomers

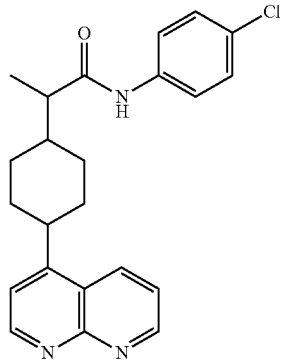 [SMILES: CC(C(=O)Nc1ccc(Cl)cc1)C1CCC(c2ccnc3ncccc23)CC1]

Intermediate 147A

Ethyl 2-(4-(1,8-naphthyridin-4-yl)cyclohex-3-en-1-yl)propanoate

A mixture of 4-bromo-1,8-naphthyridine (0.070 g, 0.335 mmol), Intermediate 143E (0.106 g, 0.345 mmol), Na$_2$CO$_3$ (0.142 g, 1.339 mmol), and Pd(Ph$_3$P)$_4$ (0.019 g, 0.017 mmol) in dioxane (3.10 ml) and water (1.034 ml) was heated at 100° C. overnight. The reaction was quenched with water and diluted with EtOAc. Layers were separated. The aqueous phase was extracted with EtOAc (2×). The organics were combined, dried over Na$_2$SO$_4$, filtered, and concentrated to afford a brown residue. Purification of the crude material by silica gel chromatography using an ISCO machine (24 g column, 35 mL/min, 0-20% MeOH in CH$_2$Cl$_2$ over 25 min, $t_r$=17 min) gave 147A (92.7 mg, 0.299 mmol, 89% yield) as a yellow residue. ESI MS (M+H)$^+$=311.2. HPLC Peak $t_r$=0.72 minutes. HPLC conditions: method A.

Intermediate 147B

Ethyl 2-(4-(1,8-naphthyridin-4-yl)cyclohexyl)propanoate

To a solution of 147A (0.0927 g, 0.299 mmol) in MeOH (1.493 ml) was added ammonium formate (0.094 g, 1.493 mmol) followed by 10% Pd/C (8.58 mg, 0.081 mmol). The reaction was heated at 70° C. for 1 h. The reaction was filtered through CELITE® and the filter cake washed with CH$_2$Cl$_2$. The filtrate was concentrated. The crude material was taken up in EtOAc and washed with a sat. aq. solution of NaHCO$_3$ (1×). The organic phase was dried over Na$_2$SO$_4$, filtered, and concentrated to afford 147B (72.5 mg, 78%) as a brown residue. ESI MS (M+H)$^+$=313.3. HPLC Peak $t_r$=0.70 minutes. HPLC conditions: method A.

Example 147

(±)-2-(Cis- and trans-4-(1,8-naphthyridin-4-yl)cyclohexyl)-N-(4-chlorophenyl)propanamide Mixture of Four Isomers To a solution of 4-chloroaniline (0.059 g, 0.464 mmol) in THF (0.4 mL) at 0° C. was added a solution of isopropylmagnesium chloride (0.232 ml, 0.464 mmol). The resulting solution was warmed to rt and stirred for 5 min, then 147B (0.0725 g, 0.232 mmol) in THF (0.76 mL) was added dropwise. The reaction was heated at 70° C. for 3 h, then allowed to cool to rt. The reaction was quenched with a sat. aq. soln. of NH$_4$Cl and diluted with EtOAc. Layers were separated. The aqueous phase was extracted with EtOAc (3×). The combined organic phases were dried over Na$_2$SO$_4$, filtered, and concentrated to afford a residue. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford the title compound as a mixture of 4 isomers (33.4 mg, 36%). ESI MS (M+H)$^+$=394.2. HPLC Peak t$_r$=1.743 minutes. Purity=98%. HPLC conditions: method B.

Example 148 (a), (b), (c), and (d)

(S)-2-((cis)-4-(1,8-Naphthyridin-4-yl)cyclohexyl)-N-(4-chlorophenyl)propanamide and (R)-2-((cis)-4-(1,8-naphthyridin-4-yl)cyclohexyl)-N-(4-chlorophenyl)propanamide and (S)-2-((trans)-4-(1,8-naphthyridin-4-yl)cyclohexyl)-N-(4-chlorophenyl)propanamide and (R)-2-((trans)-4-(1,8-naphthyridin-4-yl)cyclohexyl)-N-(4-chlorophenyl)propanamide Homochiral, Absolute and Relative Stereochemistry not Determined and Arbitrarily Assigned

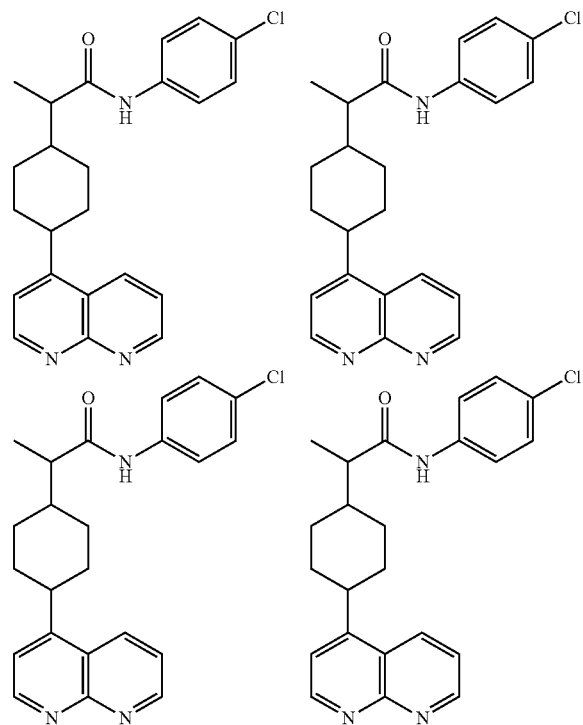

Approximately 34.3 mg of diastereomeric and racemic Example 147 was resolved. The isomeric mixture was purified via preparative SFC with the following conditions: Column: Chiral AD, 25×3 cm ID, 5-µm particles; Mobile Phase A: 70/30 CO$_2$/MeOH; Detector Wavelength: 220 nm; Flow: 85 mL/min. The fractions ("Peak-1" t$_r$=7.377, "Peak-2" t$_r$=8.774, "Peak-3" t$_r$=10.106, "Peak-4" t$_r$=14.282; analytical conditions: Column: Chiral AD, 250×4.6 mm ID, 5-µm particles; Mobile Phase A: 70/30 CO$_2$/MeOH; Flow: 2.0 mL/min) were collected in MeOH. The stereoisomeric purity of each fraction was estimated to be greater than 99% based on the prep-SFC chromatograms. Each diastereomer or enantiomer was further purified via preparative LC/MS:

Example 148 (a)

First Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 1 (5.3 mg, 5.7%). ESI MS (M+H)$^+$=394.1. HPLC Peak t$_r$=1.757 minutes. Purity=99%. HPLC conditions: method B. Absolute stereochemistry not determined.

Example 148 (b)

Second Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 2 (6.0 mg, 6.4%). ESI MS (M+H)$^+$=394.1. HPLC Peak tr=1.719 minutes. Purity=98%. HPLC conditions: method B. Absolute stereochemistry not determined.

Example 148 (c)

Third Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 3 (6.1 mg, 6.3%). ESI MS (M+H)$^+$=394.2. HPLC Peak t$_r$=1.694 minutes. Purity=95%. HPLC conditions: method B. Absolute stereochemistry not determined.

Example 148 (d)

Fourth Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 19 minutes, then a 5-minute hold at 100% B; Flow: 20 mL/min. Fractions containing the desired product were combined and dried via centrifugal evaporation to afford Isomer 4 (3.5 mg, 3.8%). ESI MS (M+H)⁺=394.3. HPLC Peak $t_r$=1.743 minutes. Purity=99%. HPLC conditions: method B. Absolute stereochemistry not determined.

Example 149

(±)-2-(Cis- and trans-4-(1H-pyrazolo[4,3-b]pyridin-7-yl)cyclohexyl)-N-(4-chlorophenyl)propanamide Mixture of Four Isomers

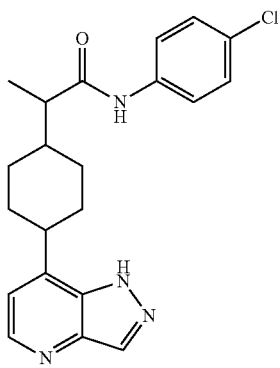 [SMILES: CC(C(=O)Nc1ccc(Cl)cc1)C1CCC(c2ccnc3cn[nH]c23)CC1]

Intermediate 149A

Ethyl 2-(4-(1H-pyrazolo[4,3-b]pyridin-7-yl)cyclohex-3-en-1-yl)propanoate

A mixture of 7-chloro-1H-pyrazolo[4,3-b]pyridine (0.048 g, 0.315 mmol), Intermediate 143E (0.100 g, 0.324 mmol), Na₂CO₃ (0.134 g, 1.260 mmol), and 10% Pd(Ph₃P)₄ (0.018 g, 0.016 mmol) in dioxane (2.92 ml) and water (0.972 ml) was heated at 100° C. overnight. The reaction was quenched with water and diluted with EtOAc. Layers were separated. The aqueous phase was extracted with EtOAc (3×). The organics were combined, dried over Na₂SO₄, filtered, and concentrated to afford a brown residue. Purification of the crude material by silica gel chromatography using an ISCO machine (40 g column, 40 mL/min, 0-100% EtOAc in hexanes over 23 min, $t_r$=18 min) gave 149A (0.039 g, 0.124 mmol, 39.3% yield) as a yellow residue. ESI MS (M+H)⁺=300.2. HPLC Peak $t_r$=0.69 minutes. HPLC conditions: method A.

Intermediate 149B

Ethyl 2-(4-(1H-pyrazolo[4,3-b]pyridin-7-yl)cyclohexyl)propanoate

To a solution of 149A (0.0395 g, 0.132 mmol) in MeOH (0.660 ml) was added ammonium formate (0.042 g, 0.660 mmol) followed by Pd/C (3.79 mg, 0.036 mmol). The reaction was heated at 70° C. for 1 h. Additional ammonium formate (0.042 g, 0.660 mmol) was added and the reaction was heated for 1 h at 70° C., then allowed to cool to rt. The reaction was filtered through CELITE® and the filter cake washed with CH₂Cl₂. The filtrate was concentrated. The crude material was taken up in EtOAc and washed with a sat. aq. solution of NaHCO₃ (1×). The organic phase was dried over Na₂SO₄, filtered, and concentrated to afford 149B (34.3 mg, 86%) as a yellow residue. Will carry forward crude. ESI MS (M+H)⁺=302.4. HPLC Peak $t_r$=0.66 minutes. HPLC conditions: method A.

Example 149

(±)-2-(Cis- and trans-4-(1H-pyrazolo[4,3-b]pyridin-7-yl)cyclohexyl)-N-(4-chlorophenyl)propanamide Mixture of Four Isomers To a solution of 4-chloroaniline (58.1 mg, 0.455 mmol) in THF (0.3 mL) at 0° C. was added a solution of isopropylmagnesium chloride (228 μl, 0.455 mmol). The resulting solution was warmed to rt and stirred for 5 min, then 149B (34.3 mg, 0.114 mmol) in THF (0.3 mL) was added dropwise. The reaction was heated at 70° C. for 2 h, then allowed to cool to rt. The reaction was quenched with a sat. aq. soln. of NH₄Cl and diluted with EtOAc. Layers were separated. The aqueous phase was extracted with EtOAc (3×). The combined organic phases were dried over Na₂SO₄, filtered, and concentrated to afford a residue. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford the title compound as a mixture of 4 isomers (25.4 mg, 58%). ESI MS (M+H)⁺=383.3. HPLC Peak $t_r$=1.662 minutes. Purity=99%. HPLC conditions: method B.

Example 150 (a), (b), (c), and (d)

(S)-2-((cis)-4-(1H-Pyrazolo[4,3-b]pyridin-7-yl)cyclohexyl)-N-(4-chlorophenyl)propanamide and (R)-2-((cis)-4-(1H-pyrazolo[4,3-b]pyridin-7-yl)cyclohexyl)-N-(4-chlorophenyl)propanamide and (S)-2-((trans)-4-(1H-pyrazolo[4,3-b]pyridin-7-yl)cyclohexyl)-N-(4-chlorophenyl)propanamide and (R)-2-((trans)-4-(1H-pyrazolo[4,3-b]pyridin-7-yl)cyclohexyl)-N-(4-chlorophenyl)propanamide Homochiral, Absolute and Relative Stereochemistry not Determined and Arbitrarily Assigned

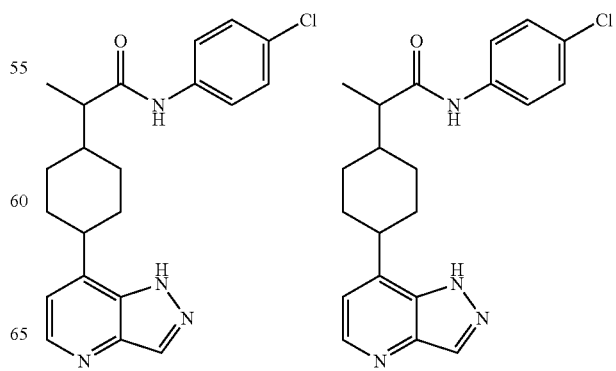

-continued

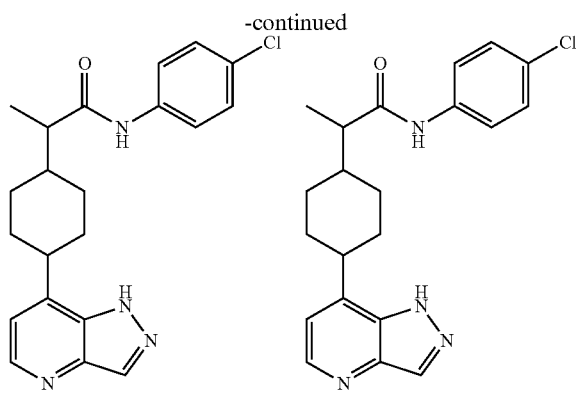

Approximately 29.3 mg of diastereomeric and racemic Example 149 was resolved. The isomeric mixture was purified via preparative SFC with the following conditions: Column: Chiral WHELK-O®, 25×3 cm ID, 5-μm particles; Mobile Phase A: 70/30 $CO_2$/MeOH; Detector Wavelength: 220 nm; Flow: 85 mL/min. The fractions (150(a) "Peak-1" $t_r$=9.587, 150(b) "Peak-2" $t_r$=10.407, 150(c) "Peak-3" $t_r$=11.794, 15-(d) "Peak-4" $t_r$=12.855; analytical conditions: Column: Chiral WHELK-O®, 250×4.6 mm ID, 5-μm particles; Mobile Phase A: 80/20 $CO_2$/MeOH; Flow: 2.0 mL/min) were collected in MeOH. The stereoisomeric purity of Peak 1, 3, and 4 were estimated to be greater than 95% based on the prep-SFC chromatograms. Peak 2 was re-purified via preparative SFC with the following conditions: Column: Chiral AS, 25×3 cm ID, 5-μm particles; Mobile Phase A: 80/20 $CO_2$/MeOH; Detector Wavelength: 220 nm; Flow: 85 mL/min. The fractions ("Peak-1" $t_r$=3.391 and "Peak-2" $t_r$=4.071; analytical conditions: Column: Chiral AS, 250×4.6 mm ID, 5-μm particles; Mobile Phase A: 80/20 $CO_2$/MeOH; Flow: 2.0 mL/min) was collected in MeOH. The stereoisomeric purity of the fractions was estimated to be greater than 99% based on the prep-SFC chromatogram. Each diastereomer or enantiomer was further purified via preparative LC/MS:

Example 150(a)

First Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford Isomer 1 (4.6 mg, 11%). ESI MS $(M+H)^+$=383.1. HPLC Peak $t_r$=1.611 minutes. Purity=100%. HPLC conditions: method B. Absolute stereochemistry not determined.

Example 150(b)

Second Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford Isomer 2 (4.6 mg, 11%). ESI MS $(M+H)^+$=383.2. HPLC Peak $t_r$=1.630 minutes. Purity=100%. HPLC conditions: method B. Absolute stereochemistry not determined.

Example 150(c)

Third Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford Isomer 3 (9.1 mg, 21%). ESI MS $(M+H)^+$=383.2. HPLC Peak $t_r$=1.659 minutes. Purity=100%. HPLC conditions: method B. Absolute stereochemistry not determined.

Example 150(d)

Fourth Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to afford Isomer 4 (4.7 mg, 10%). ESI MS $(M+H)^+$=383.3. HPLC Peak $t_r$=1.704 minutes. Purity=93%. HPLC conditions: method B. Absolute stereochemistry not determined.

Example 151

(±)-N-(Cis- and trans-4-chlorophenyl)-2-(4-(6-iodoquinolin-4-yl)cyclohexyl)propanamide

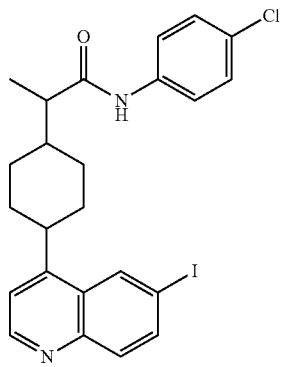

Intermediate 151A

Ethyl 2-(4-(6-nitroquinolin-4-yl)cyclohex-3-en-1-yl)propanoate

A 350 mL sealed tube was charged with a mixture of 4-chloro-6-nitroquinoline (2 g, 9.59 mmol), Intermediate 143E (3.04 g, 9.88 mmol), $Na_2CO_3$ (4.06 g, 38.4 mmol), and $Pd(Ph_3P)_4$ (0.554 g, 0.479 mmol) in dioxane (89 mL) and water (29.6 mL). The reaction was heated at 100° C. overnight. The reaction was quenched with water and diluted with EtOAc. Layers were separated. The aqueous phase was extracted with EtOAc (3×). The organics were combined, dried over $Na_2SO_4$, filtered, and concentrated to afford a brown residue. Purification of the crude material by silica gel chromatography using an ISCO machine (80 g column, 60 mL/min, 0-45% EtOAc in hexanes over 19 min, $t_r$=14 min) gave 151A (2.955 g, 8.34 mmol, 87% yield) as a yellow residue. ESI MS (M+H)$^+$=355.2. HPLC Peak $t_r$=0.98 minutes. HPLC conditions: method A.

Intermediate 151B

Ethyl 2-(4-(6-aminoquinolin-4-yl)cyclohexyl)propanoate

To a solution of 151A (0.455 g, 1.284 mmol) in MeOH (6.42 ml) was added ammonium formate (0.405 g, 6.42 mmol) followed by 10% Pd/C (0.037 g, 0.347 mmol). The reaction was heated at 70° C. for 1 h. The reaction was filtered through CELITE® and the filter cake washed with $CH_2Cl_2$. The filtrate was concentrated. The crude material was taken up in EtOAc and washed with a sat. aq. solution of $NaHCO_3$ (2×). The organic phase was dried over $Na_2SO_4$, filtered, and concentrated to afford 151B (379 mg, 90%) as a brown residue. NMR showed pure desired product in a 1.8:1 dr. ESI MS (M+H)$^+$=327.3. HPLC Peak $t_r$=0.71 minutes. HPLC conditions: method A.

Intermediate 151C

Ethyl 2-(4-(6-iodoquinolin-4-yl)cyclohexyl)propanoate

To a solution of 151B (0.379 g, 1.161 mmol) and aq. HCl (0.59 mL) in water (2.1 mL) was cooled to 0° C., then a solution of sodium nitrite (0.096 g, 1.393 mmol) in water (2.1 mL) was added. A solution of potassium iodide (0.289 g, 1.742 mmol) in water (2.1 mL) was added dropwise to the above solution after the solid dissolved completely. After addition, the mixture was stirred for 30 min at rt, then heated at 70° C. for 1 h. After cooling, the solution was neutralized by slow addition of a solution of $Na_2S_2O_3$ (1.81 mL), then extracted with $CH_2Cl_2$ (2×). The organic phase was washed with water, dried over $Na_2SO_4$, filtered, and concentrated to afford a brown residue. The crude material was dissolved in a minimal amount of $CH_2Cl_2$ and chromatographed. Purification of the crude material by silica gel chromatography using an ISCO machine (40 g column, 40 mL/min, 0-55% EtOAc in hexanes over 15 min, $t_r$=10.5 min) gave 151C (92.7 mg, 0.212 mmol, 18.26% yield) as a yellow residue. ESI MS (M+H)$^+$=438.1. HPLC Peak $t_r$=0.89 minutes. HPLC conditions: method A.

Example 151

(±)-N-(Cis- and trans-4-chlorophenyl)-2-(4-(6-iodoquinolin-4-yl)cyclohexyl)propanamide To a solution of 4-chloroaniline (0.464 g, 3.64 mmol) in THF (2.8 mL) at 0° C. was added a solution of isopropylmagnesium chloride (1.820 mL, 3.64 mmol). The resulting solution was warmed to rt and stirred for 5 min, then 151C (0.796 g, 1.820 mmol) in THF (4.8 mL) was added dropwise. The reaction was heated at 70° C. for 2 h, then allowed to cool to rt. Additional isopropylmagnesium chloride (1.820 mL, 3.64 mmol) was added. The reaction was heated an additional 2 h. The reaction was quenched with a sat. aq. soln. of $NH_4Cl$ and diluted with EtOAc. Layers were separated. The aqueous phase was extracted with EtOAc (3×). The combined organic phases were dried over $Na_2SO_4$, filtered, and concentrated to afford a residue. Purification of the crude material by silica gel chromatography using an ISCO machine (80 g column, 60 mL/min, 0-65% EtOAc in hexanes over 35 min, $t_r$=27 min) gave (±)-trans-Example 151 (455 mg, 0.702 mmol, 39% yield) and (±)-cis-Example 151 (111 mg, 12%). The trans diastereomer elutes first followed by the cis diastereomer. ESI MS (M+H)$^+$=519.1.

Example 152 (a), (b), (c), and (d)

(S)—N-(4-Chlorophenyl)-2-((cis)-4-(6-iodoquinolin-4-yl)cyclohexyl)propanamide and (R)—N-(4-chlorophenyl)-2-((cis)-4-(6-iodoquinolin-4-yl)cyclohexyl)propanamide and (S)—N-(4-chlorophenyl)-2-((trans)-4-(6-iodoquinolin-4-yl)cyclohexyl)propanamide and (R)—N-(4-chlorophenyl)-2-((trans)-4-(6-iodoquinolin-4-yl)cyclohexyl)propanamide Homochiral, Absolute and Relative Stereochemistry not Determined and Arbitrarily Assigned

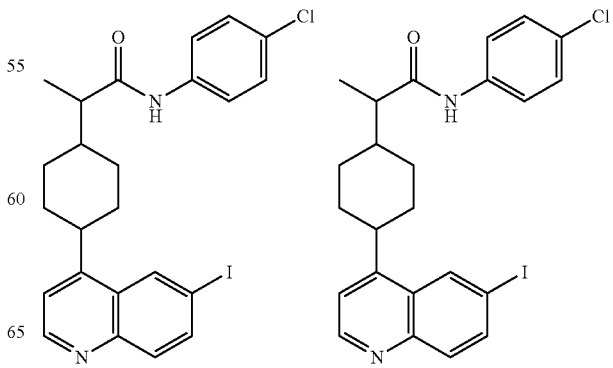

163

-continued

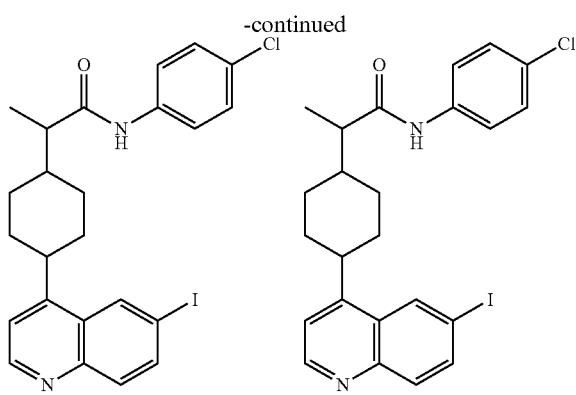

Approximately 65.1 mg of diastereomeric and racemic Example 9 was resolved. The isomeric mixture was purified via preparative SFC with the following conditions: Column: OJ-H, 25×3 cm ID, 5-μm particles; Mobile Phase A: 80/20 CO2/MeOH; Detector Wavelength: 220 nm; Flow: 150 mL/min. The fractions (152(a) "Peak-1" tr=4.64 min, 152(b) "Peak-2" tr=5.35 min, 152(c) and 152(d) "Peak-3" tr=6.43 min) were collected in MeOH. The stereoisomeric purity of Peak 1 and 2 were estimated to be greater than 95% based on the prep-SFC chromatograms. Peak 3 was re-purified via preparative SFC with the following conditions to give Isomers 3 and 4: Column: Lux-Cellulose, 25×3 cm ID, 5-μm particles; Mobile Phase A: 75/25 CO2/MeOH; Detector Wavelength: 220 nm; Flow: 180 mL/min. The fractions (152(a) "Peak-1" tr=7.63 min and 152(b) "Peak-2" tr=8.6 min) was collected in MeOH. The stereoisomeric purity of the fractions was estimated to be greater than 95% based on the prep-SFC chromatograms. Each diastereomer or enantiomer was further purified via preparative LC/MS:

Example 152(a)

First Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 1 (14.5 mg, 12%). ESI MS $(M+H)^+=519.2$. HPLC Peak $t_r=2.530$ minutes. Purity=92%. HPLC conditions: method B. Absolute stereochemistry not determined.

Example 152(b)

Second Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 2 (8.1 mg, 7.3%). ESI MS $(M+H)^+=519.1$. HPLC Peak $t_r=2.470$ minutes. Purity=100%. HPLC conditions: method B. Absolute stereochemistry not determined.

Example 152(c)

Third Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 3 (13.7 mg, 12%). ESI MS $(M+H)^+=519.1$. HPLC Peak $t_r=2.481$ minutes. Purity=97%. HPLC conditions: method B. Absolute stereochemistry not determined.

Example 152(d)

Fourth Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-100% B over 20 minutes, then a 5-minute hold at 100% B; Flow: 20 mL/min. Fractions containing the desired product were combined and dried via centrifugal evaporation to afford Isomer 4 (7.5 mg, 6.7%). ESI MS $(M+H)^+=518.9$. HPLC Peak $t_r=2.361$ minutes. Purity=99%. HPLC conditions: method B. Absolute stereochemistry not determined.

Example 153

(±)-2-((trans)-4-((1,8-Naphthyridin-4-yl)oxy)cyclohexyl)-N-(4-chlorophenyl)propanamide

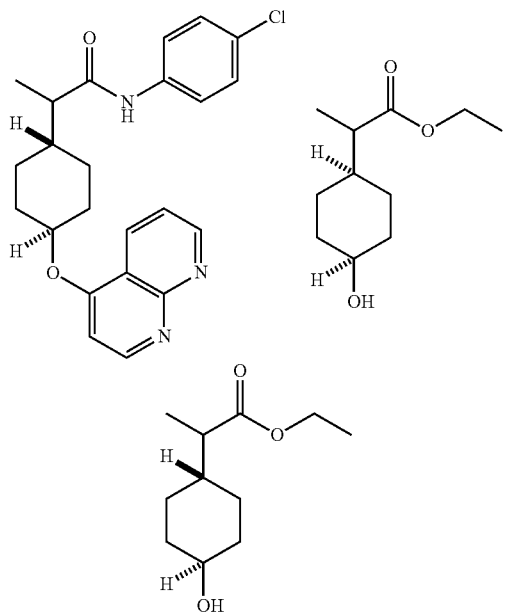

Intermediates 153A and 153B

Ethyl 2-((cis)-4-hydroxycyclohexyl)propanoate (Minor) and ethyl 2-((trans)-4-hydroxycyclohexyl)propanoate (Major)

To a solution of Intermediate 143C (0.241 g, 1.216 mmol) in MeOH (6.08 ml) was added sodium borohydride (0.047 g, 1.240 mmol). The reaction was allowed to stir at rt overnight. The reaction was quenched with water and extracted with EtOAc. Layers were separated. The aqueous phase was extracted with EtOAc (2×). The combined organic phases were dried over $Na_2SO_4$, filtered, and concentrated to afford a residue. Purification of the crude material by silica gel chromatography using an ISCO machine (40 g column, 40 mL/min, 0-100% EtOAc in hexanes over 19 min, $t_r$=10.5 min=cis, 12 min=trans) gave 153A (173 mg, 71%) and 153B (37 mg, 15%). The major product is trans. The minor product is cis. Cis elutes first. Trans elutes second. ESI MS $(M+H)^+$=201.1.

Intermediate 153C

Ethyl 2-((trans)-4-((1,8-naphthyridin-4-yl)oxy)cyclohexyl)propanoate

To a solution of 153B (59.5 mg, 0.297 mmol) in DMF (495 µl) was added NaH (19.80 mg, 0.495 mmol). After 30 min, 4-bromo-1,8-naphthyridine (51.8 mg, 0.248 mmol) as added. The reaction was heated at 80° C. overnight. Reaction quenched with a sat. aq. soln of $NH_4Cl$ and diluted with EtOAc. Layers were separated. The aqueous phase was extracted with EtOAc (2×). The combined organic phases were washed with water, dried over $Na_2SO_4$, filtered, and concentrated to afford a brown residue. Purification of the crude material by silica gel chromatography using an ISCO machine (40 g column, 40 mL/min, 0-20% MeOH in $CH_2Cl_2$ over 9 min, $t_r$=7.5 min) gave 153C (59.8 mg, 0.182 mmol, 73.5% yield) as a colorless residue. ESI MS $(M+H)^+$=329.2. HPLC Peak $t_r$=0.72 minutes. HPLC conditions: method A.

Example 153

(±)-2-((trans)-4-((1,8-naphthyridin-4-yl)oxy)cyclohexyl)-N-(4-chlorophenyl)propanamide To a solution of 4-chloroaniline (0.080 g, 0.628 mmol) in THF (0.1 mL) at 0° C. was added a solution of isopropylmagnesium chloride (0.314 ml, 0.628 mmol). The resulting solution was warmed to rt and stirred for 5 min, then Intermediate 153C (0.0516 g, 0.157 mmol) in THF (0.38 mL) was added dropwise. The reaction was heated at 70° C. for 2 h, then allowed to cool to rt. The reaction was quenched with a sat. aq. soln. of $NH_4Cl$ and diluted with EtOAc. Layers were separated. The aqueous phase was extracted with EtOAc (3×). The combined organic phases were dried over $Na_2SO_4$, filtered, and concentrated to afford a residue. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-60% B over 20 minutes, then a 5-minute hold at 100% B; Flow: 20 mL/min. Fractions containing the desired product were combined and dried via centrifugal evaporation to afford Example 153 as a racemate (6.7 mg, 10%). ESI MS $(M+H)^+$=410.2. HPLC Peak $t_r$=1.803 minutes. Purity=99%. HPLC conditions: method B.

Example 154

N-(4-Chlorophenyl)-2-(4-(6-fluoroquinolin-4-yl)cyclohexyl)butanamide

Mixture of Four Isomers

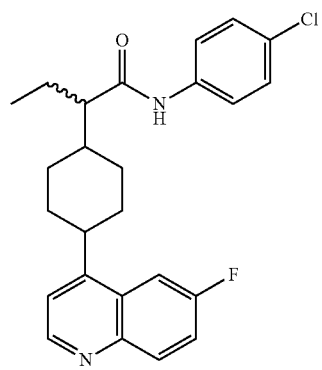 [SMILES: CCC(C(=O)Nc1ccc(Cl)cc1)C1CCC(c2ccnc3ccc(F)cc23)CC1]

Intermediate 154A

Ethyl 2-(1,4-dioxaspiro[4.5]decan-8-ylidene)acetate

To a flask containing sodium hydride (46.1 g, 1153 mmol) was added THF (1200 mL) at 0° C. under nitrogen. Then triethyl phosphonoacetate (258 g, 1153 mmol) was added dropwise. The reaction mixture was stirred at 0° C. for 30 minutes. Then 1,4-dioxaspiro[4.5]decan-8-one (150 g, 960 mmol) was added and stirred at 0° C. for 2 h. The reaction mixture was warmed to room temperature and stirred for 16 hours. The reaction mixture was quenched with water (500 ml) and the mixture was concentrated in vacuo. The residue was extracted with ethyl acetate (3×1000 mL). The combined organic layer was washed with water (500 ml) and brine (500 ml) successively. The filtrate was dried over sodium sulfate, filtered, and concentrated in vacuo. The crude material was purified via flash column chromatography, eluting with 0-30% ethyl acetate in petroleum ether to give Intermediate 154A (pale yellow oil, 135 g, 597 mmol, 62.1% yield). $^1$H NMR (400 MHz, chloroform-d) δ: 5.66 (s, 1H), 4.14 (q, J=7.2 Hz, 2H), 4.02-3.82 (m, 4H), 3.24-2.86 (m, 2H), 2.63-2.27 (m, 2H), 1.98-1.68 (m, 4H), 1.27 (t, J=7.2 Hz, 3H).

Intermediate 154B

Ethyl 2-(1,4-dioxaspiro[4.5]decan-8-yl)acetate

Intermediate 154A (13.88 g, 61.3 mmol) was taken up in EtOAc (61.3 ml) and was added to a Parr hydrogenation bottle containing palladium on carbon (1.306 g, 12.27 mmol) (54% w/w water) 10% Pd/C under an atmosphere of nitrogen. The reaction bottle was purged with nitrogen, then with hydrogen. After filling the bottle with hydrogen to 50 psi, the bottle was placed in a Parr shaker and shaken. After 4 hours, the reaction mixture was filtered over pressed CELITE® and concentrated in vacuo to give Intermediate 154B ethyl 2-(1,4-dioxaspiro[4.5]decan-8-yl)acetate (colorless oil, 13.78 g, 60.4 mmol, 98% yield). LC-MS Anal. Calc'd for $C_{12}H_{20}O_4$ 228.14. found [M+H]$^+$ 229.1. $T_r$=0.83 min (Method A). $^1$H NMR (400 MHz, chloroform-d) δ: 4.31-4.08 (m, 2H), 4.00-3.86 (m, 4H), 2.22 (d, J=7.0 Hz, 2H), 1.91-1.79 (m, 1H), 1.78-1.70 (m, 4H), 1.63-1.50 (m, 2H), 1.37-1.14 (m, 5H).

Intermediate 154C

Ethyl 2-(4-oxocyclohexyl)acetate

In a 10 liter reactor was taken Intermediate 154B (67.5 g, 296 mmol) in acetone (5000 mL). To the reaction mixture was added 1 M HCl solution (1183 mL, 1183 mmol) and the resulting mixture was heated under reflux for 2 h. The reaction mixture was concentrated to remove acetone. The residue was extracted with ethyl acetate (3×1000 mL). Combined organic layer was washed with water and brine. The organic layer was dried over sodium sulfate and concentrated in vacuo. The crude material was purified through flash column chromatography, eluting with 0-20% ethyl acetate in petroleum ether to give Intermediate 154C (pale yellow liquid, 40 g, 217 mmol, 73.4% yield). GC-MS Anal. Calc'd for $C_{10}H_{16}O_3$, 184.11 found [M+H]$^+$ 184. $T_r$=10.03 min (Method C).

Intermediate 154D

Ethyl 2-(4-(trifluoromethylsulfonyloxy)cyclohex-3-enyl)acetate

In a 2 liter 4 neck flask was taken 2,6-di-tert-butyl-4-methylpyridine (84 g, 407 mmol) in dichloromethane (500 mL) under nitrogen. Triflic anhydride (55.0 mL, 326 mmol) was added dropwise. Then a solution of Intermediate 154C (50 g, 271 mmol) in dichloromethane (500 mL) was added slowly. After completion of addition, the reaction mixture was stirred at room temperature overnight. The reaction mixture was diluted with 1000 mL of dichloromethane and washed with water and sodium carbonate solution and then water. The organic layer was dried over sodium sulfate and concentrated in vacuo. The crude material was purified through flash column chromatography, eluting with 0-10% ethyl acetate in petroleum ether to give Intermediate 154D (pale yellow oil, 65 g, 206 mmol, 76% yield). GC-MS Anal. Calc'd for $C_{11}H_{15}F_3O_5S$, 316.06 found [M+H]$^+$ 317. $T_r$=10.16 min (Method C).

Intermediate 154E

Ethyl 2-(4-(4,4,5,5-tetramethyl-1,3,2-dioxaborolan-2-yl)cyclohex-3-enyl)acetate

In 2 liter 4 neck flask was taken Intermediate 154D (120 g, 379 mmol), bis(pinacolato)diboron (106 g, 417 mmol), and potassium acetate (112 g, 1138 mmol) in 1,4-dioxane (1200 mL) under nitrogen. Nitrogen was purged inside the reaction mixture for 10 minutes. Then 1,1'-bis(diphenylphosphino)ferrocene-palladium dichloride dichloromethane complex (15.49 g, 18.97 mmol) was added. The reaction mixture was heated at 80° C. for 16 h. The reaction mixture was concentrated. The residue was partitioned between ethyl acetate and water, filtered through CELITE® bed. The organic layer was separated and the aqueous layer was extracted with ethyl acetate (3×). Combined organic layer was washed with water, brine, and dried over sodium sulfate and concentrated in vacuo. The crude material was purified through flash column chromatography, eluting with 0-10% ethyl acetate in petroleum ether to give Intermediate 154E (pale yellow oil, 56 g, 190 mmol, 50.2% yield). GC-MS Anal. Calc'd for $C_{16}H_{27}BO_4$, 294.20 found [M+H]$^+$ 295.3. $T_r$=1.10 min (Method A). $^1$H NMR (400 MHz, chloroform-d) δ: 6.52 (dd, J=4.1, 1.9 Hz, 1H), 4.14 (q, J=7.1 Hz, 2H), 2.62-1.97 (m, 6H), 1.94-1.68 (m, 2H), 1.33-1.21 (m, 16H)

Intermediate 154F

Ethyl 2-(4-(6-fluoroquinolin-4-yl)cyclohex-3-en-1-yl)acetate

Ethyl 2-(4-(4,4,5,5-tetramethyl-1,3,2-dioxaborolan-2-yl)cyclohex-3-en-1-yl)acetate (Intermediate 154E) (5 g, 17.00 mmol) was taken up in dioxane (28.3 ml) and water (7.08 ml). 4-Chloro-6-fluoroquinoline (2.57 g, 14.15 mmol) was added followed by $K_2CO_3$ (5.87 g, 42.5 mmol). Mixture was bubble with nitrogen gas for 5 minutes before the addition of Pd(Ph$_3$P)$_4$ (0.327 g, 0.283 mmol). After addition, reaction was vacated and backfilled with $N_2$ three times and then sealed (sealed vial parafilmed) and heated to 100° C. for 16 hours. The reaction was concentrated in vacuo and purified directly via silica gel flash column chromatography to give Intermediate 154F (4.22 g, 13.47 mmol, 95% yield). LC-MS Anal. Calc'd for $C_{19}H_{20}FNO_2$ 313.15. found [M+H]$^+$ 314.1 $T_r$=0.75 min (Method A).

Intermediate 154G

Ethyl 2-(4-(6-fluoroquinolin-4-yl)cyclohexyl)acetate

Intermediate 154F (4.22 g, 13.47 mmol) was dissolved in MeOH (67.3 ml) and ammonium formate (4.25 g, 67.3 mmol) was added. The vessel was equipped with a reflux condenser and vacated and flushed with nitrogen gas 3 times. Then, palladium on carbon (0.143 g, 1.347 mmol) (wet, Degussa type) was added and the reaction was heated to reflux for 1 hour. The reaction was cooled, concentrated in vacuo, and diluted with DCM. Solids were filtered off and the filtrate was concentrated to give crude Intermediate 154G (4.20 g, 13.32 mmol, 99% yield) as a mixture of cis- and trans-diastereomers. LC-MS Anal. Calc'd for $C_{19}H_{22}FNO_2$ 315.16. found [M+H] 316.2 $T_r$=0.76 min (Method A).

Intermediate 154H

Ethyl 2-(4-(6-fluoroquinolin-4-yl)cyclohexyl)butanoate

To the flask containing THF (6 mL) was added lithium diisopropylamide (2.0 M solution in THF) (3.17 mL, 6.34 mmol) at −78° C., followed by addition of 1,3-dimethyltetrahydropyrimidin-2(1H)-one (0.573 mL, 4.76 mmol) and a solution of Intermediate 154G (1.0 g, 3.17 mmol) in THF (10 mL) dropwise at −78° C. The resulting mixture turned into brown solution and stirred at −78° C. for 1 h, then iodoethane (0.51 mL, 6.34 mmol) was added slowly. The reaction mixture was then stirred at ice bath temperature for 1 h, warmed to rt overnight. The reaction was quenched by pouring into water and extracting with EtOAc. Combined organic layer was washed with brine, dried with MgSO$_4$, filtered and concentrated in vacuo. The residue was dissolved in DCM and purified by silica gel flash chromatography, eluting with 0-20% ethyl acetate in hexane to give Intermediate 154H (oil, 0.81 g, 2.359 mmol, 74.4% yield).

LC-MS Anal. Calc'd for $C_{21}H_{26}FNO_2$, 343.19 found [M+H] 344.3. $T_r$=0.87-0.88 min (Method A). $^1$H NMR (400 MHz, chloroform-d) δ: 8.88-8.77 (m, 1H), 8.18-8.06 (m, 1H), 7.66 (dd, J=10.6, 2.6 Hz, 1H), 7.47 (ddd, J=9.2, 8.0, 2.9 Hz, 1H), 7.36 (d, J=4.6 Hz, 1H), 4.25-4.15 (m, 2H), 3.34-3.09 (m, 1H), 2.70-2.16 (m, 1H), 2.13-1.49 (m, 13H), 1.36-1.24 (m, 3H), 1.00-0.90 (m, 3H)

Intermediate 154H 2-(4-(6-Fluoroquinolin-4-yl)cyclohexyl)butanoic acid

To a solution of ethyl 2-(4-(6-fluoroquinolin-4-yl)cyclohexyl)butanoate (0.81 g, 2.359 mmol) in THF (4 mL) and MeOH (7 mL) was added 2.0 M LiOH solution (7.1 mL, 14.2 mmol) slowly. The reaction mixture was stirred at rt overnight. Next day, to the reaction mixture was added more LiOH solution (7.1 mL, 14.2 mmol) and the resulting reaction mixture was heated at 70° C. for 28 h. The reaction mixture was cooled down and to the mixture was added ethyl acetate. The aqueous layer was separated and to the aqueous layer was added 1N HCl solution to adjust pH to 5-6. The resulting mixture was diluted with water and $CHCl_3$: 2-propanol (2:1). The organic layer was separated and dried over $MgSO_4$. The filtrate was concentrated in vacuo to give Intermediate 154I as a mixture of cis- and trans-(3:2) isomer (0.64 g, 2.029 mmol, 86% yield). LC-MS Anal. Calc'd for $C_{19}H_{22}FNO_2$ 315.16 found [M+H] 316.3. $T_r$=0.72 min (Method A). $^1$H NMR (400 MHz, chloroform-d) δ: 8.83 (d, J=4.4 Hz, 1H), 8.30-8.03 (m, 1H), 7.67 (dd, J=10.6, 2.4 Hz, 1H), 7.48 (ddd, J=9.2, 7.9, 2.6 Hz, 1H), 7.38 (d, J=4.6 Hz, 1H), 7.32-7.27 (m, 1H), 3.37-3.07 (m, 1H), 2.77-2.21 (m, 1H), 2.11-1.30 (m, 11H), 1.07-1.00 (m, 3H).

Example 154

N-(4-Chlorophenyl)-2-(4-(6-fluoroquinolin-4-yl)cyclohexyl)butanamide

To a solution of Intermediate 154I (60 mg, 0.190 mmol) was added thionyl chloride (0.21 mL, 2.85 mmol) and 1 drop of DMF. The reaction mixture was stirred at rt for 2 h, and the mixture was diluted with toluene 5 mL and concentrated in vacuo. The residue was dried on high vacuum for 1 h. To the residue was added acetonitrile (3 mL), 4-chloroaniline (36.4 mg, 0.285 mmol) and 4-methylmorpholine (0.13 mL, 1.14 mmol). The reaction mixture was stirred at rt for 0.6 h. The reaction mixture was heated at 70° C. for 1 h. To the reaction mixture was added more 4-methylmorpholine (0.13 mL, 1.14 mmol) and the resulting reaction mixture was heated at 70° C. over night. The reaction mixture was diluted with ethyl acetate and brine. The organic layer was separated and concentrated in vacuo. The residue was dissolved in MeOH, filtered, and purified via preparative HPLC to give Example 154 as a mixture of 4 isomers (7.1 mg, 0.017 mmol, 8.8% yield). LC-MS Anal. Calc'd for $C_{25}H_{26}ClFN_2O$, 424.17. found [M+H] 425.3. $T_r$=1.72 min (Method K). $^1$H NMR (500 MHz, DMSO-$d_6$) δ: 10.31-9.93 (m, 1H), 9.00-8.68 (m, 1H), 8.09 (dd, J=8.9, 5.9 Hz, 1H), 7.97 (d, J=9.3 Hz, 1H), 7.66 (d, J=8.7 Hz, 3H), 7.61-7.42 (m, 1H), 7.34 (d, J=8.7 Hz, 2H), 3.40-3.31 (m, 1H), 2.84-2.64 (m, 1H), 2.05-1.15 (m, 11H), 0.96-0.70 (m, 3H).

Example 155

(R)—N-(4-chlorophenyl)-4-hydroxy-2-((cis)-4-(quinolin-4-yl)cyclohexyl)butanamide

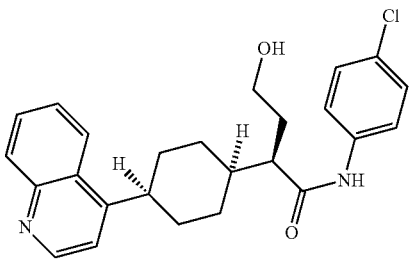 [SMILES: O=C(Nc1ccc(Cl)cc1)[C@H](CCO)[C@H]1CC[C@@H](c2ccnc3ccccc32)CC1]

Intermediate 155A (R)—N-(4-chlorophenyl)-4-oxo-2-((cis)-4-(quinolin-4-yl)cyclohexyl)butanamide

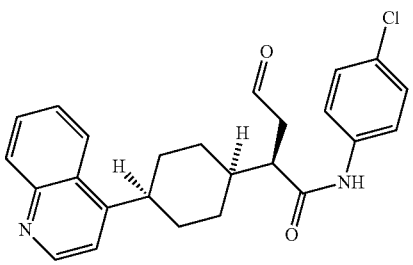 [SMILES: O=CC[C@@H](C(=O)Nc1ccc(Cl)cc1)[C@H]1CC[C@@H](c2ccnc3ccccc32)CC1]

To a solution of Example 224 (0.63 g, 1.5 mmol) in 15 mL of a 3:1 mixture of dioxane and water, was added $NaIO_4$ (1.28 g, 6 mmol) and 2,6-lutidine (0.32 g, 3 mmol) to give a white slurry. $OsO_4$ (5 vol %, 0.15 mL) was then added. After 2 hours, reaction was complete by TLC. Quenched with water and extracted thrice with EtOAc. Combined organics were washed once with brine and then dried over $MgSO_4$. Filtration and concentration afforded crude Preparation 155A as a brown oil which was carried on without further purification.

Example 155

(R)—N-(4-chlorophenyl)-4-hydroxy-2-((cis)-4-(quinolin-4-yl)cyclohexyl)butanamide To a solution of Intermediate 155A (0.16 g, 0.38 mmol) in MeOH (3.8 mL) was added sodium borohydride (0.043 g, 1.14 momol). After 1 hour, reaction was quenched with saturated aqueous NH4Cl and extracted with a solution of 10% MeOH in EtOAc. Flash chromatography on silica gel afforded 2.2 mg of Example 155 as a white solid. MS (ES): m/z=443.3 [M+H]$^+$. $T_r$=2.72 min (Method L).

Examples 156(a) and 156(b)

N-(4-chlorophenyl)-2-((cis)-4-cyano-4-(quinolin-4-yl)cyclohexyl)acetamide and N-(4-chlorophenyl)-2-((trans)-4-cyano-4-(quinolin-4-yl)cyclohexyl)acetamide Relative Stereochemistry not Determined and Arbitrarily Assigned

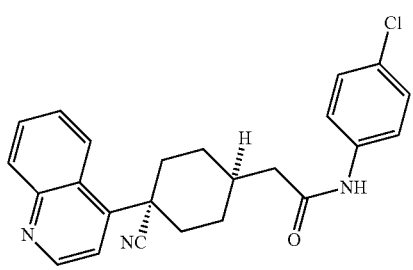

156A

156B

Intermediate 156A 4-oxo-1-(quinolin-4-yl)cyclohexane-1-carbonitrile

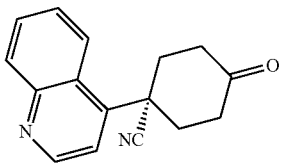

To a solution of 2-(quinolin-4-yl)acetonitrile (2.0 g, 11.4 mmol) in THF (30 mL) was added ethyl acrylate (2.38 g, 23.8 mmol) followed by potassium tert-butoxide (1.6 g, 14.3 mmol) and the mixture was stirred at room temperature. After 1 hour, water (200 mL) was added followed by heating to 85° C. for 18 hours. The reaction was then cooled to room temperature and extracted thrice with EtOAc. The combined organics were washed once with brine and dried over MgSO$_4$. Filtration and subsequent concentration gave the crude product as a brown oil. Purification via flash chromatography on silica gel (0-100% EtOAc in hexanes) gave Intermediate 156A (800 mg) as a white solid.

Intermediate 156B ethyl 2-(4-cyano-4-(quinolin-4-yl)cyclohexylidene)acetate

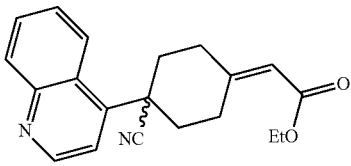 [SMILES: CCOC(=O)C=C1CCC(C#N)(c2ccnc3ccccc23)CC1]

To a solution of ethyl 2-(diethoxyphosphoryl)acetate (0.75 g, 3.36 mmol) in THF (7 mL) was added sodium tert-butoxide (0.32 g, 3.36 mmol) at 0° C. After 10 minutes, a solution of Intermediate 156A (0.80 g, 3.2 mmol) in THF (3 mL) was added to the reaction. After 2 additional hours, the reaction was quenched with water, extracted thrice with EtOAc. The combined organics were washed once with brine, dried over MgSO$_4$ and filtered to give the crude product. Purification by flash chromatography on silica gel (85% EtOAc/hexanes) gave Intermediate 156B (1.0 g) as a white solid.

Intermediate 156C ethyl 2-(4-cyano-4-(quinolin-4-yl)cyclohexyl)acetate

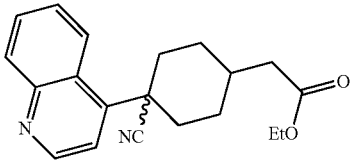 [SMILES: CCOC(=O)CC1CCC(C#N)(c2ccnc3ccccc23)CC1]

To a solution of Preparation 156 B (1.00 g, 3.13 mmol) in MeOH (31 mL) was added Pd/C (Degussa type, 0.10 g, 10% Pd). Hydrogen was introduced via a balloon. After 16 hours at RT, the reaction was purged with argon and then filtered through CELITE® rinsing with DCM. Concentration afforded the crude Preparation 156 C as a mixture of cis and trans isomers which was used without further purification.

Examples 156(a) and 156(b)

N-(4-chlorophenyl)-2-((cis)-4-cyano-4-(quinolin-4-yl)cyclohexyl)acetamide and N-(4-chlorophenyl)-2-((trans)-4-cyano-4-(quinolin-4-yl)cyclohexyl)acetamide Relative Stereochemistry not Determined and Arbitrarily Assigned Examples 156A and 156B were prepared by the method described in General Procedure G to afford a mixture of cis- and trans-isomers. These were separated by flash chromatography on silica gel to give Example 156A and Example 156B.

Example 156A

MS (ES): m/z=393.2 [M+H]$^+$. T$_r$=0.84 min (Method M).

Example 156B

MS (ES): m/z=393.2 [M+H]$^+$. T$_r$=2.77 min (Method L).

Example 157

(R)—N-(4-chlorophenyl)-5-hydroxy-2-((cis)-4-(quinolin-4-yl)cyclohexyl)pentanamide

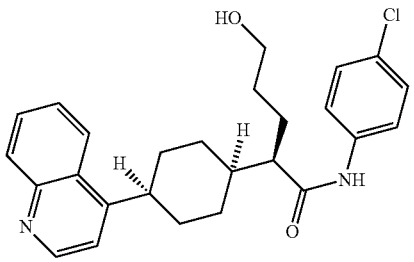 [SMILES: O=C(Nc1ccc(Cl)cc1)[C@H](CCCO)[C@H]1CC[C@@H](c2ccnc3ccccc32)CC1]

To a solution of Example 224 (0.140 g, 0.33 mmol) in THF (3.3 mL) at −78° C., was added BH$_3$-DMS (0.189 mL, 0.37 mmol, 2.0 M soln) followed by warming to RT. After 2 hours at RT, the solution was cooled to −78° C. and 5 mL of 1N NaOH and 5 mL of 30% hydrogen peroxide were added followed by warming to RT. After 5 hours, quenched with sat aq NH4Cl and extracted thrice with EtOAc. The combined organics were washed once with brine and dried over MgSO$_4$. Filtration and concentration gave the crude product. Purification by flash chromatography on silica gel gave Example 157 as a white solid. MS (ES): m/z=394.2 [M+H]$^+$. T$_r$=0.81 min (Method M).

Example 158

N-(4-chlorophenyl)-2-(1-methoxy-4-(quinolin-4-yl)cyclohexyl)acetamide

Single Diastereomer, Relative Stereochemistry not Determined

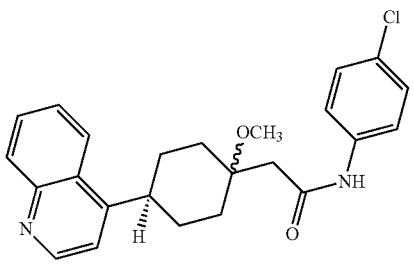

Intermediate 158A ethyl 2-(1-methoxy-4-(quinolin-4-yl)cyclohexyl)acetate

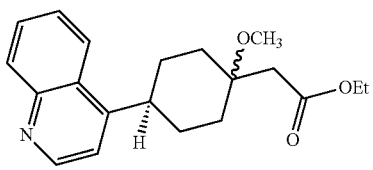

To a solution of ethyl 2-(1-hydroxy-4-(quinolin-4-yl)cyclohexyl)acetate (0.22 g, 0.69 mmol), prepared by the methods in Example 30, in DME (3 mL) at −78° C. was added KHMDS (1.5 mL, 0.5 M in toluene, 0.756 mmol) followed by 18-crown-6 (0.20 g, 0.756 mmol). After 30 minutes, MeI (0.057 mL, 0.756 mmol) was added. After an additional 30 minutes, the reaction was quenched with sat aq NH$_4$Cl and water. Extracted thrice with EtOAc, combined organics washed once with brine, dried over MgSO$_4$, filtered and concentrated to give crude Intermediate 158A as a single isomer, stereochemistry not confirmed.

Example 158

N-(4-chlorophenyl)-2-(1-methoxy-4-(quinolin-4-yl)cyclohexyl)acetamide

Example 158 was prepared from Intermediate 158A by the methods shown in Example 30. Isolated as a single isomer, relative stereochemistry not determined. MS (ES): m/z=379.2 [M+H]$^+$. T$_r$=2.29 min (Method L).

Example 159

N-(4-fluorophenyl)-2-(4-hydroxy-4-(quinolin-4-yl)cyclohexyl)acetamide

Single Diastereomer, Relative Stereochemistry not Determined

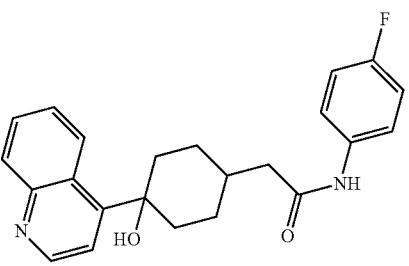 [SMILES: O=C(CC1CCC(O)(c2ccnc3ccccc23)CC1)Nc1ccc(F)cc1]

Intermediate 159A ethyl 2-(4-hydroxy-4-(quinolin-4-yl)cyclohexyl)acetate

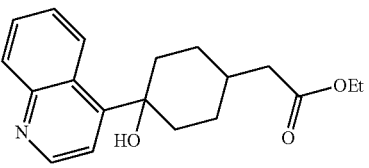 [SMILES: CCOC(=O)CC1CCC(O)(c2ccnc3ccccc23)CC1]

To a solution of 4-bromoquinoline (0.36 g, 1.75 mmol) in THF (8 mL) at −78° C. was added tert-butyl lithium (1.7 M solution, 2.1 mL, 3.51 mmol). After 5 minutes, a solution of ethyl 2-(4-oxocyclohexyl)acetate (0.294 g, 1.60 mmol) in TI-IF (2 mL) was added. After 1 hour, 1 N NaOH was added followed by warming to room temperature. The mixture was then extracted thrice with EtOAc and combined organics washed once with brine. The organics were then dried over MgSO$_4$, filtered and concentrated to give the crude product. Purified by flash chromatography on silica gel eluting with 0-100% EtOAc in hexanes to afford Intermediate 159A (214 mg) as a yellow oil.

Example 159

N-(4-fluorophenyl)-2-(4-hydroxy-4-(quinolin-4-yl)cyclohexyl)acetamide

Single Diastereomer, Relative Stereochemistry not Determined

Example 159 was prepared from Intermediate 159A and 4-fluoroaniline by the methods described in General Method G. Example 159 was isolated as a single isomer upon crystallization after concentration, stereochemistry not confirmed. MS (ES): m/z=393.2[M+H]$^+$. T$_r$=2.77 min (Method L).

Example 160

N-(4-chlorophenyl)-2-(4-hydroxy-4-(quinolin-4-yl)cyclohexyl)acetamide

Single Diastereomer, Relative Stereochemistry not Determined

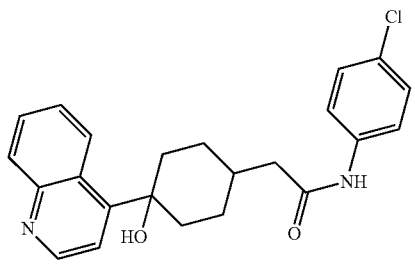 [SMILES: O=C(CC1CCC(O)(c2ccnc3ccccc23)CC1)Nc1ccc(Cl)cc1]

Example 160

N-(4-chlorophenyl)-2-(4-hydroxy-4-(quinolin-4-yl)cyclohexyl)acetamide

Example 160 was prepared from Preparation 159A and 4-chloroaniline by the methods described in General Method G. Example 160 was isolated as a single isomer upon crystallization after concentration, stereochemistry not confirmed. MS (ES): m/z=431.3 [M+H]$^+$. T$_r$=0.85 min (Method M).

TABLE 7

| Examples 161-218 prepared by methods described previously | | | | |
|---|---|---|---|---|
| Example # | | Prepared by method similar to Example | HPLC method | LC-MS RT | [M + H]+ |
| 161 | 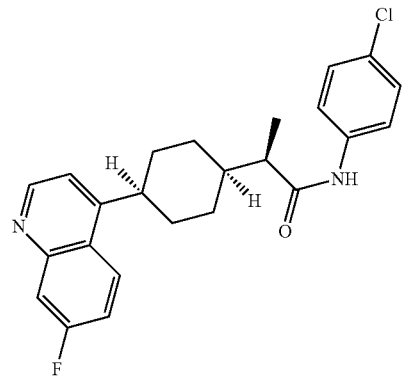 | 24 | L | 2.93 | 411.2 |
| 162 | 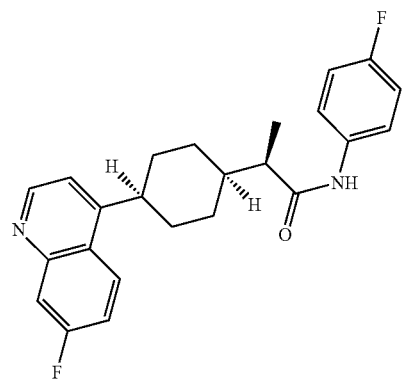 [SMILES: C[C@@H](C(=O)Nc1ccc(F)cc1)[C@H]1CC[C@@H](c2ccnc3cc(F)ccc32)CC1] | 24 | L | 2.8 | 395.3 |

TABLE 7-continued

Examples 161-218 prepared by methods described previously

| Example # | Prepared by method similar to Example | HPLC method | LC-MS RT | [M + H]+ |
|---|---|---|---|---|
| 163 | 24 | L | 2.75 | 402.3 |
| 164 | 25 | L | 3.01 | 409.3 |
| 165 | 25 | L | 2.68 | 407.3 |
| 166 | 25 | L | 2.53 | 391.3 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 167 | | 26 | L | 2.54 | 398.3 |
| 168 | | 25 | L | 2.67 | 417.2 |
| 169 | | 16 | L | 2.8 | 421.3 |
| 170 | | 157 | L | 2.42 | 451.3 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 171 | | 4 | L | 2.99 | 397.2 |
| 173 | | 5 | L | 2.86 | 381.2 |
| 174 | | 24 | L | 2.42 | 377.3 |
| 175 | | 24 | L | 2.72 | 443.3 |

TABLE 7-continued
Examples 161-218 prepared by methods described previously
| Example # | | Prepared by method similar to Example | HPLC method | LC-MS RT | [M + H]+ |
|---|---|---|---|---|---|
| 176 | 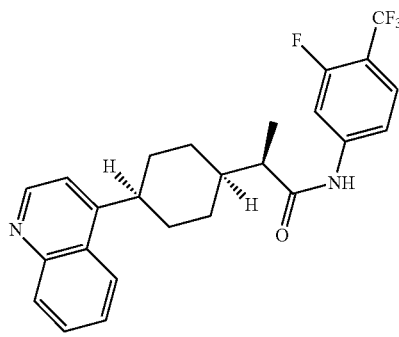 [SMILES: C[C@@H](C(=O)Nc1ccc(C(F)(F)F)c(F)c1)[C@H]1CC[C@@H](c2ccnc3ccccc32)CC1] | 24 | L | 2.81 | 445.2 |
| 177 | 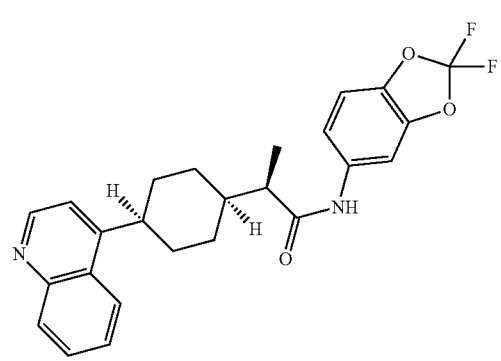 [SMILES: C[C@@H](C(=O)Nc1ccc2c(c1)OC(F)(F)O2)[C@H]1CC[C@@H](c2ccnc3ccccc32)CC1] | 24 | L | 2.7 | 439.2 |
| 178 | 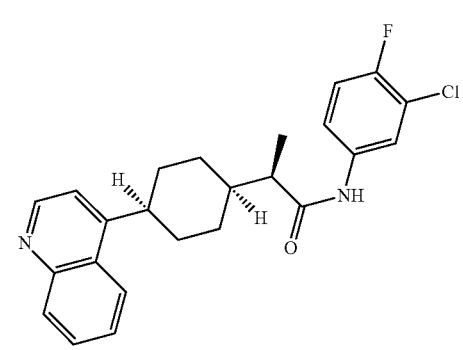 [SMILES: C[C@@H](C(=O)Nc1ccc(F)c(Cl)c1)[C@H]1CC[C@@H](c2ccnc3ccccc32)CC1] | 24 | L | 2.65 | 411.2 |
| 179 | 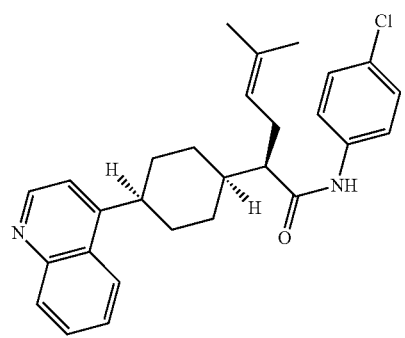 [SMILES: CC(C)=CC[C@@H](C(=O)Nc1ccc(Cl)cc1)[C@H]1CC[C@@H](c2ccnc3ccccc32)CC1] | 2524 | L | 3.01 | 447.3 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 180 | | 26 | M | 0.84 | 395.2 |
| 181 | | 24 | M | 0.8 | 411.2 |
| 182 | | 57 | M | 0.84 | 410.2 |
| 183 | | 24 | M | 0.86 | 377.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 184 | | 24 | M | 0.81 | 394.2 |
| 185 | | 24 | M | 0.78 | 427.2 |
| 186 | | 24 | M | 0.81 | 411.2 |
| 187 | | 24 | M | 0.79 | 402.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 188 | | 25 | L | 2.67 | 403.3 |
| 189 | | 24 | L | 2.71 | 395.3 |
| 190 | | 57 | L | 2.95 | 433.3 |
| 191 | | 4 | L | 3.13 | 415.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 192 | | 4 | L | 2.98 | 399.2 |
| 193 | | 3 | L | 2.94 | 399.2 |
| 194 | | 32 | L | 2.47 | 395.2 |
| 195 | | 31 | L | 2.49 | 395.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 196 | | 36 | L | 2.28 | 395.2 |
| 198 | | 32 | L | 2.24 | 386.2 |
| 199 | | 36 | L | 2.24 | 379.2 |
| 200 | | 36 | L | 2.15 | 379.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 201 | | 36 | L | 2.29 | 379.2 |
| 202 | | 36 | L | 2.37 | 409.2 |
| 203 | | 36 | L | 2.23 | 393.3 |
| 204 | | 36 | L | 2.3 | 400.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 205 | | 4 | M | 0.89 | 447.2 |
| 206 | | 1 | M | 0.86 | 447.1 |
| 207 | | 1 | M | 0.85 | 431.3 |
| 208 | | 4 | M | 0.87 | 431.2 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 209 | | 4 | M | 0.85 | 431.2 |
| 210 | | 4 | M | 0.86 | 447.2 |
| 211 | | 4 | M | 0.87 | 447.2 |
| 212 | | 24 | M | 0.88 | 395.3 |

TABLE 7-continued

Examples 161-218 prepared by methods described previously

| Example # | Structure | Prepared by method similar to Example | HPLC method | LC-MS RT | [M + H]+ |
|---|---|---|---|---|---|
| 213 | | 24 | M | 0.96 | 402.3 |
| 214 | | 137 | L | 2.516 | 527.3 |
| 215 | | 24 | M | 0.91 | 411.2 |
| 216 | | 56 | M | 0.83 | 393.2 |

TABLE 7-continued

Examples 161-218 prepared by methods described previously

| Example # | Prepared by method similar to Example | HPLC method | LC-MS RT | [M + H]+ |
|---|---|---|---|---|
| 217 | 20 | M | 0.84 | 393.2 |
| 218 | 20 | M | 0.817 | 393.3 |

TABLE 8

Examples 220-228 prepared by Methods described previously

| Example # | Structure | Prepared by method similar to Example # | $^1$H NMR |
|---|---|---|---|
| 220 | 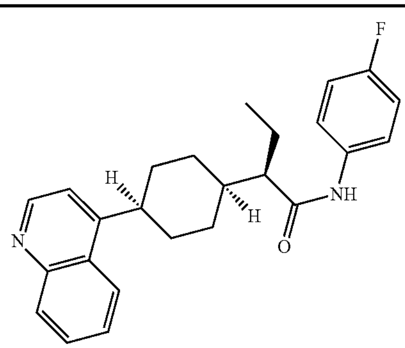 | 25 | 1H-NMR (400 MHz; CDCl3): δ 8.84 (d, J = 4.6 Hz, 1H), 8.12 (dd, J = 8.5, 0.8 Hz, 1H), 8.07 (d, J = 8.6 Hz, 1H), 7.70 (ddd, J = 8.4, 6.9, 1.4 Hz, 1H), 7.61-7.47 (m, 4H), 7.32 (d, J = 4.6 Hz, 1H), 7.11-6.91 (m, 2H), 3.51 -3.43 (m, 1H), 2.41 (td, J = 11.0, 4.2 Hz, 1H), 2.17-2.14 (m, 1H), 1.97-1.58 (m, 10H), 1.01 (t, J = 7.4 Hz, 3H). |

TABLE 8-continued

Examples 220-228 prepared by Methods described previously

| Example # | Structure | Prepared by method similar to Example # | ¹H NMR |
|---|---|---|---|
| 221 | 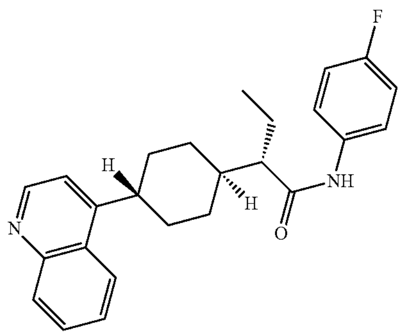 [SMILES: CC[C@H](C(=O)Nc1ccc(F)cc1)[C@H]1CC[C@H](c2ccnc3ccccc32)CC1] | 26 | 1HNMR (400 MHz; CDCl3): δ 8.84 (d, J = 4.6 Hz, 1H), 8.11 (dd, J = 8.5, 1.0 Hz, 1H), 8.06 (d, J = 8.2 Hz, 1H), 7.69 (ddd, J = 8.3, 6.8, 1.3 Hz, 1H), 7.59-7.50 (m, 3H), 7.25 (s, 1H), 7.22 (s, 1H), 7.08-6.98 (m, 2H), 3.30 (tt, J = 11.9, 2.7 Hz, 1H), 2.17-1.92 (m, 4H), 1.86-1.70 (m, 2H), 1.69-1.51 (m, 2H), 1.51-1.11 (m, 4H), 1.00 (t, J = 7.3 Hz, 3H). |
| 222 | 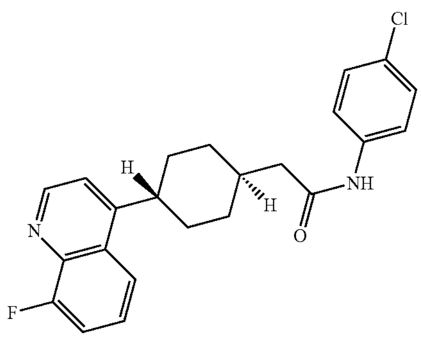 [SMILES: O=C(C[C@H]1CC[C@H](c2ccnc3c(F)cccc32)CC1)Nc1ccc(Cl)cc1] | 3 | ¹H NMR (400 MHz, CD₃OD) δ 8.79 (d, J = 12.3 Hz, 1H), 8.01 (d, J = 7.4 Hz, 1H), 7.64-7.53 (m, 4H), 7.52-7.43 (m, 1H), 7.31-7.24 (m, 2H), 3.53-3.38 (m, 1H), 2.58 (d, J = 7.4 Hz, 2H), 2.52-2.44 (m, 1H), 2.03-1.70 (m, 8H). |
| 223 | 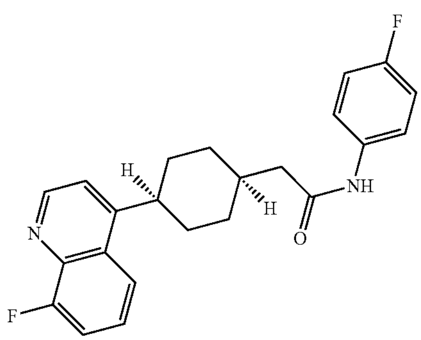 [SMILES: O=C(C[C@H]1CC[C@@H](c2ccnc3c(F)cccc32)CC1)Nc1ccc(F)cc1] | 4 | ¹H NMR (400 MHz, CDCl₃) δ 8.90 (d, J = 4.6 Hz, 1H), 7.85 (d, J = 8.7 Hz, 1H), 7.54-7.44 (m, 3H), 7.39 (ddd, J = 10.3, 7.7, 1.2 Hz, 1H), 7.35 (d, J = 4.5 Hz, 1H), 7.14 (s, 1H), 7.08- 6.98 (m, 2H), 3.36- 3.20 (m, 1H), 2.35 (d, J = 6.6 Hz, 2H), 2.16-2.01 (m, 5H), 1.75-1.59 (m, 2H), 1.45-1.28 (m, 2H). |
| 224 | 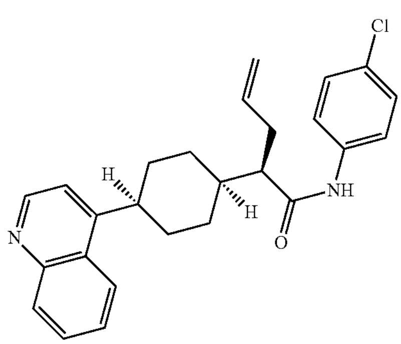 | 25 | ¹H-NMR (400 MHz; CDCl₃): δ 8.86 (d, = 4.6 Hz, 1H), 8.25 (d, J = 8.2 Hz, 1H), 8.08-8.06 (m, 1H), 7.75 (s, 1H), 7.61 (t, J = 7.9 Hz, 1H), 7.52-7.48 (m, 2H), 7.28-7.26 (m, 1H), 7.26-7.22 (m, 2H), 3.43-3.37 (m, 1H), 2.66-2.59 (m, 1H), 2.17-2.10 (m, 1H), 1.94-1.62 (m, 9H), 1.26 (d, J = 6.8 Hz, 4H). |

TABLE 8-continued

Examples 220-228 prepared by Methods described previously

| Example # | Structure | Prepared by method similar to Example # | ¹H NMR |
|---|---|---|---|
| 225 | 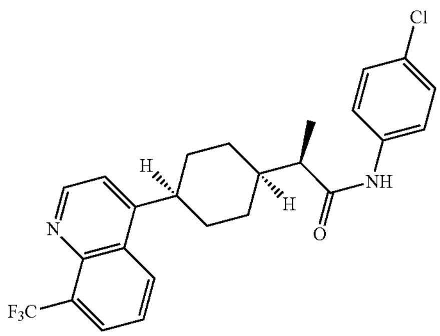 [SMILES: C[C@@H](C(=O)Nc1ccc(Cl)cc1)[C@H]1CC[C@@H](c2ccnc3c(C(F)(F)F)cccc32)CC1] | 23 | ¹H-NMR (400 MHz; CDCl₃): δ 8.15 (dd, J = 8.5, 0.9 Hz, 1H), 8.05 (d, J = 8.1 Hz, 1H), 7.86 (s, 1H), 7.75 (ddd, J = 8.4, 6.9, 1.4 Hz, 1H), 7.65 (ddd, J = 8.4, 7.0, 1.4 Hz, 1H), 7.58 (s, 1H), 7.55-7.51 (m, 2H), 7.24-7.20 (m, 2H), 3.48-3.41 (m, 1H), 2.71-2.63 (m, 1H), 2.22-2.17 (m, 1H), 2.02-1.98 (m, 1H), 1.89-1.57 (m, 8H), 1.29 (d, J = 6.8 Hz, 3H). |
| 226 | 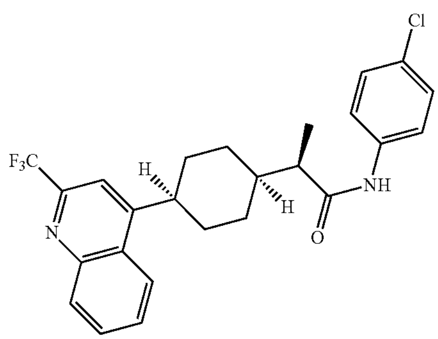 [SMILES: C[C@@H](C(=O)Nc1ccc(Cl)cc1)[C@H]1CC[C@@H](c2cc(C(F)(F)F)nc3ccccc32)CC1] | 23 | ¹H-NMR (400 MHz; CDCl₃): δ 8.86 (d, J = 4.6 Hz, 1H), 8.25 (d, J = 8.2 Hz, 1H), 8.08-8.06 (m, 1H), 7.75 (s, 1H), 7.61 (t, J = 7.9 Hz, 1H), 7.52-7.48 (m, 2H), 7.28-7.26 (m, 1H), 7.26-7.22 (m, 2H), 3.43-3.37 (m, 1H), 2.66-2.59 (m, 1H), 2.17-2.10 (m, 1H), 1.94-1.62 (m, 8H), 1.26 (d, J = 6.8 Hz, 3H). |
| 227 | 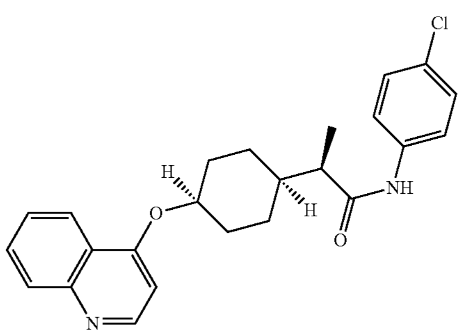 [SMILES: C[C@@H](C(=O)Nc1ccc(Cl)cc1)[C@H]1CC[C@@H](Oc2ccnc3ccccc23)CC1] | 27 | ¹H NMR (400 MHz; CDCl3): 8.69 (d, J = 6.5 Hz, 1H), 8.17 (dd, J = 1.5, 10.5 Hz, 1H), 8.00 (d, J = 10.5 Hz, 1H), 7.85 (br s, 1H), 7.66 (dt, J = 2.0, 8.5 Hz, 1H), 7.50 (d, J = 11.5 Hz, 2H), 7.43 (dt, J = 1.0, 10.0 Hz, 1H), 7.24 (d, J = 11 Hz, 2H), 6.68 (d, J = 6.5 Hz, 1H), 4.83 (br s, 1H), 2.24-2.12 (m, 3H), 1.79-1.46 (m, 7H), 1.24 (d, J = 8.5 Hz, 3H). |
| 228 | 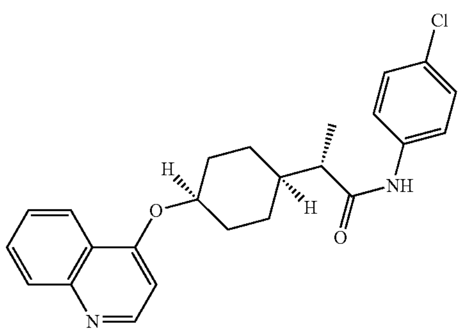 [SMILES: C[C@H](C(=O)Nc1ccc(Cl)cc1)[C@H]1CC[C@@H](Oc2ccnc3ccccc23)CC1] | 27 | ¹H NMR (400 MHz; CDCl3): 8.69 (d, J = 12 Hz, 1H), 8.18 (dd, 1.5, 10.5 Hz, 1H), 8.01 (dd, J = 1.0, 10.5 Hz, 1H), 7.69-7.65 (m, 2H), 7.49 (d, J = 11 Hz, 2H), 7.44 (dt, J = 1.0, 10.0 Hz, 1H), 7.24 (d, J = 11.5 Hz, 2H), 6.68 (d, 7 = 7.0 Hz, 1H), 4.83 (br s, 1H), 2.25-2.15 (m, 3H), 1.82-1.41 (m, 7H), 1.24 (d, 7 = 8.5 Hz, 3H). |

Examples 229 and 230

Example 229

N-(4-chlorophenyl)-2-(trans-4-(6-fluoroquinolin-4-yl)-1-hydroxycyclohexyl)propanamide

Example 230

N-(4-chlorophenyl)-2-(trans-4-(6-fluoroquinolin-4-yl)-1-hydroxycyclohexyl)propanamide Absolute Stereochemistry Unknown

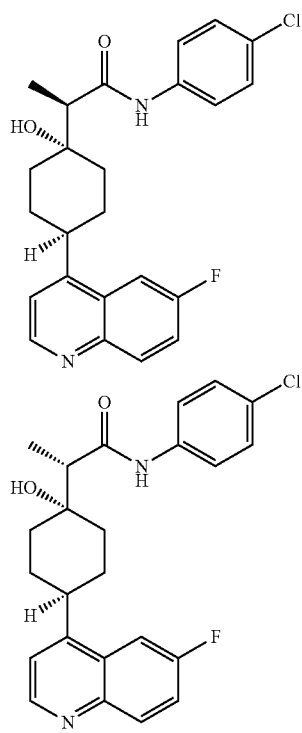

229A: methyl 2-(trans-4-(6-fluoroquinolin-4-yl)-1-hydroxycyclohexyl)propanoate

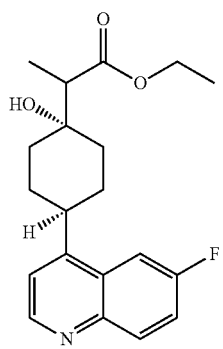 [SMILES: CCOC(=O)C(C)[C@]1(O)CC[C@H](c2ccnc3ccc(F)cc32)CC1]

229B: methyl 2-(cis-4-(6-fluoroquinolin-4-yl)-1-hydroxycyclohexyl)propanoate

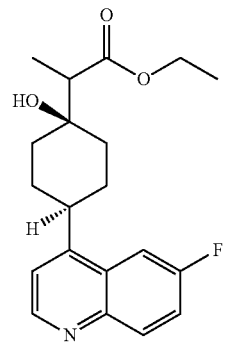 [SMILES: CCOC(=O)C(C)[C@]1(O)CC[C@@H](c2ccnc3ccc(F)cc32)CC1]

To a solution of 4-(6-fluoroquinolin-4-yl)cyclohexanone (200 mg, 0.822 mmol), methyl 2-bromopropanoate (275 mg, 1.644 mmol) in $CH_3CN$ (6 mL) at 0° C. was added tris(triphenylphoshine)rhodium(I) chloride (45.6 mg, 0.049 mmol). The reaction was stirred at 0° C. for 30 min. Then diethylzinc (1.0 M solution in heptane) (1.726 mL, 1.726 mmol) was added. The reaction was stirred at RT for 16 h. The reaction was diluted with EtOAc and saturated $NH_4Cl$. Organic was separated and washed with brine, dried over $MgSO_4$, filtered and concentrated to give a crude material. This crude material was purified with ISCO 24 g, 40 mL/min. 0-100% EtOAc/Hexane in 50 min. The product 229A (87 mg, 0.26 mmol, 32%) was eluted with 50% EtOAc/Hexane. The product 229B (122 mg, 0.364 mmol, 44%) was eluted with 60% EtOAc/Hexane.

229A: $^1$H NMR (400 MHz, CHLOROFORM-d) δ 8.83 (d, J=4.6 Hz, 1H), 8.14 (dd, J=9.2, 5.7 Hz, 1H), 7.67 (dd, J=10.5, 2.8 Hz, 1H), 7.50 (ddd, J=9.2, 8.0, 2.8 Hz, 1H), 7.33 (d, J=4.6 Hz, 1H), 3.78 (s, 3H), 3.65 (s, 1H), 3.36-3.23 (m, 1H), 3.08 (q, J=7.1 Hz, 1H), 2.18-2.08 (m, 1H), 2.06-1.94 (m, 2H), 1.94-1.81 (m, 2H), 1.79-1.68 (m, 3H), 1.68-1.51 (m, 1H), 1.36-1.23 (m, 3H) LC-MS: M+H=332.2 (tr=0.59 min) (Method A)

229B: $^1$H NMR (400 MHz, CHLOROFORM-d) δ 8.84 (d, J=4.6 Hz, 1H), 8.14 (dd, J=9.2, 5.7 Hz, 1H), 7.68 (dd, J=10.6, 2.8 Hz, 1H), 7.49 (ddd, J=9.1, 8.0, 2.8 Hz, 1H), 7.39 (d, J=4.6 Hz, 1H), 3.78 (s, 3H), 3.21-3.04 (m, 2H), 2.56 (q, J=7.2 Hz, 1H), 2.18-1.97 (m, 3H), 1.93-1.67 (m, 5H), 1.65 (s, 2H), 1.55-1.41 (m, 1H), 1.36-1.23 (m, 3H)

Examples 229 and 230

To a solution of 4-chloroaniline (63.5 mg, 0.498 mmol) in THF (1 mL) at RT was added iPrMgCl (2.0 M in THF) (0.415 mL, 0.830 mmol) drop wise. Bubbles evolved. The reaction was stirred at RT for 5 min. Then 229A (55 mg, 0.166 mmol) in THF (0.3 mL) was added. The reaction was stirred at 70° C. for 1 h. The reaction was diluted with saturated $NH_4Cl$ and EtOAc. Organic was separated and washed with brine, dried over $MgSO_4$, filtered and concentrated to dryness. The crude material was purified with ISCO 24 g column, 35 mL/min. 0-100% EtOAc/Hexane in 30 min. The desired product was eluted with 80% EtOAc/Hexane to give N-(4-chlorophenyl)-2-(trans-4-(6-fluoroquinolin-4-yl)-1-hydroxycyclohexyl)propanamide (58 mg, 0.135 mmol, 81% yield) as white solid.

The racemate was purified via preparative SFC with the following conditions: Column: Chiral OD-H 25×3 cm ID, 5-μm particles; Mobile Phase A: 70/30 CO2/MeOH; Detector Wavelength: 220 nm; Flow: 100 mL/min. The fractions ("Peak-1" tr=3.98 min (Example 229) and "Peak-2" tr=4.99 min (Example 230);

Example 229

¹H NMR (400 MHz, CHLOROFORM-d) δ 8.83 (d, J=4.6 Hz, 1H), 8.14 (dd, J=9.2, 5.7 Hz, 1H), 7.67 (dd, J=10.5, 2.8 Hz, 1H), 7.50 (ddd, J=9.2, 8.0, 2.8 Hz, 1H), 7.33 (d, J=4.6 Hz, 1H), 3.78 (s, 3H), 3.65 (s, 1H), 3.36-3.23 (m, 1H), 3.08 (q, J=7.1 Hz, 1H), 2.18-2.08 (m, 1H), 2.06-1.94 (m, 2H), 1.94-1.81 (m, 2H), 1.79-1.68 (m, 3H), 1.68-1.51 (m, 1H), 1.36-1.23 (m, 3H) LC-MS: M+H=332.2 (tr=0.59 min)

Example 230

¹H NMR (400 MHz, CHLOROFORM-d) δ 8.83 (d, J=4.6 Hz, 1H), 8.14 (dd, J=9.2, 5.7 Hz, 1H), 7.67 (dd, J=10.5, 2.8 Hz, 1H), 7.50 (ddd, J=9.2, 8.0, 2.8 Hz, 1H), 7.33 (d, J=4.6 Hz, 1H), 3.78 (s, 3H), 3.65 (s, 1H), 3.36-3.23 (m, 1H), 3.08 (q, J=7.1 Hz, 1H), 2.18-2.08 (m, 1H), 2.06-1.94 (m, 2H), 1.94-1.81 (m, 2H), 1.79-1.68 (m, 3H), 1.68-1.51 (m, 1H), 1.36-1.23 (m, 3H) LC-MS: M+H=332.2 (tr=0.59 min) (Method A)

Example 231 and 232

Example 231

N-(4-chlorophenyl)-2-(cis-4-(6-fluoroquinolin-4-yl)-1-hydroxycyclohexyl)propanamide Example 232

N-(4-chlorophenyl)-2-(cis-4-(6-fluoroquinolin-4-yl)-1-hydroxycyclohexyl)propanamide Absolute Stereochemistry Unknown

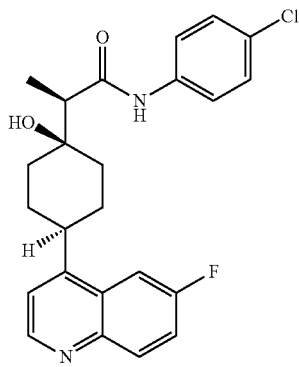

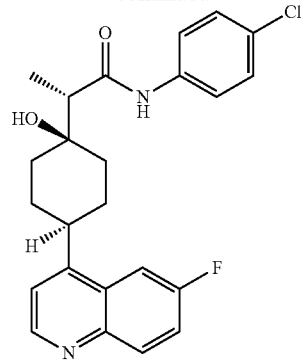

To a solution of 4-chloroaniline (61.2 mg, 0.480 mmol) in THF (2 mL) at RT was added iPrMgCl (2.0 M in THF) (0.400 mL, 0.800 mmol) drop wise. The bubbles evolved. The mixture was stirred at RT for 5 min. Then Preparation 229B (53 mg, 0.160 mmol) was added. The reaction was heated at 70° C. for 1 h. Cooled to RT. The mixture was diluted with saturated $NH_4Cl$ and EtOAc. Organic was separated and washed with brine, dried over $MgSO_4$, filtered and concentrated to dryness. The crude material was purified with ISCO 24 g column, 35 mL/min. 0-100% EtOAc/Hexane in 45 min. The desired product was eluted with 75% EtOAc/Hexane to afford N-(4-chlorophenyl)-2-((1s, 4s)-4-(6-fluoroquinolin-4-yl)-1-hydroxycyclohexyl)propanamide (55 mg, 0.128 mmol, 80% yield) as white solid. The racemate was purified via preparative SFC with the following conditions: Column: Chiral OD-H 25×3 cm ID, 5-μm particles; Mobile Phase A: 70/30 $CO_2$/MeOH; Detector Wavelength: 220 nm; Flow: 100 mL/min. The fractions ("Peak-1" tr=4.58 min (Example 231) and "Peak-2" tr=5.33 min (Example 232);

Example 231

¹H NMR (400 MHz, CHLOROFORM-d) δ 8.83 (d, J=4.5 Hz, 1H), 8.14 (dd, J=9.2, 5.7 Hz, 1H), 7.94 (s, 1H), 7.66 (dd, J=10.6, 2.8 Hz, 1H), 7.55-7.45 (m, 3H), 7.38 (d, J=4.6 Hz, 1H), 7.35-7.31 (m, 2H), 3.60 (br. s., 1H), 3.24-3.02 (m, 1H), 2.38 (q, J=7.1 Hz, 1H), 2.21-1.95 (m, 3H), 1.95-1.83 (m, 2H), 1.80-1.64 (m, 2H), 1.49 (td, J=13.3, 4.1 Hz, 1H), 1.42 (d, J=7.1 Hz, 3H) LC-MS: M+H=332.2 (tr=0.78 min) (Method A)

Example 232

¹H NMR (400 MHz, CHLOROFORM-d) δ 8.83 (d, J=4.5 Hz, 1H), 8.14 (dd, J=9.2, 5.7 Hz, 1H), 7.94 (s, 1H), 7.66 (dd, J=10.6, 2.8 Hz, 1H), 7.55-7.45 (m, 3H), 7.38 (d, J=4.6 Hz, 1H), 7.35-7.31 (m, 2H), 3.60 (br. s., 1H), 3.24-3.02 (m, 1H), 2.38 (q, J=7.1 Hz, 1H), 2.21-1.95 (m, 3H), 1.95-1.83 (m, 2H), 1.80-1.64 (m, 2H), 1.49 (td, J=13.3, 4.1 Hz, 1H), 1.42 (d, J=7.1 Hz, 3H) LC-MS: M+H=332.2 (tr=0.78 min) (Method A)

Example 233

(+/−)-N-(4-chlorophenyl)-2-(trans-1-fluoro-4-(6-fluoroquinolin-4-yl)cyclohexyl)propanamide

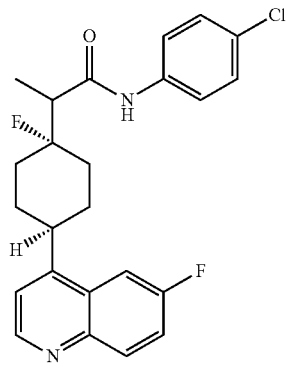 [SMILES: CC(C(=O)Nc1ccc(Cl)cc1)[C@]1(F)CC[C@H](c2ccnc3ccc(F)cc32)CC1]

To a solution of 229B (20 mg, 0.047 mmol) in CH$_2$Cl$_2$ (1 mL) at RT was added diethylaminosulfur trifluoride (0.019 mL, 0.141 mmol). The reaction was stirred at RT for 3 h. The reaction was diluted with water and EtOAc. Organic was separated and washed with brine, dried over MgSO4, filtered and concentrated to dryness. The crude material was purified via preparative LC/MS with the following conditions: Column: XBridge Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 25-50% B over 25 minutes, then a 2-minute hold at 50% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 50-75% B over 25 minutes, then a 2-minute hold at 75% B; Flow: 20 mL/min. Fractions containing the desired product were combined and dried via centrifugal evaporation. The yield of Example 233 was 0.5 mg (1.17 mmol, 2.5%) $^1$H NMR (500 MHz, DMSO-d$_6$) δ 10.13 (s, 1H), 8.84 (d, J=4.4 Hz, 1H), 8.15-8.00 (m, 2H), 7.72-7.55 (m, 4H), 7.36 (d, J=8.7 Hz, 2H), 3.21-3.12 (m, 1H), 2.15 (br. s., 1H), 2.06 (br. s., 1H), 1.94 (d, J=9.0 Hz, 3H), 1.88 (br. s., 2H), 1.66 (d, J=11.4 Hz, 1H), 1.24 (d, J=6.9 Hz, 3H) LC-MS: M+H=429.0 (tr=0.82 min) (Method A)

Examples 234, 235, 236, 237

Example 234

N-(4-chlorophenyl)-2-(trans-4-(6-fluoroquinolin-4-yl)-4-hydroxycyclohexyl)propanamide Absolute Stereochemistry Unknown

Example 235

N-(4-chlorophenyl)-2-(trans-4-(6-fluoroquinolin-4-yl)-4-hydroxycyclohexyl)propanamide Absolute Stereochemistry Unknown

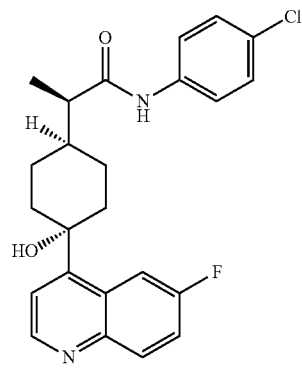

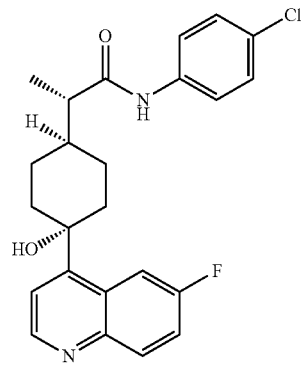

Example 236

N-(4-chlorophenyl)-2-(cis-4-(6-fluoroquinolin-4-yl)-4-hydroxycyclohexyl)propanamide Absolute Stereochemistry Unknown

Example 237

N-(4-chlorophenyl)-2-(cis-4-(6-fluoroquinolin-4-yl)-4-hydroxycyclohexyl)propanamide Absolute Stereochemistry Unknown

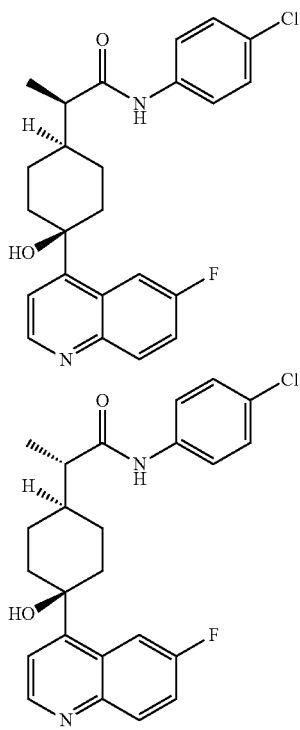

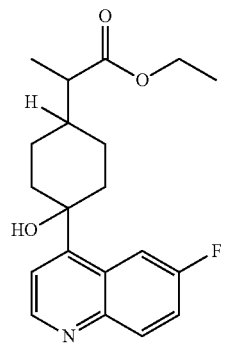 [SMILES: CCOC(=O)C(C)C1CCC(O)(c2ccnc3ccc(F)cc23)CC1]

234A: ethyl 2-(4-(6-fluoroquinolin-4-yl)-4-hydroxycyclohexyl) propionate

To a solution of 4-bromo-6-fluoroquinoline (163 mg, 0.721 mmol) in THF (5 mL) at −78° C. was added t-BuLi (1.7M-3.2M in Heptane) (0.849 mL, 1.443 mmol) drop wise. It turned from clear to dark brown color. The reaction was stirred at −78° C. for 3 min. Then ethyl 2-(4-oxocyclohexyl)propanoate (130 mg, 0.656 mmol) in THF (1 mL) was added drop wise. The reaction was stirred at −78° C. for 1 h. The reaction was diluted with saturated $NH_4Cl$ and EtOAc. Organic was separated and washed with brine, dried over $MgSO_4$, filtered and concentrated to give a crude material. This material was purified with ISCO 40 g, 40 mL/min. 0-100% EtOAc/Hexane in 35 min. The desired product was eluted with 55% EtOAc/Hexane to give 234A (100 mg, 0.290 mmol, 44%) as the mixture of the diastereomers.

234B: N-(4-chlorophenyl)-2-(4-(6-fluoroquinolin-4-yl)-4-hydroxycyclohexyl)propanamide

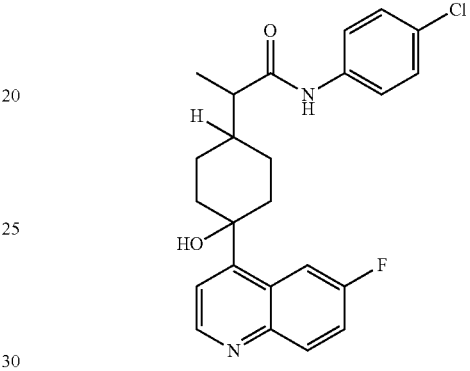

To a solution of 4-chloroaniline (111 mg, 0.869 mmol) in THF (2 mL) at RT was added iPrMgBr (2.0M in THF) (0.724 mL, 1.448 mmol) drop wise. Bubbles evolved. The reaction was stirred at RT for 5 min. Then 234A (100 mg, 0.29 mmol) n THF (1 mL) was added. The reaction was stirred at 70° C. for 1 h. Then it was cooled to RT and diluted with saturated $NH_4Cl$ and EtOAc. Organic was separated and washed with brine, dried over $MgSO_4$, filtered and concentrated to dryness. The crude material was purified with ISCO 24 g column, 35 mL/min. 0-100% EtOAc/Hexane in 30 min. The desired product was eluted with 80% EtOAc/Hexane to give 234B (110 mg, 0.258 mmol, 89%) as the mixture of diastereomers.

The mixture of diastereomers 234B was purified via preparative SFC with the following conditions: Column: Whelk-O R, R Kromasil 25×3 cm ID, 5-μm particles; Mobile Phase A: 75/25 CO2/MeOH; Detector Wavelength: 220 nm; Flow: 100 mL/min. The fractions ("Peak-1" tr=9.94 min (Example 234) and "Peak-2" tr=11.49 min (Example 236); "Peak-3" tr=13.23 min (Example 235) and "Peak-4" tr=14.63 min (Example 237);

Examples 234 and 235

5 mg each (0.011 mmol, 4.44%) $^1$H NMR (400 MHz, CHLOROFORM-d) δ 8.86-8.74 (m, 1H), 8.53 (dd, J=11.7, 2.8 Hz, 1H), 8.13 (dd, J=9.2, 5.9 Hz, 1H), 7.57-7.39 (m, 4H), 7.35-7.26 (m, 2H), 7.22 (s, 1H), 2.59 (d, J=7.3 Hz, 2H), 2.27-2.16 (m, 1H), 2.09-1.86 (m, 5H), 1.38-1.18 (m, 6H); LC-MS: M+H=427.1 (tr=0.78 min) (Method A)

Examples 236 and 237

40 mg each (0.093 mmol, 36.2%) $^1$H NMR (400 MHz, CHLOROFORM-d) δ 8.83 (d, J=4.6 Hz, 1H), 8.52 (dd, J=11.7, 2.8 Hz, 1H), 8.14 (dd, J=9.3, 6.0 Hz, 1H), 7.58-7.53 (m, J=8.8 Hz, 2H), 7.49 (ddd, J=9.2, 7.6, 2.8 Hz, 1H), 7.42

(d, J=4.5 Hz, 1H), 7.39-7.30 (m, 2H), 7.20 (s, 1H), 2.38-2.16 (m, 3H), 2.09-1.91 (m, 3H), 1.88-1.71 (m, 5H), 1.40-1.30 (m, 3H); LC-MS: M+H=427.1 (tr=0.78 min) (Method A)

Examples 238-241 were obtained following the procedures in Example 58 using the corresponding acids and anilines.

| Number | Name | R | Tr (min)[method] | [M + H]+ |
|---|---|---|---|---|
| Example 238 | (R)-N-(4-chloro-2-hydroxyphenyl)-2-(cis-4-(6-fluoroquinolin-4-yl)cyclohexyl)propanamide | | 0.83[a] | 427.2 |
| Example 239 | (R)-N-(4-chloro-3-hydroxyphenyl)-2-(cis-4-(6-fluoroquinolin-4-yl)cyclohexyl)propanamide | | 0.76[a] | 427.2 |
| Example 240 | (2R)-N-((2S)-bicyclo[2.2.1]heptan-2-yl)-2-(cis-4-(6-fluoroquinolin-4-yl)cyclohexyl)propanamide | | 2.02[b] | 395.0 |
| Example 241 | (R)-N-(2-amino-4-chlorophenyl)-2-(cis-4-(6-fluoroquinolin-4-yl)cyclohexyl)pent-4-enamide | | 0.80[a] | 452.3 |

Example 242

2-(1-(6-Fluoroquinolin-4-yl)-4-methylpiperidin-4-yl)-N-(1-methylcyclohexyl)acetamide

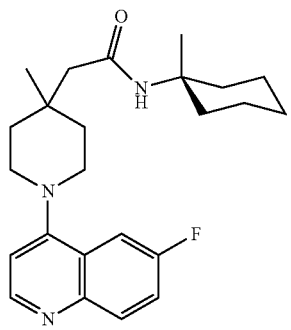

242A. Methyl 2-(4-methylpiperidin-4-yl)acetate

To a flask charged with MeOH (7.5 mL), at 0° C. under nitrogen atmosphere, was slowly added acetyl chloride (1.1 mL, 15.2 mmol). After the addition was complete, the mixture was stirred at 0° C. for 5 minutes before a homogeneous mixture of 2-(4-methylpiperidin-4-yl)acetic acid, HCl (675.0 mg, 3.5 mmol) in MeOH (1.5 mL) was added slowly dropwise. The resultant homogeneous mixture was stirred at 0° C. for 5 minutes then at 60° C. for 8 hours, before being concentrated in vacuo to afford the HCl salt of the title compound as a white solid (718.0 mg; 99% yield) which was used without further purification. $^1$H NMR (400 MHz, DMSO-$d_6$) δ 9.41-9.12 (m, 1H), 3.60 (s, 3H), 3.25-3.15 (m, 2H), 2.93-2.82 (m, 2H), 2.39-2.30 (m, 2H), 1.74-1.64 (m, 4H), 1.02 (s, 3H).

242B. Methyl 2-(1-(6-fluoroquinolin-4-yl)-4-methylpiperidin-4-yl)acetate

To a homogeneous mixture of 4-chloro-6-fluoroquinoline (350.0 mg, 1.9 mmol) in anhydrous NMP (5 mL), in a sealable vial, was added the HCl salt of methyl 2-(4-methylpiperidin-4-yl)acetate (242A, 480.0 mg, 2.3 mmol) followed by DIPEA (1.6 mL, 9.2 mmol). The vial was sealed and the mixture was stirred at 120° C. After 26 hours, the reaction mixture was cooled to room temperature then partitioned between water and EtOAc. The layers were separated and the aqueous layer was extracted once more with EtOAc. The organic layers were combined, washed with brine, then concentrated in vacuo to afford the crude product. Purification by Isco chromatography afforded methyl 2-(1-(6-fluoroquinolin-4-yl)-4-methylpiperidin-4-yl)acetate as an oil (565.8 mg; 93% yield). MS (ES): m/z=317 [M+H]$^+$. $t_R$=0.66 min (Method A). $^1$H NMR (400 MHz, DMSO-$d_6$) δ 8.38 (d, J=5.4 Hz, 1H), 7.96 (dd, J=11.7, 2.8 Hz, 1H), 7.89-7.84 (m, 1H), 7.55-7.49 (m, 1H), 6.54 (d, J=5.5 Hz, 1H), 3.82-3.63 (m, 2H), 3.59 (s, 3H), 3.54-3.34 (m, 2H), 2.45-2.38 (m, 2H), 1.87-1.72 (m, 4H), 1.05 (s, 3H).

242C. 2-(1-(6-Fluoroquinolin-4-yl)-4-methylpiperidin-4-yl)acetic acid

To a homogeneous mixture of methyl 2-(1-(6-fluoroquinolin-4-yl)-4-methylpiperidin-4-yl)acetate (321.0 mg, 1.0 mmol) in MeOH (5 mL), under nitrogen atmosphere, was added dropwise 2M NaOH aqueous solution (1 mL, 2.0 mmol). The reaction was then stirred at ambient temperature for 20 hours before being treated with 1N HCl (aq) until pH 6 to pH test strips. The mixture was then partitioned between water and EtOAc, the layers were separated and the aqueous layer was twice extracted with EtOAc. The aqueous layer from the extraction was lyophilized to afford the crude product as an off-white solid (302.1 mg, 98% yield) which was used without further purification. MS (ES): m/z=303 [M+H]$^+$. $t_R$=0.58 min (Method A). $^1$H NMR (400 MHz, DMSO-$d_6$) δ 12.12 (br. s, 1H), 8.41 (d, J=6.1 Hz, 1H), 8.14-8.08 (m, 1H), 8.00 (dd, 0.1=9.3, 5.7 Hz, 1H), 7.75-7.64 (m, 1H), 6.64 (d, J=6.2 Hz, 1H), 3.98-3.87 (m, 1H), 3.87-3.78 (m, 1H), 3.69-3.49 (m, 2H), 2.38-2.29 (m, 2H), 1.92-1.70 (m, 4H), 1.06 (s, 3H).

Example 242

2-(1-(6-Fluoroquinolin-4-yl)-4-methylpiperidin-4-yl)-N-(1-methylcyclohexyl)acetamide To a mixture of 2-(1-(6-fluoroquinolin-4-yl)-4-methylpiperidin-4-yl)acetic acid (26.5 mg, 0.09 mmol) in anhydrous DMF (1 mL), in a sealable vial, was added PyBOP (45.6 mg, 0.09 mmol) followed by DIPEA (0.06 mL, 0.34 mmol). The mixture was stirred for 15 minutes before 1-methylcyclohexanamine, HCl (15.7 mg, 0.11 mmol) was added and the vial was sealed. The reaction was stirred at ambient temperature for 21 hours, before being diluted with DMF, passed through a syringe filter, then purified via preparative HPLC/MS to afford the title compound (17.2 mg; 38% yield). MS (ES): m/z=398 [M+H]$^+$. $t_R$=1.61 min (Method B). $^1$H NMR (500 MHz, DMSO-$d_6$) δ 8.38 (d, J=5.6 Hz, 1H), 8.02 (d, J=9.7 Hz, 1H), 7.90-7.84 (m, 1H), 7.60 (t, J=7.6 Hz, 1H), 7.19 (s, 1H), 6.57 (d, J=5.8 Hz, 1H), 3.94-3.64 (m, 2H), 2.16 (t, J=7.8 Hz, 2H), 2.02-1.92 (m, 2H), 1.88-1.73 (m, 2H), 1.67 (t, J=7.3 Hz, 2H), 1.47-1.31 (m, 5H), 1.30-1.10 (m, 8H), 1.04 (s, 3H).

Example 243

(±)-N-(4-Chlorophenyl)-2-(1-(6-fluoroquinolin-4-yl)piperidin-4-yl)butanamide

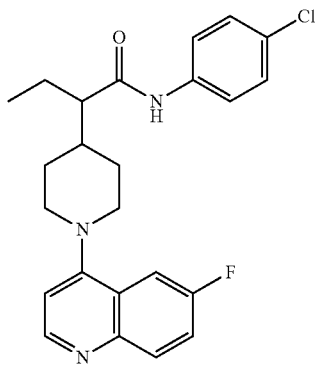

243A. tert-Butyl 4-(1-ethoxy-1-oxobutan-2-ylidene)piperidine-1-carboxylate

To a suspension of NaH (0.29 g, 7.18 mmol) in anhydrous THF (10 mL), under nitrogen atmosphere, was added triethyl 2-phosphonobutyrate (1.81 g, 7.18 mmol) over 5 minutes. The resultant mixture was stirred at ambient temperature for 20 minutes, during which time it became homogeneous. To this solution was added dropwise a homogeneous mixture of 1-Boc-4-piperidone (1.10 g, 5.52 mmol) in anhydrous THF (2.5 mL). After stirring for 1.5 hours, the reaction was quenched with saturated NH$_4$Cl (aq) solution before being thoroughly extracted with EtOAc. The organic fractions were combined, washed with brine, dried (MgSO4), filtered and concentrated in vacuo to afford tert-butyl 4-(1-ethoxy-1-oxobutan-2-ylidene)piperidine-1-carboxylate a clear oil (1.64 g; 100% yield) which was used without further purification. $^1$H NMR (400 MHz, DMSO-d$_6$) δ 4.13 (q, J=7.1 Hz, 2H), 3.39-3.35 (m, 2H), 3.35-3.31 (m, 2H), 2.45-2.39 (m, 2H), 2.31-2.22 (m, 4H), 1.40 (s, 9H), 1.21 (t, J=7.2 Hz, 3H), 0.93 (t, J=7.5 Hz, 3H).

243B. tert-Butyl 4-(1-ethoxy-1-oxobutan-2-yl)piperidine-1-carboxylate

To a flask charged with tert-butyl 4-(1-ethoxy-1-oxobutan-2-ylidene)piperidine-1-carboxylate (1.64 g, 5.52 mmol) and under nitrogen atmosphere, was added platinum(IV) oxide (0.07 g, 0.31 mmol) followed by careful addition of EtOH (5 mL). The nitrogen line was then replaced with a hydrogen balloon and the mixture was stirred at ambient temperature. After 15 hours, the reaction mixture was purged with nitrogen before being filtered through a pad of CELITE®. The pad was thoroughly rinsed with EtOAc before the combined filtrates were concentrated in vacuo to afford tert-butyl 4-(1-ethoxy-1-oxobutan-2-yl)piperidine-1-carboxylate as a clear oil (1.65 g; 100% yield) which was used without further purification. $^1$H NMR (400 MHz, DMSO-d$_6$) δ 4.08 (q, J=7.1 Hz, 2H), 3.98-3.83 (m, 2H), 2.78-2.52 (m, 2H), 2.13-2.03 (m, 1H), 1.69-1.62 (m, 1H), 1.52-1.43 (m, 2H), 1.38 (s, 9H), 1.28-1.13 (m, 5H), 1.10-0.98 (m, 2H), 0.80 (t, J=7.3 Hz, 3H).

243C. Ethyl 2-(piperidin-4-yl)butanoate

To a homogeneous mixture of tert-butyl 4-(1-ethoxy-1-oxobutan-2-yl)piperidine-1-carboxylate (1.65 g, 5.52 mmol) in anhydrous dioxane (5 mL), under nitrogen atmosphere, was added HCl (4N in dioxane, 10 mL, 40.0 mmol). The mixture was stirred at ambient temperature for two hours before being concentrated in vacuo to remove volatiles. The resultant oil was treated with saturated aqueous NaHCO$_3$ solution until pH5 and then 1N NaOH (aq) until pH 8, before the mixture was thoroughly extracted with EtOAc. The layers were separated and the aqueous layer was lyophilized to afford the title compound as a pale yellow solid (1.20 g; 92% yield) which was used in the next step without further purification. MS (ES): m/z=200 [M+H]$^+$. t$_R$=0.57 min (Method A). $^1$H NMR (500 MHz, DMSO-d$_6$) δ 4.07 (q, J=7.2 Hz, 2H), 3.01-2.78 (m, 2H), 2.48-2.29 (m, 3H), 2.07-1.98 (m, 1H), 1.60-1.35 (m, 5H), 1.18 (t, J=7.1 Hz, 3H), 1.11-0.88 (m, 2H), 0.80 (t, J=7.4 Hz, 3H).

243D. Ethyl 2-(1-(6-fluoroquinolin-4-yl)piperidin-4-yl)butanoate

To a homogeneous mixture of 4-chloro-6-fluoroquinoline (365.0 mg, 2.01 mmol) in anhydrous NMP (5 mL), in a sealable vial, was added ethyl 2-(piperidin-4-yl)butanoate (243C, 544.0 mg, 2.31 mmol) followed by DIPEA (1.6 mL, 9.16 mmol). The vial was sealed and the mixture was stirred at 120° C. for three hours before being allowed to cool to room temperature. After stirring 7 days, the mixture was heated at 120° C. for three days, then allowed to cool to room temperature, before being partitioned between water and EtOAc. The layers were separated and the aqueous layer was extracted once more with EtOAc. This organic extract was combined with the original organic layer and was washed with water then concentrated in vacuo to afford a dark brown residue. Purification by Isco chromatography afforded ethyl 2-(1-(6-fluoroquinolin-4-yl)piperidin-4-yl)butanoate as a gold oil (76.1 mg; 11% yield). MS (ES): m/z=345 [M+H]$^+$. t$_R$=0.77 min (Method A). $^1$H NMR (400 MHz, CHLOROFORM-d) δ 8.68 (d, J=5.0 Hz, 1H), 8.06-8.03 (m, 1H), 7.59-7.55 (m, 1H), 7.43-7.38 (m, 1H), 6.84 (d, J=4.9 Hz, 1H), 4.21 (q, J=7.1 Hz, 2H), 3.62-3.52 (m, 2H), 2.84-2.71 (m, 2H), 2.29-2.20 (m, 1H), 2.01-1.93 (m, 1H), 1.82-1.60 (m, 6H), 1.31 (t, J=7.2 Hz, 3H), 0.94 (t, J=7.4 Hz, 3H).

243E. 2-(1-(6-Fluoroquinolin-4-yl)piperidin-4-yl)butanoic acid

To a homogeneous mixture of ethyl 2-(1-(6-fluoroquinolin-4-yl)piperidin-4-yl)butanoate (76.1 mg, 0.22 mmol) in EtOH (4 mL), under nitrogen atmosphere, was added NaOH (2M aqueous solution, 0.2 mL, 0.40 mmol). The mixture was stirred at ambient temperature for 21 hours before NaOH (2M aqueous solution, 0.2 mL, 0.40 mmol) was added and stirring continued. After 22 hours NaOH (2M aqueous solution, 0.2 mL, 0.40 mmol) was added and the reaction was warmed to 40° C. The reaction was stirred for 4 days before NaOH (2M aqueous solution, 0.2 mL, 0.40 mmol) was added and stirring was continued for 21 hours. After cooling to room temperature, the reaction was quenched with 4N HCl in dioxane (until pH 5-6 on pH test strips), stirred for 5 minutes at room temperature then concentrated in vacuo to afford the crude product as a pale yellow solid, which was used in the next step without further purification. MS (ES): m/z=317 [M+H]$^+$. t$_R$=0.63 min (Method A).

Example 243

(±)-N-(4-Chlorophenyl)-2-(1-(6-fluoroquinolin-4-yl)piperidin-4-yl)-butanamide

To a mixture of 2-(1-(6-fluoroquinolin-4-yl)piperidin-4-yl)butanoic acid (35.0 mg, 0.11 mmol) and 4-chloroaniline (17.0 mg, 0.13 mmol) in anhydrous DMF, under nitrogen atmosphere, was added DIPEA (0.1 mL, 0.57 mmol) followed by PyBOP (57.6 mg, 0.11 mmol). The resulting mixture was stirred at ambient temperature for 98 hours before being diluted with DMF, passed through a syringe filter, then purified via preparative HPLC/MS to afford the title compound (2.5 mg; 3% yield). MS (ES): m/z=426 [M+H]$^+$. t$_R$=2.22 min (Method B). $^1$H NMR (500 MHz, DMSO-d$_6$) δ 10.15 (s, 1H), 8.64 (d, J=4.9 Hz, 1H), 8.00 (dd, J=9.0, 5.7 Hz, 1H), 7.67 (d, J=8.7 Hz, 2H), 7.64-7.51 (m, 2H), 7.35 (d, J=8.7 Hz, 2H), 7.07-6.96 (m, J=4.9 Hz, 1H), 3.52-3.43 (m, 1H), 2.84-2.66 (m, 2H), 2.55-2.53 (m, 1H), 2.27-2.18 (m, 1H), 2.02-1.92 (m, J=11.9 Hz, 1H), 1.78-1.43 (m, 6H), 0.86 (t, J=7.2 Hz, 3H).

Example 244

(±)-N-(4-Chlorophenyl)-2-(4-(6-fluoroquinolin-4-yl)piperazin-1-yl)pentanamide

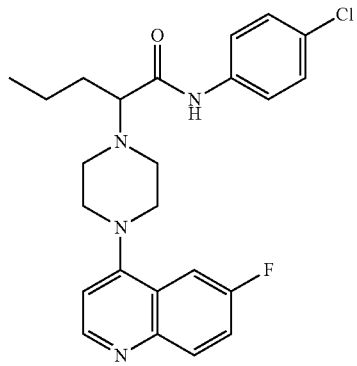

244A. tert-Butyl 4-(6-fluoroquinolin-4-yl)piperazine-1-carboxylate

To a mixture of 4-chloro-6-fluoroquinoline (500.0 mg, 2.8 mmol) in anhydrous NMP (5 mL), in a sealable vial, was added 1-Boc-piperazine (750.0 mg, 4.0 mmol) followed by DIPEA (2.0 mL, 11.5 mmol). The vial was capped and the mixture was stirred at 120° C. for 15.5 hours. The reaction mixture was cooled to room temperature before being partitioned between water and Et$_2$O. The layers were separated and the aqueous layer was extracted twice more with Et$_2$O. These organic extracts were combined with the original organic layer and were washed with brine, dried (Na$_2$SO$_4$), filtered and concentrated in vacuo to afford the crude product. Purification by Isco chromatography afforded tert-butyl 4-(6-fluoroquinolin-4-yl)piperazine-1-carboxylate as an oil (719.3 mg; 77% yield). MS (ES): m/z=332 [M+H]$^+$. $t_R$=0.70 min (Method A). $^1$H NMR (400 MHz, DMSO-d$_6$) δ 8.70 (d, J=4.9 Hz, 1H), 8.09-8.00 (m, 1H), 7.77-7.67 (m, 1H), 7.67-7.62 (m, 1H), 7.07 (d, j=4.9 Hz, 1H), 3.67-3.57 (m, 4H), 3.15-3.06 (m, 4H), 1.44 (s, 9H).

244B. 6-Fluoro-4-(piperazin-1-yl)quinoline

To a homogeneous mixture of tert-butyl 4-(6-fluoroquinolin-4-yl)piperazine-1-carboxylate (600.0 mg, 1.8 mmol) in dioxane (4 mL), under nitrogen atmosphere, was added 4M HCl in dioxane (10 mL, 40.0 mmol). The resultant mixture was stirred at ambient temperature for 2.5 hours, during which time a precipitate formed. The heterogeneous mixture was concentrated to approximately ½ of its original volume. Vacuum filtration afforded the HCl salt of the title compound as an off-white solid (490.0 mg; 100% yield) which was used without further purification. MS (ES): m/z=232 [M+H]$^+$. $t_R$=0.38 min (Method A).

244C. (±)-Ethyl 2-(4-(6-fluoroquinolin-4-yl)piperazin-1-yl)pentanoate

To a heterogeneous mixture of the HCl salt of 6-fluoro-4-(piperazin-1-yl)quinoline (244B, 200.0 mg, 0.75 mmol) in anhydrous DMF (5 mL), in a sealable reaction vial, was added K$_2$CO$_3$ (288.0 mg, 2.08 mmol) followed by ethyl 2-bromovalerate (234.0 mg, 1.12 mmol). The flask was then sealed and the mixture was stirred at 60° C. After 16 hours, the reaction was cooled to room temperature then partitioned between water and EtOAc. The layers were separated and the aqueous layer was extracted once more with EtOAc. The organic layers were combined, washed with brine, dried (anhydrous Na$_2$SO$_4$), filtered and concentrated in vacuo to afford the product as a yellow oil which was used in the next step without further purification. MS (ES): m/z=360 [M+H]$^+$. $t_R$=0.62 min (Method A).

244D. (±)-2-(4-(6-Fluoroquinolin-4-yl)piperazin-1-yl)pentanoic acid

To a homogeneous mixture of ethyl 2-(4-(6-fluoroquinolin-4-yl)piperazin-1-yl)propanoate (244C, 0.75 mmol) in MeOH (4 mL), under nitrogen atmosphere, was added dropwise 2M NaOH (aq) (0.8 mL, 1.6 mmol). The resultant mixture was stirred at ambient temperature for 64 hours before 2M NaOH (aq) (0.8 mL, 1.6 mmol) was added. After 6 hours of stirring, 2M NaOH (aq) (0.8 mL, 1.6 mmol) was added and stirring was continued. After 115 hours, the reaction was treated with HCl (4N in dioxane) until pH 5 to pH test strips. The mixture was then partitioned between water and EtOAc. The layers were separated and the aqueous layer was lyophilized to afford a pale yellow solid. Purification by RP Preparative HPLC (YMC-ODS 5µ 250×30 column. Conditions: 30 mL/min flow rate; 40 minute gradient from 30-100% B (Solvent A=95:5 H2O/MeCN with 0.05% TFA. Solvent B=5:95 H2O/MeCN with 0.05% TFA) afforded the TFA salt of 2-(4-(6-fluoroquinolin-4-yl)piperazin-1-yl)pentanoic acid as a pale yellow solid (160.0 mg; 58% yield). MS (ES): m/z=332 [M+H]$^+$. $t_R$=0.46 min (Method A). $^1$H NMR (400 MHz, DMSO-d$_6$) δ 8.77 (d, J=6.4 Hz, 1H), 8.10 (dd, J=10.1, 5.2 Hz, 1H), 7.93-7.86 (m, 2H), 7.28 (d, J=6.5 Hz, 1H), 3.84-3.73 (m, 4H), 3.72-3.51 (m, 1H), 3.38-2.99 (m, 4H), 1.86-1.68 (m, 2H), 1.46-1.33 (m, 2H), 0.94 (t, J=7.3 Hz, 3H).

Example 244

(±)-N-(4-Chlorophenyl)-2-(4-(6-fluoroquinolin-4-yl)piperazin-1-yl)pentanamide

To a mixture of the salt of (±)-2-(4-(6-fluoroquinolin-4-yl)piperazin-1-yl)pentanoic acid (244D, 32.0 mg, 0.10 mmol) in anhydrous DMF (1.5 mL), in a sealable vial, was added PyBOP (50.3 mg, 0.10 mmol) followed by DIPEA (0.06 mL, 0.34 mmol). The resulting mixture was stirred at ambient temperature for 10 minutes before 4-chloroaniline (14.8 mg, 0.12 mmol) was added. The vial was sealed and the reaction was stirred at ambient temperature for 63 hours, before being diluted with DMF, passed through a syringe filter, then purified via preparative HPLC/MS to afford the title compound as a racemate (15.9 mg; 37% yield). MS (ES): m/z=441 [M+H]$^+$. $t_R$=2.24 min (Method B). $^1$H NMR (500 MHz, DMSO-d$_6$) δ 10.15 (s, 1H), 8.66 (d, J=4.8 Hz, 1H), 8.08-7.95 (m, 1H), 7.68 (d, J=8.7 Hz, 2H), 7.64-7.53 (m, 2H), 7.37 (d, J=8.7 Hz, 2H), 7.02 (d, J=4.8 Hz, 1H), 3.57-3.43 (m, 1H), 3.35-3.08 (m, 4H), 2.94-2.78 (m, 4H), 1.81-1.58 (m, 2H), 1.40-1.24 (m, 2H), 0.92 (t, J=7.3 Hz, 3H).

Example 245

N-(4-Chlorophenyl)-2-(4-(6-fluoroquinolin-4-yl)piperazin-1-yl)pentanamide

Enantiomer 1

Absolute Stereochemistry not Assigned

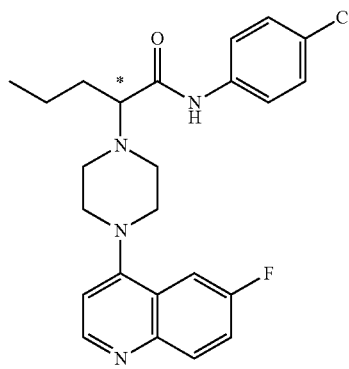

and

Example 246

N-(4-Chlorophenyl)-2-(4-(6-fluoroquinolin-4-yl)piperazin-1-yl)pentanamide

Enantiomer 2

Absolute Stereochemistry not Assigned

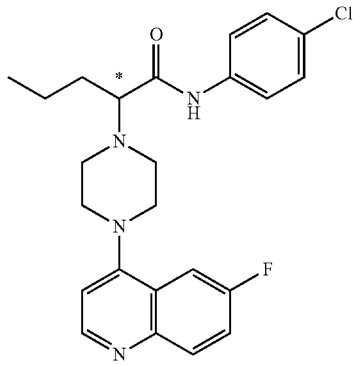

Racemic Example 244 (15.9 mg) was purified by chiral SFC (82/18 CO$_2$/MeOH with 0.1% DEA mobile phase, Chiral OJ 25×3 cm, 5 μm column, 85 ml/min, detector wavelength=220 nm). Concentration of the appropriate (earlier eluting) fractions afforded Example 245 (6.7 mg) assigned as N-(4-chlorophenyl)-2-(4-(6-fluoroquinolin-4-yl)piperazin-1-yl)pentanamide (Enantiomer 1). MS (ES): m/z=441 [M+H]$^+$. T$_r$=2.21 min (Method B). $^1$H NMR (500 MHz, DMSO-d$_6$): superimposable upon racemate NMR. Concentration of the later eluting fractions afforded Example 246 (6.8 mg) assigned as N-(4-chlorophenyl)-2-(4-(6-fluoroquinolin-4-yl)piperazin-1-yl)pentanamide (Enantiomer 2). MS (ES): m/z=441 [M+H]$^+$. T$_r$=2.21 min (Method B). $^1$H NMR (500 MHz, DMSO-d$_6$): superimposable upon racemate NMR.

Example 247

(±)-2-(4-(6-Fluoroquinolin-4-yl)piperazin-1-yl)-N-(1-methylcyclohexyl)pentanamide

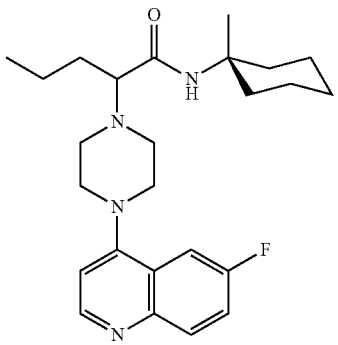

Example 247 (17.5 mg; 42% yield) was prepared following a procedure analogous to that for the synthesis of Example 244 except that 1-methylcyclohexanamine, HCl (17.3 mg, 0.12 mmol) was used instead of 4-chloroaniline. MS (ES): m/z=427 [M+H]$^+$. T$_r$=2.23 min (Method B). $^1$H NMR (500 MHz, DMSO-d$_6$) δ 8.64 (d, J=4.8 Hz, 1H), 8.01 (dd, J=9.0, 5.7 Hz, 1H), 7.68-7.52 (m, 2H), 7.35-7.23 (m, 1H), 7.03 (d, J=4.9 Hz, 1H), 3.19-3.09 (m, 4H), 2.90-2.77 (m, 3H), 2.56-2.51 (m, 2H), 2.11-2.00 (m, 2H), 1.70-1.58 (m, 1H), 1.53-1.35 (m, 6H), 1.30-1.19 (m, 8H), 0.88 (t, J=7.2 Hz, 3H).

Example 248

2-(4-(6-Fluoroquinolin-4-yl)piperazin-1-yl)-N-(1-methylcyclohexyl)pentanamide

Enantiomer 1, Absolute Stereochemistry not Assigned

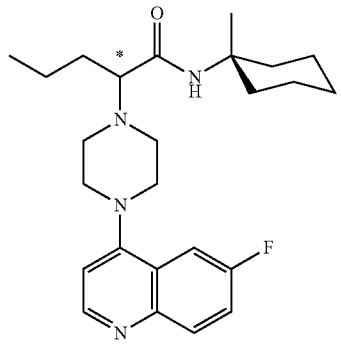

and

Example 249

2-(4-(6-Fluoroquinolin-4-yl)piperazin-1-yl)-N-(1-methylcyclohexyl)pentanamide

Enantiomer 2

Absolute Stereochemistry not Assigned

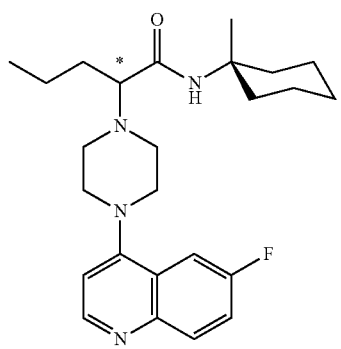

Racemic Example 247 (16.7 mg) was purified by chiral SFC (80/20 CO$_2$/MeOH with 0.1% DEA mobile phase, Chiral AD 25×3 cm, 5 μL m column, 85 ml/min, detector wavelength=220 nm). Concentration of the appropriate (earlier eluting) fractions afforded Example 248 (7.4 mg) assigned as 2-(4-(6-fluoroquinolin-4-yl)piperazin-1-yl)-N-(1-methylcyclohexyl)pentanamide (Enantiomer 1). MS (ES): m/z 427 [M+H]$^+$. T$_r$=2.28 min (Method B). $^1$H NMR (500 MHz, DMSO-d$_6$): superimposable upon racemate NMR. Concentration of the later eluting fractions afforded Example 249 (6.5 mg) assigned as 2-(4-(6-fluoroquinolin-4-yl)piperazin-1-yl)-N-(1-methylcyclohexyl)pentanamide (Enantiomer 2). MS (ES): m/z=427 [M+H]$^+$. T$_r$=2.28 min (Method B). $^1$H NMR (500 MHz, DMSO-d$_6$): superimposable upon racemate NMR.

Example 250

(+/−)-Cis and trans-N-(4-chlorophenyl)-2-(4-(3-methyl-3H-imidazo[4,5-b]pyridin-7-yl)cyclohexyl)propanamide

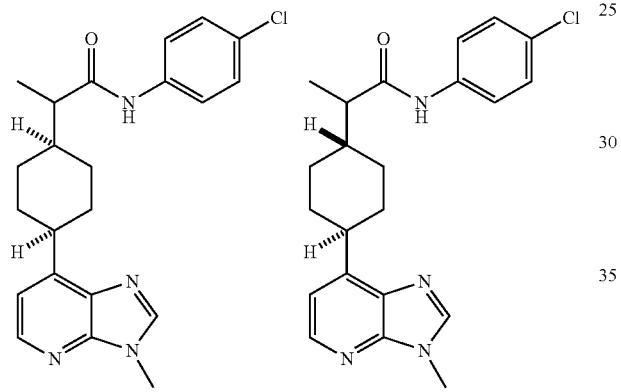

Preparation 250A 7-chloro-3-methyl-3H-imidazo[4,5-b]pyridine

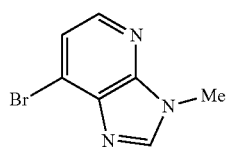

To a solution of 7-chloro-3H-imidazo[4,5-b]pyridine, formic acid salt (0.2 g, 0.820 mmol) in DMSO (4.10 ml) was added cesium carbonate (0.534 g, 1.639 mmol) and iodomethane (0.054 ml, 0.860 mmol). Reaction stirred at rt for 28 h, then quenched with H$_2$O and extracted with EtOAc (5×). Organics combined, dried over Na$_2$SO$_4$, filtered, and concentrated to afford an orange liquid, which was further dried under high vacuum overnight. TLC and LC-MS showed ~1:1 product/SM. The crude material was dissolved in a minimal amount of CH$_2$Cl$_2$ and chromatographed. Purification of the crude material by silica gel chromatography using an ISCO machine (40 g column, 40 mL/min, 0-20% MeOH in CH$_2$Cl$_2$ over 24 min, t$_r$=17 min) gave the title compound (0.0729 g, 0.344 mmol, 42.0% yield) as a white solid and 2.8:1 mixture of isomers. ESI MS (M+H)+=212.0. HPLC Peak t$_r$=0.55 minutes. HPLC conditions: Method A.

Preparation 250B ethyl 2-(4-(3-methyl-3H-imidazo[4,5-b]pyridin-7-yl)cyclohex-3-en-1-yl)propanoate

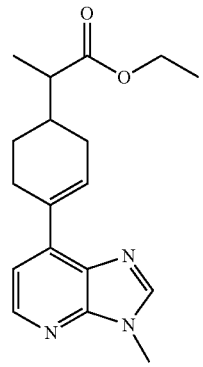 [SMILES: CCOC(=O)C(C)C1CC=C(c2ccnc3c2ncn3C)CC1]

A mixture of Preparation 250A (0.0729 g, 0.435 mmol), ethyl 2-(4-(4,4,5,5-tetramethyl-1,3,2-dioxaborolan-2-yl)cyclohex-3-en-1-yl)propanoate (0.138 g, 0.448 mmol), Na$_2$CO$_3$ (0.184 g, 1.740 mmol), and Pd(Ph$_3$P)$_4$ (0.025 g, 0.022 mmol) in dioxane (3.5 mL) and water (0.5 mL) was heated at 100° C. overnight. The reaction was quenched with water and diluted with EtOAc. Layers were separated. The aqueous phase was extracted with EtOAc (3×). The organics were combined, dried over Na$_2$SO$_4$, filtered, and concentrated to afford a brown residue. Purification of the crude material by silica gel chromatography using an ISCO machine (40 g column, 40 mL/min, 0-20% MeOH in CH$_2$Cl$_2$ over 25 min, t$_r$=12, 16 min) gave the title compound (79 mg, 0.253 mmol, 58% yield) as a colorless residue and its regioisomer (21 mg, 0.067 mmol, 15.41% yield) as a colorless residue. ESI MS (M+H)+=314.3. HPLC Peak t$_r$=0.75 minutes. HPLC conditions: Method A.

Preparation 250C ethyl 2-(4-(3-methyl-3H-imidazo[4,5-b]pyridin-7-yl)cyclohexyl)propanoate

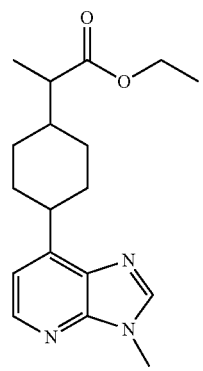 [SMILES: CCOC(=O)C(C)C1CCC(c2ccnc3c2ncn3C)CC1]

To a solution of Preparation 250B (0.0792 g, 0.253 mmol) in MeOH (1.264 ml) was added ammonium formate (0.080 g, 1.264 mmol) followed by Pd/C (7.26 mg, 0.068 mmol). The reaction was heated at 70° C. for 1 h. The reaction was filtered through CELITE® and the filter cake washed with CH$_2$Cl$_2$. The filtrate was concentrated. The crude material was taken up in EtOAc and washed with a sat. aq. solution of NaHCO$_3$ (2×). The organic phase was dried over Na$_2$SO$_4$, filtered, and concentrated to afford the title compound (59.7 mg, 0.180 mmol, 71% yield) as a green residue. ESI MS (M+H)+=316.2. HPLC Peak t$_r$=0.72 minutes. HPLC conditions: Method A.

Example 250

(+/−)-Cis and trans-N-(4-chlorophenyl)-2-(4-(3-methyl-3H-imidazo[4,5-b]pyridin-7-yl)cyclohexyl) propanamide To a solution of 4-chloroaniline (0.097 g, 0.757 mmol) in THF (0.4 mL) at 0° C. was added a solution of isopropylmagnesium chloride (0.379 ml, 0.757 mmol). The resulting solution was warmed to rt and stirred for 5 min, then Preparation 250C (0.0597 g, 0.189 mmol) in THF (0.6 mL) was added dropwise. The reaction was heated at 70° C. for 2.5 h, then allowed to cool to rt. The reaction was quenched with a sat. aq. soln. of NH$_4$Cl and diluted with EtOAc. Layers were separated. The aqueous phase was extracted with EtOAc (3×). The combined organic phases were dried over Na$_2$SO$_4$, filtered, and concentrated to afford a residue. The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford the title compound as a mixture of 4 isomers (26.6 mg, 35%). ESI MS (M+H)+=397.3. HPLC Peak t$_r$=1.775 minutes and 1.793 minutes. Purity=99%. HPLC conditions: Method B.

Example 251

N-(4-chlorophenyl)-2-(4-(3-methyl-3H-imidazo[4,5-b]pyridin-7-yl)cyclohexyl)propanamide, Absolute and Relative Stereochemistry not Confirmed

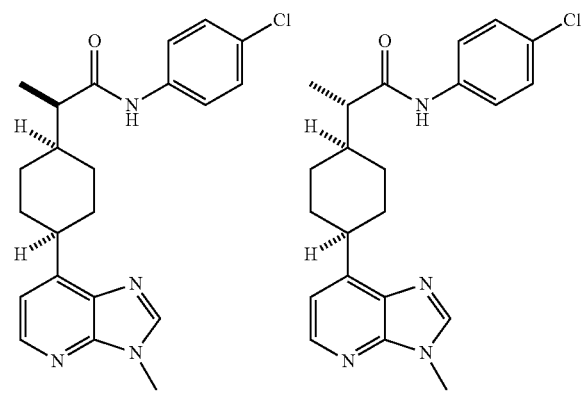

-continued

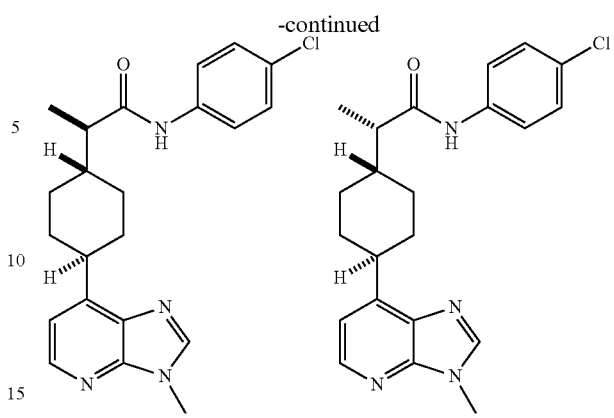

Approximately 25.4 mg of diastereomeric and racemic Example 250 was resolved. The isomeric mixture was purified via preparative SFC with the following conditions: Column: Chiral OZ-H, 25×3 cm ID, 5-µm particles; Mobile Phase A: 82/18 CO$_2$/MeOH with 0.1% DEA; Detector Wavelength: 220 nm; Flow: 100 mL/min. The fractions ("Peak-1" t$_r$=11.910 min, "Peak-2" t$_r$=15.648 min, "Peak-3" t$_r$=16.927 min, "Peak-4" t$_r$=19.403; analytical conditions: Column: Chiral OZ-H, 250×4.6 mm ID, 5-µm particles; Mobile Phase A: 80/20 CO$_2$/MeOH with 0.1% DEA; Flow: 2.0 mL/min) were collected in MeOH with 0.1% DEA. The stereoisomeric purity of each fraction was estimated to be greater than 99% based on the prep-SFC chromatograms. Each diastereomer or enantiomer was further purified via preparative LC/MS:

Example 250a

First Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 35-60% B over 25 minutes, then a 2-minute hold at 60% B; Flow: 20 mL/min. Fractions containing the desired product were combined and dried via centrifugal evaporation to afford Isomer 1 (3.1 mg, 4%). ESI MS (M+H)+=397.3. HPLC Peak t$_r$=1.840 minutes. Purity=95%. HPLC conditions: Method B. Absolute stereochemistry not determined.

Example 250b

Second Eluting Isomer

The crude material was purified via preparative LC/MS with the following conditions: Column: XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate;

Gradient: 30-70% B over 20 minutes, then a 5-minute hold at 100% B; Flow: 20 mL/min. Fractions containing the desired product were combined and dried via centrifugal evaporation to afford Isomer 2 (3.0 mg, 4%). ESI MS (M+H)+=397.3. HPLC Peak $t_r$=1.804 minutes. Purity=93%. HPLC conditions: Method B. Absolute stereochemistry not determined.

Example 250c

Third Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford Isomer 3 (3.2 mg, 4%). ESI MS (M+H)+=397.3. HPLC Peak $t_r$=1.806 minutes. Purity=96%. HPLC conditions: Method B. Absolute stereochemistry not determined.

Example 250d

Fourth Eluting Isomer

The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 30-70% B over 20 minutes, then a 5-minute hold at 100% B; Flow: 20 mL/min. Fractions containing the desired product were combined and dried via centrifugal evaporation to afford Isomer 4 (3.0 mg, 4%). ESI MS (M+H)+=397.2. HPLC Peak $t_r$=1.841 minutes. Purity=94%. HPLC conditions: Method B. Absolute stereochemistry not determined.

BIOLOGICAL EXAMPLES

Example 251

Assessment of Inhibitor Activity in HeLa Cell-Based Indoleamine 2,3-Dioxygenase (IDO) Assay HeLa (ATCC® CCL-2) cells were obtained from the ATCC and cultured in Dulbecco's Modified Eagle Medium supplemented with 4.5 g/L glucose, 4.5 g/L L-glutamine and 4.5 g/L sodium pyruvate (#10-013-CV, Corning), 2 mM L-alanyl-L-glutamine dipeptide (#35050-061, Gibco), 100 U/mL penicillin, 100 μg/mL streptomycin (#5V30010, Hyclone) and 10% fetal bovine serum (#SH30071.03 Hyclone). Cells were maintained in a humidified incubator at 37° C. in 5% $CO_2$.

IDO activity was assessed as a function of kynurenine production as follows: HeLa cells were seeded in a 96-well culture plate at a density of 5,000 cells/well and allowed to equilibrate overnight. After 24 hours, the media was aspirated and replaced with media containing IFNγ (#285-IF/CF, R&D Systems) at a final concentration of 25 ng/mL. A serial dilution of each test compound was added to the cells in a total volume of 200 μL of culture medium. After a further 48 hour incubation, 170 μL of supernatant was transferred from each well to a fresh 96-well plate. 12.1 μL of 6.1N trichloroacetic acid (#T0699, Sigma-Aldrich) was added to each well and mixed, followed by incubation at 65° C. for 20 minutes to hydrolyze N-formylkynurenine, the product of indoleamine 2,3-dioxygenase, to kynurenine. The reaction mixture was then centrifuged for 10 mins at 500×g to sediment the precipitate. 100 μL of the supernatant was transferred from each well to a fresh 96-well plate. 100 μL of 2% (w/v) p-dimethylaminobenzaldehyde (#15647-7, Sigma-Aldrich) in acetic acid (#A6283, Sigma-Aldrich) was added to each well mixed and incubated at room temperature for 20 mins. Kynurenine concentrations were determined by measuring absorbance at 480 nm and calibrating against an L-kynurenine (#K8625, Sigma-Aldrich) standard curve using a SPECTRAMAX® M2e microplate reader (Molecular Devices). The percentage activity at each inhibitor concentration was determined and $IC_{50}$ values assessed using nonlinear regression.

Figure 1P:
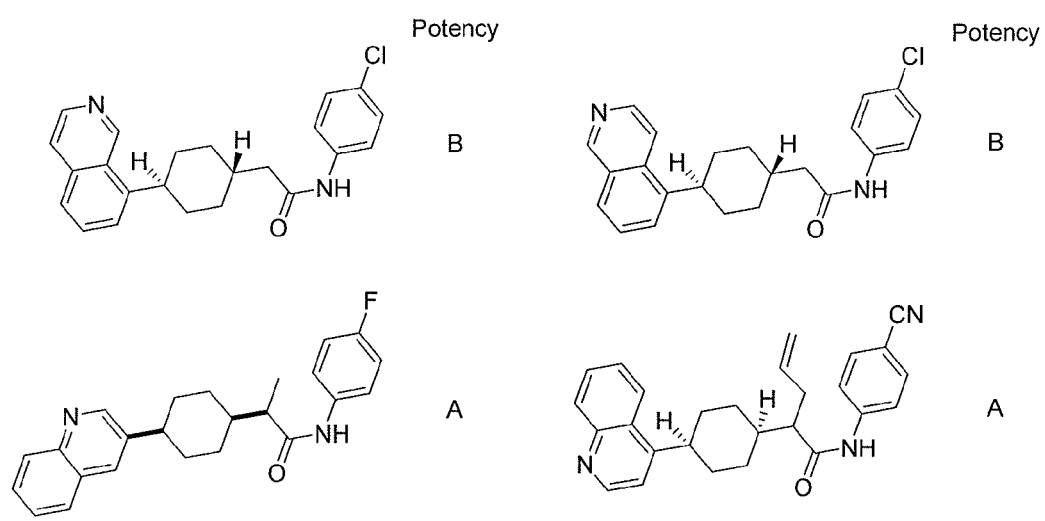

Activity for compounds described herein is provided in FIGS. 1A-1P, wherein potency levels are provided as follows: (Potency: IDO $IC_{50}$: A<0.1 μM; B<1 μM; C<10 μM)

Example 252

1HEK293 cells were transfected with a pCDNA-based mammalian expression vector harboring human IDOL cDNA (NM 002164.2) by electroporation. They were cultured in medium (DMEM with 10% FBS) containing 1 mg/ml G418 for two weeks. Clones of HEK293 cells that stably expressed human IDO1 protein were selected and expanded for IDO inhibition assay.

The human IDO1/HEK293 cells were seeded at 10,000 cells per 50 μL per well with RPMI/phenol red free media contains 10% FBS in a 384-well black wall clear bottom tissue culture plate (Matrix Technologies LLC) 100 nL of certain concentration of compound was then added to each well using ECHO liquid handling systems. The cells were incubated for 20 hours in 37° C. incubator with 5% $CO_2$.

The compound treatments were stopped by adding Trichloroacetic Acid (Sigma-Aldrich) to a final concentration at 0.2%. The cell plate was further incubated at 50° C. for 30 minute. The equal volume supernatant (20 μL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Compounds with an $IC_{50}$ greater than 250 nM are shown with (C), compounds with an $IC_{50}$ less than 250 nM are shown with (B) and those with an $IC_{50}$ less than 50 nM are shown with (A) in Table X below.

TABLE X

Biological activity for Examples tested in the biological assay described in Example 252.

| Example No. | HEK Human IDO-1 Potency |
|---|---|
| 58 | A |
| 59 | C |
| 60 | A |

TABLE X-continued

Biological activity for Examples tested in the biological assay described in Example 252.

| Example No. | HEK Human IDO-1 Potency |
|---|---|
| 61 | A |
| 62 | B |
| 63 | A |
| 64 | B |
| 65 | A |
| 66 | A |
| 67 | A |
| 68 | A |
| 69 | C |
| 70 | A |
| 71 | A |
| 72 | A |
| 73 | B |
| 73a | C |
| 74 | A |
| 75 | B |
| 76 | A |
| 77 | A |
| 78 | A |
| 79 | B |
| 80 | A |
| 82 | B |
| 83 | B |
| 83a | C |
| 83b | B |
| 84 | C |
| 85 | A |
| 86 | A |
| 87a | A |
| 87b | A |
| 88 | A |
| 88a | A |
| 88b | B |
| 89 | C |
| 89a | B |
| 89b | C |
| 90 | C |
| 92 | C |
| 93 | A |
| 94 | B |
| 95 | B |
| 96 | A |
| 97 | B |
| 98 | B |
| 99 | A |
| 100 | A |
| 101 | A |
| 102 | C |
| 103 | B |
| 104 | A |
| 105 | A |
| 106 | C |
| 107 | A |
| 108 | B |
| 109 | A |
| 110 | C |
| 111 | B |
| 112 | C |
| 113 | A |
| 114 | B |
| 115 | C |
| 116 | C |
| 117 | C |
| 118 | C |
| 119 | C |
| 120 | C |
| 121 | C |
| 122 | C |
| 123 | A |
| 124 | C |
| 125 | B |
| 126 | C |
| 127 | C |
| 128 | C |
| 129 | B |
| 130 | C |
| 131 | A |
| 132 | C |
| 133 | C |
| 134 | B |
| 135 | C |
| 136 | C |
| 137 | A |
| 138 | A |
| 139 | A |
| 140 | A |
| 141 | A |
| 142 | B |
| 143 | B |
| 144a | A |
| 144b | C |
| 144c | B |
| 144d | C |
| 147 | A |
| 148a | C |
| 148b | A |
| 148c | A |
| 148d | B |
| 149 | A |
| 150a | A |
| 150b | C |
| 150c | C |
| 150d | A |
| 152a | A |
| 152b | A |
| 152c | B |
| 152d | A |
| 153 | A |
| 154 | A |
| 229 | A |
| 230 | B |
| 231 | B |
| 232 | A |
| 233 | A |
| 234 | |
| 235 | |
| 236 | |
| 237 | |
| 238 | A |
| 239 | A |
| 240 | B |
| 241 | A |
| 242 | A |
| 243 | C |
| 244 | B |
| 245 | B |
| 246 | C |
| 247 | C |
| 248 | C |
| 249 | A |
| 250 | B |
| 251a | A |
| 251b | C |
| 251c | A |
| 251d | C |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the formula (I):

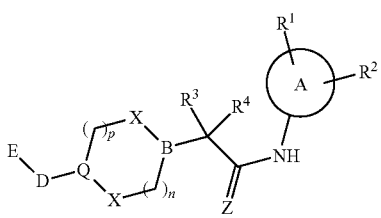

or a pharmaceutically acceptable salt, hydrate or solvate thereof, wherein, the subscript n is 1; the subscript p is 1;

the ring designated as A is phenyl, 5- or 6-membered heteroaryl, or $C_{5-7}$ cycloalkyl;

Z is O;

B is N, $C(OR^{5a})$, or $C(R^{3a})$;

each X is independently $CHR^5$, $C(O)$, or $CH(OR^{5a})$;

Q is N, $C(CN)$, or $CR^6$;

D is a bond, O, $C(R^5)_2$, or $NR^{5a}$;

E is an optionally substituted 9- or 10-membered fused bicyclic heteroaryl;

$R^1$ and $R^2$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl;

$R^3$, $R^{3a}$ and $R^4$ are independently hydrogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ haloalkyl, optionally substituted $C_3$-$C_6$ cycloalkyl-$C_1$-$C_4$ alkyl, optionally substituted aryl-$C_1$-$C_6$ alkyl, fluorine, OH, CN, $CO_2H$, $C(O)NH_2$, $N(R^5)_2$, optionally substituted —O—$C_1$-$C_6$ alkyl, —$(CR^5R^5)_m$—OH, —$(CR^5R^5)_m$—$CO_2H$, —$(CR^5R^5)_m$—$C(O)NH_2$, —$(CR^5R^5)_m$—$C(O)NHR^5$, —$(CR^5R^5)_m$N$(R^5)_2$, —NH$(CR^5R^5)_m$$CO_2H$ or —NH$(CR^5R^5)_m$—$C(O)NH_2$;

each $R^5$ is independently H, F, OH, or optionally substituted $C_1$-$C_6$ alkyl;

each $R^{5a}$ is independently H, or optionally substituted $C_1$-$C_6$ alkyl;

$R^6$ is H, OH, F, optionally substituted $C_1$-$C_6$ alkyl, optionally substituted —O—$C_1$-$C_6$ alkyl, or —N$(R^{5a})_2$;

and each m is independently 1, 2, or 3.

2. The compound of claim 1, or a pharmaceutically acceptable salt, hydrate or solvate thereof, wherein, the subscript n is 1; the subscript p is 1;

the ring designated as A is phenyl, 5- or 6-membered heteroaryl, or $C_{5-7}$ cycloalkyl;

Z is O;

B is N, $C(OR^{5a})$, or $C(R^{3a})$;

each X is independently $CHR^5$, $C(O)$, or $CH(OR^{5a})$;

Q is N, $C(CN)$, or $CR^6$;

D is a bond, O, $C(R^5)_2$, or $NR^{5a}$;

E is an optionally substituted 9- or 10-membered fused bicyclic heteroaryl;

$R^1$ and $R^2$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl;

$R^3$, $R^{3a}$ and $R^4$ are independently hydrogen, optionally substituted $C_1$-$C_6$ alkyl, optionally substituted $C_1$-$C_6$ haloalkyl, fluorine, OH, CN, $CO_2H$, $C(O)NH_2$, $N(R^5)_2$, optionally substituted —O—$C_1$-$C_6$ alkyl, —$(CR^5R^5)_m$—OH, —$(CR^5R^5)_m$—$CO_2H$, —$(CR^5R^5)_m$—$C(O)NH_2$, —$(CR^5R^5)_m$—$C(O)NHR^5$, —$(CR^5R^5)_m$N$(R^5)_2$, —NH$(CR^5R^5)_m$$CO_2H$ or —NH$(CR^5R^5)_m$—$C(O)NH_2$;

each $R^5$ is independently H, F, OH, or optionally substituted $C_1$-$C_6$ alkyl;

each $R^{5a}$ is independently H, or optionally substituted $C_1$-$C_6$ alkyl;

$R^6$ is H, OH, F, optionally substituted $C_1$-$C_6$ alkyl, optionally substituted —O—$C_1$-$C_6$ alkyl, or —N$(R^{5a})_2$;

and each m is independently 1, 2, or 3.

3. The compound of claim 1, having the formula:

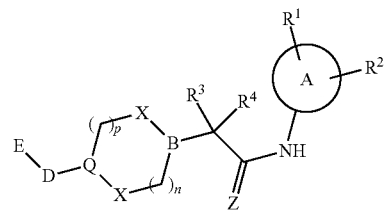

wherein Q is $C(CN)$ or $CR^6$.

4. The compound of claim 3, having the formula:

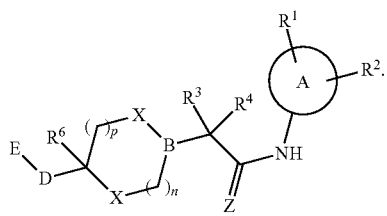

5. The compound of claim 4, having the formula:

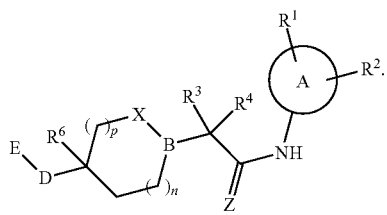

6. The compound of claim 5, having the formula:

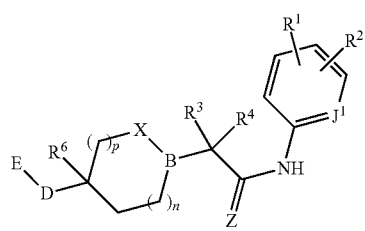

wherein $J^1$ is CH, N or optionally $C(R^2)$ when $R^2$ is attached to the ring vertex identified as $J^1$.

7. The compound of claim 6, having the formula:

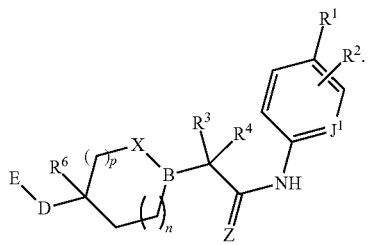

8. The compound of claim 7, having the formula:

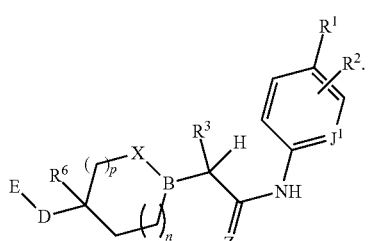

9. The compound of claim 8, having the formula:

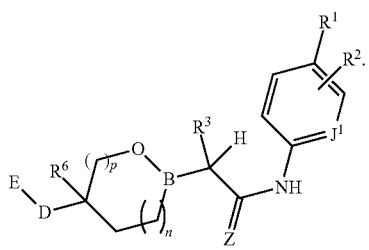

10. The compound of claim 8, having the formula:

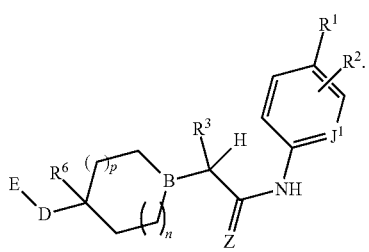

11. The compound of claim 10, having the formula:

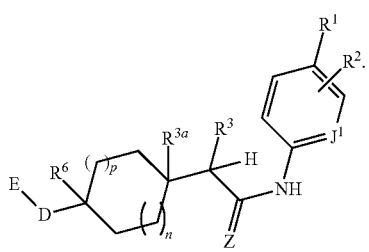

12. The compound of claim 11, having the formula:

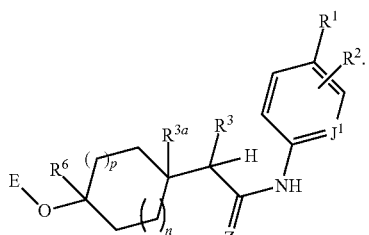

13. The compound of claim 11, having the formula:

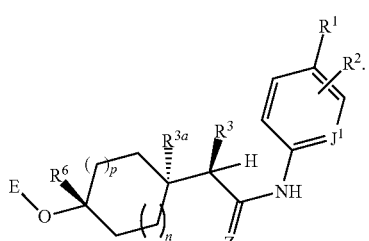

14. The compound of claim 11, having the formula:

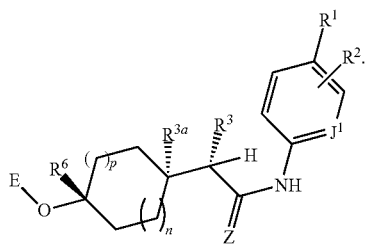

15. The compound of claim 11, having the formula:

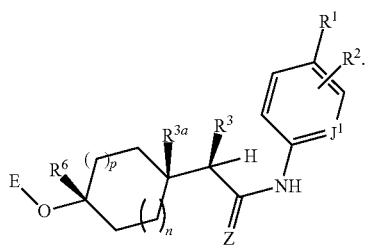

16. The compound of claim 11, having the formula:

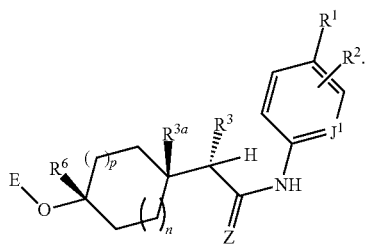

17. The compound of claim 11, having the formula:

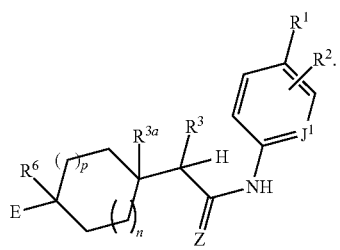

18. The compound of claim 11, having the formula:

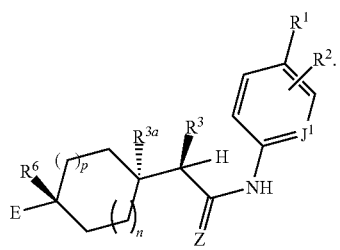

19. The compound of claim 11, having the formula:

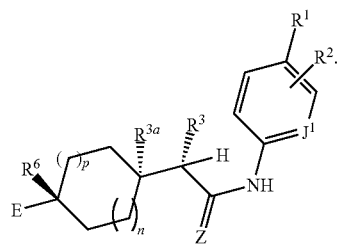

20. The compound of claim 11, having the formula:

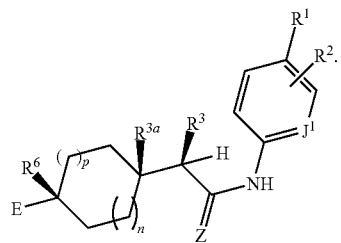

21. The compound of claim 11, having the formula:

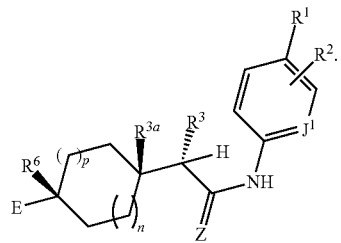

22. The compound of claim 17, having the formula:

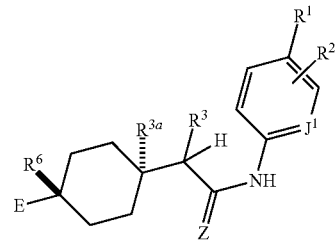

which is substantially free of other isomers at the carbon atoms to which each of $R^{3a}$ and $R^6$ are attached.

23. The compound of claim 17, having the formula:

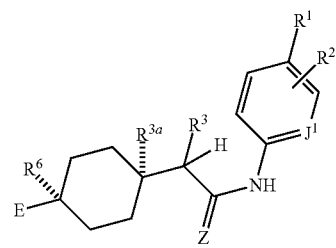

which is substantially free of other isomers at the carbon atoms to which each of $R^{3a}$ and $R^6$ are attached.

24. The compound of claim 17, having the formula:

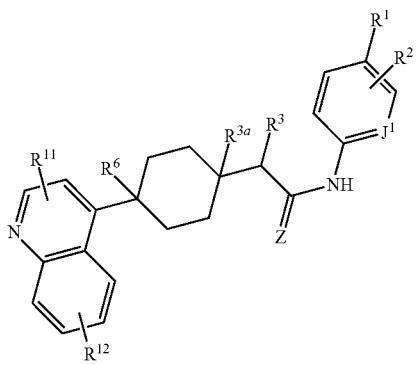

wherein:

$R^{11}$ and $R^{12}$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl.

25. The compound of claim 24, wherein $R^6$ is H, and $R^{11}$ and $R^{12}$ are each independently selected from the group consisting of halogen, CN and optionally substituted $C_1$-$C_4$ alkyl.

26. The compound of claim 17, having the formula:

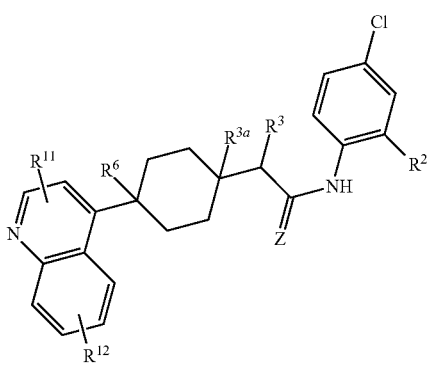

wherein:

$R^{11}$ and $R^{12}$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl.

27. The compound of claim 17, having the formula:

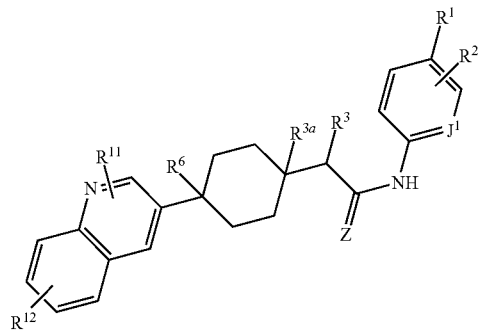

wherein:

$R^{11}$ and $R^{12}$ are independently hydrogen, halogen, optionally substituted $C_1$-$C_4$ haloalkyl, optionally substituted $C_3$-$C_6$ cycloalkyl, optionally substituted 3- to 6-membered cycloheteroalkyl, optionally substituted phenyl, optionally substituted heteroaryl, optionally substituted $C_1$-$C_4$ alkyl, optionally substituted $C_1$-$C_4$ alkoxy, CN, $SO_2NH_2$, $NHSO_2CH_3$, $NHSO_2CF_3$, $OCF_3$, $SO_2CH_3$, $SO_2CF_3$, or $CONH_2$, and when $R^1$ and $R^2$ are on adjacent vertices of a phenyl ring they may be joined together to form a 5- or 6-membered cycloheteroalkyl ring having one or two ring vertices independently selected from O, N and S, wherein said cycloheteroalkyl ring is optionally substituted with from one to three members selected from fluoro and $C_1$-$C_3$ alkyl.

28. The compound of claim 17, having the formula:

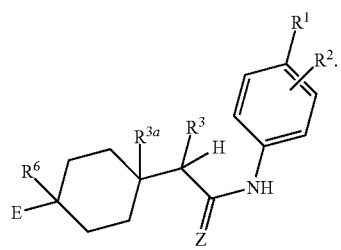

29. The compound of claim 27, having the formula:

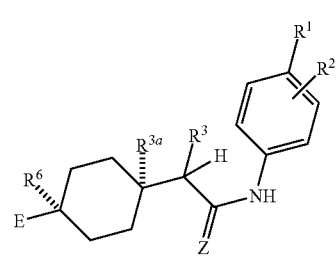

which is substantially free of other isomers at the stereocenters of the cyclohexane ring.

30. The compound of claim 27, having the formula:

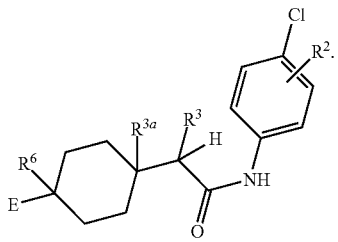

31. The compound of claim 27, having the formula:

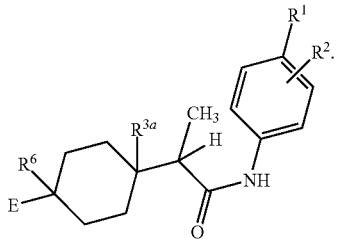

32. The compound of claim 28, having the formula:

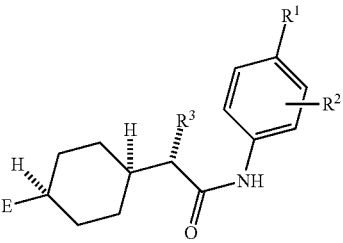

which is substantially free of other isomers at each of the three stereocenters shown.

33. The compound of claim 28, having the formula:

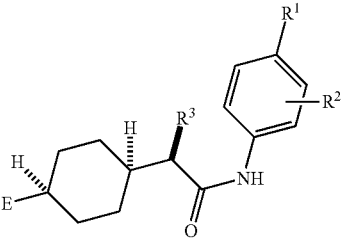

which is substantially free of other isomers at each of the three stereocenters shown.

34. The compound of claim 31, wherein $R^1$ is Cl, F, optionally substituted phenyl, or CN.

35. The compound of claim 31, having the formula:

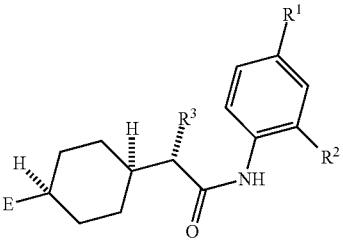

wherein $R^1$ is Cl, F, optionally substituted phenyl, or CN; and $R^2$ is H or F; and which is substantially free of other isomers at each of the three stereocenters shown.

36. The compound of claim 34, wherein $R^1$ is Cl.

37. The compound of claim 34, wherein $R^1$ is Cl; and $R^3$ is $CH_3$.

38. The compound of claim 34, having the formula:

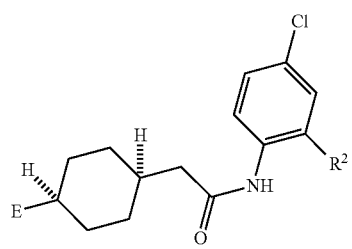

which is substantially free of other isomers at each of the two stereocenters shown.

39. The compound of claim 34, having the formula:

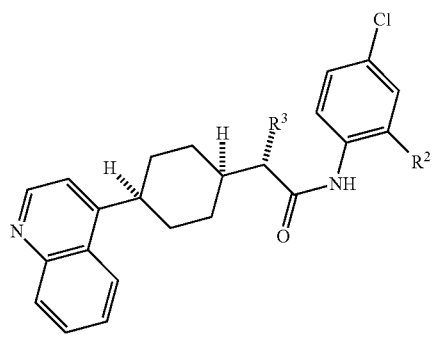

which is substantially free of other isomers at each of the two stereocenters shown.

40. The compound of claim 34, having the formula:

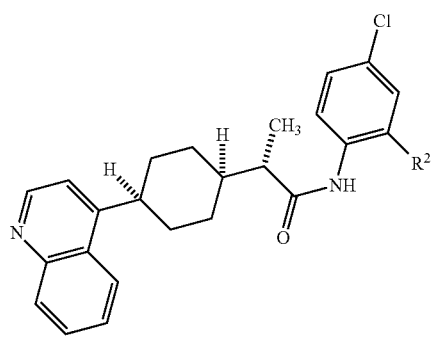

which is substantially free of other isomers at each of the three stereocenters shown.

41. The compound of claim 1 that is
N-(4-chlorophenyl)-2-(trans-4-(quinolin-4-yl)cyclohexyl)acetamide;
N-(4-chlorophenyl)-2-(cis-4-(quinolin-4-yl)cyclohexyl)acetamide;
N-(4-cyanophenyl)-2-(trans-4-(quinolin-4-yl)cyclohexyl)acetamide;
N-(4-cyanophenyl)-2-(cis-4-(quinolin-4-yl)cyclohexyl)acetamide;
N-(4-fluorophenyl)-2-(trans-4-(quinolin-4-yl)cyclohexyl)acetamide;
N-(4-fluorophenyl)-2-(cis-4-(quinolin-4-yl)cyclohexyl)acetamide;

N-(4-fluorophenyl)-2-(cis-4-(quinolin-3-yl)cyclohexyl) acetamide;
N-(4-fluorophenyl)-2-(trans-4-(quinolin-3-yl)cyclohexyl) acetamide;
N-(4-chlorophenyl)-2-(cis-4-(quinolin-3-yl)cyclohexyl) acetamide;
N-(4-chlorophenyl)-2-(trans-4-(quinolin-3-yl)cyclohexyl)acetamide;
N-(4-cyanophenyl)-2-(cis-4-(quinolin-3-yl)cyclohexyl) acetamide;
N-(4-cyanophenyl)-2-(trans-4-(quinolin-3-yl)cyclohexyl) acetamide;
2-(4-(cis-1H-indazol-4-yl)cyclohexyl)-N-(4-cyanophenyl)acetamide;
2-(4-(trans-1H-indazol-4-yl)cyclohexyl)-N-(4-cyanophenyl)acetamide;
2-(4-(1H-indazol-4-yl)cyclohexyl)-N-(4-chlorophenyl) acetamide;
N-(4-fluorophenyl)-2-(cis-4-(quinolin-4-yl)cyclohexyl) propanamide;
N-(4-chlorophenyl)-2-(trans-4-(quinolin-4-yl)cyclohexyl)propanamide;
N-(4-chlorophenyl)-2-(cis-4-(quinolin-4-yl)cyclohexyl) propanamide;
(R)—N-(4-chlorophenyl)-2-(cis-4-(6-fluoroquinolin-4-yl)cyclohexyl)propanamide;
(S)—N-(4-chlorophenyl)-2-(trans-4-(quinolin-3-yl)cyclohexyl)propanamide;
(R)—N-(4-cyanophenyl)-2-(cis-4-(7-fluoroquinolin-4-yl)cyclohexyl)butanamide;
(R)—N-(4-chlorophenyl)-2-(cis-4-(7-fluoroquinolin-4-yl)cyclohexyl)butanamide;
(R)—N-(4-chlorophenyl)-2-(cis-4-(quinolin-4-yl)cyclohexyl)propamide;
(R)—N-(4-cyanophenyl)-2-(cis-4-(quinolin-4-yl)cyclohexyl)propamide;
(R)—N-(4-chlorophenyl)-2-(cis-4-(quinolin-4-yl)cyclohexyl)butanamide;
(S)—N-(4-chlorophenyl)-2-(trans-4-(quinolin-4-yl)cyclohexyl)butanamide;
N-(4-chlorophenyl)-2-(cis-4-(quinolin-4-yloxy)cyclohexyl)propanamide;
N-(4-chlorophenyl)-2-(cis-1-hydroxy-4-(quinolin-4-yl) cyclohexyl)acetamide;
N-(4-fluorophenyl)-2-(cis-4-(isoquinolin-4-yloxy)cyclohexyl)acetamide;
N-(4-fluorophenyl)-2-(trans-4-(isoquinolin-4-yloxy)cyclohexyl)acetamide;
N-(4-cyanophenyl)-2-(cis-4-(quinolin-4-yloxy)cyclohexyl)acetamide;
N-(4-chlorophenyl)-2-(trans-1-hydroxy-4-(quinolin-4-yl) cyclohexyl)acetamide;
N-(4-fluorophenyl)-2-(trans-1-hydroxy-4-(quinolin-4-yl) cyclohexyl)acetamide;
(R)—N-(4-cyanophenyl)-2-(cis-4-(quinolin-4-yloxy)cyclohexyl)propanamide;
(S)—N-(4-fluorophenyl)-2-(cis-4-(quinolin-4-yloxy)cyclohexyl)propanamide;
N-(4-chlorophenyl)-2-(trans-4-(quinolin-4-yl)cyclohexyl)pent-4-enamide;
2-(4-(1H-pyrazolo[3,4-b]pyridin-4-yl)cyclohexyl)-N-(4-chlorophenyl) acetamide;
N-(4-fluorophenyl)-2-(cis-4-(quinazolin-4-yl)cyclohexyl)acetamide;
N-(4-fluorophenyl)-2-(4-(quinazolin-4-yl)cyclohexyl)acetamide;
N-(4-chlorophenyl)-2-(cis-4-(quinazolin-4-yl)cyclohexyl)acetamide;
N-(4-chlorophenyl)-2-(trans-4-(quinazolin-4-yl)cyclohexyl)acetamide;
N-(4-chlorophenyl)-2-(4-(1,5-naphthyridin-4-yl)cyclohexyl)acetamide;
N-(4-chlorophenyl)-2-(cis-4-(quinolin-3-yl)cyclohexyl) propanamide;
N-(4-fluorophenyl)-2-(trans-4-(quinolin-3-yl)cyclohexyl) propanamide;
N-(4-chlorophenyl)-2-((trans)-4-(isoquinolin-1-yl)cyclohexyl)acetamide;
N-(4-chlorophenyl)-2-((cis)-4-(isoquinolin-1-yl)cyclohexyl)acetamide;
N-(4-chlorophenyl)-2-((cis)-4-(isoquinolin-8-yl)cyclohexyl)acetamide;
N-(4-chlorophenyl)-2-((trans)-4-isoquinolin-8-yl)cyclohexyl)acetamide;
N-(4-chlorophenyl)-2-((trans)-4-(isoquinolin-5-yl)cyclohexyl)acetamide;
N-(4-fluorophenyl)-2-(cis-4-(quinolin-3-yl)cyclohexyl) propanamide;
N-(4-cyanophenyl)-2-((cis)-4-(quinolin-4-yl)cyclohexyl) pent-4-enamide;
(R)-2-((cis)-4-(6-fluoroquinolin-4-yl)cyclohexyl)-N-phenylpropanamide;
(R)—N-(4-fluoro-2-methylphenyl)-2-((cis)-4-(6-fluoroquinolin-4-yl)cyclohexyl)propanamide;
(R)-2-((cis)-4-(6-fluoroquinolin-4-yl)cyclohexyl)-N-(4-(trifluoromethyl)phenyl)propanamide;
(R)—N-(2,2-difluorobenzo[d][1,3]dioxol-5-yl)-2-((cis)-4-(6-fluoroquinolin-4-yl)cyclohexyl)propanmide;
(R)—N-(2-ethoxyphenyl)-2-((cis)-4-(6-fluoroquinolin-4-yl)cyclohexyl)propanamide;
(R)—N-(3-(difluoromethyl)phenyl)-2-((cis)-4-(6-fluoroquinolin-4-yl)cyclohexyl)propanamide;
(R)—N-(4-chloro-2-methylphenyl)-2-((cis)-4-(6-fluoroquinolin-4-yl)cyclohexyl)propanamide;
(R)—N-(3-chlorophenyl)-2-((cis)-4-(6-fluoroquinolin-4-yl)cyclohexyl)propanamide;
(R)—N-(3,4-dichlorophenyl)-2-((cis)-4-(6-fluoroquinolin-4-yl)cyclohexyl)propanamide;
methyl 3-((R)-2-((cis)-4-(6-fluoroquinolin-4-yl)cyclohexyl)propanamido)benzoate;
methyl 4-((R)-2-((cis)-4-(6-fluoroquinolin-4-yl)cyclohexyl)propanamido)benzoate;
(R)-2-((cis)-4-(6-fluoroquinolin-4-yl)cyclohexyl)-N-methyl-N-phenylpropanamide;
(R)-2-((cis)-4-(6-fluoroquinolin-4-yl)cyclohexyl)-N-(3-(trifluoromethyl)phenyl)propanamide;
(R)-2-((cis)-4-(6-fluoroquinolin-4-yl)cyclohexyl)-N-(4-phenoxyphenyl)propanamide;
(R)-2-((cis)-4-(6-fluoroquinolin-4-yl)cyclohexyl)-N-(m-tolyl)propanamide;
(R)-2-((cis)-4-(6-fluoroquinolin-4-yl)cyclohexyl)-N-(3-phenoxyphenyl)propanamide;
(R)-2-((cis)-4-(6-fluoroquinolin-4-yl)cyclohexyl)-N-(2-phenoxyphenyl)propanamide;
(R)-2-((cis)-4-(6-fluoroquinolin-4-yl)cyclohexyl)-N-(pyridin-4-yl)propanamide;
(R)-2-((cis)-4-(6-fluoroquinolin-4-yl)cyclohexyl)-N-(thiazol-2-yl)propanamide;
(R)-2-((cis)-4-(6-fluoroquinolin-4-yl)cyclohexyl)-N-(pyridin-3-yl)propanamide;
(R)—N-(2-fluorophenyl)-2-((cis)-4-(6-fluoroquinolin-4-yl)cyclohexyl)propanamide;

(R)—N-(4-ethoxyphenyl)-2-((cis)-4-(6-fluoroquinolin-4-yl)cyclohexyl)propanamide;
(R)—N-(3-cyanophenyl)-2-((cis)-4-(6-fluoroquinolin-4-yl)cyclohexyl)propanamide;
(R)—N-(3-chloro-4-methylphenyl)-2-((cis)-4-(6-fluoroquinolin-4-yl)cyclohexyl)propanamide;
(R)—N-(3-fluorophenyl)-2-((cis)-4-(6-fluoroquinolin-4-yl)cyclohexyl)propanamide;
(R)—N-(3-cyano-4-(trifluoromethyl)phenyl)-2-((cis)-4-(6-fluoroquinolin-4-yl)cyclohexyl)propanamide;
N-(4-chlorophenyl)-2-((trans)-4-((7-(trifluoromethyl)quinolin-4-yl)oxy)cyclohexyl)butanamide;
N-(4-chlorophenyl)-2-((trans)-4-((2-(trifluoromethyl)quinolin-4-yl)oxy)cyclohexyl)butanamide;
N-(4-chlorophenyl)-2-((trans)-4-(quinolin-4-yloxy)cyclohexyl)butanamide;
N-(4-chlorophenyl)-2-((trans)-4-((8-(trifluoromethyl)quinolin-4-yl)oxy)cyclohexyl)butanamide;
2-(4-((R)-3-((4-Chlorophenyl)amino)-2-((cis)-4-(6-fluoroquinolin-4-yl)cyclohexyl)-3-oxopropyl)phenyl)-2-propanoic acid;
N-(4-chlorophenyl)-2-((cis)-4-((2-(trifluoromethyl)quinolin-4-yl)oxy)cyclohexyl)butanamide;
N-(4-chlorophenyl)-2-((cis)-4-((6-(trifluoromethyl)quinolin-4-yl)oxy)cyclohexyl)butanamide;
N-(4-chlorophenyl)-2-(4-((4-chloroquinolin-6-yl)oxy)piperidin-1-yl)acetamide;
N-(4-chlorophenyl)-2-(4-((4-chloroquinolin-6-yl)oxy)piperidin-1-yl)propanamide;
2-(4-((4-chloroquinolin-6-yl)oxy)piperidin-1-yl)-N-(p-tolyl)propanamide;
N-(4-chlorophenyl)-2-(4-((6-fluoroquinolin-4-yl)oxy)piperidin-1-yl)acetamide;
N-(4-chlorophenyl)-2-(4-((6-fluoroquinolin-4-yl)oxy)piperidin-1-yl)propanamide;
2-(4-((6-fluoroquinolin-4-yl)oxy)piperidin-1-yl)-N-(p-tolyl)butanamide;
N-(4-chlorophenyl)-2-(4-((6-fluoroquinolin-4-yl)oxy)piperidin-1-yl)butanamide;
N-(4-fluorophenyl)-2-(4-((6-fluoroquinolin-4-yl)oxy)piperidin-1-yl)propanamide;
N-(4-ethoxyphenyl)-2-(4-((6-fluoroquinolin-4-yl)oxy)piperidin-1-yl)propanamide;
2-(4-((6-fluoroquinolin-4-yl)oxy)piperidin-1-yl)-N-(p-tolyl)propanamide;
N-(4-chlorophenyl)-2-(4-((6-fluoroquinolin-4-yl)oxy)piperidin-1-yl)-3-methylbutanamide;
N-(4-chlorophenyl)-2-(1-(quinolin-4-ylmethyl)piperidin-4-yl)acetamide;
N-(4-fluorophenyl)-(1-(quinolin-4-ylmethyl)piperidin-4-yl)acetamide;
N-(4-fluorophenyl)-2-(1-(6-fluoroquinolin-4-yl)piperidin-4-yl)acetamide;
N-(4-chlorophenyl)-2-(1-(6-fluoroquinolin-4-yl)piperidin-4-yl)acetamide;
N-(4-bromophenyl)-2-(1(6-fluoroquinolin-4-yl)piperidin-4-yl)acetamide;
N-(2-fluoro-4-methylphenyl)-2-(1-(6-fluoroquinolin-4-yl)piperidin-4-yl)acetamide;
N-(4-chloro-2-methylphenyl)-2-(1-(6-fluoroquinolin-4-yl)piperidin-4-yl)acetamide;
N-(4-fluorophenyl)-2-(1-(6-fluoroquinolin-4-yl)-4-methylpiperidin-4-yl)acetamide;
N-(4-chlorophenyl)-2-(1-(6-fluoroquinolin-4-yl)-4-methylpiperidin-4-yl)acetamide;
2-(1-(6-fluoroquinolin-4-yl)-4-methylpiperidin-4-yl)-N-(2-methoxypyrimidin-5-yl)acetamide;
N-(4-ethoxyphenyl)-2-(1-(6-fluoroquinolin-4-yl)-4-methylpiperidin-4-yl)acetamide;
N-(4-chlorophenyl)-2-(4-(6-fluoroquinolin-4-yl)piperazin-1-yl)propanamide;
N-(4-fromophenyl)-2-(4-(6-fluoroquinolin-4-yl)piperazin-1-yl)propanamide;
2-(4-(6-fluoroquinolin-4-yl)piperazin-1-yl)-N-phenylpropanamide;
N-(4-chlorophenyl)-2-(4-(6-fluoroquinolin-4-yl)piperazin-1-yl)butanamide;
2-(4-(6-fluoroquinolin-4-yl)piperazin-1-yl)-N-phenylbutanamide;
N-(4-chlorophenyl)-2-(4-(6-fluoroquinolin-4-yl)piperazin-1-yl)-3-methoxypropanamide;
N-(4-fluorophenyl)-2-(4-(6-fluoroquinolin-4-yl)piperazin-1-yl)-3-methoxypropanamide;
2-(4-((R)-3-((4-cyanophenyl)amino)-2-((cis)-4-(6-fluoroquinolin-4-yl)cyclohexyl)-3-oxopropyl)phenyl)propanoic acid;
(R)—N-cyclohexyl-2-((cis)-4-(6-fluoroquinolin-4-yl)cyclohexyl)propanamide;
N-cyclohexyl-2-((cis)-4-(6-fluoroquinolin-4-yl)cyclohexyl)acetamide;
N-(4-chlorophenyl)-2-(cis-trans-4-(pyrazolo[1,5-a]pyrimidin-7-yl)cyclohexyl)propanamide;
N-(4-chlorophenyl)-2-(trans-4-(pyrazolo[1,5-a]pyrimidin-7-yl)cyclohexyl)propanamide;
(S)—N-(4-chlorophenyl)-2-((cis)-4-(pyrazolo[1,5-a]pyrimidin-7-yl)cyclohexyl)propanamide;
(R)—N-(4-chlorophenyl)-2-((cis)-4-(pyrazolo[1,5-a]pyrimidin-7-yl)cyclohexyl)propanamide;
(R)—N-(4-chlorophenyl)-2-((trans)-4-(pyrazolo[1,5-a]pyrimidin-7-yl)cyclohexyl)propanamide;
2-(cis-4-(1,8-naphthyridin-4-yl)cyclohexyl)-N-(4-chlorophenyl)propanamide;
2-trans-4-(1,8-naphthyridin-4-yl)cyclohexyl)-N-(4-chlorophenyl)propanamide;
(S)-2-((cis)-4-(1,8-naphthyridin-4-yl)cyclohexyl)-N-(4-chlorophenyl)propanamide;
(R)-2-((cis)-4-(1,8-naphthyridin-4-yl)cyclohexyl)-N-(4-chlorophenyl)propanamide;
2-(trans-4-(1H-pyrazolo[4,3-b]pyridin-7-yl)cyclohexyl)-N-(4-chlorophenyl)propanamide;
(S)-2-((cis)-4-(1H-pyrazolo[4,3-b]pyridin-7-yl)cyclohexyl)-N-(4-chlorophenyl)propanamide;
(R)-2-((cis)-4-(1H-pyrazolo[4,3-b]pyridin-7-yl)cyclohexyl)-N-(4-chlorophenyl)propanamide;
(S)-2-((trans)-4-(1H-pyrazolo[4,3-b]pyridin-7-yl)cyclohexyl)-N-(4-chlorophenyl)propanamide;
(R)-2-((trans)-4-(1H-pyrazolo[4,3-b]pyridin-7-yl)cyclohexyl)-N-(4-chlorophenyl)propanamide;
N-(cis-4-chlorophenyl)-2-(4-(6-iodoquinolin-4-yl)cyclohexyl)propanamide;
N-(trans-4-chlorophenyl)-2-(4-(6-iodoquinolin-4-yl)cyclohexyl)propanamide;
(S)—N-(4-chlorophenyl)-2-((cis)-4-(6-iodoquinolin-4-yl)cyclohexyl)propanamide;
(R)—N-(4-chlorophenyl)-2-((cis)-4-(6-iodoquinolin-4-yl)cyclohexyl)propanamide;
(S)—N-(4-chlorophenyl)-2-((trans)-4-(6-iodoquinolin-4-yl)cyclohexyl)propanamide;
(R)—N-(4-chlorophenyl)-2-((trans)-4-(6-iodoquinolin-4-yl)cyclohexyl)propanamide;
2-((trans)-4-((1,8-naphthyridin-4-yl)oxy)cyclohexyl)-N-(4-chlorophenyl)propanamide;
N-(4-chlorophenyl)-2-(4-(6-fluoroquinolin-4-yl)cyclohexyl)butanamide;

(R)—N-(4-chlorophenyl)-4-hydroxy-2-((cis)-4-(quinolin-4-yl)cyclohexyl)butanamide;
N-(4-chlorophenyl)-2-((cis)-4-cyano-4-(quinolin-4-yl)cyclohexyl)acetamide;
N-(4-chlorophenyl)-2-((trans)-4-cyano-4-(quinolin-4-yl)cyclohexyl)acetamide;
(R)—N-(4-chlorophenyl)-5-hydroxy-2-((cis)-4-(quinolin-4-yl)cyclohexyl)pentanamide;
N-(4-chlorophenyl)-2-(1-methoxy-4-(quinolin-4-yl)cyclohexyl)acetamide;
N-(4-fluorophenyl)-2-(4-hydroxy-4-(quinolin-4-yl)cyclohexyl)acetamide;
N-(4-chlorophenyl)-2-(4-hydroxy-4-(quinolin-4-yl)cyclohexyl)acetamide;
(R)—N-(4-chlorophenyl)-2-((1S,4S)-4-(7-fluoroquinolin-4-yl)cyclohexyl)propanamide;
(R)—N-(4-fluorophenyl)-2-((1S,4S)-4-(7-fluoroquinolin-4-yl)cyclohexyl)propanamide;
(R)—N-(4-cyanophenyl)-2-((1S,4S)-4-(7-fluoroquinolin-4-yl)cyclohexyl)propanamide;
(R)—N-(4-fluorophenyl)-2-((1S,4S)-4-(7-fluoroquinolin-4-yl)cyclohexyl)butanamide;
(R)—N-(4-chlorophenyl)-2-((1R,4R)-4-(quinolin-4-yl)cyclohexyl)butanamide;
(R)—N-(4-fluorophenyl)-2-((1R,4R)-4-(quinolin-4-yl)cyclohexyl)butanamide;
(S)—N-(4-cyanophenyl)-2-((1R,4S)-4-(quinolin-4-yl)cyclohexyl)butanamide;
(R)—N-(4-chlorophenyl)-2-((1S,4R)-4-(quinolin-4-yl)cyclohexyl)pent-4-ynamide;
N-(4-chlorophenyl)-2-((1S,4S)-4-(quinolin-4-yl)cyclohexyl)pentanamide;
5-((4-chlorophenyl)amino)-5-oxo-4-((1S,4S)-4-(quinolin-4-yl)cyclohexyl)pentanoic acid;
N-(4-chlorophenyl)-2-((1S,4S)-4-(8-fluoroquinolin-4-yl)cyclohexyl)acetamide;
N-(4-fluorophenyl)-2-((1R,4R)-4-(8-fluoroquinolin-4-yl)cyclohexyl)acetamide;
(R)—N-(2-fluorophenyl)-2-((1S,4S)-4-(quinolin-4-yl)cyclohexyl)propanamide;
(R)-2-((1S,4S)-4-(quinolin-4-yl)cyclohexyl)-N-(4-(trifluoromethoxy)phenyl)propanamide;
(R)—N-(3-fluoro-4-(trifluoromethyl)phenyl)-2-((1S,4S)-4-(quinolin-4-yl)cyclohexyl)propanamide;
(R)—N-(2,2-difluorobenzo[d][1,3]dioxol-5-yl)-2-((1S,4S)-4-(quinolin-4-yl)cyclohexyl)propanamide;
(R)—N-(3-chloro-4-fluorophenyl)-2-((1S,4S)-4-(quinolin-4-yl)cyclohexyl)propanamide;
(R)—N-(4-chlorophenyl)-5-methyl-2-((1S,4S)-4-(quinolin-4-yl)cyclohexyl)hex-4-enamide;
(S)—N-(4-chlorophenyl)-2-((1S,4R)-4-(quinolin-4-yl)cyclohexyl)propanamide;
(R)—N-(4-chloro-2-fluorophenyl)-2-((1S,4S)-4-(quinolin-4-yl)cyclohexyl)propanamide;
N-(4-cyanophenyl)-2-((1R,4R)-4-(quinolin-4-yl)cyclohexyl)pent-4-enamide;
(R)—N-(4-fluorophenyl)-2-((1S,4S)-4-(quinolin-4-yl)cyclohexyl)propanamide;
(R)—N-(5-chloropyridin-2-yl)-2-((1S,4S)-4-(quinolin-4-yl)cyclohexyl)propanamide;
(R)-2-((1S,4S)-4-(quinolin-4-yl)cyclohexyl)-N-(4-(trifluoromethyl)phenyl)propanamide;
(R)—N-(4-chloro-3-fluorophenyl)-2-((1S,4S)-4-(quinolin-4-yl)cyclohexyl)propanamide;
(R)—N-(4-cyano-3-fluorophenyl)-2-((1S,4S)-4-(quinolin-4-yl)cyclohexyl)propanamide;
(R)—N-(4-fluorophenyl)-2-((1S,4S)-4-(quinolin-4-yl)cyclohexyl)pent-4-enamide;
(R)—N-(3,4-difluorophenyl)-2-((1S,4S)-4-(quinolin-4-yl)cyclohexyl)propanamide;
N-(4-chlorophenyl)-2-((1S,4S)-4-(6,8-difluoroquinolin-4-yl)cyclohexyl)acetamide;
2-((1S,4S)-4-(6,8-difluoroquinolin-4-yl)cyclohexyl)-N-(4-fluorophenyl)acetamide;
2-((1R,4R)-4-(6,8-difluoroquinolin-4-yl)cyclohexyl)-N-(4-fluorophenyl)acetamide;
N-(4-chlorophenyl)-2-((1R,4R)-4-(quinolin-4-yloxy)cyclohexyl)acetamide;
N-(4-chlorophenyl)-2-((1S,4S)-4-(quinolin-4-yloxy)cyclohexyl)acetamide;
N-(4-chlorophenyl)-2-(1-hydroxy-4-(quinolin-4-yl)cyclohexyl)acetamide;
N-(4-cyanophenyl)-2-((1R,4R)-4-(quinolin-4-yloxy)cyclohexyl)acetamide;
N-(4-chlorophenyl)-2-((1R,4R)-1-hydroxy-4-(quinolin-4-yl)cyclohexyl)acetamide;
N-(4-fluorophenyl)-2-((1R,4R)-1-hydroxy-4-(quinolin-4-yl)cyclohexyl)acetamide;
N-(4-chlorophenyl)-2-((1S,4S)-1-hydroxy-4-(quinolin-4-yl)cyclohexyl)acetamide;
(S)—N-(4-fluorophenyl)-2-((1R,4S)-1-hydroxy-4-(quinolin-4-yl)cyclohexyl)propanamide;
(S)—N-(4-cyanophenyl)-2-((1R,4S)-1-hydroxy-4-(quinolin-4-yl)cyclohexyl)propanamide;
N-(4-chlorophenyl)-2-((1S,4S)-4-(2-(trifluoromethyl)quinolin-4-yl)cyclohexyl)acetamide;
N-(4-chlorophenyl)-2-((1R,4R)-4-(2-(trifluoromethyl)quinolin-4-yl)cyclohexyl)acetamide;
N-(4-fluorophenyl)-2-((1R,4R)-4-(2-(trifluoromethyl)quinolin-4-yl)cyclohexyl)acetamide;
N-(4-fluorophenyl)-2-((1S,4S)-4-(2-(trifluoromethyl)quinolin-4-yl)cyclohexyl)acetamide;
N-(4-fluorophenyl)-2-((1S,4S)-4-(8-(trifluoromethyl)quinolin-4-yl)cyclohexyl)acetamide;
N-(4-chlorophenyl)-2-((1R,4R)-4-(8-(trifluoromethyl)quinolin-4-yl)cyclohexyl)acetamide;
N-(4-chlorophenyl)-2-((1S,4S)-4-(8-trifluoromethyl)quinolin-4-yl)cyclohexyl)acetamide;
(R)—N-(4-fluorophenyl)-2-((1S,4S)-4-(6-fluoroquinolin-4-yl)cyclohexyl)propanamide;
(R)—N-(4-cyanophenyl)-2-((1S,4S)-4-(8-fluoroquinolin-4-yl)cyclohexyl)propanamide;
2-(4-((R)-3-((4-chlorophenyl)amino)-3-oxo-2-((1S,4S)-4-(quinolin-4-yl)cyclohexyl)propyl)phenyl)acetic acid;
(R)—N-(4-chlorophenyl)-2-((1S,4S)-4-(8-fluoroquinolin-4-yl)cyclohexyl)propanamide;
(R)—N-(4-chlorophenyl)-2-((1S,4S)-4-(quinolin-3-yl)cyclohexyl)propanamide;
(R)—N-(4-chlorophenyl)-2-((1R,4R)-4-(quinolin-3-yl)cyclohexyl)propanamide;
(S)—N-(4-chlorophenyl)-2-((1S,4R)-4-(quinolin-3-yl)cyclohexyl)propanamide;
(R)—N-(4-fluorophenyl)-2-((1S,4S)-4-(quinolin-4-yl)cyclohexyl)butanamide;
(S)—N-(4-fluorophenyl)-2-((1R,4S)-4-(quinolin-4-yl)cyclohexyl)butanamide;
N-(4-chlorophenyl)-2-((1R,4R)-4-(8-fluoroquinolin-4-yl)cyclohexyl)acetamide;
N-(4-fluorophenyl)-2-((1S,4S)-4-(8-fluoroquinolin-4-yl)cyclohexyl)acetamide;
(R)—N-(4-chlorophenyl)-2-((1S,4S)-4-(quinolin-4-yl)cyclohexyl)pent-4-enamide;

(R)—N-(4-chlorophenyl)-2-((1S,4S)-4-(8-(trifluoromethyl)quinolin-4-yl)cyclohexyl)propanamide;
(R)—N-(4-chlorophenyl)-2-((1S,4S)-4-(2-(trifluoromethyl)quinolin-4-yl)cyclohexyl)propanamide;
(R)—N-(4-chlorophenyl)-2-((1S,4S)-4-(quinolin-4-yloxy)cyclohexyl)propanamide;
(S)—N-(4-chlorophenyl)-2-((1S,4R)-4-(quinolin-4-yloxy)cyclohexyl)propanamide;
N-(4-chlorophenyl)-2-(trans-4-(6-fluoroquinolin-4-yl)-1-hydroxycyclohexyl)propanamide;
N-(4-chlorophenyl)-2-(cis-4-(6-fluoroquinolin-4-yl)-1-hydroxycyclohexyl)propanamide;
N-(4-chlorophenyl)-2-(trans-1-fluoro-4-(6-fluoroquinolin-4-yl)cyclohexyl)propanamide;
N-(4-chlorophenyl)-2-(trans-4-(6-fluoroquinolin-4-yl)-4-hydroxycyclohexyl)propanamide;
N-(4-chlorophenyl)-2-(cis-4-(6-fluoroquinolin-4-yl)-4-hydroxycyclohexyl)propanamide;
(R)—N-(4-chloro-2-hydroxyphenyl)-2-(cis-4-(6-fluoroquinolin-4-yl)cyclohexyl)propanamide;
(R)—N-(4-chloro-3-hydroxyphenyl)-2-(cis-4-(6-fluoroquinolin-4-yl)cyclohexyl)propanamide;
(R)—N-((2S)-bicyclo[2.2.1]heptan-2-yl)-2-(cis-4-(6-fluoroquinolin-4-yl)cyclohexyl)propanamide;
(R)—N-(2-amino-4-chlorophenyl)-2-(cis-4-(6-fluoroquinolin-4-yl)cyclohexyl)pent-4-enamide;
2-(1-(6-fluoroquinolin-4-yl)-4-methylpiperidin-4-yl)-N-(1-methylcyclohexyl)acetamide;
N-(4-chlorophenyl)-2-(1-(6-fluoroquinolin-4-yl)piperidin-4-yl)butanamide;
N-(4-chlorophenyl)-2-(4-(6-fluoroquinolin-4-yl)piperazin-1-yl)pentanamide;
2-(4-(6-fluoroquinolin-4-yl)piperazin-1-yl)-N-(1-methylcyclohexyl)pentanamide;
cis-N-(4-chlorophenyl)-2-(4-(3-methyl-3H-imidazo[4,5-b]pyridin-7-yl)cyclohexyl)propanamide;
trans-N-(4-chlorophenyl)-2-(4-(3-methyl-3H-imidazo[4,5-b]pyridin-7-yl)cyclohexyl)propanamide; or
N-(4-chlorophenyl)-2-(4-(3-methyl-3H-imidazo[4,5-b]pyridin-7-yl)cyclohexyl)propanamide;
or a stereoisomer thereof or a pharmaceutically acceptable salt thereof.

42. A pharmaceutical composition comprising a compound of claim 1 and a pharmaceutically acceptable excipient.

43. A combination comprising a compound of claim 1 and at least one additional therapeutic agent.

44. The combination of claim 43, wherein the at least one additional therapeutic agent is a chemotherapeutic agent, an immune- and/or inflammation-modulating agent, an anti-hypercholesterolemia agent, or an anti-infective agent.

45. The combination of claim 43, wherein the at least one additional therapeutic agent is an immune checkpoint inhibitor.

46. The combination of claim 45, wherein said immune checkpoint inhibitor is selected from the group consisting of ipilimumab, nivolumab and pembroluzimab.

47. The compound of claim 1 that is
(R)—N-(4-chlorophenyl)-2-(cis-4-(6-fluoroquinolin-4-yl)cyclohexyl)propanamide;
(R)—N-(4-cyanophenyl)-2-(cis-4-(7-fluoroquinolin-4-yl)cyclohexyl)butanamide;
(R)—N-(4-chlorophenyl)-2-(cis-4-(7-fluoroquinolin-4-yl)cyclohexyl)butanamide;
(R)-2-((cis)-4-(6-fluoroquinolin-4-yl)cyclohexyl)-N-phenylpropanamide;
(R)—N-(4-fluoro-2-methylphenyl)-2-((cis)-4-(6-fluoroquinolin-4-yl)cyclohexyl)propanamide;
(R)-2-((cis)-4-(6-fluoroquinolin-4-yl)cyclohexyl)-N-(4-(trifluoromethyl)phenyl)propanamide;
(R)—N-(2,2-difluorobenzo[d][1,3]dioxol-5-yl)-2-((cis)-4-(6-fluoroquinolin-4-yl)cyclohexyl)propanmide;
(R)—N-(2-ethoxyphenyl)-2-((cis)-4-(6-fluoroquinolin-4-yl)cyclohexyl)propanamide;
(R)—N-(3-(difluoromethyl)phenyl)-2-((cis)-4-(6-fluoroquinolin-4-yl)cyclohexyl)propanamide;
(R)—N-(4-chloro-2-methylphenyl)-2-((cis)-4-(6-fluoroquinolin-4-yl)cyclohexyl)propanamide;
(R)—N-(3-chlorophenyl)-2-((cis)-4-(6-fluoroquinolin-4-yl)cyclohexyl)propanamide;
(R)—N-(3,4-dichlorophenyl)-2-((cis)-4-(6-fluoroquinolin-4-yl)cyclohexyl)propanamide;
methyl 3-((R)-2-((cis)-4-(6-fluoroquinolin-4-yl)cyclohexyl)propanamido)benzoate;
methyl 4-((R)-2-((cis)-4-(6-fluoroquinolin-4-yl)cyclohexyl)propanamido)benzoate;
(R)-2-((cis)-4-(6-fluoroquinolin-4-yl)cyclohexyl)-N-methyl-N-phenylpropanamide;
(R)-2-((cis)-4-(6-fluoroquinolin-4-yl)cyclohexyl)-N-(3-(trifluoromethyl)phenyl)propanamide;
(R)-2-((cis)-4-(6-fluoroquinolin-4-yl)cyclohexyl)-N-(4-phenoxyphenyl)propanamide;
(R)-2-((cis)-4-(6-fluoroquinolin-4-yl)cyclohexyl)-N-(m-tolyl)propanamide;
(R)-2-((cis)-4-(6-fluoroquinolin-4-yl)cyclohexyl)-N-(3-phenoxyphenyl)propanamide;
(R)-2-((cis)-4-(6-fluoroquinolin-4-yl)cyclohexyl)-N-(2-phenoxyphenyl)propanamide;
(R)-2-((cis)-4-(6-fluoroquinolin-4-yl)cyclohexyl)-N-(pyridin-4-yl)propanamide;
(R)-2-((cis)-4-(6-fluoroquinolin-4-yl)cyclohexyl)-N-(thiazol-2-yl)propanamide;
(R)-2-((cis)-4-(6-fluoroquinolin-4-yl)cyclohexyl)-N-(pyridin-3-yl)propanamide;
(R)—N-(2-fluorophenyl)-2-((cis)-4-(6-fluoroquinolin-4-yl)cyclohexyl)propanamide;
(R)—N-(4-ethoxyphenyl)-2-((cis)-4-(6-fluoroquinolin-4-yl)cyclohexyl)propanamide;
(R)—N-(3-cyanophenyl)-2-((cis)-4-(6-fluoroquinolin-4-yl)cyclohexyl)propanamide;
(R)—N-(3-chloro-4-methylphenyl)-2-((cis)-4-(6-fluoroquinolin-4-yl)cyclohexyl)propanamide;
(R)—N-(3-fluorophenyl)-2-((cis)-4-(6-fluoroquinolin-4-yl)cyclohexyl)propanamide;
(R)—N-(3-cyano-4-(trifluoromethyl)phenyl)-2-((cis)-4-(6-fluoroquinolin-4-yl)cyclohexyl)propanamide;
N-(cis-4-chlorophenyl)-2-(4-(6-iodoquinolin-4-yl)cyclohexyl)propanamide;
N-(trans-4-chlorophenyl)-2-(4-(6-iodoquinolin-4-yl)cyclohexyl)propanamide;
(S)—N-(4-chlorophenyl)-2-((cis)-4-(6-iodoquinolin-4-yl)cyclohexyl)propanamide;
(R)—N-(4-chlorophenyl)-2-((cis)-4-(6-iodoquinolin-4-yl)cyclohexyl)propanamide;
(S)—N-(4-chlorophenyl)-2-((trans)-4-(6-iodoquinolin-4-yl)cyclohexyl)propanamide;
(R)—N-(4-chlorophenyl)-2-((trans)-4-(6-iodoquinolin-4-yl)cyclohexyl)propanamide;
N-(4-chlorophenyl)-2-(4-(6-fluoroquinolin-4-yl)cyclohexyl)butanamide;
(R)—N-(4-chlorophenyl)-2-((1S,4S)-4-(7-fluoroquinolin-4-yl)cyclohexyl)propanamide;

(R)—N-(4-fluorophenyl)-2-((1S,4S)-4-(7-fluoroquinolin-4-yl)cyclohexyl)propanamide;
(R)—N-(4-cyanophenyl)-2-((1S,4S)-4-(7-fluoroquinolin-4-yl)cyclohexyl)propanamide;
(R)—N-(4-fluorophenyl)-2-((1S,4S)-4-(7-fluoroquinolin-4-yl)cyclohexyl)butanamide;
N-(4-chlorophenyl)-2-((1S,4S)-4-(8-fluoroquinolin-4-yl)cyclohexyl)acetamide;
N-(4-fluorophenyl)-2-((1R,4R)-4-(8-fluoroquinolin-4-yl)cyclohexyl)acetamide;
N-(4-chlorophenyl)-2-((1S,4S)-4-(6,8-difluoroquinolin-4-yl)cyclohexyl)acetamide;
2-((1S,4S)-4-(6,8-difluoroquinolin-4-yl)cyclohexyl)-N-(4-fluorophenyl)acetamide;
2-((1R,4R)-4-(6,8-difluoroquinolin-4-yl)cyclohexyl)-N-(4-fluorophenyl)acetamide;
(R)—N-(4-fluorophenyl)-2-((1S,4S)-4-(6-fluoroquinolin-4-yl)cyclohexyl)propanamide;
(R)—N-(4-cyanophenyl)-2-((1S,4S)-4-(8-fluoroquinolin-4-yl)cyclohexyl)propanamide;
(R)—N-(4-chlorophenyl)-2-((1S,4S)-4-(8-fluoroquinolin-4-yl)cyclohexyl)propanamide;
N-(4-chlorophenyl)-2-((1R,4R)-4-(8-fluoroquinolin-4-yl)cyclohexyl)acetamide;
N-(4-fluorophenyl)-2-((1S,4S)-4-(8-fluoroquinolin-4-yl)cyclohexyl)acetamide;
N-(4-chlorophenyl)-2-(trans-4-(6-fluoroquinolin-4-yl)-1-hydroxycyclohexyl)propanamide;
N-(4-chlorophenyl)-2-(cis-4-(6-fluoroquinolin-4-yl)-1-hydroxycyclohexyl)propanamide;
N-(4-chlorophenyl)-2-(trans-1-fluoro-4-(6-fluoroquinolin-4-yl)cyclohexyl)propanamide;
N-(4-chlorophenyl)-2-(trans-4-(6-fluoroquinolin-4-yl)-4-hydroxycyclohexyl)propanamide;
N-(4-chlorophenyl)-2-(cis-4-(6-fluoroquinolin-4-yl)-4-hydroxycyclohexyl)propanamide;
(R)—N-(4-chloro-2-hydroxyphenyl)-2-(cis-4-(6-fluoroquinolin-4-yl)cyclohexyl)propanamide; or
(R)—N-(4-chloro-3-hydroxyphenyl)-2-(cis-4-(6-fluoroquinolin-4-yl)cyclohexyl)propanamide;
or a stereoisomer thereof or a pharmaceutically acceptable salt thereof.

* * * * *

UNITED STATES PATENT AND TRADEMARK OFFICE
CERTIFICATE OF CORRECTION

PATENT NO. : 9,643,972 B2  
APPLICATION NO. : 14/933863  
DATED : May 9, 2017  
INVENTOR(S) : Beck et al.

Page 1 of 1

It is certified that error appears in the above-identified patent and that said Letters Patent is hereby corrected as shown below:

In the Claims

At Column 251, Line 58 (Claim 46), delete "pembroluzimab" and substitute therefor
-- pembrolizumab --

Signed and Sealed this
Sixth Day of February, 2018

Joseph Matal
*Performing the Functions and Duties of the
Under Secretary of Commerce for Intellectual Property and
Director of the United States Patent and Trademark Office*